United States Patent
Davydov et al.

(10) Patent No.: US 12,094,604 B2
(45) Date of Patent: Sep. 17, 2024

(54) WELLNESS AGGREGATOR

(71) Applicant: Apple Inc., Cupertino, CA (US)

(72) Inventors: Anton M. Davydov, Gilroy, CA (US); Adam L. Beberg, San Jose, CA (US); Dylan R. Edwards, San Jose, CA (US); Zachery W. Kennedy, Marina Del Rey, CA (US); Zachury B. Minjack, San Francisco, CA (US); Afshad M. Mistri, Mountain View, CA (US); Dennis S. Park, San Francisco, CA (US); Lawrence Y. Yang, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/951,945

(22) Filed: Sep. 23, 2022

(65) Prior Publication Data

US 2023/0014290 A1 Jan. 19, 2023

Related U.S. Application Data

(63) Continuation of application No. 17/735,395, filed on May 3, 2022, which is a continuation of application
(Continued)

(51) Int. Cl.
*G16H 40/67* (2018.01)
*G06Q 50/00* (2012.01)
(Continued)

(52) U.S. Cl.
CPC ............ *G16H 40/67* (2018.01); *G06Q 50/01* (2013.01); *G16H 10/60* (2018.01); *G16H 50/30* (2018.01); *G16H 50/70* (2018.01); *G16H 80/00* (2018.01)

(58) Field of Classification Search
CPC ........ G16H 40/67; G16H 10/60; G16H 50/30; G16H 50/70; G16H 80/60; G06Q 50/01
(Continued)

(56) References Cited

U.S. PATENT DOCUMENTS 4,205,628 A 6/1980 Null
4,842,266 A 6/1989 Sweeney et al.
(Continued)

FOREIGN PATENT DOCUMENTS

AU 2011302438 A1 5/2013
CA 2815518 A1 5/2012
(Continued)

OTHER PUBLICATIONS

Adeniyi Samuel, "How to connect a second PS4 controller to a PlayStation 4 console", Online available on:—https://www.youtube.com/watch?v=mOZX_SrNISE, May 28, 2017, 2 pages.
(Continued)

*Primary Examiner* — Hai Tao Sun
(74) *Attorney, Agent, or Firm* — DLA Piper LLP (US)

(57) ABSTRACT

The present disclosure relates to aggregating and sharing wellness data. The wellness data can be received by a user device from any number of sensors external or internal to the user device, from a user manually entering the wellness data, or from other users or entities. The user device can securely store the wellness data on the user device and transmit the wellness data to be stored on a remote database. A user of the device can share some or all of the wellness data with friends, relatives, caregivers, healthcare providers, or the like. The user device can further display a user's wellness data in an aggregated view of different types of wellness data. Wellness data of other users can also be viewed if authorizations from those users have been received.

9 Claims, 99 Drawing Sheets

Related U.S. Application Data

No. 16/820,383, filed on Mar. 16, 2020, now Pat. No. 11,996,190, which is a continuation of application No. 14/732,773, filed on Jun. 7, 2015, now abandoned, which is a continuation-in-part of application No. PCT/US2013/073195, filed on Dec. 4, 2013, and a continuation-in-part of application No. PCT/US2015/032474, filed on May 26, 2015, said application No. 14/732,773 is a continuation-in-part of application No. 14/599,424, filed on Jan. 16, 2015, now Pat. No. 10,270,898.

(60) Provisional application No. 62/129,945, filed on Mar. 8, 2015, provisional application No. 62/006,032, filed on May 30, 2014.

(51) Int. Cl.
  *G16H 10/60* (2018.01)
  *G16H 50/30* (2018.01)
  *G16H 50/70* (2018.01)
  *G16H 80/00* (2018.01)

(58) Field of Classification Search
  USPC .................................................. 705/3
  See application file for complete search history.

(56) References Cited

U.S. PATENT DOCUMENTS

| | | | |
|---|---|---|---|
| 5,349,962 | A | 9/1994 | Lockard et al. |
| 5,423,863 | A | 6/1995 | Felblinger et al. |
| 5,458,548 | A | 10/1995 | Crossing et al. |
| 5,474,077 | A | 12/1995 | Suga |
| 5,642,731 | A | 7/1997 | Kehr |
| 5,685,723 | A | 11/1997 | Ladin et al. |
| 5,730,141 | A | 3/1998 | Fain et al. |
| 5,788,655 | A | 8/1998 | Yoshimura et al. |
| 5,845,235 | A | 12/1998 | Luukkanen et al. |
| 5,944,633 | A | 8/1999 | Wittrock |
| 6,013,008 | A | 1/2000 | Fukushima |
| 6,061,592 | A | 5/2000 | Nigam |
| 6,095,949 | A | 8/2000 | Arai |
| 6,095,984 | A | 8/2000 | Amano et al. |
| 6,097,371 | A | 8/2000 | Siddiqui et al. |
| 6,097,385 | A | 8/2000 | Robinson |
| 6,199,012 | B1 | 3/2001 | Hasegawa |
| 6,244,988 | B1 | 6/2001 | Delman |
| 6,302,789 | B2 | 10/2001 | Harada et al. |
| 6,323,846 | B1 | 11/2001 | Westerman et al. |
| 6,416,471 | B1 | 7/2002 | Kumar et al. |
| 6,570,557 | B1 | 5/2003 | Westerman et al. |
| 6,603,477 | B1 | 8/2003 | Tittle |
| 6,639,584 | B1 | 10/2003 | Li |
| 6,662,023 | B1 | 12/2003 | Helle |
| 6,677,932 | B1 | 1/2004 | Westerman |
| 6,705,972 | B1 | 3/2004 | Takano et al. |
| 6,837,827 | B1 | 1/2005 | Lee |
| 6,866,613 | B1 | 3/2005 | Brown et al. |
| 7,020,514 | B1 | 3/2006 | Wiesel |
| 7,081,905 | B1 | 7/2006 | Raghunath |
| 7,107,546 | B2 | 9/2006 | Coulthard et al. |
| 7,128,693 | B2 | 10/2006 | Brown et al. |
| 7,130,664 | B1 | 10/2006 | Williams |
| 7,251,454 | B2 | 7/2007 | White |
| 7,302,272 | B2 | 11/2007 | Ackley |
| 7,534,206 | B1 | 5/2009 | Lovitt et al. |
| 7,614,008 | B2 | 11/2009 | Ording |
| 7,633,076 | B2 | 12/2009 | Huppi et al. |
| 7,653,883 | B2 | 1/2010 | Hotelling et al. |
| 7,657,849 | B2 | 2/2010 | Chaudhri et al. |
| 7,662,065 | B1 | 2/2010 | Kahn |
| 7,663,607 | B2 | 2/2010 | Hotelling et al. |
| 7,695,406 | B2 | 4/2010 | Waters |
| 7,739,148 | B2 | 6/2010 | Suzuki et al. |
| 7,771,320 | B2 | 8/2010 | Riley et al. |
| 7,844,914 | B2 | 11/2010 | Andre et al. |
| 7,853,428 | B2 | 12/2010 | Usui et al. |
| 7,870,013 | B1 | 1/2011 | Allemann et al. |
| 7,957,762 | B2 | 6/2011 | Herz et al. |
| 7,970,827 | B1 | 6/2011 | Cumberbatch et al. |
| 8,006,002 | B2 | 8/2011 | Kalayjian et al. |
| 8,060,229 | B2 | 11/2011 | Gupta et al. |
| 8,105,208 | B2 | 1/2012 | Oleson et al. |
| 8,152,694 | B2 | 4/2012 | Srinivasan et al. |
| 8,200,323 | B2 | 6/2012 | Dibenedetto et al. |
| 8,239,784 | B2 | 8/2012 | Hotelling et al. |
| 8,279,180 | B2 | 10/2012 | Hotelling et al. |
| 8,321,006 | B1 | 11/2012 | Snyder et al. |
| 8,341,557 | B2 | 12/2012 | Pisula et al. |
| 8,381,135 | B2 | 2/2013 | Hotelling et al. |
| 8,475,339 | B2 | 7/2013 | Hwang et al. |
| 8,479,122 | B2 | 7/2013 | Hotelling et al. |
| 8,496,563 | B2 | 7/2013 | Komatsu et al. |
| 8,543,081 | B2 | 9/2013 | Scott et al. |
| 8,595,798 | B2 | 11/2013 | Anand et al. |
| 8,666,361 | B2 | 3/2014 | Chu et al. |
| 8,676,170 | B2 | 3/2014 | Porrati et al. |
| 8,700,158 | B2 | 4/2014 | Mass et al. |
| 8,725,527 | B1 | 5/2014 | Kahn et al. |
| 8,734,296 | B1 | 5/2014 | Brumback et al. |
| 8,768,648 | B2 | 7/2014 | Panther et al. |
| 8,784,115 | B1 | 7/2014 | Chuang |
| 8,784,271 | B2 | 7/2014 | Brumback et al. |
| 8,825,445 | B2 | 9/2014 | Hoffman et al. |
| 8,849,610 | B2 | 9/2014 | Molettiere et al. |
| 8,888,707 | B2 | 11/2014 | Shirasaki et al. |
| 8,910,299 | B2 | 12/2014 | Michalske |
| 8,934,963 | B1 | 1/2015 | Farazi |
| 8,947,239 | B1 | 2/2015 | Park |
| 8,990,006 | B1 | 3/2015 | Wallace et al. |
| 9,011,292 | B2 | 4/2015 | Weast et al. |
| 9,020,538 | B1 | 4/2015 | White et al. |
| 9,063,164 | B1 | 6/2015 | Yuen et al. |
| 9,087,234 | B2 | 7/2015 | Hoffman et al. |
| 9,148,483 | B1 | 9/2015 | Molettiere et al. |
| 9,164,663 | B1 | 10/2015 | Berard |
| 9,173,576 | B2 | 11/2015 | Yuen et al. |
| 9,224,291 | B2 | 12/2015 | Moll-Carrillo et al. |
| 9,230,076 | B2 | 1/2016 | King et al. |
| 9,449,365 | B2 | 9/2016 | Roberts |
| 9,532,734 | B2 | 1/2017 | Hoffman et al. |
| 9,557,881 | B1 | 1/2017 | Jain et al. |
| 9,579,060 | B1 | 2/2017 | Lisy et al. |
| 9,582,165 | B2 | 2/2017 | Wilson et al. |
| 9,589,445 | B2 | 3/2017 | White et al. |
| 9,606,695 | B2 | 3/2017 | Matas |
| 9,712,629 | B2 | 7/2017 | Molettiere et al. |
| 9,721,066 | B1 | 8/2017 | Funaro et al. |
| 9,723,381 | B2 | 8/2017 | Swanson |
| 9,730,621 | B2 | 8/2017 | Cohen et al. |
| 9,734,477 | B2 | 8/2017 | Weast et al. |
| 9,740,825 | B2 | 8/2017 | Sansale et al. |
| 9,798,443 | B1 | 10/2017 | Gray |
| 9,800,525 | B1 | 10/2017 | Lerner et al. |
| 9,808,206 | B1 | 11/2017 | Zhao et al. |
| 9,813,642 | B1 | 11/2017 | Chen et al. |
| 9,817,481 | B2 | 11/2017 | Pantelopoulos et al. |
| 9,854,653 | B1 | 12/2017 | Ackmann et al. |
| 9,880,805 | B1 | 1/2018 | Guralnick |
| 9,910,571 | B2 | 3/2018 | Chen et al. |
| 9,918,664 | B2 | 3/2018 | Blahnik et al. |
| 9,931,539 | B1 | 4/2018 | De Pablos et al. |
| 9,940,682 | B2 | 4/2018 | Hoffman et al. |
| 10,056,006 | B1 | 8/2018 | Hsu-Hoffman et al. |
| 10,105,573 | B2 | 10/2018 | Park et al. |
| 10,150,002 | B2 | 12/2018 | Kass et al. |
| 10,220,258 | B2 | 3/2019 | Gu et al. |
| 10,226,195 | B2 | 3/2019 | Briante et al. |
| 10,254,911 | B2 | 4/2019 | Yang |
| 10,270,898 | B2 | 4/2019 | Soli et al. |
| 10,272,294 | B2 | 4/2019 | Williams et al. |
| 10,275,262 | B1 | 4/2019 | Bull et al. |
| 10,300,334 | B1 | 5/2019 | Chuang |

(56) References Cited

U.S. PATENT DOCUMENTS

| | | |
|---|---|---|
| 10,304,347 B2 | 5/2019 | Wilson et al. |
| 10,339,830 B2 | 7/2019 | Han et al. |
| 10,365,811 B2 | 7/2019 | Robinson et al. |
| 10,398,381 B1 | 9/2019 | Heneghan et al. |
| 10,489,508 B2 | 11/2019 | Zhai et al. |
| 10,500,441 B2 | 12/2019 | Lagree |
| 10,576,327 B2 | 3/2020 | Kim et al. |
| 10,592,088 B2 | 3/2020 | Robinson et al. |
| 10,602,964 B2 | 3/2020 | Kerber |
| 10,635,267 B2 | 4/2020 | Williams |
| 10,639,521 B2 | 5/2020 | Foley et al. |
| 10,674,942 B2 | 6/2020 | Williams et al. |
| 10,692,593 B1 | 6/2020 | Young et al. |
| 10,736,543 B2 | 8/2020 | Chen et al. |
| 10,762,990 B1 | 9/2020 | Schilling et al. |
| 10,777,314 B1 | 9/2020 | Williams et al. |
| 10,796,549 B2 | 10/2020 | Roberts et al. |
| 10,898,132 B2 | 1/2021 | White et al. |
| 10,978,195 B2 | 4/2021 | Blahnik et al. |
| 11,103,161 B2 | 8/2021 | Williams et al. |
| 11,107,567 B2 | 8/2021 | Blahnik et al. |
| 11,107,569 B1 | 8/2021 | Devoto |
| 11,107,580 B1 | 8/2021 | Felton et al. |
| 11,152,100 B2 | 10/2021 | Crowley et al. |
| 11,202,598 B2 | 12/2021 | Soli et al. |
| 11,209,957 B2 | 12/2021 | Dryer et al. |
| 11,216,119 B2 | 1/2022 | De Vries et al. |
| 11,317,833 B2 | 5/2022 | Williams et al. |
| 11,446,548 B2 | 9/2022 | Devine et al. |
| 11,452,915 B2 | 9/2022 | Devine et al. |
| 11,458,363 B2 | 10/2022 | Powers et al. |
| 11,529,074 B2 | 12/2022 | Vaterlaus |
| 11,801,423 B2 | 10/2023 | Bissonnette et al. |
| 2001/0049470 A1 | 12/2001 | Mault et al. |
| 2002/0015024 A1 | 2/2002 | Westerman et al. |
| 2002/0045960 A1 | 4/2002 | Phillips et al. |
| 2002/0086774 A1 | 7/2002 | Warner |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0140044 A1 | 7/2003 | Mok et al. |
| 2003/0179229 A1 | 9/2003 | Van Erlach et al. |
| 2003/0181291 A1 | 9/2003 | Ogawa |
| 2003/0182628 A1 | 9/2003 | Lira |
| 2003/0216971 A1 | 11/2003 | Sick et al. |
| 2003/0226695 A1 | 12/2003 | Mault |
| 2004/0014567 A1 | 1/2004 | Mendel |
| 2004/0034288 A1 | 2/2004 | Hennessy et al. |
| 2004/0077462 A1 | 4/2004 | Brown et al. |
| 2004/0077958 A1 | 4/2004 | Kato et al. |
| 2004/0128286 A1 | 7/2004 | Yasushi et al. |
| 2004/0236189 A1 | 11/2004 | Hawthorne et al. |
| 2005/0015803 A1 | 1/2005 | Macrae et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0130802 A1 | 6/2005 | Kinnunen et al. |
| 2005/0139852 A1 | 6/2005 | Chen et al. |
| 2005/0165627 A1* | 7/2005 | Fotsch ............... G16H 10/60 707/999.009 |
| 2005/0171410 A1 | 8/2005 | Hjelt et al. |
| 2005/0172311 A1 | 8/2005 | Hjelt et al. |
| 2005/0190059 A1 | 9/2005 | Wehrenberg |
| 2005/0197063 A1 | 9/2005 | White et al. |
| 2005/0215848 A1 | 9/2005 | Lorenzato et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2006/0017692 A1 | 1/2006 | Wehrenberg et al. |
| 2006/0020174 A1 | 1/2006 | Matsumura et al. |
| 2006/0026536 A1 | 2/2006 | Hotelling et al. |
| 2006/0033724 A1 | 2/2006 | Chaudhri et al. |
| 2006/0047208 A1 | 3/2006 | Yoon |
| 2006/0048076 A1 | 3/2006 | Vronay et al. |
| 2006/0052727 A1 | 3/2006 | Palestrant |
| 2006/0094969 A1 | 5/2006 | Nissila |
| 2006/0098109 A1 | 5/2006 | Ooki |
| 2006/0106741 A1 | 5/2006 | Janarthanan |
| 2006/0117014 A1 | 6/2006 | Qi |
| 2006/0136173 A1 | 6/2006 | Case, Jr. et al. |
| 2006/0155578 A1 | 7/2006 | Eisenberger et al. |
| 2006/0160090 A1 | 7/2006 | Macina et al. |
| 2006/0184800 A1 | 8/2006 | Rosenberg |
| 2006/0197753 A1 | 9/2006 | Hotelling |
| 2006/0205564 A1 | 9/2006 | Peterson |
| 2006/0240959 A1 | 10/2006 | Huang |
| 2006/0250524 A1 | 11/2006 | Roche |
| 2007/0016091 A1 | 1/2007 | Butt et al. |
| 2007/0021269 A1 | 1/2007 | Shum |
| 2007/0032733 A1 | 2/2007 | Burton |
| 2007/0033069 A1 | 2/2007 | Rao et al. |
| 2007/0056727 A1 | 3/2007 | Newman |
| 2007/0071256 A1 | 3/2007 | Ito |
| 2007/0113726 A1 | 5/2007 | Oliver et al. |
| 2007/0135043 A1 | 6/2007 | Hayes et al. |
| 2007/0136093 A1 | 6/2007 | Rankin et al. |
| 2007/0143433 A1 | 6/2007 | Daigle |
| 2007/0169614 A1 | 7/2007 | Sasaki et al. |
| 2007/0249949 A1 | 10/2007 | Hadley |
| 2007/0250505 A1 | 10/2007 | Yang et al. |
| 2007/0250613 A1 | 10/2007 | Gulledge |
| 2007/0271065 A1 | 11/2007 | Gupta et al. |
| 2008/0012701 A1 | 1/2008 | Kass et al. |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0076637 A1 | 3/2008 | Gilley et al. |
| 2008/0077026 A1 | 3/2008 | Banet et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0133742 A1 | 6/2008 | Southiere et al. |
| 2008/0141135 A1 | 6/2008 | Mason et al. |
| 2008/0146892 A1 | 6/2008 | Leboeuf et al. |
| 2008/0150731 A1 | 6/2008 | Laukkanen et al. |
| 2008/0161161 A1 | 7/2008 | Pipinich et al. |
| 2008/0161707 A1 | 7/2008 | Farringdon et al. |
| 2008/0195600 A1* | 8/2008 | Deakter ............... G16H 70/20 707/999.005 |
| 2008/0200312 A1 | 8/2008 | Tagliabue |
| 2008/0228045 A1 | 9/2008 | Gao et al. |
| 2008/0229226 A1 | 9/2008 | Rowbottom et al. |
| 2008/0254767 A1 | 10/2008 | Jin |
| 2008/0262946 A1 | 10/2008 | Wren |
| 2008/0278333 A1 | 11/2008 | Fennell et al. |
| 2008/0300110 A1 | 12/2008 | Smith et al. |
| 2008/0320391 A1 | 12/2008 | Lemay et al. |
| 2009/0007017 A1 | 1/2009 | Anzures et al. |
| 2009/0012821 A1 | 1/2009 | Besson et al. |
| 2009/0012988 A1 | 1/2009 | Brown |
| 2009/0047645 A1 | 2/2009 | Dibenedetto et al. |
| 2009/0054743 A1 | 2/2009 | Stewart |
| 2009/0065578 A1 | 3/2009 | Peterson et al. |
| 2009/0075782 A1 | 3/2009 | Joubert et al. |
| 2009/0106685 A1 | 4/2009 | Care et al. |
| 2009/0118100 A1 | 5/2009 | Oliver et al. |
| 2009/0144639 A1 | 6/2009 | Nims et al. |
| 2009/0149299 A1 | 6/2009 | Tchao et al. |
| 2009/0158167 A1 | 6/2009 | Wang et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0199130 A1 | 8/2009 | Tsern et al. |
| 2009/0205041 A1 | 8/2009 | Michalske |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0222761 A1 | 9/2009 | Hayashi |
| 2009/0233771 A1 | 9/2009 | Quatrochi et al. |
| 2009/0249076 A1 | 10/2009 | Reed et al. |

(56) References Cited

U.S. PATENT DOCUMENTS

| | | |
|---|---|---|
| 2009/0259134 A1 | 10/2009 | Levine |
| 2009/0262088 A1 | 10/2009 | Moll-Carrillo et al. |
| 2009/0268949 A1 | 10/2009 | Ueshima et al. |
| 2009/0276463 A1 | 11/2009 | Miller et al. |
| 2009/0287103 A1 | 11/2009 | Pillai |
| 2009/0291805 A1 | 11/2009 | Blum et al. |
| 2009/0292561 A1 | 11/2009 | Itoh |
| 2009/0307105 A1 | 12/2009 | Lemay et al. |
| 2009/0319243 A1 | 12/2009 | Suarez-Rivera et al. |
| 2010/0030094 A1 | 2/2010 | Lundback |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1 | 3/2010 | Rottler et al. |
| 2010/0063840 A1 | 3/2010 | Hoyme et al. |
| 2010/0064255 A1 | 3/2010 | Rottler et al. |
| 2010/0076331 A1 | 3/2010 | Chan et al. |
| 2010/0079291 A1 | 4/2010 | Kroll et al. |
| 2010/0094658 A1 | 4/2010 | Mok et al. |
| 2010/0099539 A1 | 4/2010 | Haataja |
| 2010/0103101 A1 | 4/2010 | Song et al. |
| 2010/0121700 A1 | 5/2010 | Wigder et al. |
| 2010/0130890 A1 | 5/2010 | Matsumura et al. |
| 2010/0137106 A1 | 6/2010 | Oshima et al. |
| 2010/0145209 A1 | 6/2010 | Lee et al. |
| 2010/0152600 A1 | 6/2010 | Droitcour et al. |
| 2010/0161353 A1 | 6/2010 | Mayaud |
| 2010/0179832 A1 | 7/2010 | Van Deursen et al. |
| 2010/0179833 A1 | 7/2010 | Roizen et al. |
| 2010/0184564 A1 | 7/2010 | Molyneux et al. |
| 2010/0190468 A1 | 7/2010 | Scott et al. |
| 2010/0194692 A1 | 8/2010 | Orr et al. |
| 2010/0197463 A1 | 8/2010 | Haughay et al. |
| 2010/0198453 A1 | 8/2010 | Dorogusker et al. |
| 2010/0202368 A1 | 8/2010 | Hans |
| 2010/0222645 A1 | 9/2010 | Nadler et al. |
| 2010/0222859 A1 | 9/2010 | Govari et al. |
| 2010/0231612 A1 | 9/2010 | Chaudhri et al. |
| 2010/0264097 A1 | 10/2010 | Sun et al. |
| 2010/0269055 A1 | 10/2010 | Daikeler et al. |
| 2010/0269157 A1* | 10/2010 | Experton ............ G06F 21/6245 726/28 |
| 2010/0273610 A1 | 10/2010 | Johnson |
| 2010/0281374 A1 | 11/2010 | Schulz et al. |
| 2010/0292599 A1 | 11/2010 | Oleson et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0010195 A1 | 1/2011 | Cohn et al. |
| 2011/0016120 A1 | 1/2011 | Haughay et al. |
| 2011/0032105 A1 | 2/2011 | Hoffman et al. |
| 2011/0052005 A1 | 3/2011 | Selner |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0087076 A1 | 4/2011 | Brynelsen et al. |
| 2011/0088086 A1 | 4/2011 | Swink et al. |
| 2011/0098928 A1 | 4/2011 | Hoffman et al. |
| 2011/0106553 A1 | 5/2011 | Tanaka et al. |
| 2011/0106557 A1 | 5/2011 | Gazula |
| 2011/0112418 A1 | 5/2011 | Feild et al. |
| 2011/0113430 A1 | 5/2011 | Fuse |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van Os |
| 2011/0201911 A1 | 8/2011 | Johnson et al. |
| 2011/0213276 A1 | 9/2011 | Sarussi et al. |
| 2011/0214162 A1 | 9/2011 | Brakensiek et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0257638 A1 | 10/2011 | Boukhny et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1* | 1/2012 | Lee ................... A63B 71/0686 482/8 |
| 2012/0015779 A1 | 1/2012 | Powch et al. |
| 2012/0022884 A1 | 1/2012 | Chillemi |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0046784 A1 | 2/2012 | Malina et al. |
| 2012/0059664 A1 | 3/2012 | Georgiev et al. |
| 2012/0060118 A1 | 3/2012 | Gupta et al. |
| 2012/0071770 A1 | 3/2012 | Grey et al. |
| 2012/0092379 A1 | 4/2012 | Tsuji et al. |
| 2012/0092383 A1 | 4/2012 | Hysek et al. |
| 2012/0105225 A1 | 5/2012 | Valtonen |
| 2012/0112908 A1 | 5/2012 | Prykaeri et al. |
| 2012/0116550 A1 | 5/2012 | Hoffman et al. |
| 2012/0116684 A1 | 5/2012 | Ingrassia et al. |
| 2012/0119911 A1 | 5/2012 | Jeon et al. |
| 2012/0143094 A1 | 6/2012 | Jallon |
| 2012/0143095 A1 | 6/2012 | Nakamura |
| 2012/0150759 A1 | 6/2012 | Tarjan |
| 2012/0159380 A1 | 6/2012 | Kocienda et al. |
| 2012/0169882 A1 | 7/2012 | Millar et al. |
| 2012/0171649 A1 | 7/2012 | Wander et al. |
| 2012/0179278 A1 | 7/2012 | Riley et al. |
| 2012/0179319 A1 | 7/2012 | Gilman et al. |
| 2012/0203124 A1 | 8/2012 | Lim |
| 2012/0209829 A1 | 8/2012 | Thomas et al. |
| 2012/0215115 A1 | 8/2012 | Takahashi |
| 2012/0215328 A1 | 8/2012 | Schmelzer |
| 2012/0232414 A1 | 9/2012 | Mollicone et al. |
| 2012/0232929 A1 | 9/2012 | Experton |
| 2012/0245447 A1 | 9/2012 | Karan et al. |
| 2012/0251079 A1 | 10/2012 | Meschter et al. |
| 2012/0253485 A1 | 10/2012 | Weast et al. |
| 2012/0253488 A1 | 10/2012 | Shaw et al. |
| 2012/0254263 A1 | 10/2012 | Hiestermann et al. |
| 2012/0258684 A1 | 10/2012 | Franz et al. |
| 2012/0272186 A1 | 10/2012 | Kraut |
| 2012/0274508 A1 | 11/2012 | Brown et al. |
| 2012/0283524 A1 | 11/2012 | Kiani et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0310389 A1 | 12/2012 | Martin |
| 2012/0310674 A1 | 12/2012 | Faulkner et al. |
| 2012/0313776 A1 | 12/2012 | Utter |
| 2012/0317167 A1 | 12/2012 | Rahman et al. |
| 2012/0317430 A1 | 12/2012 | Rahman et al. |
| 2012/0323129 A1 | 12/2012 | Fujita et al. |
| 2012/0326873 A1 | 12/2012 | Utter, II |
| 2013/0011819 A1 | 1/2013 | Horseman |
| 2013/0012788 A1 | 1/2013 | Horseman |
| 2013/0013331 A1 | 1/2013 | Horseman |
| 2013/0053990 A1 | 2/2013 | Ackland |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0072765 A1 | 3/2013 | Kahn et al. |
| 2013/0081083 A1 | 3/2013 | Yu et al. |
| 2013/0093715 A1 | 4/2013 | Marsden et al. |
| 2013/0095459 A1 | 4/2013 | Tran |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |
| 2013/0117696 A1 | 5/2013 | Robertson et al. |
| 2013/0132028 A1 | 5/2013 | Crankson et al. |

(56) References Cited

U.S. PATENT DOCUMENTS

| | | |
|---|---|---|
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0143512 A1 | 6/2013 | Hernandez et al. |
| 2013/0144653 A1 | 6/2013 | Poe et al. |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0191034 A1 | 7/2013 | Weast et al. |
| 2013/0191647 A1 | 7/2013 | Ferrara et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0215119 A1 | 8/2013 | Vanhoecke |
| 2013/0217253 A1 | 8/2013 | Golko et al. |
| 2013/0217979 A1 | 8/2013 | Blackadar et al. |
| 2013/0223707 A1 | 8/2013 | Stephenson |
| 2013/0225118 A1 | 8/2013 | Jang et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0238287 A1 | 9/2013 | Hoffman et al. |
| 2013/0245966 A1 | 9/2013 | Burroughs et al. |
| 2013/0262155 A1 | 10/2013 | Hinkamp |
| 2013/0263719 A1 | 10/2013 | Watterson et al. |
| 2013/0290013 A1 | 10/2013 | Forrester et al. |
| 2013/0295872 A1 | 11/2013 | Guday et al. |
| 2013/0310726 A1 | 11/2013 | Miller et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0325493 A1 | 12/2013 | Wong et al. |
| 2013/0325758 A1 | 12/2013 | Alphin et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0005947 A1 | 1/2014 | Jeon et al. |
| 2014/0019162 A1 | 1/2014 | Skowronski et al. |
| 2014/0035761 A1 | 2/2014 | Burton et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0073486 A1 | 3/2014 | Ahmed et al. |
| 2014/0081666 A1 | 3/2014 | Teller et al. |
| 2014/0088995 A1 | 3/2014 | Damani |
| 2014/0089836 A1 | 3/2014 | Damani et al. |
| 2014/0100885 A1 | 4/2014 | Stern |
| 2014/0107524 A1 | 4/2014 | Brull et al. |
| 2014/0108998 A1 | 4/2014 | Chaudhri et al. |
| 2014/0127996 A1 | 5/2014 | Park et al. |
| 2014/0129007 A1 | 5/2014 | Utter, II |
| 2014/0129243 A1 | 5/2014 | Utter, II |
| 2014/0135955 A1 | 5/2014 | Burroughs |
| 2014/0139637 A1 | 5/2014 | Mistry et al. |
| 2014/0142403 A1 | 5/2014 | Brumback et al. |
| 2014/0143678 A1 | 5/2014 | Mistry et al. |
| 2014/0156292 A1 | 6/2014 | Kozicki et al. |
| 2014/0164611 A1 | 6/2014 | Molettiere et al. |
| 2014/0172460 A1 | 6/2014 | Kohli |
| 2014/0176335 A1 | 6/2014 | Brumback et al. |
| 2014/0176346 A1 | 6/2014 | Brumback et al. |
| 2014/0176475 A1 | 6/2014 | Myers et al. |
| 2014/0180595 A1 | 6/2014 | Brumback et al. |
| 2014/0180786 A1 | 6/2014 | Sullivan |
| 2014/0184422 A1 | 7/2014 | Mensinger et al. |
| 2014/0189584 A1 | 7/2014 | Weng et al. |
| 2014/0197946 A1 | 7/2014 | Park et al. |
| 2014/0199966 A1 | 7/2014 | Schushan |
| 2014/0200426 A1 | 7/2014 | Taub et al. |
| 2014/0200691 A1 | 7/2014 | Lee et al. |
| 2014/0213415 A1 | 7/2014 | Parker et al. |
| 2014/0218369 A1 | 8/2014 | Yuen et al. |
| 2014/0221790 A1 | 8/2014 | Pacione et al. |
| 2014/0222446 A1 | 8/2014 | Ash et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0266731 A1 | 9/2014 | Malhotra |
| 2014/0266776 A1 | 9/2014 | Miller et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278220 A1 | 9/2014 | Yuen |
| 2014/0278229 A1 | 9/2014 | Hong et al. |
| 2014/0280498 A1 | 9/2014 | Frankel et al. |
| 2014/0282153 A1 | 9/2014 | Christiansen et al. |
| 2014/0288680 A1 | 9/2014 | Hoffman et al. |
| 2014/0297217 A1 | 10/2014 | Yuen |
| 2014/0310598 A1 | 10/2014 | Sprague et al. |
| 2014/0310643 A1 | 10/2014 | Karmanenko et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344687 A1 | 11/2014 | Durham et al. |
| 2014/0344693 A1 | 11/2014 | Reese et al. |
| 2014/0344723 A1 | 11/2014 | Malik et al. |
| 2014/0344951 A1 | 11/2014 | Brewer |
| 2014/0354494 A1 | 12/2014 | Katz |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2015/0004578 A1 | 1/2015 | Gilley et al. |
| 2015/0011204 A1 | 1/2015 | Seo et al. |
| 2015/0018632 A1 | 1/2015 | Khair |
| 2015/0033149 A1 | 1/2015 | Kuchoor |
| 2015/0046814 A1 | 2/2015 | Haughay et al. |
| 2015/0052618 A1 | 2/2015 | Michalske |
| 2015/0057942 A1 | 2/2015 | Self et al. |
| 2015/0057943 A1 | 2/2015 | Self et al. |
| 2015/0057945 A1 | 2/2015 | White et al. |
| 2015/0058093 A1 | 2/2015 | Jakobs |
| 2015/0058263 A1 | 2/2015 | Landers |
| 2015/0065095 A1 | 3/2015 | Seo et al. |
| 2015/0065302 A1 | 3/2015 | Ou et al. |
| 2015/0066172 A1 | 3/2015 | Yi |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0082167 A1 | 3/2015 | Yeh et al. |
| 2015/0083970 A1 | 3/2015 | Koh et al. |
| 2015/0089536 A1 | 3/2015 | Byerley |
| 2015/0098309 A1 | 4/2015 | Adams et al. |
| 2015/0100245 A1 | 4/2015 | Huang et al. |
| 2015/0100348 A1 | 4/2015 | Connery et al. |
| 2015/0106025 A1 | 4/2015 | Keller et al. |
| 2015/0112700 A1 | 4/2015 | Sublett et al. |
| 2015/0112990 A1 | 4/2015 | Van Os et al. |
| 2015/0113553 A1 | 4/2015 | Pan |
| 2015/0118657 A1 | 4/2015 | Shrake et al. |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0130830 A1 | 5/2015 | Nagasaki et al. |
| 2015/0133748 A1 | 5/2015 | Edmonds et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0173686 A1 | 6/2015 | Furuta et al. |
| 2015/0180746 A1 | 6/2015 | Day et al. |

(56) References Cited

U.S. PATENT DOCUMENTS

| | | |
|---|---|---|
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0186602 A1 | 7/2015 | Pipke et al. |
| 2015/0193217 A1 | 7/2015 | Xiang et al. |
| 2015/0193805 A1 | 7/2015 | Filipiak |
| 2015/0196804 A1 | 7/2015 | Koduri et al. |
| 2015/0196805 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0205947 A1 | 7/2015 | Berman et al. |
| 2015/0217163 A1 | 8/2015 | Amis et al. |
| 2015/0220523 A1 | 8/2015 | Lagree |
| 2015/0220883 A1 | 8/2015 | Bfar et al. |
| 2015/0230717 A1 | 8/2015 | Wan |
| 2015/0248535 A1 | 9/2015 | Cho |
| 2015/0251053 A1 | 9/2015 | Hoffman et al. |
| 2015/0261918 A1 | 9/2015 | Thornbury, Jr. |
| 2015/0262497 A1 | 9/2015 | Landau et al. |
| 2015/0262499 A1 | 9/2015 | Wicka et al. |
| 2015/0269848 A1 | 9/2015 | Yuen et al. |
| 2015/0286800 A1 | 10/2015 | Kanagala et al. |
| 2015/0289823 A1 | 10/2015 | Rack-Gomer et al. |
| 2015/0293592 A1 | 10/2015 | Cheong et al. |
| 2015/0294440 A1 | 10/2015 | Roberts |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0334546 A1 | 11/2015 | Diamond |
| 2015/0343709 A1 | 12/2015 | Gerstle et al. |
| 2015/0347690 A1 | 12/2015 | Keen et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0364057 A1 | 12/2015 | Catani et al. |
| 2015/0374267 A1 | 12/2015 | Laughlin |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0034133 A1 | 2/2016 | Wilson et al. |
| 2016/0034148 A1 | 2/2016 | Wilson et al. |
| 2016/0048298 A1 | 2/2016 | Choi et al. |
| 2016/0055420 A1 | 2/2016 | Karanam et al. |
| 2016/0058331 A1 | 3/2016 | Keen et al. |
| 2016/0058336 A1 | 3/2016 | Blahnik et al. |
| 2016/0058337 A1 | 3/2016 | Blahnik et al. |
| 2016/0062464 A1 | 3/2016 | Moussette et al. |
| 2016/0062540 A1 | 3/2016 | Yang et al. |
| 2016/0062582 A1 | 3/2016 | Wilson et al. |
| 2016/0062589 A1 | 3/2016 | Wan et al. |
| 2016/0063215 A1 | 3/2016 | Zamer |
| 2016/0065505 A1 | 3/2016 | Iskander |
| 2016/0066842 A1 | 3/2016 | Kokkoneva et al. |
| 2016/0070275 A1 | 3/2016 | Anderson et al. |
| 2016/0072896 A1 | 3/2016 | Petersen et al. |
| 2016/0078778 A1 | 3/2016 | Holland |
| 2016/0085937 A1 | 3/2016 | Dettinger et al. |
| 2016/0086500 A1 | 3/2016 | Kaleal, III |
| 2016/0089569 A1 | 3/2016 | Blahnik |
| 2016/0098160 A1 | 4/2016 | Groset |
| 2016/0098522 A1 | 4/2016 | Weinstein |
| 2016/0103985 A1 | 4/2016 | Shim et al. |
| 2016/0107031 A1 | 4/2016 | Palatsi et al. |
| 2016/0110523 A1 | 4/2016 | Francois |
| 2016/0132645 A1 | 5/2016 | Charpentier et al. |
| 2016/0135731 A1 | 5/2016 | Drennan |
| 2016/0140828 A1 | 5/2016 | Deforest |
| 2016/0150978 A1 | 6/2016 | Yuen et al. |
| 2016/0156584 A1 | 6/2016 | Hum et al. |
| 2016/0180026 A1 | 6/2016 | Kim et al. |
| 2016/0189051 A1 | 6/2016 | Mahmood |
| 2016/0193500 A1 | 7/2016 | Webster et al. |
| 2016/0196635 A1 | 7/2016 | Cho et al. |
| 2016/0196759 A1 | 7/2016 | Kim et al. |
| 2016/0203691 A1 | 7/2016 | Arnold et al. |
| 2016/0210099 A1 | 7/2016 | Hampapuram et al. |
| 2016/0210434 A1 | 7/2016 | Al-sharif |
| 2016/0210568 A1 | 7/2016 | Krupa et al. |
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0249864 A1 | 9/2016 | Kang et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0270717 A1 | 9/2016 | Luna et al. |
| 2016/0270740 A1 | 9/2016 | Raisoni et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0285985 A1 | 9/2016 | Molettiere et al. |
| 2016/0287177 A1 | 10/2016 | Huppert et al. |
| 2016/0296798 A1 | 10/2016 | Balakrishnan et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0313869 A1 | 10/2016 | Jang et al. |
| 2016/0314670 A1 | 10/2016 | Roberts et al. |
| 2016/0317341 A1 | 11/2016 | Galvan |
| 2016/0321932 A1 | 11/2016 | Mitchell et al. |
| 2016/0324457 A1 | 11/2016 | Dagum |
| 2016/0324488 A1 | 11/2016 | Olsen |
| 2016/0328736 A1 | 11/2016 | Wang et al. |
| 2016/0332025 A1 | 11/2016 | Repka |
| 2016/0346607 A1 | 12/2016 | Rapfogel |
| 2016/0357403 A1 | 12/2016 | Chang et al. |
| 2016/0357616 A1 | 12/2016 | Yu et al. |
| 2016/0360972 A1 | 12/2016 | Kusakabe et al. |
| 2016/0367138 A1 | 12/2016 | Kim et al. |
| 2016/0371464 A1 | 12/2016 | Bricker |
| 2016/0373631 A1 | 12/2016 | Titi et al. |
| 2016/0375306 A1 | 12/2016 | Gu et al. |
| 2016/0379511 A1 | 12/2016 | Dawson et al. |
| 2017/0000348 A1 | 1/2017 | Karsten et al. |
| 2017/0001073 A1 | 1/2017 | Krueger et al. |
| 2017/0007882 A1 | 1/2017 | Werner |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0039327 A1 | 2/2017 | Bitran et al. |
| 2017/0042485 A1 | 2/2017 | Chung et al. |
| 2017/0043214 A1 | 2/2017 | Higashi |
| 2017/0045866 A1 | 2/2017 | Hou et al. |
| 2017/0046052 A1 | 2/2017 | Lee et al. |
| 2017/0046108 A1 | 2/2017 | Kang et al. |
| 2017/0053542 A1 | 2/2017 | Wilson et al. |
| 2017/0056722 A1 | 3/2017 | Singh et al. |
| 2017/0065224 A1 | 3/2017 | Rahko et al. |
| 2017/0071551 A1 | 3/2017 | Jain et al. |
| 2017/0075551 A1 | 3/2017 | Robinson et al. |
| 2017/0083542 A1 | 3/2017 | Roskowick et al. |
| 2017/0087412 A1 | 3/2017 | Blahnik |
| 2017/0087469 A1 | 3/2017 | Hardee et al. |
| 2017/0095695 A1 | 4/2017 | Mangusson et al. |
| 2017/0124276 A1 | 5/2017 | Tee |
| 2017/0128003 A1 | 5/2017 | Lim |
| 2017/0132395 A1 | 5/2017 | Futch |
| 2017/0136297 A1 | 5/2017 | Penie |
| 2017/0140143 A1 | 5/2017 | Ahmad et al. |
| 2017/0143262 A1 | 5/2017 | Kurunmäki et al. |
| 2017/0147197 A1 | 5/2017 | Yang et al. |
| 2017/0153606 A1 | 6/2017 | Pitis et al. |
| 2017/0153804 A1 | 6/2017 | Kim et al. |
| 2017/0156593 A1 | 6/2017 | Ferber et al. |
| 2017/0161014 A1 | 6/2017 | Kikugawa et al. |

(56) References Cited

U.S. PATENT DOCUMENTS

| | | |
|---|---|---|
| 2017/0161462 A1 | 6/2017 | Parker et al. |
| 2017/0177086 A1 | 6/2017 | Yuen et al. |
| 2017/0177797 A1 | 6/2017 | Kurniawan et al. |
| 2017/0181645 A1 | 6/2017 | Mahalingam et al. |
| 2017/0188893 A1 | 7/2017 | Venkatraman et al. |
| 2017/0209766 A1 | 7/2017 | Riley et al. |
| 2017/0225034 A1 | 8/2017 | Kass et al. |
| 2017/0237694 A1 | 8/2017 | Choudhary et al. |
| 2017/0239524 A1 | 8/2017 | Lee et al. |
| 2017/0239525 A1 | 8/2017 | Kim et al. |
| 2017/0243508 A1 | 8/2017 | Cheng et al. |
| 2017/0249417 A1 | 8/2017 | Gosieski et al. |
| 2017/0255169 A1 | 9/2017 | Lee et al. |
| 2017/0266494 A1 | 9/2017 | Crankson et al. |
| 2017/0266531 A1 | 9/2017 | Elford et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0300643 A1 | 10/2017 | Bezark et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0332980 A1 | 11/2017 | Fifield et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2017/0359623 A1 | 12/2017 | Folse et al. |
| 2017/0364637 A1 | 12/2017 | Kshepakaran et al. |
| 2018/0000426 A1 | 1/2018 | Li |
| 2018/0001184 A1 | 1/2018 | Tran et al. |
| 2018/0032234 A1 | 2/2018 | Michalske |
| 2018/0036591 A1 | 2/2018 | King et al. |
| 2018/0042559 A1 | 2/2018 | Cabrera et al. |
| 2018/0053200 A1 | 2/2018 | Cronin et al. |
| 2018/0056130 A1 | 3/2018 | Bitran et al. |
| 2018/0056132 A1 | 3/2018 | Foley et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0078197 A1 | 3/2018 | Ware et al. |
| 2018/0081918 A1 | 3/2018 | Gravenites et al. |
| 2018/0085058 A1 | 3/2018 | Chakravarthi et al. |
| 2018/0107962 A1 | 4/2018 | Lundin et al. |
| 2018/0110465 A1 | 4/2018 | Naima |
| 2018/0117414 A1 | 5/2018 | Miyasaka et al. |
| 2018/0120985 A1 | 5/2018 | Wallace et al. |
| 2018/0126248 A1 | 5/2018 | Dion et al. |
| 2018/0132768 A1 | 5/2018 | Sasahara et al. |
| 2018/0133537 A1 | 5/2018 | Montantes |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0150709 A1 | 5/2018 | Ha |
| 2018/0154212 A1 | 6/2018 | Park et al. |
| 2018/0177437 A1 | 6/2018 | Yoshioka |
| 2018/0182491 A1 | 6/2018 | Belliveau et al. |
| 2018/0189077 A1 | 7/2018 | Gupta et al. |
| 2018/0189343 A1 | 7/2018 | Embiricos et al. |
| 2018/0206766 A1 | 7/2018 | Blahnik et al. |
| 2018/0211020 A1 | 7/2018 | Fukuda |
| 2018/0232494 A1 | 8/2018 | Leppala et al. |
| 2018/0239869 A1 | 8/2018 | Laing et al. |
| 2018/0247706 A1 | 8/2018 | Riley et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0272190 A1 | 9/2018 | Miura et al. |
| 2018/0279885 A1 | 10/2018 | Bulut |
| 2018/0294053 A1 | 10/2018 | Runyon et al. |
| 2018/0300037 A1 | 10/2018 | Takeda et al. |
| 2018/0316964 A1 | 11/2018 | Dillon et al. |
| 2018/0318647 A1 | 11/2018 | Foley et al. |
| 2018/0329584 A1 | 11/2018 | Williams et al. |
| 2018/0336530 A1 | 11/2018 | Johnson et al. |
| 2018/0339195 A1 | 11/2018 | Bernotas |
| 2018/0345078 A1 | 12/2018 | Blahnik et al. |
| 2018/0350453 A1 | 12/2018 | Nag et al. |
| 2018/0367484 A1 | 12/2018 | Rodriguez et al. |
| 2018/0376107 A1 | 12/2018 | Shibaev et al. |
| 2019/0008467 A1 | 1/2019 | Averina et al. |
| 2019/0014205 A1 | 1/2019 | Miloseski et al. |
| 2019/0018588 A1 | 1/2019 | Debates et al. |
| 2019/0025995 A1 | 1/2019 | Williams |
| 2019/0026011 A1 | 1/2019 | Wang et al. |
| 2019/0034049 A1 | 1/2019 | Williams et al. |
| 2019/0034050 A1 | 1/2019 | Williams et al. |
| 2019/0034494 A1 | 1/2019 | Bradley et al. |
| 2019/0089701 A1 | 3/2019 | Mercury et al. |
| 2019/0090800 A1 | 3/2019 | Bosworth et al. |
| 2019/0090816 A1 | 3/2019 | Horseman |
| 2019/0102049 A1 | 4/2019 | Anzures et al. |
| 2019/0104951 A1 | 4/2019 | Valys et al. |
| 2019/0108908 A1 | 4/2019 | Faulks et al. |
| 2019/0122523 A1 | 4/2019 | Roberts et al. |
| 2019/0126099 A1 | 5/2019 | Hoang |
| 2019/0138696 A1 | 5/2019 | Carpenter et al. |
| 2019/0143194 A1 | 5/2019 | Evancha et al. |
| 2019/0150854 A1 | 5/2019 | Chung et al. |
| 2019/0184234 A1 | 6/2019 | Packles et al. |
| 2019/0192086 A1 | 6/2019 | Menon et al. |
| 2019/0206538 A1 | 7/2019 | Xing et al. |
| 2019/0209777 A1 | 7/2019 | O'Connell et al. |
| 2019/0228179 A1 | 7/2019 | Rakshit et al. |
| 2019/0228847 A1 | 7/2019 | Soli |
| 2019/0232110 A1 | 8/2019 | Williams et al. |
| 2019/0232111 A1 | 8/2019 | Williams et al. |
| 2019/0240534 A1 | 8/2019 | Black |
| 2019/0240536 A1 | 8/2019 | Dibenedetto et al. |
| 2019/0252054 A1 | 8/2019 | Dirani et al. |
| 2019/0274563 A1 | 9/2019 | Soli et al. |
| 2019/0274565 A1 | 9/2019 | Soli et al. |
| 2019/0279520 A1 | 9/2019 | Wilson et al. |
| 2019/0298230 A1 | 10/2019 | Nicholson et al. |
| 2019/0302995 A1 | 10/2019 | Robinson et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0339860 A1 | 11/2019 | Chen et al. |
| 2019/0342616 A1 | 11/2019 | Domm et al. |
| 2019/0364120 A1 | 11/2019 | Bandela et al. |
| 2019/0365332 A1 | 12/2019 | Fedichev et al. |
| 2019/0380624 A1 | 12/2019 | Ota et al. |
| 2019/0380653 A1 | 12/2019 | Benson et al. |
| 2019/0385708 A1 | 12/2019 | Hong et al. |
| 2019/0387982 A1 | 12/2019 | Buller |
| 2020/0014967 A1 | 1/2020 | Putnam |
| 2020/0026398 A1 | 1/2020 | Kim |
| 2020/0054931 A1 | 2/2020 | Martin et al. |
| 2020/0069258 A1 | 3/2020 | Grinberg |
| 2020/0098278 A1 | 3/2020 | Doti et al. |
| 2020/0100693 A1 | 4/2020 | Velo |
| 2020/0101365 A1 | 4/2020 | Wilson et al. |
| 2020/0110814 A1 | 4/2020 | Abuelsaad et al. |
| 2020/0126673 A1 | 4/2020 | Tanabe et al. |
| 2020/0149921 A1 | 5/2020 | Hoffman et al. |
| 2020/0160961 A1 | 5/2020 | Wadhawan et al. |
| 2020/0203012 A1 | 6/2020 | Kamath et al. |
| 2020/0214650 A1 | 7/2020 | Lee et al. |
| 2020/0245928 A1 | 8/2020 | Kang et al. |
| 2020/0261011 A1 | 8/2020 | Seppänen et al. |

(56) References Cited

U.S. PATENT DOCUMENTS

| | | |
|---|---|---|
| 2020/0261763 A1 | 8/2020 | Park et al. |
| 2020/0273566 A1 | 8/2020 | Bhowmik et al. |
| 2020/0289919 A1 | 9/2020 | Gruben |
| 2020/0297249 A1 | 9/2020 | Williams et al. |
| 2020/0323441 A1 | 10/2020 | Deno et al. |
| 2020/0356242 A1 | 11/2020 | Wilson et al. |
| 2020/0356687 A1 | 11/2020 | Salzman et al. |
| 2020/0357522 A1 | 11/2020 | Pahwa et al. |
| 2020/0374682 A1 | 11/2020 | Newman et al. |
| 2020/0381099 A1 | 12/2020 | Crowley et al. |
| 2020/0381100 A1 | 12/2020 | Williams et al. |
| 2020/0382613 A1 | 12/2020 | Sundstrom et al. |
| 2020/0384314 A1 | 12/2020 | Lee et al. |
| 2021/0001226 A1 | 1/2021 | Suzuki et al. |
| 2021/0007632 A1 | 1/2021 | Blahnik et al. |
| 2021/0007633 A1 | 1/2021 | Blahnik et al. |
| 2021/0008413 A1 | 1/2021 | Asikainen et al. |
| 2021/0042132 A1 | 2/2021 | Park et al. |
| 2021/0093919 A1 | 4/2021 | Lyke et al. |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0204815 A1 | 7/2021 | Koskela et al. |
| 2021/0210182 A1 | 7/2021 | Nag et al. |
| 2021/0225482 A1 | 7/2021 | Crowley et al. |
| 2021/0236903 A1 | 8/2021 | Briel |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0294438 A1 | 9/2021 | Yang et al. |
| 2021/0316185 A1 | 10/2021 | Mckenna et al. |
| 2021/0350900 A1 | 11/2021 | Blahnik et al. |
| 2021/0352118 A1 | 11/2021 | Ahn et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375450 A1 | 12/2021 | Felton et al. |
| 2021/0379447 A1 | 12/2021 | Lee |
| 2021/0394020 A1 | 12/2021 | Killen et al. |
| 2022/0047212 A1 | 2/2022 | Balsamo et al. |
| 2022/0047918 A1 | 2/2022 | Williams et al. |
| 2022/0062707 A1 | 3/2022 | Bedekar et al. |
| 2022/0066902 A1 | 3/2022 | Narra et al. |
| 2022/0121299 A1 | 4/2022 | De Vries et al. |
| 2022/0157143 A1 | 5/2022 | Panneer Selvam et al. |
| 2022/0157184 A1 | 5/2022 | Wilson et al. |
| 2022/0160258 A1 | 5/2022 | Williams et al. |
| 2022/0262485 A1 | 8/2022 | Meschter et al. |
| 2022/0262509 A1 | 8/2022 | Pahwa et al. |
| 2022/0328161 A1 | 10/2022 | Gilravi et al. |
| 2022/0336077 A1 | 10/2022 | Chen et al. |
| 2022/0386901 A1 | 12/2022 | Chen et al. |
| 2023/0012755 A1 | 1/2023 | D'auria et al. |
| 2023/0013809 A1 | 1/2023 | D'auria et al. |
| 2023/0013932 A1 | 1/2023 | Blahnik et al. |
| 2023/0014053 A1 | 1/2023 | Devine et al. |
| 2023/0017793 A1 | 1/2023 | Williams et al. |
| 2023/0019337 A1 | 1/2023 | D'auria et al. |
| 2023/0024084 A1 | 1/2023 | D'auria et al. |
| 2023/0025724 A1 | 1/2023 | Gilravi et al. |
| 2023/0027358 A1 | 1/2023 | Williams et al. |
| 2023/0066552 A1 | 3/2023 | Van Os et al. |
| 2023/0107803 A1 | 4/2023 | Dugan |
| 2023/0114054 A1 | 4/2023 | Crowley et al. |
| 2023/0119253 A1 | 4/2023 | Sundstrom et al. |
| 2023/0136700 A1 | 5/2023 | Williams et al. |
| 2023/0191198 A1 | 6/2023 | Lee et al. |
| 2023/0260416 A1 | 8/2023 | Wilson et al. |
| 2023/0390606 A1 | 12/2023 | Bolton et al. |
| 2023/0390626 A1 | 12/2023 | Bolton et al. |
| 2023/0390627 A1 | 12/2023 | Bolton et al. |
| 2023/0393723 A1 | 12/2023 | Arney et al. |
| 2024/0013889 A1 | 1/2024 | Crowley et al. |
| 2024/0077309 A1 | 3/2024 | Felton et al. |
| 2024/0081751 A1 | 3/2024 | Murphy et al. |
| 2024/0139608 A1 | 5/2024 | Bolton et al. |

FOREIGN PATENT DOCUMENTS

| | | |
|---|---|---|
| CA | 2826239 C | 1/2017 |
| CN | 1337638 A | 2/2002 |
| CN | 1397904 A | 2/2003 |
| CN | 1443427 A | 9/2003 |
| CN | 1523500 A | 8/2004 |
| CN | 1585943 A | 2/2005 |
| CN | 1628609 A | 6/2005 |
| CN | 1767789 A | 5/2006 |
| CN | 1824358 A | 8/2006 |
| CN | 1997050 A | 7/2007 |
| CN | 101061484 A | 10/2007 |
| CN | 101150810 A | 3/2008 |
| CN | 101219046 A | 7/2008 |
| CN | 101444419 A | 6/2009 |
| CN | 101541387 A | 9/2009 |
| CN | 101651870 A | 2/2010 |
| CN | 101658423 A | 3/2010 |
| CN | 101668482 A | 3/2010 |
| CN | 101836894 A | 9/2010 |
| CN | 101890217 A | 11/2010 |
| CN | 101894206 A | 11/2010 |
| CN | 101910992 A | 12/2010 |
| CN | 101978374 A | 2/2011 |
| CN | 102339201 A | 2/2012 |
| CN | 102438521 A | 5/2012 |
| CN | 102448555 | 5/2012 |
| CN | 102449560 A | 5/2012 |
| CN | 102449566 A | 5/2012 |
| CN | 102549590 A | 7/2012 |
| CN | 102804238 A | 11/2012 |
| CN | 102814037 A | 12/2012 |
| CN | 102834079 A | 12/2012 |
| CN | 102989159 A | 3/2013 |
| CN | 103154954 A | 6/2013 |
| CN | 103182175 A | 7/2013 |
| CN | 103210355 A | 7/2013 |
| CN | 103212197 A | 7/2013 |
| CN | 103270540 A | 8/2013 |
| CN | 103294124 A | 9/2013 |
| CN | 103297610 A | 9/2013 |
| CN | 103370924 A | 10/2013 |
| CN | 103403627 A | 11/2013 |
| CN | 203276086 U | 11/2013 |
| CN | 103561640 A | 2/2014 |
| CN | 103581456 A | 2/2014 |
| CN | 103646570 A | 3/2014 |
| CN | 103682785 A | 3/2014 |
| CN | 103701504 A | 4/2014 |
| CN | 104288983 A | 1/2015 |
| CN | 104501043 A | 4/2015 |
| CN | 104508426 A | 4/2015 |
| CN | 104815428 A | 8/2015 |
| CN | 105187282 A | 12/2015 |
| CN | 105260078 A | 1/2016 |
| CN | 105320454 A | 2/2016 |
| CN | 105388998 A | 3/2016 |
| CN | 105392064 A | 3/2016 |
| CN | 105681328 A | 6/2016 |
| CN | 105721667 A | 6/2016 |
| CN | 105808959 A | 7/2016 |
| CN | 106310638 A | 1/2017 |
| CN | 106415559 A | 2/2017 |
| CN | 106510719 A | 3/2017 |
| CN | 106537397 A | 3/2017 |
| CN | 106709235 A | 5/2017 |
| CN | 106878550 A | 6/2017 |
| CN | 107469327 A | 12/2017 |
| CN | 107545930 A | 1/2018 |

(56) References Cited

FOREIGN PATENT DOCUMENTS

| | | |
|---|---|---|
| CN | 107580776 A | 1/2018 |
| CN | 107749310 A | 3/2018 |
| CN | 107921317 A | 4/2018 |
| CN | 108200464 A | 6/2018 |
| CN | 108211310 A | 6/2018 |
| CN | 108604327 A | 9/2018 |
| EP | 0943290 A1 | 9/1999 |
| EP | 1559372 A1 | 8/2005 |
| EP | 1935339 A1 | 6/2008 |
| EP | 2025368 A2 | 2/2009 |
| EP | 2529663 A1 | 12/2012 |
| EP | 2568409 A1 | 3/2013 |
| EP | 2631830 A2 | 8/2013 |
| EP | 2632139 A2 | 8/2013 |
| EP | 2728680 A1 | 5/2014 |
| EP | 2921899 A2 | 9/2015 |
| EP | 2993602 A1 | 3/2016 |
| EP | 3096235 A1 | 11/2016 |
| EP | 3101882 A2 | 12/2016 |
| EP | 3117767 A1 | 1/2017 |
| EP | 3122038 A1 | 1/2017 |
| EP | 3130997 A1 | 2/2017 |
| EP | 3557590 A1 | 10/2019 |
| JP | 5-288869 A | 11/1993 |
| JP | 6-187118 A | 7/1994 |
| JP | 8-126632 A | 5/1996 |
| JP | 11-84030 A | 3/1999 |
| JP | 2001-76078 A | 3/2001 |
| JP | 2001-216336 A | 8/2001 |
| JP | 2002-190007 A | 7/2002 |
| JP | 2002-346013 A | 12/2002 |
| JP | 2003-102868 A | 4/2003 |
| JP | 2003-157323 A | 5/2003 |
| JP | 2003-248721 A | 9/2003 |
| JP | 2003-319912 A | 11/2003 |
| JP | 2003-337863 A | 11/2003 |
| JP | 2004-102609 A | 4/2004 |
| JP | 2004-113466 A | 4/2004 |
| JP | 2004-174006 A | 6/2004 |
| JP | 2005-79814 A | 3/2005 |
| JP | 3635663 B2 | 4/2005 |
| JP | 2006-107134 A | 4/2006 |
| JP | 2006-155104 A | 6/2006 |
| JP | 2006-180899 A | 7/2006 |
| JP | 2006-230679 A | 9/2006 |
| JP | 2007-260288 A | 10/2007 |
| JP | 2007-330513 A | 12/2007 |
| JP | 2008-104758 A | 5/2008 |
| JP | 2008-183339 A | 8/2008 |
| JP | 2008-272301 A | 11/2008 |
| JP | 2009-78134 A | 4/2009 |
| JP | 2009-88989 A | 4/2009 |
| JP | 2009-112731 A | 5/2009 |
| JP | 2009-211241 A | 9/2009 |
| JP | 2009-282670 A | 12/2009 |
| JP | 2010-12335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2010-182287 A | 8/2010 |
| JP | 2010-186249 A | 8/2010 |
| JP | 2010-206668 A | 9/2010 |
| JP | 2011-514192 A | 5/2011 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-200575 A | 10/2011 |
| JP | 2011-206323 A | 10/2011 |
| JP | 2011-210119 A | 10/2011 |
| JP | 2011-229141 A | 11/2011 |
| JP | 2011-259253 A | 12/2011 |
| JP | 2012-20134 A | 2/2012 |
| JP | 2012-35071 A | 2/2012 |
| JP | 2012-45373 A | 3/2012 |
| JP | 2012-59264 A | 3/2012 |
| JP | 2012-86088 A | 5/2012 |
| JP | 2012-524640 A | 10/2012 |
| JP | 2012-230503 A | 11/2012 |
| JP | 2012-232114 A | 11/2012 |
| JP | 2012-239808 A | 12/2012 |
| JP | 2012-533117 A | 12/2012 |
| JP | 2013-103020 A | 5/2013 |
| JP | 2013-117690 A | 6/2013 |
| JP | 2013-146557 A | 8/2013 |
| JP | 2013-530776 A | 8/2013 |
| JP | 2013-192608 A | 9/2013 |
| JP | 2013-543156 A | 11/2013 |
| JP | 5346115 B1 | 11/2013 |
| JP | 2013-544140 A | 12/2013 |
| JP | 2014-500740 A | 1/2014 |
| JP | 2014-45782 A | 3/2014 |
| JP | 2014-104139 A | 6/2014 |
| JP | 2014-143473 A | 8/2014 |
| JP | 2014-168685 A | 9/2014 |
| JP | 2014-171831 A | 9/2014 |
| JP | 2015-58218 A | 3/2015 |
| JP | 2015-507811 A | 3/2015 |
| JP | 2015-509019 A | 3/2015 |
| JP | 2015-509755 A | 4/2015 |
| JP | 2015-531916 A | 11/2015 |
| JP | 2015-213686 A | 12/2015 |
| JP | 2016-17331 A | 2/2016 |
| JP | 2016-502875 A | 2/2016 |
| JP | 2016-52512 A | 4/2016 |
| JP | 2016-517329 A | 6/2016 |
| JP | 2016-158867 A | 9/2016 |
| JP | 2016-528016 A | 9/2016 |
| JP | 2016-177151 A | 10/2016 |
| JP | 2016-185288 A | 10/2016 |
| JP | 2016-202751 A | 12/2016 |
| JP | 2016-538926 A | 12/2016 |
| JP | 2017-83978 A | 5/2017 |
| JP | 2017-117265 A | 6/2017 |
| JP | 2017-515520 A | 6/2017 |
| JP | 2017-134689 A | 8/2017 |
| JP | 2017-156267 A | 9/2017 |
| JP | 2017-526073 A | 9/2017 |
| JP | 2017-182393 A | 10/2017 |
| JP | 2017-529880 A | 10/2017 |
| JP | 2017-531235 A | 10/2017 |
| JP | 2017-211994 A | 11/2017 |
| JP | 2017-532069 A | 11/2017 |
| JP | 2018-504660 A | 2/2018 |
| JP | 2018-102908 A | 7/2018 |
| JP | 2018-523554 A | 8/2018 |
| JP | 6382433 B1 | 8/2018 |
| JP | 2018-202174 A | 12/2018 |
| JP | 2019-3670 A | 1/2019 |
| JP | 2019-28806 A | 2/2019 |
| JP | 2019-32461 A | 2/2019 |
| JP | 2019-505035 A | 2/2019 |
| JP | 2019-55076 A | 4/2019 |
| JP | 2019-207536 A | 12/2019 |
| KR | 10-2006-0117570 A | 11/2006 |
| KR | 10-2011-0017076 A | 2/2011 |
| KR | 10-2011-0121394 A | 11/2011 |
| KR | 10-2012-0023657 A | 3/2012 |
| KR | 10-2012-0076559 A | 7/2012 |
| KR | 10-2012-0098854 A | 9/2012 |
| KR | 10-2012-0132732 A | 12/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2016-0027943 A | 3/2016 |
| KR | 10-2016-0028351 A | 3/2016 |
| KR | 10-2016-0076264 A | 6/2016 |
| KR | 10-2016-0077199 A | 7/2016 |
| KR | 10-2016-0084705 A | 7/2016 |
| KR | 10-2016-0105129 A | 9/2016 |
| KR | 10-2016-0142418 A | 12/2016 |

(56) References Cited

FOREIGN PATENT DOCUMENTS

| | | |
|---|---|---|
| KR | 10-2017-0003608 A | 1/2017 |
| KR | 10-2017-0019040 A | 2/2017 |
| KR | 10-2017-0019745 A | 2/2017 |
| KR | 10-2017-0020085 A | 2/2017 |
| KR | 10-2017-0029014 A | 3/2017 |
| KR | 10-2017-0032471 A | 3/2017 |
| KR | 10-2018-0026066 A | 3/2018 |
| KR | 10-2018-0129188 A | 12/2018 |
| KR | 10-2019-0022883 A | 3/2019 |
| KR | 10-2019-0141702 A | 12/2019 |
| TW | 201210368 A | 3/2012 |
| TW | 201240499 A | 10/2012 |
| WO | 97/38626 A1 | 10/1997 |
| WO | 99/41682 A2 | 8/1999 |
| WO | 02/27530 A2 | 4/2002 |
| WO | 02/41134 A2 | 5/2002 |
| WO | 2005/029242 A2 | 3/2005 |
| WO | 2005/070289 A1 | 8/2005 |
| WO | 2006/103965 A1 | 10/2006 |
| WO | 2007/081629 A2 | 7/2007 |
| WO | 2009/129402 A1 | 10/2009 |
| WO | 2009/152608 A1 | 12/2009 |
| WO | 2010/126821 A1 | 11/2010 |
| WO | 2010/126825 A1 | 11/2010 |
| WO | 2011/072111 A2 | 6/2011 |
| WO | 2011/108335 A1 | 9/2011 |
| WO | 2012/021507 A2 | 2/2012 |
| WO | 2012/036891 A2 | 3/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2012/095712 A1 | 7/2012 |
| WO | 2013/052789 A1 | 4/2013 |
| WO | 2013/109762 A1 | 7/2013 |
| WO | 2013/109776 A1 | 7/2013 |
| WO | 2013/109777 A1 | 7/2013 |
| WO | 2013/109916 A1 | 7/2013 |
| WO | 2013/157307 A1 | 10/2013 |
| WO | 2013/169870 A1 | 11/2013 |
| WO | 2013/173838 A2 | 11/2013 |
| WO | 2014/006862 A1 | 1/2014 |
| WO | 2014/022711 A1 | 2/2014 |
| WO | 2014/059259 A1 | 4/2014 |
| WO | 2014/105276 A1 | 7/2014 |
| WO | 2014/200730 A1 | 12/2014 |
| WO | 2014/207294 A1 | 12/2014 |
| WO | 2014/207875 A1 | 12/2014 |
| WO | 2015/027133 A1 | 2/2015 |
| WO | 2015/084353 A1 | 6/2015 |
| WO | 2015/179592 A1 | 11/2015 |
| WO | 2015/183828 A1 | 12/2015 |
| WO | 2015/198488 A1 | 12/2015 |
| WO | 2016/022203 A1 | 2/2016 |
| WO | 2016/025036 A1 | 2/2016 |
| WO | 2016/036472 A1 | 3/2016 |
| WO | 2016/036582 A2 | 3/2016 |
| WO | 2016/036582 A3 | 6/2016 |
| WO | 2017/014403 A1 | 1/2017 |
| WO | 2017/030646 A1 | 2/2017 |
| WO | 2017/037242 A1 | 3/2017 |
| WO | 2017/172046 A1 | 10/2017 |
| WO | 2018/048510 A1 | 3/2018 |
| WO | 2018/213066 A1 | 11/2018 |
| WO | 2018/222313 A1 | 12/2018 |
| WO | 2018/236291 A1 | 12/2018 |
| WO | 2019/017508 A1 | 1/2019 |
| WO | 2019/024383 A1 | 2/2019 |
| WO | 2019/024603 A1 | 2/2019 |
| WO | 2019/183422 A1 | 9/2019 |
| WO | 2019/190001 A1 | 10/2019 |
| WO | 2019/217249 A2 | 11/2019 |
| WO | 2019/231982 A1 | 12/2019 |
| WO | 2019/240513 A1 | 12/2019 |

OTHER PUBLICATIONS

Advisory Action received for U.S. Appl. No. 16/144,864, mailed on Jul. 29, 2019, 6 pages.
Advisory Action received for U.S. Appl. No. 14/732,773, mailed on Aug. 23, 2019, 6 pages.
Advisory Action received for U.S. Appl. No. 14/732,773, mailed on Nov. 9, 2018, 6 pages.
Advisory Action received for U.S. Appl. No. 14/839,922, mailed on Mar. 24, 2017, 4 pages.
Advisory Action received for U.S. Appl. No. 16/144,849, mailed on Aug. 12, 2019, 5 pages.
Advisory Action received for U.S. Appl. No. 16/144,864, mailed on Jul. 6, 2020, 6 pages.
Advisory Action received for U.S. Appl. No. 16/377,892, mailed on Apr. 9, 2021, 4 pages.
Advisory Action received for U.S. Appl. No. 16/378,136, mailed on Apr. 12, 2021, 4 pages.
Allison Conor, "Working out with Fiit's wearable-powered boutique fitness classes", Online available at:—<https://www.wareable.com/wearable-tech/fiit-fitness-classes-review-3849>, May 14, 2018, 8 pages.
Apple Inc., "iPhone User Guide For iOS 7.1 Software", available online at <https://manuals.info.apple.com/MANUALS/1000/MA1681/en_US/iphone_ios7_user_guide.pdf>, Mar. 10, 2014, pp. 1-162.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant Initiated Interview Summary received for U.S. Appl. No. 16/994,352, mailed on Nov. 2, 2021, 4 pages.
Applicant Initiated Interview Summary received for U.S. Appl. No. 15/608,848, mailed on Apr. 13, 2021, 4 pages.
Applicant Initiated Interview Summary received for U.S. Appl. No. 15/608,848, mailed on May 12, 2020, 5 pages.
Applicant Initiated Interview Summary received for U.S. Appl. No. 15/608,848, mailed on Oct. 26, 2020, 3 pages.
Applicant Initiated Interview Summary received for U.S. Appl. No. 15/627,069, mailed on Nov. 4, 2019, 6 pages.
Applicant Initiated Interview Summary received for U.S. Appl. No. 16/144,735, mailed on Jun. 18, 2020, 3 pages.
Applicant Initiated Interview Summary received for U.S. Appl. No. 16/144,753, mailed on Jun. 18, 2020, 3 pages.
Applicant Initiated Interview Summary received for U.S. Appl. No. 16/144,849, mailed on Jan. 21, 2020, 6 pages.
Applicant Initiated Interview Summary received for U.S. Appl. No. 16/144,864, mailed on Apr. 29, 2020, 4 pages.
Applicant Initiated Interview Summary received for U.S. Appl. No. 16/894,309, mailed on Jan. 26, 2021, 3 pages.
Applicant Initiated Interview Summary received for U.S. Appl. No. 17/030,318, mailed on Jul. 30, 2021, 4 pages.
Applicant Initiated Interview Summary received for U.S. Appl. No. 17/030,321, mailed on Jul. 30, 2021, 2 pages.
Applicant Initiated Interview Summary received for U.S. Appl. No. 17/381,570, mailed on Apr. 26, 2022, 5 pages.
Applicant-Initiated Interview Summary received for U.S. Appl. No. 15/600,243, mailed on Nov. 1, 2019, 6 pages.
Applicant-Initiated Interview Summary received for U.S. Appl. No. 15/608,848, mailed on Nov. 1, 2019, 3 pages.
Applicant-Initiated Interview Summary received for U.S. Appl. No. 15/627,069, mailed on Jan. 22, 2021, 4 pages.
Applicant-Initiated Interview Summary received for U.S. Appl. No. 15/627,069, mailed on Jul. 20, 2020, 5 pages.
Applicant-Initiated Interview Summary received for U.S. Appl. No. 15/705,849, mailed on Feb. 14, 2020, 3 pages.
Applicant-Initiated Interview Summary received for U.S. Appl. No. 15/705,849, mailed on Jun. 29, 2020, 3 pages.
Applicant-Initiated Interview Summary received for U.S. Appl. No. 15/925,652, mailed on Nov. 3, 2020, 4 pages.
Applicant-Initiated Interview Summary received for U.S. Appl. No. 15/978,126, mailed on Jan. 19, 2021, 4 pages.
Applicant-Initiated Interview Summary received for U.S. Appl. No. 15/978,126, mailed on Jul. 1, 2020, 6 pages.

(56) References Cited

OTHER PUBLICATIONS

Applicant-Initiated Interview Summary received for U.S. Appl. No. 16/138,809, mailed on Dec. 16, 2020, 7 pages.
Applicant-Initiated Interview Summary received for U.S. Appl. No. 16/138,809, mailed on Jun. 9, 2020, 4 pages.
Applicant-Initiated Interview Summary received for U.S. Appl. No. 16/144,753, mailed on Nov. 4, 2020, 3 pages.
Applicant-Initiated Interview Summary received for U.S. Appl. No. 16/144,864, mailed on Jun. 22, 2020, 3 pages.
Applicant-Initiated Interview Summary received for U.S. Appl. No. 16/249,627, mailed on Jun. 2, 2021, 5 pages.
Applicant-Initiated Interview Summary received for U.S. Appl. No. 16/249,627, mailed on Mar. 23, 2022, 3 pages.
Applicant-Initiated Interview Summary received for U.S. Appl. No. 16/249,627, mailed on Oct. 6, 2021, 4 pages.
Applicant-Initiated Interview Summary received for U.S. Appl. No. 16/377,892, mailed on Mar. 26, 2021, 2 pages.
Applicant-Initiated Interview Summary received for U.S. Appl. No. 16/377,892, mailed on Oct. 13, 2020, 5 pages.
Applicant-Initiated Interview Summary received for U.S. Appl. No. 16/378,136, mailed on Mar. 26, 2021, 2 pages.
Applicant-Initiated Interview Summary received for U.S. Appl. No. 16/378,136, mailed on Oct. 13, 2020, 4 pages.
Applicant-Initiated Interview Summary received for U.S. Appl. No. 16/418,786, mailed on Mar. 30, 2021, 4 pages.
Applicant-Initiated Interview Summary received for U.S. Appl. No. 16/418,786, mailed on May 9, 2022, 2 pages.
Applicant-Initiated Interview Summary received for U.S. Appl. No. 16/820,383, mailed on Aug. 12, 2022, 2 pages.
Applicant-Initiated Interview Summary received for U.S. Appl. No. 16/820,383, mailed on Mar. 11, 2021, 2 pages.
Applicant-Initiated Interview Summary received for U.S. Appl. No. 16/820,383, mailed on May 10, 2022, 2 pages.
Applicant-Initiated Interview Summary received for U.S. Appl. No. 16/880,714, mailed on Feb. 26, 2021, 5 pages.
Applicant-Initiated Interview Summary received for U.S. Appl. No. 16/888,629, mailed on Aug. 4, 2021, 5 pages.
Applicant-Initiated Interview Summary received for U.S. Appl. No. 16/894,309, mailed on Jun. 25, 2021, 4 pages.
Applicant-Initiated Interview Summary received for U.S. Appl. No. 16/987,275, mailed on Feb. 3, 2022, 4 pages.
Applicant-Initiated Interview Summary received for U.S. Appl. No. 17/030,337, mailed on Jul. 27, 2022, 2 pages.
Applicant-Initiated Interview Summary received for U.S. Appl. No. 17/031,543, mailed on Apr. 21, 2022, 2 pages.
Applicant-Initiated Interview Summary received for U.S. Appl. No. 17/031,704, mailed on Feb. 9, 2021, 3 pages.
Applicant-Initiated Interview Summary received for U.S. Appl. No. 17/031,704, mailed on Jun. 25, 2021, 3 pages.
Applicant-Initiated Interview Summary received for U.S. Appl. No. 17/031,717, mailed on Jan. 29, 2021, 5 pages.
Applicant-Initiated Interview Summary received for U.S. Appl. No. 17/031,717, mailed on May 17, 2021, 5 pages.
Applicant-Initiated Interview Summary received for U.S. Appl. No. 17/031,717, mailed on Nov. 4, 2021, 5 pages.
Applicant-Initiated Interview Summary received for U.S. Appl. No. 17/031,723, mailed on Aug. 30, 2022, 4 pages.
Applicant-Initiated Interview Summary received for U.S. Appl. No. 17/031,723, mailed on Mar. 21, 2021, 5 pages.
Applicant-Initiated Interview Summary received for U.S. Appl. No. 17/031,779, mailed on Aug. 29, 2022, 2 pages.
Applicant-Initiated Interview Summary received for U.S. Appl. No. 17/031,779, mailed on Mar. 10, 2022, 2 pages.
Applicant-Initiated Interview Summary received for U.S. Appl. No. 17/031,854, mailed on Feb. 25, 2022, 5 pages.
Applicant-Initiated Interview Summary received for U.S. Appl. No. 17/031,854, mailed on Jul. 27, 2022, 5 pages.
Applicant-Initiated Interview Summary received for U.S. Appl. No. 17/031,859, mailed on Feb. 25, 2022, 4 pages.
Applicant-Initiated Interview Summary received for U.S. Appl. No. 17/031,859, mailed on Feb. 26, 2021, 4 pages.
Applicant-Initiated Interview Summary received for U.S. Appl. No. 17/031,859, mailed on Jul. 28, 2022, 3 pages.
Applicant-Initiated Interview Summary received for U.S. Appl. No. 17/031,859, mailed on Jun. 30, 2021, 4 pages.
Applicant-Initiated Interview Summary received for U.S. Appl. No. 17/031,874, mailed on Feb. 25, 2022, 4 pages.
Applicant-Initiated Interview Summary received for U.S. Appl. No. 17/031,874, mailed on Feb. 26, 2021, 4 pages.
Applicant-Initiated Interview Summary received for U.S. Appl. No. 17/031,874, mailed on Jul. 27, 2022, 5 pages.
Applicant-Initiated Interview Summary received for U.S. Appl. No. 17/031,874, mailed on Jun. 30, 2021, 4 pages.
Applicant-Initiated Interview Summary received for U.S. Appl. No. 17/041,415, mailed on Jun. 29, 2022, 2 pages.
Applicant-Initiated Interview Summary received for U.S. Appl. No. 17/157,728, mailed on Feb. 3, 2022, 5 pages.
Applicant-Initiated Interview Summary received for U.S. Appl. No. 17/192,161, mailed on Dec. 24, 2021, 4 pages.
Applicant-Initiated Interview Summary received for U.S. Appl. No. 17/192,161, mailed on Jun. 29, 2021, 4 pages.
Applicant-Initiated Interview Summary received for U.S. Appl. No. 17/192,161, mailed on Sep. 29, 2021, 3 pages.
Applicant-Initiated Interview Summary received for U.S. Appl. No. 17/381,570, mailed on Aug. 24, 2022, 5 pages.
Applicant-Initiated Interview Summary received for U.S. Appl. No. 17/516,537, mailed on Jul. 5, 2022, 4 pages.
Bagala et al., "Evaluation of Accelerometer-Based Fall Detection Algorithms on Real-World Falls", PloS One, vol. 7, No. 5, May 16, 2012, 9 pages.
Board Decision received for Chinese Patent Application No. 201380081349.6, mailed on Nov. 23, 2020, 2 pages.
Brief Communication Regarding Oral Proceedings received for European Patent Application No. 20182116.2, mailed on Apr. 13, 2022, 3 pages.
CBS This Morning, "This smart mirror puts a personal trainer in your reflection", Available on: https://www.youtube.com/watch?v=nSmTTZcpVGg, Oct. 13, 2018, 4 pages.
Certificate of Examination received for Australian Patent Application No. 2018101855, mailed on Aug. 6, 2019, 2 pages.
Certification of Examination received for Australian Patent Application No. 2018100158, mailed on Oct. 23, 2018, 2 pages.
Cho H.S., "Satisfactory Innovative Smart-watch (fitbit force) . . . review after seven days of use, such as the amount of sleep and movement improving sleep is the object of X-Blue", Online Available at: <https://x-blueuv.blogspot.com/2013/12/fitbit-force.html>, Dec. 3, 2013, 8 pages.
CNET, "Google Fit's automatic activity tracking is getting smarter on Android Wear", Available online at: https://www.youtube.com/watch?v=IttzlCid_d8, May 18, 2016, 1 page.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Communication of the Board of Appeal received for European Patent Application No. 13811085.3, mailed on Jul. 28, 2022, 13 pages.
Communication of the Board of Appeal received for European Patent Application No. 15771747.1, mailed on Aug. 25, 2021, 9 pages.
Corrected Notice of Allowance received for U.S. Appl. No. 14/732,773, mailed on Feb. 10, 2020, 3 pages.
Corrected Notice of Allowance received for U.S. Appl. No. 14/732,773, mailed on Mar. 24, 2020, 3 pages.
Corrected Notice of Allowance received for U.S. Appl. No. 15/183,663, mailed on Feb. 25, 2019, 3 pages.
Corrected Notice of Allowance received for U.S. Appl. No. 15/183,663, mailed on Mar. 27, 2019, 2 pages.
Corrected Notice of Allowance received for U.S. Appl. No. 15/600,243, mailed on Feb. 5, 2020, 3 pages.
Corrected Notice of Allowance received for U.S. Appl. No. 15/600,243, mailed on Mar. 13, 2020, 3 pages.

(56) References Cited

OTHER PUBLICATIONS

Corrected Notice of Allowance received for U.S. Appl. No. 15/600,243, mailed on Mar. 31, 2020, 5 pages.
Corrected Notice of Allowance received for U.S. Appl. No. 16/377,892, mailed on Aug. 11, 2021, 3 pages.
Corrected Notice of Allowance received for U.S. Appl. No. 16/378,136, mailed on Aug. 11, 2021, 2 pages.
Corrected Notice of Allowance received for U.S. Appl. No. 16/378,136, mailed on Jun. 11, 2021, 2 pages.
Corrected Notice of Allowance received for U.S. Appl. No. 16/418,786, mailed on Jan. 5, 2022, 3 pages.
Corrected Notice of Allowance received for U.S. Appl. No. 16/418,786, mailed on Jun. 23, 2022, 2 pages.
Corrected Notice of Allowance received for U.S. Appl. No. 16/820,383, mailed on Aug. 13, 2021, 2 pages.
Corrected Notice of Allowance received for U.S. Appl. No. 16/820,383, mailed on Aug. 19, 2021, 2 pages.
Corrected Notice of Allowance received for U.S. Appl. No. 16/820,383, mailed on Oct. 5, 2021, 2 pages.
Corrected Notice of Allowance received for U.S. Appl. No. 16/888,629, mailed on Jan. 21, 2022, 2 pages.
Corrected Notice of Allowance received for U.S. Appl. No. 16/987,275, mailed on Jun. 8, 2022, 3 pages.
Corrected Notice of Allowance received for U.S. Appl. No. 17/030,318, mailed on Jan. 24, 2022, 2 pages.
Corrected Notice of Allowance received for U.S. Appl. No. 17/030,321, mailed on Aug. 15, 2022, 3 pages.
Corrected Notice of Allowance received for U.S. Appl. No. 17/030,337, mailed on Aug. 31, 2022, 2 pages.
Corrected Notice of Allowance received for U.S. Appl. No. 17/031,543, mailed on Aug. 22, 2022, 2 pages.
Corrected Notice of Allowance received for U.S. Appl. No. 17/031,543, mailed on Jul. 18, 2022, 2 pages.
Corrected Notice of Allowance received for U.S. Appl. No. 17/031,543, mailed on Jun. 8, 2022, 3 pages.
Corrected Notice of Allowance received for U.S. Appl. No. 17/031,704, mailed on Nov. 2, 2021, 7 pages.
Corrected Notice of Allowance received for U.S. Appl. No. 17/031,717, mailed on Apr. 15, 2022, 3 pages.
Corrected Notice of Allowance received for U.S. Appl. No. 17/031,717, mailed on May 19, 2022, 3 pages.
Corrected Notice of Allowance received for U.S. Appl. No. 17/157,728, mailed on Apr. 4, 2022, 3 pages.
Corrected Notice of Allowance received for U.S. Appl. No. 17/157,728, mailed on Apr. 14, 2022, 6 pages.
Corrected Notice of Allowance received for U.S. Appl. No. 17/192,161, mailed on Apr. 22, 2022, 2 pages.
Corrected Notice of Allowance received for U.S. Appl. No. 17/192,161, mailed on Mar. 23, 2022, 2 pages.
Corrected Notice of Allowance received for U.S. Appl. No. 17/197,628, mailed on Apr. 27, 2022, 3 pages.
Corrected Notice of Allowance received for U.S. Appl. No. 17/197,628, mailed on Jul. 29, 2022, 2 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
DC Rainmaker, "Garmin Fenix3 New Auto Climb Functionality", Available online at: https://www.youtube.com/watch?v=iuavOSNpVRc, Feb. 19, 2015, 1 page.
Decision of Appeal received for European Patent Application No. 15771747.1, mailed on Dec. 14, 2021, 21 pages.
Decision on Appeal received for Korean Patent Application No. 10-2019-7025538, mailed on Feb. 24, 2021, 20 pages.
Decision to Grant received for Danish Patent Application No. PA201670656, mailed on Jun. 21, 2021, 2 pages.
Decision to Grant received for Danish Patent Application No. PA201870379, mailed on Jul. 5, 2019, 2 pages.
Decision to Grant received for Danish Patent Application No. PA202070615, mailed on Jul. 29, 2022, 2 pages.
Decision to Grant received for Danish Patent Application No. PA202070619, mailed on Aug. 11, 2022, 2 pages.
Decision to Grant received for German Patent Application No. 112015002326.7, mailed on Jun. 15, 2021, 10 pages.
Decision to Refuse received for European Patent Application No. 13811085.3, mailed on Sep. 11, 2018, 21 pages.
Decision to Refuse received for European Patent Application No. 15771747.1, mailed on Aug. 10, 2018, 22 pages.
Decision to Refuse received for European Patent Application No. 17810749.6, mailed on Jan. 29, 2021, 24 pages.
Decision to Refuse received for European Patent Application No. 18154145.9, mailed on Feb. 17, 2021, 20 pages.
DwProgressBar v2: Stepping and Events, davidwalsh.name/dwprogressbar-2-stepping-events-mootools-progress-bar, retrieved from the Wayback Machine, Aug. 31, 2008, 4 pages.
European Search Report received for European Patent Application No. 20182116.2, mailed on Oct. 21, 2020, 4 pages.
European Search Report received for European Patent Application No. 21165295.3, mailed on Jun. 18, 2021, 4 pages.
European Search Report received for European Patent Application No. 21168916.1, mailed on Jul. 14, 2021, 5 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 16837432.0, mailed on Mar. 11, 2019, 10 pages.
Extended European Search Report received for European Patent Application No. 18154145.9, mailed on Mar. 2, 2018, 8 pages.
Extended European Search Report received for European Patent Application No. 19163212.4, mailed on Jun. 25, 2019, 11 pages.
Extended European Search Report received for European Patent Application No. 20203526.7, mailed on Jan. 29, 2021, 13 pages.
FAQ|SleepScore, Available Online at: https://www.sleepscore.com/sleepscore-app/faq/, Retrieved on May 26, 2021, 31 pages.
Final Office Action received for U.S. Appl. No. 16/994,352, mailed on Dec. 6, 2021, 14 pages.
Final Office Action received for U.S. Appl. No. 12/205,847, mailed on Apr. 25, 2012, 42 pages.
Final Office Action received for U.S. Appl. No. 14/599,424, mailed on Jun. 28, 2018, 12 pages.
Final Office Action received for U.S. Appl. No. 14/599,425, mailed on Jun. 12, 2018, 45 pages.
Final Office Action received for U.S. Appl. No. 14/599,425, mailed on May 19, 2017, 24 pages.
Final Office Action received for U.S. Appl. No. 14/599,425, mailed on Oct. 8, 2015, 20 pages.
Final Office Action received for U.S. Appl. No. 14/732,773, mailed on Jul. 13, 2018, 48 pages.
Final Office Action received for U.S. Appl. No. 14/732,773, mailed on Jun. 21, 2019, 32 pages.
Final Office Action received for U.S. Appl. No. 14/839,922, mailed on Dec. 14, 2016, 22 pages.
Final Office Action received for U.S. Appl. No. 15/608,848, mailed on Aug. 21, 2020, 15 pages.
Final Office Action received for U.S. Appl. No. 15/608,848, mailed on Jun. 26, 2019, 27 pages.
Final Office Action received for U.S. Appl. No. 15/627,069, mailed on Mar. 2, 2020, 22 pages.
Final Office Action received for U.S. Appl. No. 15/627,069, mailed on Oct. 20, 2020, 25 pages.
Final Office Action received for U.S. Appl. No. 15/705,849, mailed on May 1, 2020, 17 pages.
Final Office Action received for U.S. Appl. No. 15/925,652, mailed on Aug. 1, 2019, 30 Pages.
Final Office Action received for U.S. Appl. No. 15/978,126, mailed on Sep. 30, 2020, 23 pages.
Final Office Action received for U.S. Appl. No. 16/138,809, mailed on Aug. 27, 2020, 24 pages.
Final Office Action received for U.S. Appl. No. 16/144,735, mailed on May 4, 2020, 12 pages.
Final Office Action received for U.S. Appl. No. 16/144,753, mailed on Sep. 22, 2020, 9 pages.

(56) References Cited

OTHER PUBLICATIONS

Final Office Action received for U.S. Appl. No. 16/144,849, mailed on Jun. 7, 2019, 29 pages.
Final Office Action received for U.S. Appl. No. 16/144,864, mailed on May 17, 2019, 24 pages.
Final Office Action received for U.S. Appl. No. 16/144,864, mailed on May 28, 2020, 29 pages.
Final Office Action received for U.S. Appl. No. 16/249,627, mailed on Feb. 14, 2022, 19 pages.
Final Office Action received for U.S. Appl. No. 16/377,892, mailed on Jan. 28, 2021, 11 pages.
Final Office Action received for U.S. Appl. No. 16/378,136, mailed on Jan. 28, 2021, 9 pages.
Final Office Action received for U.S. Appl. No. 16/418,786, mailed on Jan. 13, 2021, 14 pages.
Final Office Action received for U.S. Appl. No. 16/820,383, mailed on Jun. 22, 2022, 21 pages.
Final Office Action received for U.S. Appl. No. 16/894,309, mailed on Feb. 24, 2021, 30 pages.
Final Office Action received for U.S. Appl. No. 17/030,318, mailed on Sep. 30, 2021, 28 pages.
Final Office Action received for U.S. Appl. No. 17/030,321, mailed on Apr. 2, 2021, 28 pages.
Final Office Action received for U.S. Appl. No. 17/031,704, mailed on Apr. 1, 2021, 31 pages.
Final Office Action received for U.S. Appl. No. 17/031,717, mailed on Feb. 24, 2021, 23 pages.
Final Office Action received for U.S. Appl. No. 17/031,723, mailed on Jul. 12, 2022, 25 pages.
Final Office Action received for U.S. Appl. No. 17/031,779, mailed on Jul. 14, 2022, 19 pages.
Final Office Action received for U.S. Appl. No. 17/031,854, mailed on Jun. 10, 2022, 15 pages.
Final Office Action received for U.S. Appl. No. 17/031,859, mailed on Apr. 16, 2021, 14 pages.
Final Office Action received for U.S. Appl. No. 17/031,859, mailed on Jun. 10, 2022, 13 pages.
Final Office Action received for U.S. Appl. No. 17/031,874, mailed on Apr. 16, 2021, 17 pages.
Final Office Action received for U.S. Appl. No. 17/031,874, mailed on Jun. 2, 2022, 19 pages.
Final Office Action received for U.S. Appl. No. 17/192,161, mailed on Aug. 16, 2021, 22 pages.
Final Office Action received for U.S. Appl. No. 17/192,161, mailed on Oct. 18, 2021, 22 pages.
Final Office Action received for U.S. Appl. No. 17/381,570, mailed on Jul. 20, 2022, 22 pages.
Fitbit App, Available online at: <http://web.archive.org/web/20180114083150/https://www.fitbit.com/au/app>, Jan. 14, 2018, 8 pages.
Garmin Edge 520, Owner's Manual, Online available at: https://www8.garmin.com/manuals/webhelp/edge520/EN-US/Edge_520_OM_EN-US.pdf, 2015, 24 pages.
Garmin, "Fenix 5x Owner's Manual", Online Available at:—https://web.archive.org/web/20180127170640/https://static.garmin.com/pumac/fenix5x_OM_EN.pdf, Jan. 27, 2018, 42 pages.
Graphs and Charts, online available at: <https://www.teachervision.com/lesson-planning/graph-chart-teacher-resources, retrieved on Dec. 12, 2018, 4 pages.
Gym Book—Strength Training Planner, Logger and Analyzer, GymBookApp, Available Online at: https://web.archive.org/web/20160401104508/https://gymbookapp.com/, Apr. 1, 2016, 10 pages.
Hamilton Jim, "Peloton Tips", Online available on:—<https://www.youtube.com/watch?app=desktop&v=OneXtB0kaD4>, Oct. 22, 2015, 3 pages.
Intention to Grant received for Danish Patent Application No. PA201570668, mailed on Mar. 27, 2017, 2 pages.
Intention to Grant received for Danish Patent Application No. PA201670656, mailed on Jan. 18, 2021, 2 pages.
Intention to Grant received for Danish Patent Application No. PA201870379, mailed on May 2, 2019, 2 pages.
Intention to Grant received for Danish Patent Application No. PA202070614, mailed on Aug. 8, 2022, 2 pages.
Intention to Grant received for Danish Patent Application No. PA202070615, mailed on Jan. 27, 2022, 2 pages.
Intention to Grant received for Danish Patent Application No. PA202070619, mailed on Jan. 17, 2022, 2 pages.
Intention to Grant received for European Patent Application No. 20182116.2, mailed on Jun. 2, 2022, 8 pages.
International Preliminary Report on Patentability received for PCT Patent Application No. PCT/US2016/037686, mailed on Mar. 1, 2018, 12 pages.
International Preliminary Report on Patentability received for PCT Patent Application No. PCT/US2020/035164, mailed on Dec. 16, 2021, 19 pages.
International Preliminary Report on Patentability received for PCT Patent Application No. PCT/US2020/035199, mailed on Dec. 16, 2021, 14 pages.
International Preliminary Report on Patentability received for PCT Patent Application No. PCT/US2013/073195, mailed on Jun. 16, 2016, 10 pages.
International Preliminary Report on Patentability received for PCT Patent Application No. PCT/US2015/032474, mailed on Dec. 15, 2016, 7 pages.
International Preliminary Report on Patentability received for PCT Patent Application No. PCT/US2015/047282, mailed on Mar. 16, 2017, 26 pages.
International Preliminary Report on Patentability received for PCT Patent Application No. PCT/US2017/035554, mailed on Dec. 20, 2018, 39 pages.
International Preliminary Report on Patentability received for PCT Patent Application No. PCT/US2018/023303, mailed on Dec. 12, 2019, 8 pages.
International Preliminary Report on Patentability received for PCT Patent Application No. PCT/US2018/031662, mailed on Nov. 28, 2019, 12 pages.
International Preliminary Report on Patentability received for PCT Patent Application No. PCT/US2019/014215, mailed on Aug. 6, 2020, 14 pages.
International Preliminary Report on Patentability received for PCT Patent Application No. PCT/US2019/024570, mailed on Nov. 19, 2020, 10 pages.
International Preliminary Report on Patentability received for PCT Patent Application No. PCT/US2020/025997, mailed on Nov. 18, 2021, 10 pages.
International Preliminary Report on Patentability received for PCT Patent Application No. PCT/US2021/017736, mailed on Aug. 25, 2022, 19 pages.
International Search Report and Written Opinion received for PCT Patent Application No. PCT/US2015/032474, mailed on Aug. 19, 2015, 8 pages.
International Search Report and Written Opinion received for PCT Patent Application No. PCT/US2015/047282, mailed on May 9, 2016, 33 pages.
International Search Report and Written Opinion received for PCT Patent Application No. PCT/US2016/037686, mailed on Sep. 9, 2016, 19 pages.
International Search Report and Written Opinion received for PCT Patent Application No. PCT/US2017/035554, mailed on Sep. 22, 2017, 42 pages.
International Search Report and Written Opinion received for PCT Patent Application No. PCT/US2018/023303, mailed on Jun. 19, 2018, 10 pages.
International Search Report and Written Opinion received for PCT Patent Application No. PCT/US2018/031662, mailed on Sep. 27, 2018, 17 pages.
International Search Report and Written Opinion received for PCT Patent Application No. PCT/US2019/014215, mailed on Jun. 4, 2019, 17 pages.
International Search Report and Written Opinion received for PCT Patent Application No. PCT/US2019/024570, mailed on Aug. 8, 2019, 18 pages.

(56) References Cited

OTHER PUBLICATIONS

International Search Report and written Opinion received for PCT Patent Application No. PCT/US2020/025997, mailed on Jul. 1, 2020, 16 pages.
International Search Report and Written Opinion received for PCT Patent Application No. PCT/US2020/025997, mailed on Jul. 14, 2020, 15 pages.
International Search Report and Written Opinion received for PCT Patent Application No. PCT/US2020/035164, mailed on Feb. 8, 2021, 26 pages.
International Search Report and Written Opinion received for PCT Patent Application No. PCT/US2020/035199, mailed on Oct. 30, 2020, 20 pages.
International Search Report and Written Opinion received for PCT Patent Application No. PCT/US2021/017736, mailed on Sep. 2, 2021, 25 pages.
International Search Report and Written Opinion received for PCT Patent Application No. PCT/US2021/035227, mailed on Oct. 6, 2021, 17 pages.
International Search Report and Written Opinion received for PCT Patent Application No. PCT/US2021/045375, mailed on Jan. 10, 2022, 21 pages.
International Search Report received for PCT Patent Application No. PCT/US2013/073195, mailed on Jun. 23, 2014, 3 pages.
International Written Opinion received for PCT Patent Application No. PCT/US2013/073195, mailed on Jun. 23, 2014, 8 pages.
Invitation to Pay Addition Fees and Partial International Search Report received for PCT Patent Application No. PCT/US2018/031662, mailed on Jul. 16, 2018, 13 pages.
Invitation to Pay Addition Fees and Partial International Search Report received for PCT Patent Application No. PCT/US2019/014215, mailed on Apr. 12, 2019, 13 pages.
Invitation to Pay Additional Fees and Partial International Search Report received for PCT Patent Application No. PCT/US2020/035164, mailed on Oct. 16, 2020, 14 pages.
Invitation to Pay Additional Fees received for PCT Patent Application No. PCT/US2015/047282, mailed on Dec. 22, 2015, 7 pages.
Invitation to Pay Additional Fees received for PCT Patent Application No. PCT/US2017/035554, mailed on Jul. 20, 2017, 2 pages.
Invitation to Pay Additional Fees received for PCT Patent Application No. PCT/US2020/035199, mailed on Sep. 8, 2020, 12 pages.
Invitation to Pay Additional Fees received for PCT Patent Application No. PCT/US2021/017736, mailed on Jun. 15, 2021, 14 pages.
Invitation to Pay Additional Fees received for PCT Patent Application No. PCT/US2021/045375, mailed on Nov. 16, 2021, 12 pages.
Jenbsjourney, "Wondering About a Fitbit?", Available at: https://jenbsjourney.blogspot.kr/2013/08/wondering-about-fitbit.html, Aug. 6, 2013, 12 pages.
Kamijo Noboru, "Next Generation Mobile System—WatchPad1.5", Available at <http://researcher.ibm.com/researcher/view_group_subpage.php?id=5617>, retrieved on Jul. 4, 2015, 2 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Minutes of the Oral Proceedings received for European Patent Application No. 15771747.1, mailed on Dec. 1, 2021, 4 pages.
Minutes of the Oral Proceedings received for European Patent Application No. 17810749.6, mailed on Jan. 26, 2021, 8 pages.
Minutes of the Oral Proceedings received for European Patent Application No. 18154145.9, mailed on Feb. 12, 2021, 8 pages.
Minutes of the Oral Proceedings received for European Patent Application No. 20182116.2, mailed on May 24, 2022, 7 pages.
Mugs, Online Available at: https://web.archive.org/web/20151029034349/http://le-mugs.com/, Oct. 29, 2015, 14 pages.
Multi-Set Bar Chart, The Data Visualization Catalogue, Available Online at: https://datavizcatalogue.com/methods/multiset_barchart.html, Feb. 8, 2014, 3 pages.
My CalStep, http://www.surprisesoftware.com/mycalstep/, retireved from the Wayback Machine, May 9, 2007, 2 pages.
Non-Final Office Action received for U.S. Appl. No. 14/839,916, mailed on Feb. 4, 2016, 19 pages.
Non-Final Office Action received for U.S. Appl. No. 14/839,922, mailed on Feb. 25, 2016, 20 pages.
Non-Final Office Action Received for U.S. Appl. No. 16/144,864, mailed on Dec. 18, 2018, 19 pages.
Non-Final Office Action received for U.S. Appl. No. 16/994,352, mailed on Jul. 30, 2021, 11 pages.
Non-Final Office Action received for U.S. Appl. No. 12/205,847, mailed on Oct. 3, 2011, 59 pages.
Non-Final Office Action received for U.S. Appl. No. 14/503,372, mailed on Dec. 5, 2014, 11 pages.
Non-Final Office Action received for U.S. Appl. No. 14/599,424, mailed on Jan. 17, 2018, 13 pages.
Non-Final Office Action received for U.S. Appl. No. 14/599,425, mailed on Jan. 11, 2018, 42 pages.
Non-Final Office Action received for U.S. Appl. No. 14/599,425, mailed on Mar. 17, 2015, 16 pages.
Non-Final Office Action received for U.S. Appl. No. 14/599,425, mailed on Oct. 26, 2016., 22 pages.
Non-Final Office Action received for U.S. Appl. No. 14/732,773, mailed on Feb. 8, 2019, 32 pages.
Non-Final Office Action received for U.S. Appl. No. 14/732,773, mailed on Jan. 19, 2018., 45 pages.
Non-Final Office Action received for U.S. Appl. No. 14/839,916, mailed on May 1, 2017, 18 pages.
Non-Final Office Action received for U.S. Appl. No. 14/839,922, mailed on Aug. 17, 2016, 25 pages.
Non-Final Office Action received for U.S. Appl. No. 15/183,663, mailed on Jul. 9, 2018, 13 pages.
Non-Final Office Action received for U.S. Appl. No. 15/600,243, mailed on Jun. 27, 2019, 17 Pages.
Non-Final Office Action received for U.S. Appl. No. 15/608,848, mailed on Feb. 6, 2020, 12 pages.
Non-Final Office Action received for U.S. Appl. No. 15/608,848, mailed on Feb. 12, 2021, 14 pages.
Non-Final Office Action received for U.S. Appl. No. 15/608,848, mailed on Nov. 2, 2018, 21 pages.
Non-Final Office Action received for U.S. Appl. No. 15/627,069, mailed on Jun. 21, 2019, 22 pages.
Non-Final Office Action received for U.S. Appl. No. 15/627,069, mailed on May 26, 2020, 25 pages.
Non-Final Office Action received for U.S. Appl. No. 15/705,849, mailed on Nov. 12, 2019, 15 pages.
Non-Final Office Action received for U.S. Appl. No. 15/925,652, mailed on Apr. 5, 2019, 28 pages.
Non-Final Office Action received for U.S. Appl. No. 15/925,652, mailed on Aug. 7, 2020, 39 pages.
Non-Final Office Action received for U.S. Appl. No. 15/978,126, mailed on Mar. 26, 2020, 16 pages.
Non-Final Office Action received for U.S. Appl. No. 16/138,809, mailed on Feb. 28, 2020, 22 pages.
Non-Final Office Action received for U.S. Appl. No. 16/144,735, mailed on Feb. 19, 2020, 10 pages.
Non-Final Office Action received for U.S. Appl. No. 16/144,753, mailed on Mar. 5, 2020, 9 pages.
Non-Final Office Action received for U.S. Appl. No. 16/144,849, mailed on Dec. 31, 2018, 28 pages.
Non-Final Office Action received for U.S. Appl. No. 16/144,849, mailed on Sep. 17, 2019, 9 pages.
Non-Final Office Action received for U.S. Appl. No. 16/144,864, mailed on Jan. 31, 2020, 29 pages.
Non-Final Office Action received for U.S. Appl. No. 16/249,627, mailed on Aug. 22, 2022, 21 pages.
Non-Final Office Action received for U.S. Appl. No. 16/249,627, mailed on Aug. 31, 2021, 18 pages.
Non-Final Office Action received for U.S. Appl. No. 16/249,627, mailed on Mar. 11, 2021, 21 pages.
Non-Final Office Action received for U.S. Appl. No. 16/377,892, mailed on May 21, 2020, 9 pages.

(56) References Cited

OTHER PUBLICATIONS

Non-Final Office Action received for U.S. Appl. No. 16/378,136, mailed on Jun. 2, 2020, 8 pages.
Non-Final Office Action received for U.S. Appl. No. 16/418,786, mailed on Apr. 24, 2020, 16 pages.
Non-Final Office Action received for U.S. Appl. No. 16/418,786, mailed on Aug. 1, 2022, 18 pages.
Non-Final Office Action received for U.S. Appl. No. 16/418,786, mailed on Mar. 28, 2022, 14 pages.
Non-Final Office Action received for U.S. Appl. No. 16/418,786, mailed on Oct. 4, 2021, 10 pages.
Non-Final Office Action received for U.S. Appl. No. 16/820,383, mailed on Dec. 14, 2020, 11 pages.
Non-Final Office Action received for U.S. Appl. No. 16/820,383, mailed on Jan. 10, 2022, 18 pages.
Non-Final Office Action received for U.S. Appl. No. 16/880,714, mailed on Oct. 28, 2020, 11 pages.
Non-Final Office Action received for U.S. Appl. No. 16/888,629, mailed on Mar. 31, 2021, 14 pages.
Non-Final Office Action received for U.S. Appl. No. 16/894,309, mailed on Oct. 15, 2020, 24 pages.
Non-Final Office Action received for U.S. Appl. No. 16/987,275, mailed on Nov. 23, 2021, 17 pages.
Non-Final Office Action received for U.S. Appl. No. 17/030,318, mailed on Apr. 2, 2021, 28 pages.
Non-Final Office Action received for U.S. Appl. No. 17/030,318, mailed on Dec. 3, 2020, 22 pages.
Non-Final Office Action received for U.S. Appl. No. 17/030,318, mailed on Jun. 14, 2022, 9 pages.
Non-Final Office Action received for U.S. Appl. No. 17/030,321, mailed on Dec. 15, 2020, 25 pages.
Non-Final Office Action received for U.S. Appl. No. 17/030,321, mailed on Oct. 18, 2021, 28 pages.
Non-Final Office Action received for U.S. Appl. No. 17/030,337, mailed on Jun. 14, 2022, 13 pages.
Non-Final Office Action received for U.S. Appl. No. 17/030,340, mailed on Jun. 14, 2022, 15 pages.
Non-Final Office Action received for U.S. Appl. No. 17/031,543, mailed on Apr. 1, 2022, 9 pages.
Non-Final Office Action received for U.S. Appl. No. 17/031,704, mailed on Dec. 10, 2020, 30 pages.
Non-Final Office Action received for U.S. Appl. No. 17/031,717, mailed on Nov. 19, 2020, 22 pages.
Non-Final Office Action received for U.S. Appl. No. 17/031,717, mailed on Sep. 14, 2021, 35 pages.
Non-Final Office Action received for U.S. Appl. No. 17/031,723, mailed on Jan. 24, 2022, 17 pages.
Non-Final Office Action received for U.S. Appl. No. 17/031,779, mailed on Feb. 16, 2022, 17 pages.
Non-Final Office Action received for U.S. Appl. No. 17/031,854, mailed on Dec. 27, 2021, 13 pages.
Non-Final Office Action received for U.S. Appl. No. 17/031,859, mailed on Dec. 15, 2020, 13 pages.
Non-Final Office Action received for U.S. Appl. No. 17/031,859, mailed on Dec. 24, 2021, 16 pages.
Non-Final Office Action received for U.S. Appl. No. 17/031,874, mailed on Dec. 28, 2020, 14 pages.
Non-Final Office Action received for U.S. Appl. No. 17/031,874, mailed on Jan. 24, 2022, 18 pages.
Non-Final Office Action received for U.S. Appl. No. 17/041,415, mailed on Mar. 29, 2022, 11 pages.
Non-Final Office Action received for U.S. Appl. No. 17/157,728, mailed on Nov. 26, 2021, 18 pages.
Non-Final Office Action received for U.S. Appl. No. 17/192,161, mailed on May 13, 2021, 28 pages.
Non-Final Office Action received for U.S. Appl. No. 17/381,570, mailed on Apr. 1, 2022, 29 pages.
Non-Final Office Action received for U.S. Appl. No. 17/516,537, mailed on May 5, 2022, 8 pages.
Non-Final Office Action received for U.S. Appl. No. 17/591,184, mailed on Aug. 4, 2022, 18 pages.
Notice of Acceptance received for Australian Patent Application No. 2015267240, mailed on Apr. 10, 2018, 3 pages.
Notice of Acceptance received for Australian Patent Application No. 2015312215, mailed on Oct. 9, 2017, 3 pages.
Notice of Acceptance received for Australian Patent Application No. 2017277971, mailed on Feb. 17, 2021, 3 pages.
Notice of Acceptance received for Australian Patent Application No. 2018268972, mailed on Dec. 18, 2020, 3 pages.
Notice of Acceptance received for Australian Patent Application No. 2019201583, mailed on Jul. 15, 2019, 3 pages.
Notice of Acceptance received for Australian Patent Application No. 2019210192, mailed on Dec. 2, 2021, 3 pages.
Notice of Acceptance received for Australian Patent Application No. 2019222943, mailed on May 5, 2020, 3 pages.
Notice of Acceptance received for Australian Patent Application No. 2019250251, mailed on Feb. 18, 2021, 3 pages.
Notice of Acceptance received for Australian Patent Application No. 2020204153, mailed on Jul. 6, 2020, 3 pages.
Notice of Acceptance received for Australian Patent Application No. 2020239692, mailed on Apr. 6, 2022, 3 pages.
Notice of Acceptance received for Australian Patent Application No. 2020239740, mailed on Feb. 22, 2022, 3 pages.
Notice of Acceptance received for Australian Patent Application No. 2020239743, mailed on Jan. 13, 2022, 3 pages.
Notice of Acceptance received for Australian Patent Application No. 2020239752, mailed on Jan. 31, 2022, 3 pages.
Notice of Acceptance received for Australian Patent Application No. 2020256383, mailed on Aug. 3, 2021, 3 pages.
Notice of Acceptance received for Australian Patent Application No. 2021200787, mailed on Mar. 19, 2021, 3 pages.
Notice of Acceptance received for Australian Patent Application No. 2021201130, mailed on Mar. 28, 2022, 3 pages.
Notice of Acceptance received for Australian Patent Application No. 2021203636, mailed on Apr. 14, 2022, 3 pages.
Notice of Acceptance received for Australian Patent Application No. 2021204422, mailed on Aug. 15, 2022, 3 pages.
Notice of Allowance received for Australian Patent Application No. 2020239748, mailed on Mar. 7, 2022, 3 pages.
Notice of Allowance received for Chinese Patent Application No. 201380081349.6, mailed on Dec. 17, 2021, 2 pages.
Notice of Allowance received for Chinese Patent Application No. 201520358505.5, issued on Jan. 13, 2016, 3 pages.
Notice of Allowance received for Chinese Patent Application No. 201580028677.9, mailed on Apr. 2, 2019, 2 pages.
Notice of Allowance received for Chinese Patent Application No. 201580037927.5, mailed on Oct. 17, 2019, 3 pages.
Notice of Allowance received for Chinese Patent Application No. 201680047983.1, mailed on Apr. 28, 2021, 3 pages.
Notice of Allowance received for Chinese Patent Application No. 201710439448.7, mailed on Jan. 26, 2021, 2 pages.
Notice of Allowance received for Chinese Patent Application No. 201780034203.4, mailed on Jan. 17, 2022, 2 pages.
Notice of Allowance received for Chinese Patent Application No. 201810105846.X, mailed on Feb. 18, 2020, 2 pages.
Notice of Allowance received for Chinese Patent Application No. 202010606407.4, mailed on Jan. 24, 2022, 2 pages.
Notice of Allowance received for Danish Patent Application No. PA201570666, mailed on Sep. 15, 2016, 1 page.
Notice of Allowance received for Danish Patent Application No. PA201570668, mailed on Oct. 30, 2017, 2 pages.
Notice of Allowance received for Japanese Patent Application No. 2016-535045, mailed on Mar. 2, 2018, 4 pages.
Notice of Allowance received for Japanese Patent Application No. 2016-557650, mailed on Apr. 9, 2019, 4 pages.
Notice of Allowance received for Japanese Patent Application No. 2018-014096, mailed on Jan. 5, 2021, 3 pages.
Notice of Allowance received for Japanese Patent Application No. 2018-068846, mailed on Dec. 9, 2019, 4 pages.
Notice of Allowance received for Japanese Patent Application No. 2018-184532, mailed on Jan. 17, 2022, 4 pages.

(56) References Cited

OTHER PUBLICATIONS

Notice of Allowance received for Japanese Patent Application No. 2019-044107, mailed on Jul. 11, 2022, 31 pages.
Notice of Allowance received for Japanese Patent Application No. 2019-162293, mailed on Apr. 9, 2021, 4 pages.
Notice of Allowance received for Japanese Patent Application No. 2019-563407, mailed on Aug. 20, 2021, 4 pages.
Notice of Allowance received for Japanese Patent Application No. 2020-000492, mailed on Jul. 16, 2021, 4 pages.
Notice of Allowance received for Japanese Patent Application No. 2020-104679, mailed on Jan. 4, 2021, 4 pages.
Notice of Allowance received for Japanese Patent Application No. 2020-115940, mailed on Oct. 22, 2021, 4 pages.
Notice of Allowance received for Japanese Patent Application No. 2020-160023, mailed on Apr. 11, 2022, 4 pages.
Notice of Allowance received for Japanese Patent Application No. 2020-160052, mailed on Jun. 3, 2022, 4 pages.
Notice of Allowance received for Japanese Patent Application No. 2020-160054, mailed on Apr. 4, 2022, 4 pages.
Notice of Allowance received for Japanese Patent Application No. 2020-551585, mailed on Jul. 22, 2022, 4 pages.
Notice of Allowance received for Japanese Patent Application No. 2020-560883, mailed on Oct. 29, 2021, 4 pages.
Notice of Allowance received for Korean Patent Application No. 10-2016-7014577, mailed on May 30, 2019, 5 pages.
Notice of Allowance received for Korean Patent Application No. 10-2016-7033638, issued on May 31, 2017, 5 pages.
Notice of Allowance received for Korean Patent Application No. 10-2019-7025538, mailed on Mar. 10, 2021, 5 pages.
Notice of Allowance received for Korean Patent Application No. 10-2019-7025781, mailed on Jun. 29, 2021, 5 pages.
Notice of Allowance received for Korean Patent Application No. 10-2019-7033834, mailed on Jul. 3, 2021, 4 pages.
Notice of Allowance received for Korean Patent Application No. 10-2020-7023277, mailed on Jul. 18, 2022, 5 pages.
Notice of Allowance received for Korean Patent Application No. 10-2020-7026035, mailed on Aug. 23, 2021, 4 pages.
Notice of Allowance received for Korean Patent Application No. 10-2021-7026284, mailed on Jul. 28, 2022, 6 pages.
Notice of Allowance received for Korean Patent Application No. 10-2021-7031939, mailed on Apr. 5, 2022, 4 pages.
Notice of Allowance received for Korean Patent Application No. 10-2021-7038005, mailed on Dec. 14, 2021, 4 pages.
Notice of Allowance received for Korean Patent Application No. 10-2022-7008569, mailed on May 19, 2022, 5 pages.
Notice of Allowance received for Korean Patent Application No. 10-2022-7017918, mailed on Jun. 13, 2022, 6 pages.
Notice of Allowance received for Taiwanese Patent Application No. 104117509, mailed on Mar. 31, 2017, 3 pages.
Notice of Allowance received for Taiwanese Patent Application No. 104128685, mailed on May 3, 2017, 3 pages.
Notice of Allowance received for U.S. Appl. No. 12/205,847, mailed on Aug. 20, 2012, 13 pages.
Notice of Allowance received for U.S. Appl. No. 14/599,424, mailed on Dec. 13, 2018, 6 pages.
Notice of Allowance received for U.S. Appl. No. 14/599,425, mailed on Dec. 19, 2018, 9 pages.
Notice of Allowance received for U.S. Appl. No. 14/732,773, mailed on Dec. 18, 2019, 21 pages.
Notice of Allowance received for U.S. Appl. No. 14/839,916, mailed on Aug. 31, 2016, 11 pages.
Notice of Allowance received for U.S. Appl. No. 14/839,916, mailed on Jan. 10, 2018, 19 pages.
Notice of Allowance received for U.S. Appl. No. 14/839,922, mailed on Jan. 26, 2018, 2 pages.
Notice of Allowance received for U.S. Appl. No. 14/839,922, mailed on Jul. 6, 2017, 8 pages.
Notice of Allowance received for U.S. Appl. No. 14/839,922, mailed on Nov. 2, 2017, 8 pages.
Notice of Allowance received for U.S. Appl. No. 15/183,663, mailed on Jan. 17, 2019, 6 pages.
Notice of Allowance received for U.S. Appl. No. 15/600,243, mailed on Dec. 12, 2019, 7 pages.
Notice of Allowance received for U.S. Appl. No. 15/608,848, mailed on Aug. 25, 2021, 9 pages.
Notice of Allowance received for U.S. Appl. No. 15/608,848, mailed on Oct. 29, 2021, 7 pages.
Notice of Allowance received for U.S. Appl. No. 15/616,480, mailed on Jan. 3, 2019, 8 pages.
Notice of Allowance received for U.S. Appl. No. 15/627,069, mailed on Jun. 17, 2021, 14 pages.
Notice of Allowance received for U.S. Appl. No. 15/705,849, mailed on July 28, 2020, 10 pages.
Notice of Allowance received for U.S. Appl. No. 15/705,849, mailed on Oct. 16, 2020, 14 pages.
Notice of Allowance received for U.S. Appl. No. 15/925,652, mailed on Mar. 9, 2021, 9 pages.
Notice of Allowance received for U.S. Appl. No. 15/925,652, mailed on Nov. 20, 2020, 9 pages.
Notice of Allowance received for U.S. Appl. No. 15/978,126, mailed on Feb. 4, 2021, 10 pages.
Notice of Allowance received for U.S. Appl. No. 16/138,809, mailed on Apr. 16, 2021, 11 pages.
Notice of Allowance received for U.S. Appl. No. 16/138,809, mailed on Jul. 20, 2021, 6 pages.
Notice of Allowance received for U.S. Appl. No. 16/144,671, mailed on Feb. 10, 2020, 17 pages.
Notice of Allowance received for U.S. Appl. No. 16/144,735, mailed on Jul. 21, 2020, 13 pages.
Notice of Allowance received for U.S. Appl. No. 16/144,735, mailed on Oct. 28, 2020, 13 pages.
Notice of Allowance received for U.S. Appl. No. 16/144,753, mailed on Dec. 4, 2020, 22 pages.
Notice of Allowance received for U.S. Appl. No. 16/144,753, mailed on Feb. 10, 2021, 8 pages.
Notice of Allowance received for U.S. Appl. No. 16/144,849, mailed on Apr. 17, 2020, 2 pages.
Notice of Allowance received for U.S. Appl. No. 16/144,849, mailed on Mar. 6, 2020, 9 pages.
Notice of Allowance received for U.S. Appl. No. 16/144,864, mailed on Feb. 9, 2021, 13 pages.
Notice of Allowance received for U.S. Appl. No. 16/144,864, mailed on Jul. 28, 2020, 27 pages.
Notice of Allowance received for U.S. Appl. No. 16/144,864, mailed on Mar. 12, 2021, 2 pages.
Notice of Allowance received for U.S. Appl. No. 16/144,864, mailed on Mar. 30, 2021, 2 pages.
Notice of Allowance received for U.S. Appl. No. 16/144,864, mailed on Sep. 10, 2020, 3 pages.
Notice of Allowance received for U.S. Appl. No. 16/144,864, mailed on Sep. 16, 2020, 2 pages.
Notice of Allowance received for U.S. Appl. No. 16/144,864, mailed on Sep. 29, 2020, 2 pages.
Notice of Allowance received for U.S. Appl. No. 16/377,892, mailed on May 24, 2021, 9 pages.
Notice of Allowance received for U.S. Appl. No. 16/377,892, mailed on Sep. 9, 2021, 9 pages.
Notice of Allowance received for U.S. Appl. No. 16/378,136, mailed on Jun. 3, 2021, 7 pages.
Notice of Allowance received for U.S. Appl. No. 16/378,136, mailed on Sep. 22, 2021, 7 pages.
Notice of Allowance received for U.S. Appl. No. 16/418,786, mailed on Dec. 9, 2021, 9 pages.
Notice of Allowance received for U.S. Appl. No. 16/418,786, mailed on Jun. 14, 2022, 9 pages.
Notice of Allowance received for U.S. Appl. No. 16/556,023, mailed on Jan. 13, 2021, 8 pages.
Notice of Allowance received for U.S. Appl. No. 16/556,023, mailed on Oct. 15, 2020, 8 pages.
Notice of Allowance received for U.S. Appl. No. 16/588,950, mailed on Feb. 10, 2020, 9 pages.

(56) References Cited

OTHER PUBLICATIONS

Notice of Allowance received for U.S. Appl. No. 16/588,950, mailed on May 5, 2020, 9 pages.
Notice of Allowance received for U.S. Appl. No. 16/820,383, mailed on Jul. 21, 2021, 11 pages.
Notice of Allowance received for U.S. Appl. No. 16/820,383, mailed on Mar. 31, 2021, 11 pages.
Notice of Allowance received for U.S. Appl. No. 16/880,714, mailed on Jun. 9, 2021, 6 pages.
Notice of Allowance received for U.S. Appl. No. 16/880,714, mailed on Mar. 19, 2021, 7 pages.
Notice of Allowance received for U.S. Appl. No. 16/888,629, mailed on Nov. 9, 2021, 11 pages.
Notice of Allowance received for U.S. Appl. No. 16/894,309, mailed on Feb. 25, 2022, 9 pages.
Notice of Allowance received for U.S. Appl. No. 16/894,309, mailed on Nov. 5, 2021, 12 pages.
Notice of Allowance received for U.S. Appl. No. 16/987,275, mailed on Jul. 27, 2022, 6 pages.
Notice of Allowance received for U.S. Appl. No. 16/987,275, mailed on May 16, 2022, 7 pages.
Notice of Allowance received for U.S. Appl. No. 16/994,352, mailed on Jun. 3, 2022, 9 pages.
Notice of Allowance received for U.S. Appl. No. 16/994,352, mailed on Mar. 2, 2022, 14 pages.
Notice of Allowance received for U.S. Appl. No. 17/030,318, mailed on Jan. 5, 2022, 8 pages.
Notice of Allowance received for U.S. Appl. No. 17/030,321, mailed on Apr. 1, 2022, 8 pages.
Notice of Allowance received for U.S. Appl. No. 17/030,337, mailed on Aug. 22, 2022, 10 pages.
Notice of Allowance received for U.S. Appl. No. 17/031,543, mailed on May 11, 2022, 6 pages.
Notice of Allowance received for U.S. Appl. No. 17/031,704, mailed on Jul. 21, 2021, 10 pages.
Notice of Allowance received for U.S. Appl. No. 17/031,717, mailed on Jul. 7, 2022, 12 pages.
Notice of Allowance received for U.S. Appl. No. 17/031,717, mailed on Mar. 16, 2022, 12 pages.
Notice of Allowance received for U.S. Appl. No. 17/031,727, mailed on Dec. 24, 2020, 12 pages.
Notice of Allowance received for U.S. Appl. No. 17/031,727, mailed on Jun. 25, 2021, 6 pages.
Notice of Allowance received for U.S. Appl. No. 17/031,727, mailed on Mar. 12, 2021, 7 pages.
Notice of Allowance received for U.S. Appl. No. 17/041,415, mailed on Aug. 31, 2022, 7 pages.
Notice of Allowance received for U.S. Appl. No. 17/157,728, mailed on Feb. 24, 2022, 7 pages.
Notice of Allowance received for U.S. Appl. No. 17/192,161, mailed on Feb. 16, 2022, 8 pages.
Notice of Allowance received for U.S. Appl. No. 17/192,161, mailed on May 27, 2022, 8 pages.
Notice of Allowance received for U.S. Appl. No. 17/197,628, mailed on Jun. 24, 2022, 8 pages.
Notice of Allowance received for U.S. Appl. No. 17/197,628, mailed on Mar. 23, 2022, 35 pages.
Notice of Allowance received for U.S. Appl. No. 17/317,084, mailed on Aug. 29, 2022, 10 pages.
Office Action received for Japanese Patent Application No. 2016-569945, mailed on Nov. 10, 2017, 8 pages.
Office Action received for Australian Patent Application No. 2015100734, issued on Jul. 29, 2015, 5 pages.
Office Action received for Australian Patent Application No. 2015267240, mailed on Apr. 10, 2017, 5 pages.
Office Action received for Australian Patent Application No. 2015267240, mailed on Mar. 21, 2018, 5 pages.
Office Action received for Australian Patent Application No. 2015312215, mailed on Oct. 13, 2016, 3 pages.
Office Action received for Australian Patent Application No. 2017100667, mailed on Aug. 3, 2017, 9 pages.
Office Action received for Australian Patent Application No. 2017277971, mailed on Aug. 12, 2020, 3 pages.
Office Action received for Australian Patent Application No. 2017277971, mailed on Jun. 3, 2020, 3 pages.
Office Action received for Australian Patent Application No. 2018100158, mailed on Apr. 23, 2018, 5 pages.
Office Action received for Australian Patent Application No. 2018101855, mailed on Feb. 22, 2019, 4 pages.
Office Action received for Australian Patent Application No. 2018200428, mailed on Mar. 7, 2018, 4 pages.
Office Action received for Australian Patent Application No. 2018200428, mailed on Nov. 15, 2018, 4 pages.
Office Action received for Australian Patent Application No. 2018206772, mailed on Apr. 1, 2019, 4 pages.
Office Action received for Australian Patent Application No. 2018206772, mailed on Nov. 6, 2019, 4 pages.
Office Action received for Australian Patent Application No. 2018268972, mailed on Jul. 9, 2020, 4 pages.
Office Action received for Australian Patent Application No. 2019100495, mailed on Mar. 6, 2020, 3 pages.
Office Action received for Australian Patent Application No. 2019100495, mailed on Mar. 16, 2020, 3 pages.
Office Action received for Australian Patent Application No. 2019100495, mailed on Sep. 17, 2019, 7 pages.
Office Action received for Australian Patent Application No. 2019210192, mailed on May 25, 2021, 4 pages.
Office Action received for Australian Patent Application No. 2019210192, mailed on Sep. 9, 2021, 4 pages.
Office Action received for Australian Patent Application No. 2019222943, mailed on Oct. 3, 2019, 3 pages.
Office Action received for Australian Patent Application No. 2019250251, mailed on Aug. 6, 2020, 3 pages.
Office Action received for Australian Patent Application No. 2020239692, mailed on Jan. 27, 2022, 3 pages.
Office Action received for Australian Patent Application No. 2020239692, mailed on Jul. 20, 2021, 5 pages.
Office Action received for Australian Patent Application No. 2020239740, mailed on Jul. 9, 2021, 4 pages.
Office Action received for Australian Patent Application No. 2020239740, mailed on Sep. 28, 2021, 5 pages.
Office Action received for Australian Patent Application No. 2020239743, mailed on Mar. 25, 2021, 8 pages.
Office Action received for Australian Patent Application No. 2020239743, mailed on Sep. 3, 2021, 4 pages.
Office Action received for Australian Patent Application No. 2020239748, mailed on Apr. 21, 2021, 6 pages.
Office Action received for Australian Patent Application No. 2020239748, mailed on Feb. 11, 2022, 2 pages.
Office Action received for Australian Patent Application No. 2020239748, mailed on Sep. 1, 2021, 4 pages.
Office Action received for Australian Patent Application No. 2020239752, mailed on Jun. 4, 2021, 8 pages.
Office Action received for Australian Patent Application No. 2020239752, mailed on Oct. 25, 2021, 5 pages.
Office Action received for Australian Patent Application No. 2020256383, mailed on Jun. 4, 2021, 3 pages.
Office Action received for Australian Patent Application No. 2021201130, mailed on Jan. 27, 2022, 2 pages.
Office Action received for Australian Patent Application No. 2021203636, mailed on Mar. 23, 2022, 3 pages.
Office Action received for Australian Patent Application No. 2021204422, mailed on May 31, 2022, 2 pages.
Office Action received for Chinese Patent Application No. 201380081349.6, mailed on Feb. 26, 2019, 12 pages.
Office Action received for Chinese Patent Application No. 201380081349.6, mailed on Jan. 5, 2021, 16 pages.
Office Action received for Chinese Patent Application No. 201380081349.6, mailed on Jan. 16, 2020, 11 pages.
Office Action received for Chinese Patent Application No. 201380081349.6, mailed on Jul. 15, 2019, 10 pages.

(56) References Cited

OTHER PUBLICATIONS

Office Action received for Chinese Patent Application No. 201380081349.6, mailed on Jul. 15, 2020, 9 pages.
Office Action received for Chinese Patent Application No. 201380081349.6, mailed on Jun. 2, 2021, 17 pages.
Office Action received for Chinese Patent Application No. 201510284850.3, mailed on Jul. 9, 2018, 11 pages.
Office Action received for Chinese Patent Application No. 201510284850.3, mailed on Jun. 21, 2019, 10 pages.
Office Action received for Chinese Patent Application No. 201510284850.3, mailed on Nov. 28, 2017, 15 pages.
Office Action received for Chinese Patent Application No. 201580028677.9, mailed on May 25, 2018, 14 pages.
Office Action received for Chinese Patent Application No. 201580037927.5, mailed on Apr. 22, 2019, 9 pages.
Office Action received for Chinese Patent Application No. 201580037927.5, mailed on Jul. 20, 2018, 21 pages.
Office Action received for Chinese Patent Application No. 201680047983.1, mailed on Feb. 1, 2021, 6 pages.
Office Action received for Chinese Patent Application No. 201680047983.1, mailed on Jul. 1, 2020, 6 pages.
Office Action received for Chinese Patent Application No. 201680047983.1, mailed on Mar. 18, 2019, 18 pages.
Office Action received for Chinese Patent Application No. 201680047983.1, mailed on Nov. 28, 2019, 9 pages.
Office Action received for Chinese Patent Application No. 201710439448.7, mailed on Mar. 27, 2020, 13 pages.
Office Action received for Chinese Patent Application No. 201710439448.7, mailed on Oct. 10, 2020, 19 pages.
Office Action received for Chinese Patent Application No. 201780034203.4, mailed on Jul. 14, 2021, 12 pages.
Office Action received for Chinese Patent Application No. 201780034203.4, mailed on Sep. 24, 2021, 7 pages.
Office Action received for Chinese Patent Application No. 201810105846.X, mailed on Aug. 27, 2019, 12 pages.
Office Action received for Chinese Patent Application No. 201810105846.X, mailed on Feb. 25, 2019, 10 pages.
Office Action received for Chinese Patent Application No. 201810105846.X, mailed on Nov. 28, 2019, 9 pages.
Office Action received for Chinese Patent Application No. 201910858933.7, mailed on Aug. 18, 2020, 14 pages.
Office Action received for Chinese Patent Application No. 201910858933.7, mailed on Dec. 30, 2021, 9 pages.
Office Action received for Chinese Patent Application No. 201910858933.7, mailed on Jun. 29, 2021, 8 pages.
Office Action received for Chinese Patent Application No. 201911401161.0, mailed on Jan. 24, 2022, 6 pages.
Office Action received for Chinese Patent Application No. 202010606407.4, mailed on Jan. 27, 2021, 16 pages.
Office Action received for Chinese Patent Application No. 202010606407.4, mailed on Jun. 2, 2021, 12 pages.
Office Action received for Chinese Patent Application No. 202010606407.4, mailed on Nov. 18, 2021, 6 pages.
Office Action received for Chinese Patent Application No. 202110363565.6, mailed on May 7, 2022, 12 pages.
Office Action received for Chinese Patent Application No. 202110363565.6, mailed on Nov. 16, 2021, 16 pages.
Office Action received for Chinese Patent Application No. 202110783860.7, mailed on Mar. 10, 2022, 15 pages.
Office Action received for Chinese Patent Application No. 202111611270.2, mailed on May 10, 2022, 16 pages.
Office Action Received for Danish Patent Application No. PA201670656, mailed on Nov. 3, 2016, 8 pages.
Office Action received for Danish Patent Application No. PA 2020 70612, mailed on Mar. 1, 2022, 2 pages.
Office Action received for Danish Patent Application No. PA201570666, mailed on Feb. 2, 2016, 9 pages.
Office Action received for Danish Patent Application No. PA201570666, mailed on Jun. 27, 2016, 4 pages.
Office Action received for Danish Patent Application No. PA201570668, mailed on Apr. 8, 2016, 8 pages.
Office Action received for Danish Patent Application No. PA201570668, mailed on Sep. 9, 2016, 3 pages.
Office Action Received for Danish Patent Application No. PA201670656, mailed on Jul. 1, 2020, 4 pages.
Office Action received for Danish Patent Application No. PA201670656, mailed on Jun. 14, 2017, 3 pages.
Office Action Received for Danish Patent Application No. PA201670656, mailed on May 2, 2019, 4 pages.
Office Action Received for Danish Patent Application No. PA201670656, mailed on May 30, 2018, 5 pages.
Office Action received for Danish Patent Application No. PA201770191, mailed on Jan. 25, 2018, 3 pages.
Office Action received for Danish Patent Application No. PA201770191, mailed on Nov. 21, 2018, 4 pages.
Office Action received for Danish Patent Application No. PA201770191, mailed on Oct. 25, 2019, 4 pages.
Office Action received for Danish Patent Application No. PA201770423, mailed on Jun. 12, 2018, 7 pages.
Office Action received for Danish Patent Application No. PA201770423, mailed on Mar. 29, 2019, 6 pages.
Office Action received for Danish Patent Application No. PA201870378, mailed on Feb. 25, 2019, 3 pages.
Office Action received for Danish Patent Application No. PA201870378, mailed on Jan. 6, 2020, 3 pages.
Office Action received for Danish Patent Application No. PA201870379, mailed on Feb. 28, 2019, 3 pages.
Office Action received for Danish Patent Application No. PA201870380, mailed on Mar. 5, 2020, 2 pages.
Office Action received for Danish Patent Application No. PA201870380, mailed on Mar. 27, 2019, 4 pages.
Office Action received for Danish Patent Application No. PA201870380, mailed on Sep. 11, 2018, 9 pages.
Office Action received for Danish Patent Application No. PA201970532, mailed on May 29, 2020, 3 pages.
Office Action received for Danish Patent Application No. PA202070612, mailed on May 10, 2022, 2 pages.
Office Action received for Danish Patent Application No. PA202070613, mailed on May 10, 2022, 2 pages.
Office Action received for Danish Patent Application No. PA202070613, mailed on Sep. 30, 2021, 4 pages.
Office Action received for Danish Patent Application No. PA202070614, mailed on Apr. 28, 2022, 4 pages.
Office Action received for Danish Patent Application No. PA202070614, mailed on Sep. 28, 2021, 4 pages.
Office Action received for Danish Patent Application No. PA202070615, mailed on Nov. 16, 2021, 4 pages.
Office Action received for Danish Patent Application No. PA202070616, mailed on Jan. 27, 2022, 2 pages.
Office Action received for Danish Patent Application No. PA202070616, mailed on May 5, 2022, 3 pages.
Office Action received for Danish Patent Application No. PA202070619, mailed on Aug. 27, 2021, 12 pages.
Office Action received for Danish Patent Application No. PA202070619, mailed on Oct. 14, 2021, 3 pages.
Office Action received for Danish Patent Application No. PA202070620, mailed on May 10, 2021, 5 pages.
Office Action received for Danish Patent Application No. PA202070620, mailed on Nov. 19, 2021, 2 pages.
Office Action received for Danish Patent Application No. PA202070815, mailed on Jun. 14, 2022, 3 pages.
Office Action received for Danish Patent Application No. PA202070815, mailed on Oct. 18, 2021, 2 pages.
Office Action received for Danish Patent Application No. PA202170113, mailed on Apr. 15, 2021, 2 pages.
Office Action received for Danish Patent Application No. PA202170113, mailed on Aug. 18, 2022, 2 pages.
Office Action received for Danish Patent Application No. PA202170113, mailed on May 3, 2022, 2 pages.
Office Action received for European Patent Application No. 13811085.3, mailed on Apr. 20, 2018, 15 pages.

(56) References Cited

OTHER PUBLICATIONS

Office Action received for European Patent Application No. 15730890.9, mailed on Aug. 3, 2017, 4 pages.
Office Action received for European Patent Application No. 16837432.0, mailed on Jan. 10, 2020, 7 pages.
Office Action received for European Patent Application No. 16837432.0, mailed on Jan. 27, 2021, 7 pages.
Office Action received for European Patent Application No. 17810749.6, mailed on Aug. 20, 2019, 9 pages.
Office Action received for European Patent Application No. 18154145.9, mailed on Apr. 3, 2018, 6 pages.
Office Action received for European Patent Application No. 18727543.3, mailed on Mar. 26, 2021, 7 pages.
Office Action received for European Patent Application No. 19721883.7, mailed on Jan. 10, 2020, 4 pages.
Office Action received for European Patent Application No. 19721883.7, mailed on Jun. 15, 2021, 9 pages.
Office Action received for European Patent Application No. 19721883.7, mailed on May 28, 2020, 11 pages.
Office Action received for European Patent Application No. 20182116.2, mailed on May 25, 2021, 9 pages.
Office Action received for European Patent Application No. 20182116.2, mailed on Nov. 6, 2020, 9 pages.
Office Action received for European Patent Application No. 20203526.7, mailed on Nov. 23, 2021, 9 pages.
Office Action received for European Patent Application No. 20721342.2, mailed on Nov. 4, 2021, 9 pages.
Office Action received for European Patent Application No. 21165295.3, mailed on Jul. 1, 2021, 10 pages.
Office Action received for European Patent Application No. 21168916.1, mailed on Aug. 23, 2021, 8 pages.
Office Action received for European Patent Application No. 15771747.1, mailed on Oct. 31, 2017, 7 pages.
Office Action received for German Patent Application No. 112015002326.7, mailed on Feb. 20, 2019, 7 pages.
Office Action received for Indian Patent Application No. 202014041484, mailed on Dec. 8, 2021, 8 pages.
Office Action received for Indian Patent Application No. 202014041563, mailed on Dec. 30, 2021, 6 pages.
Office Action received for Indian Patent Application No. 202014041571, mailed on Dec. 17, 2021, 5 pages.
Office Action received for Japanese Patent Application No. 2016-535045, mailed on May 12, 2017, 10 pages.
Office Action received for Japanese Patent Application No. 2016-557650, mailed on Apr. 13, 2018, 9 pages.
Office Action received for Japanese Patent Application No. 2016-557650, mailed on Aug. 10, 2017, 10 pages.
Office Action received for Japanese Patent Application No. 2016-557650, mailed on Nov. 9, 2018, 6 pages.
Office Action received for Japanese Patent Application No. 2016-569945, mailed on Jul. 29, 2019, 6 pages.
Office Action received for Japanese Patent Application No. 2016-569945, mailed on Sep. 10, 2018, 11 pages.
Office Action received for Japanese Patent Application No. 2018-014096, mailed on Aug. 28, 2020, 4 pages.
Office Action received for Japanese Patent Application No. 2018-014096, mailed on Jan. 6, 2020, 17 pages.
Office Action received for Japanese Patent Application No. 2018-014096, mailed on Jun. 29, 2018, 20 pages.
Office Action received for Japanese Patent Application No. 2018-014096, mailed on May 8, 2019, 14 pages.
Office Action received for Japanese Patent Application No. 2018-014096, mailed on Nov. 6, 2018, 15 pages.
Office Action received for Japanese Patent Application No. 2018-068846, mailed on Jan. 8, 2019, 6 pages.
Office Action received for Japanese Patent Application No. 2018-184532, mailed on Mar. 1, 2021, 11 pages.
Office Action received for Japanese Patent Application No. 2019-044107, mailed on Jul. 30, 2021, 9 pages.
Office Action received for Japanese Patent Application No. 2019-044107, mailed on May 29, 2020, 6 pages.
Office Action received for Japanese Patent Application No. 2019-162293, mailed on Jan. 31, 2020, 8 pages.
Office Action received for Japanese Patent Application No. 2019-162293, mailed on Jul. 27, 2020, 9 pages.
Office Action received for Japanese Patent Application No. 2019-563407, mailed on Feb. 5, 2021, 5 pages.
Office Action received for Japanese Patent Application No. 2020-000492, mailed on Dec. 11, 2020, 6 pages.
Office Action received for Japanese Patent Application No. 2020-104679, mailed on Sep. 18, 2020, 13 pages.
Office Action received for Japanese Patent Application No. 2020-115940, mailed on May 7, 2021, 3 pages.
Office Action received for Japanese Patent Application No. 2020-160023, mailed on Jan. 17, 2022, 11 pages.
Office Action received for Japanese Patent Application No. 2020-160052, mailed on Dec. 17, 2021, 10 pages.
Office Action received for Japanese Patent Application No. 2020-160053, mailed on Aug. 1, 2022, 8 pages.
Office Action received for Japanese Patent Application No. 2020-160053, mailed on Jan. 31, 2022, 8 pages.
Office Action received for Japanese Patent Application No. 2020-160054, mailed on Jan. 21, 2022, 8 pages.
Office Action received for Japanese Patent Application No. 2020-551585, mailed on Jan. 6, 2022, 11 pages.
Office Action received for Japanese Patent Application No. 2021-131726, mailed on Aug. 22, 2022, 8 pages.
Office Action received for Korean Patent Application No. 10-2016-7014577, mailed on Dec. 26, 2017, 14 pages.
Office Action received for Korean Patent Application No. 10-2016-7014577, mailed on Oct. 31, 2018, 11 pages.
Office Action received for Korean Patent Application No. 10-2016-7033638, mailed on Jan. 31, 2017, 6 pages.
Office Action received for Korean Patent Application No. 10-2019-7025538, mailed on Aug. 15, 2020, 8 pages.
Office Action received for Korean Patent Application No. 10-2019-7025538, mailed on Feb. 17, 2020, 12 pages.
Office Action received for Korean Patent Application No. 10-2019-7025781, mailed on Nov. 26, 2019, 10 pages.
Office Action received for Korean Patent Application No. 10-2019-7025781, mailed on Oct. 30, 2020, 10 pages.
Office Action received for Korean Patent Application No. 10-2019-7033834, mailed on Jan. 22, 2021, 13 pages.
Office Action received for Korean Patent Application No. 10-2020-0123815, mailed on May 31, 2022, 10 pages.
Office Action received for Korean Patent Application No. 10-2020-0124134, mailed on Jul. 28, 2022, 22 pages.
Office Action received for Korean Patent Application No. 10-2020-7023277, mailed on Jan. 26, 2022, 11 pages.
Office Action received for Korean Patent Application No. 10-2020-7026035, mailed on Feb. 19, 2021, 13 pages.
Office Action received for Korean Patent Application No. 10-2021-7026284, mailed on Aug. 31, 2021, 10 pages.
Office Action received for Korean Patent Application No. 10-2021-7031939, mailed on Oct. 19, 2021, 11 pages.
Office Action received for Taiwanese Patent Application No. 104117509, issued on Aug. 22, 2016, 6 pages.
Office Action received for Taiwanese Patent Application No. 104128685, mailed on Jan. 4, 2017, 40 pages.
Partial Supplementary European Search Report received for European Patent Application No. 17810749.6, mailed on Apr. 25, 2019, 8 pages.
Preliminary Opinion received for European Patent Application No. 15730890.9, mailed on Mar. 7, 2019, 4 pages.
Razykdreviews, "In Depth Review of Apple Watch Activity and Workout App", available at <URL: https://www.youtube.com/watch?v=GkKI3qIK0ow>, Category: X Claims: 1-5Category: L Reason: Internet citation/video, May 11, 2015, 1 page.
Result of Consultation received for European Patent Application No. 17810749.6, mailed on Dec. 15, 2020, 3 pages.
Result of Consultation received for European Patent Application No. 17810749.6, mailed on Jan. 18, 2021, 3 pages.

(56) References Cited

OTHER PUBLICATIONS

Result of Consultation received for European Patent Application No. 17810749.6, mailed on Jan. 21, 2021, 18 pages.
Result of Consultation received for European Patent Application No. 18154145.9, mailed on Nov. 30, 2020, 17 pages.
Result of Consultation received for European Patent Application No. 18154145.9, mailed on Sep. 4, 2020, 3 pages.
Result of Consultation received for European Patent Application No. 19721883.7, mailed on Oct. 7, 2020, 3 pages.
Rizknows, "Garmin Connect Mobile App—Review #2", https://www.youtube.com/watch?v=7my3wMpeRbE, Category: X Claims: 1-5 Category: L Reason: Internet citation/video, Oct. 22, 2015, 1 page.
Rizknows, "TomTom Multisport Cardio Review", Online available at:—https://www.youtube.com/watch?v=WoVCzLrSN9A, Sep. 4, 2015, 1 page.
Search report and opinion received for Danish Patent Application No. PA201770191, mailed on Jun. 30, 2017, 9 pages.
Search Report and Opinion received for Danish Patent Application No. PA201770423, mailed on Oct. 4, 2017, 10 pages.
Search Report and Opinion received for Danish Patent Application No. PA201870378, mailed on Sep. 10, 2018, 9 pages.
Search Report and Opinion received for Danish Patent Application No. PA201870379, mailed on Sep. 14, 2018, 9 pages.
Search Report and Opinion received for Danish Patent Application No. PA201970532, mailed on Nov. 8, 2019, 9 pages.
Search Report and Opinion received for Danish Patent Application No. PA202070612, mailed on Jun. 7, 2021, 9 pages.
Search Report and Opinion received for Danish Patent Application No. PA202070613, mailed on Jan. 22, 2021, 9 pages.
Search Report and Opinion received for Danish Patent Application No. PA202070614, mailed on Jan. 14, 2021, 9 pages.
Search Report and Opinion received for Danish Patent Application No. PA202070615, mailed on Jan. 22, 2021, 9 pages.
Search Report and Opinion received for Danish Patent Application No. PA202070616, mailed on Feb. 3, 2021, 8 pages.
Search Report and Opinion received for Danish Patent Application No. PA202070619, mailed on Dec. 2, 2020, 11 pages.
Search Report and Opinion received for Danish Patent Application No. PA202070620, mailed on Dec. 11, 2020, 9 pages.
Search Report and Opinion received for Danish Patent Application No. PA202070815, mailed on Mar. 16, 2021, 8 pages.
Search Report and Opinion received for Danish Patent Application No. PA202170113, mailed on Nov. 30, 2021, 9 pages.
Smith, "Garmin Fenix 5 Activity/Smart Watch Review", Online Available at:—https://www.youtube.com/watch?v=6PkQxXQxpoU, Sep. 2, 2017, 1 page.
Sportstechguides, "Garmin Fenix 5: How to Add Power Data Fields", Online Available at:—https://www.youtube.com/watch?v=ZkPptnnXEiQ, Apr. 29, 2017, 2 pages.
Sportstechguides, "Garmin Fenix 5: How To Set Up Run Alerts", Online Available at:—https://www.youtube.com/watch?v=gSMwv8vlhB4, May 13, 2017, 2 pages.
Summons to attend oral proceedings received for European Patent Application No. 13811085.3, mailed on Jan. 26, 2018., 14 pages.
Summons to Attend Oral Proceedings received for European Patent Application No. 13811085.3, mailed on Mar. 3, 2022, 3 pages.
Summons to Attend Oral Proceedings received for European Patent Application No. 15730890.9, mailed on Sep. 10, 2018, 11 pages.
Summons to Attend Oral Proceedings received for European Patent Application No. 17810749.6, mailed on Aug. 12, 2020, 11 pages.
Summons to Attend Oral Proceedings received for European Patent Application No. 18154145.9, mailed on Sep. 17, 2020, 11 pages.
Summons to Attend Oral Proceedings received for European Patent Application No. 20182116.2, mailed on Dec. 21, 2021, 7 pages.
Summons to Attend Oral Proceedings received for European Patent Application No. 20203526.7, mailed on Jun. 23, 2022, 9 pages.
Summons to Attend Oral Proceedings received for European Patent Application No. 20721342.2, mailed on May 20, 2022, 11 pages.
Summons to Attend Oral Proceedings received for European Patent Application No. 15771747.1, mailed on May 25, 2018, 17 pages.
Summon to Oral Proceedings received for European Patent Application No. 15771747.1, mailed on Apr. 29, 2021, 8 pages.
Supplemental Notice of Allowance received for U.S. Appl. No. 15/616,480, mailed on Mar. 28, 2019, 2 pages.
Supplemental Notice of Allowance received for U.S. Appl. No. 15/627,069, mailed on Jul. 12, 2021, 2 pages.
Supplemental Notice of Allowance received for U.S. Appl. No. 15/925,652, mailed on Feb. 17, 2021, 3 pages.
Supplemental Notice of Allowance received for U.S. Appl. No. 15/925,652, filed Jan. 6, 2021, 3 pages.
Supplemental Notice of Allowance received for U.S. Appl. No. 15/925,652, mailed on Jan. 26, 2021, 3 pages.
Supplemental Notice of Allowance received for U.S. Appl. No. 16/144,849, mailed on Mar. 31, 2020, 2 pages.
Supplemental Notice of Allowance received for U.S. Appl. No. 16/556,023, mailed on Feb. 3, 2021, 2 pages.
Supplemental Notice of Allowance received for U.S. Appl. No. 16/588,950, mailed on Apr. 1, 2020, 2 pages.
Supplemental Notice of Allowance received for U.S. Appl. No. 16/588,950, mailed on Jul. 29, 2020, 2 pages.
Supplemental Notice of Allowance received for U.S. Appl. No. 16/588,950, mailed on Jun. 18, 2020, 2 pages.
Supplemental Notice of Allowance received for U.S. Appl. No. 16/880,714, mailed on Sep. 16, 2021, 2 pages.
Supplemental Notice of Allowance received for U.S. Appl. No. 16/894,309, mailed on Apr. 8, 2022, 3 pages.
Supplemental Notice of Allowance received for U.S. Appl. No. 16/894,309, mailed on Dec. 24, 2021, 2 pages.
Supplemental Notice of Allowance received for U.S. Appl. No. 16/894,309, mailed on Jan. 25, 2022, 2 pages.
Supplemental Notice of Allowance received for U.S. Appl. No. 16/994,352, mailed on Jun. 20, 2022, 2 pages.
Supplemental Notice of Allowance received for U.S. Appl. No. 17/030,318, mailed on Apr. 4, 2022, 2 pages.
Supplemental Notice of Allowance received for U.S. Appl. No. 17/030,318, mailed on Feb. 22, 2022, 2 pages.
Supplemental Notice of Allowance received for U.S. Appl. No. 17/030,318, mailed on Mar. 16, 2022, 2 pages.
Supplemental Notice of Allowance received for U.S. Appl. No. 17/030,321, mailed on Apr. 15, 2022, 2 pages.
Supplemental Notice of Allowance received for U.S. Appl. No. 17/030,321, mailed on Jul. 27, 2022, 2 pages.
Supplemental Notice of Allowance received for U.S. Appl. No. 17/030,321, mailed on Jun. 10, 2022, 2 pages.
Supplemental Notice of Allowance received for U.S. Appl. No. 17/030,321, mailed on May 27, 2022, 2 pages.
Supplemental Notice of Allowance received for U.S. Appl. No. 17/031,727, mailed on Jan. 15, 2021, 2 pages.
Supplemental Notice of Allowance received for U.S. Appl. No. 17/192,161, mailed on Jun. 13, 2022, 2 pages.
Supplemental Notice of Allowance received for U.S. Appl. No. 17/192,161, mailed on May 13, 2022, 2 pages.
Supplementary European Search Report received for European Patent Application No. 17810749.6, mailed on Aug. 6, 2019, 6 pages.
Suunto Spartan Trainer Wrist HR 1.12, Online Available at:—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at:—https://www.youtube.com/watch?v=aixfoCnS0OU, Mar. 19, 2018, 2 page.
Tech, Kalyani, "I See Some problems in Honor Band 5", Retrieved from: https://www.youtube.com/watch?v=5XPnYJFqajl, May 19, 2020, 1 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.

(56) References Cited

OTHER PUBLICATIONS

Ticks, Smartwatch, "Senbono S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
TomTom, "TomTom Runner & Multi-Sport Reference Guide", Online available at:—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Utilization of Galaxy S4—S Health, ChatOn and Samsung Hub, Available at: http://seeit.kr/1263, Jun. 12, 2013, 25 pages.
Vicky's Blog, "How to Log In to PS4 Automatically with Particular User?", Online available on :—https://www.youtube.com/watch?v=kqdlzXAvOkY, May 30, 2018, 3 pages.
Visual Pace Alarm app, Available Online at: https://apps.garmin.com/en-US/apps/3940f3a2-4847-4078-a911-d77422966c82, Oct. 19, 2016, 1 page.
Wesley, "Apple Watch Series 1", online available at:—http://toolbox.info/blog/archives/1737-unknown.html, May 28, 2015, 5 pages.
Wikipedia, "Enhanced Multi-Level Precedence and Pre-emption Service", Available online at: https://de.wikipedia.org/w/index.php?%20title=Enhanced%20Multi%E3%83%BCLevel_Precedence_And_Pre-emption_Service&oldid=123047429, Oct. 2013, 2 pages.
Youtube, "Apple Watch Series 3", Online available at:—https://www.youtube.com/watch?v=iBPr9gEfkK8, Nov. 21, 2017, 15 pages.
Yoyodavid, "How to Use Multiple Accounts on the Playstation 4", Online available at:—https://www.youtube.com/watch?v=5V21obRMeKE, Jan. 9, 2014, 3 pages.
Zlelik, "Garmin Fenix 5 Open Water Swimming Activity Demo", Online Available at:—https://www.youtube.com/watch?v=iSVhdvw2dcs, Jun. 9, 2017, 1 page.
Brief Communication Regarding Oral Proceedings received for European Patent Application No. 20721342.2, mailed on Oct. 18, 2022, 1 page.
Result of Consultation received for European Patent Application No. 20721342.2, mailed on Oct. 18, 2022, 3 pages.
Summons to Attend Oral Proceedings received for European Patent Application No. 18727543.3, mailed on Oct. 25, 2022, 8 pages.
Updated Notice of Allowance received for U.S. Appl. No. 17/030,340, mailed on Nov. 2, 2022, 2 pages.
Advisory Action received for U.S. Appl. No. 17/031,779, mailed on Oct. 20, 2022, 5 pages.
Applicant-Initiated Interview Summary received for U.S. Appl. No. 16/249,627, mailed on Sep. 28, 2022, 4 pages.
Applicant-Initiated Interview Summary received for U.S. Appl. No. 16/418,786, mailed on Sep. 23, 2022, 2 pages.
Applicant-Initiated Interview Summary received for U.S. Appl. No. 17/591,184, mailed on Sep. 23, 2022, 2 pages.
Corrected Notice of Allowance received for U.S. Appl. No. 17/030,337, mailed on Oct. 18, 2022, 2 pages.
Corrected Notice of Allowance received for U.S. Appl. No. 17/030,337, mailed on Sep. 21, 2022, 2 pages.
Final Office Action received for U.S. Appl. No. 17/516,537, mailed on Oct. 11, 2022, 9 pages.
Intention to Grant received for Danish Patent Application No. PA202070815, mailed on Sep. 13, 2022, 2 pages.
Invitation to Pay Search Fees received for European Patent Application No. 19703582.7, mailed on Sep. 12, 2022, 3 pages.
Non-Final Office Action received for U.S. Appl. No. 17/031,854, mailed on Sep. 26, 2022, 17 pages.
Non-Final Office Action received for U.S. Appl. No. 17/031,859, mailed on Sep. 12, 2022, 17 pages.
Non-Final Office Action received for U.S. Appl. No. 17/031,874, mailed on Oct. 4, 2022, 20 pages.
Non-Final Office Action received for U.S. Appl. No. 17/381,570, mailed on Sep. 28, 2022, 20 pages.
Notice of Allowance received for Chinese Patent Application No. 202111611270.2, mailed on Sep. 21, 2022, 4 pages (1 page of English Translation and 3 pages of Official Copy).
Notice of Allowance received for Japanese Patent Application No. 2022-107902, mailed on Aug. 26, 2022, 4 pages (1 page of English Translation and 3 pages of Official Copy).
Notice of Allowance received for Korean Patent Application No. 10-2020-0123815, mailed on Aug. 26, 2022, 7 pages (2 pages of English Translation and 5 pages of Official Copy).
Notice of Allowance received for U.S. Appl. No. 17/030,340, mailed on Sep. 28, 2022, 7 pages.
Notice of Allowance received for U.S. Appl. No. 17/030,343, mailed on Sep. 16, 2022, 11 pages.
Office Action received for Chinese Patent Application No. 201911401161.0, mailed on Aug. 9, 2022, 17 pages (9 pages of English Translation and 8 pages of Official Copy).
Office Action received for Danish Patent Application No. PA202070612, mailed on Sep. 12, 2022, 3 pages.
Office Action received for Danish Patent Application No. PA202070613, mailed on Oct. 13, 2022, 7 pages.
Office Action received for Korean Patent Application No. 10-2020-0123821, mailed on Sep. 20, 2022, 11 pages (5 pages of English Translation and 6 pages of Official Copy).
Office Action received for Korean Patent Application No. 10-2020-7033395, mailed on Aug. 29, 2022, 11 pages (4 pages of English Translation and 7 pages of Official Copy).
Office Action received for Korean Patent Application No. 10-2022-0061486, mailed on Aug. 29, 2022, 5 pages (2 pages of English Translation and 3 pages of Official Copy).
Supplemental Notice of Allowance received for U.S. Appl. No. 17/030,343, mailed on Oct. 5, 2022, 2 pages.
Supplemental Notice of Allowance received for U.S. Appl. No. 17/041,415, mailed on Oct. 13, 2022, 2 pages.
Supplemental Notice of Allowance received for U.S. Appl. No. 17/041,415, mailed on Sep. 20, 2022, 2 pages.
Supplemental Notice of Allowance received for U.S. Appl. No. 17/317,084, mailed on Sep. 20, 2022, 2 pages.
Androidandyuk, "Endomondo Android App Review", Available online at: https://www.youtube.com/watch?v=Wyjyrza-P1E, Jan. 9, 2013, 17 pages.
GPSCity, "Garmin Connect 2.0 Overview with GPS City", Available online at: https://www.youtube.com/watch?v=EJ6U10y_8y0, Feb. 28, 2014, 8 pages.
Heinrich Peter, "More Player Engagement Potential: GameCircle Now Rewards Player Experience across Games", Available online at: https://www.developer.amazon.com/es-mx/blogs/home/tag/badges, Apr. 11, 2014, 9 pages.
Venusivenus, "Nike Training Club", Available online at: https://www.youtube.com/watch?v=_pe6fqJPA04, Mar. 28, 2011, 6 pages.
Corrected Notice of Allowance received for U.S. Appl. No. 17/030,337, mailed on Nov. 3, 2022, 2 pages.
Corrected Notice of Allowance received for U.S. Appl. No. 17/030,337, mailed on Nov. 15, 2022, 2 pages.
Decision to Refuse received for European Patent Application No. 20721342.2, mailed on Nov. 10, 2022, 14 pages.
Intention to Grant received for European Patent Application No. 20182116.2, mailed on Nov. 11, 2022, 9 pages.
Garmin, "Edge 520 Plus Owner's Manual", Online Available at: https://www8.garmin.com/manuals/webhelp/edge520plus/EN-US/Edge_520_Plus_OM_EN-US.pdf, 2018, 30 pages.
Minutes of Oral Proceedings received for European Patent Application No. 20721342.2, mailed on Nov. 8, 2022, 5 pages.
Office Action received for Australian Patent Application No. 2020268150, mailed on Nov. 3, 2022, 4 pages.
Office Action received for Australian Patent Application No. 2020288139, mailed on Oct. 31, 2022, 3 pages.
Office Action received for Australian Patent Application No. 2021266294, mailed on Nov. 11, 2022, 3 pages.
Supplemental Notice of Allowance received for U.S. Appl. No. 17/030,343, mailed on Nov. 9, 2022, 2 pages.
Updated Notice of Allowance received for U.S. Appl. No. 17/030,340, mailed on Nov. 10, 2022, 2 pages.
Applicant-Initiated Interview Summary received for U.S. Appl. No. 17/892,534, mailed on Feb. 10, 2023, 2 pages.
Corrected Notice of Allowance received for U.S. Appl. No. 17/030,337, mailed on Feb. 10, 2023, 2 pages.

(56) References Cited

OTHER PUBLICATIONS

Corrected Notice of Allowance received for U.S. Appl. No. 17/030,337, mailed on Feb. 17, 2023, 2 pages.
Final Office Action received for U.S. Appl. No. 17/031,859, mailed on Feb. 8, 2023, 15 pages.
Final Office Action received for U.S. Appl. No. 17/381,570, mailed on Feb. 10, 2023, 22 pages.
Intention to Grant received for European Patent Application No. 20203526.7, mailed on Feb. 10, 2023, 9 pages.
Non-Final Office Action received for U.S. Appl. No. 17/666,301, mailed on Feb. 16, 2023, 24 pages.
Non-Final Office Action received for U.S. Appl. No. 17/735,395, mailed on Feb. 10, 2023, 28 pages.
Notice of Acceptance received for Australian Patent Application No. 2020288139, mailed on Feb. 2, 2023, 3 pages.
Notice of Allowance received for Japanese Patent Application No. 2021-188824, mailed on Feb. 13, 2023, 4 pages (1 page of English Translation and 3 pages of Official Copy).
Notice of Allowance received for U.S. Appl. No. 17/591,184, mailed on Feb. 22, 2023, 5 pages.
Office Action received for Australian Patent Application No. 2020268150, mailed on Feb. 6, 2023, 5 pages.
Allen Ray, "Join the Nike Training Club and let your iPhone be your fitness instructor", Apr. 19, 2011, 26 pages.
Applicant-Initiated Interview Summary received for U.S. Appl. No. 17/381,570, mailed on Nov. 28, 2022, 5 pages.
Applicant-Initiated Interview Summary received for U.S. Appl. No. 17/516,537, mailed on Nov. 22, 2022, 2 pages.
Decision to Grant received for Danish Patent Application No. PA202070614, mailed on Nov. 10, 2022, 2 pages.
Final Office Action received for U.S. Appl. No. 17/030,318, mailed on Nov. 28, 2022, 13 pages.
International Search Report and Written Opinion received for PCT Patent Application No. PCT/US2022/029297, mailed on Aug. 11, 2022, 13 pages.
Invitation to Pay Search Fees received for European Patent Application No. 20760607.0, mailed on Nov. 21, 2022, 3 pages.
Notice of Allowance received for U.S. Appl. No. 16/418,786, mailed on Nov. 22, 2022, 6 pages.
Notice of Allowance received for U.S. Appl. No. 16/820,383, mailed on Nov. 22, 2022, 16 pages.
Applicant-Initiated Interview Summary received for U.S. Appl. No. 17/031,723, mailed on Jan. 23, 2023, 4 pages.
Applicant-Initiated Interview Summary received for U.S. Appl. No. 17/031,854, mailed on Jan. 24, 2023, 6 pages.
Applicant-Initiated Interview Summary received for U.S. Appl. No. 17/031,859, mailed on Dec. 27, 2022, 5 pages.
Applicant-Initiated Interview Summary received for U.S. Appl. No. 17/031,874, mailed on Jan. 24, 2023, 5 pages.
Applicant-Initiated Interview Summary received for U.S. Appl. No. 17/892,534, mailed on Feb. 6, 2023, 2 pages.
Brief Communication Regarding Oral Proceedings received for European Patent Application No. 20203526.7, mailed on Dec. 23, 2022, 4 pages.
Brief Communication Regarding Oral Proceedings received for European Patent Application No. 20203526.7, mailed on Jan. 18, 2023, 1 page.
Decision to Grant received for Danish Patent Application No. PA202070815, mailed on Dec. 23, 2022, 1 page.
Extended European Search Report received for European Patent Application No. 22194355.8, mailed on Dec. 23, 2022, 10 pages.
Final Office Action received for U.S. Appl. No. 17/591,184, mailed on Dec. 23, 2022, 10 pages.
International Preliminary Report on Patentability received for PCT Patent Application No. PCT/US2021/035227, mailed on Dec. 15, 2022, 10 pages.
Li-Yu et al., "Influence of exercise prescription on body composition of college students", Clinical Rehabilitation in China, vol. 9 Issue 24, Jun. 28, 2005, pp. 147-149. (Official Copy only) (See Communication under 37 CFR § 1.98(a) (3)).
Non-Final Office Action received for U.S. Appl. No. 16/249,627, mailed on Jan. 19, 2023, 19 pages.
Non-Final Office Action received for U.S. Appl. No. 17/031,723, mailed on Dec. 5, 2022, 27 pages.
Non-Final Office Action received for U.S. Appl. No. 17/892,534, mailed on Dec. 19, 2022, 20 pages.
Non-Final Office Action received for U.S. Appl. No. 17/951,875, mailed on Jan. 23, 2023, 12 pages.
Notice of Allowance received for Chinese Patent Application No. 202210238202.4, mailed on Jan. 13, 2023, 7 pages (3 pages of English Translation and 4 pages of Official Copy).
Notice of Allowance received for Japanese Patent Application No. 2020-160053, mailed on Jan. 16, 2023, 4 pages (1 page of English Translation and 3 pages of Official Copy).
Notice of Allowance received for Korean Patent Application No. 10-2022-0061486, mailed on Nov. 22, 2022, 7 pages (2 pages of English Translation and 5 pages of Official Copy).
Notice of Allowance received for U.S. Appl. No. 17/030,318, mailed on Jan. 25, 2023, 10 pages.
Notice of Allowance received for U.S. Appl. No. 17/030,337, mailed on Dec. 23, 2022, 9 pages.
Notice of Allowance received for U.S. Appl. No. 17/030,343, mailed on Dec. 15, 2022, 9 pages.
Notice of Allowance received for U.S. Appl. No. 17/031,779, mailed on Feb. 1, 2023, 11 pages.
Notice of Allowance received for U.S. Appl. No. 17/317,084, mailed on Jan. 6, 2023, 6 pages.
Notice of Allowance received for U.S. Appl. No. 17/516,537, mailed on Dec. 27, 2022, 7 pages.
Office Action received for Chinese Patent Application No. 201811303556.2, mailed on Nov. 28, 2022, 18 pages (7 pages of English Translation and 11 pages of Official Copy).
Office Action received for Chinese Patent Application No. 201880032190.1, mailed on Nov. 14, 2022, 23 pages (12 pages of English Translation and 11 pages of Official Copy).
Office Action received for Chinese Patent Application No. 201911401161.0, mailed on Dec. 15, 2022, 14 pages (7 pages of English Translation and 7 pages of Official Copy).
Office Action received for Chinese Patent Application No. 202110783860.7, mailed on Nov. 15, 2022, 8 pages (2 pages of English Translation and 6 pages of Official Copy).
Office Action received for European Patent Application No. 19703582.7, mailed on Jan. 11, 2023, 11 pages.
Office Action received for European Patent Application No. 20760607.0, mailed on Feb. 1, 2023, 13 pages.
Office Action received for Japanese Patent Application No. 2021-131726, mailed on Dec. 2, 2022, 4 pages (2 pages of English Translation and 2 pages of Official Copy).
Office Action received for Japanese Patent Application No. 2021-153558, mailed on Nov. 21, 2022, 8 pages (4 pages of English Translation and 4 pages of Official Copy).
Office Action received for Japanese Patent Application No. 2021-192437, mailed on Dec. 16, 2022, 4 pages (2 pages of English Translation and 2 pages of Official Copy).
Office Action received for Japanese Patent Application No. 2021-565912, mailed on Jan. 12, 2023, 9 pages (5 pages of English Translation and 4 pages of Official Copy).
Office Action received for Japanese Patent Application No. 2021-571468, mailed on Jan. 5, 2023, 14 pages (7 pages of English Translation & 7 pages of Official Copy).
Office Action received for Korean Patent Application No. 10-2020-0123840, mailed on Nov. 21, 2022, 18 pages (8 pages of English Translation and 10 pages of Official Copy).
Office Action received for Korean Patent Application No. 10-2022-7031866, mailed on Nov. 18, 2022, 11 pages (5 pages of English Translation and 6 pages of Official Copy).
Office Action received for Korean Patent Application No. 10-2022-7036381, mailed on Jan. 6, 2023, 10 pages (5 pages of English Translation and 5 pages of Official Copy).
Result of Consultation received for European Patent Application No. 20203526.7, mailed on Jan. 13, 2023, 3 pages.
Supplemental Notice of Allowance received for U.S. Appl. No. 17/030,343, mailed on Jan. 6, 2023, 2 pages.

(56) References Cited

OTHER PUBLICATIONS

Supplemental Notice of Allowance received for U.S. Appl. No. 17/317,084, mailed on Jan. 19, 2023, 2 pages.
Updated Notice of Allowance received for U.S. Appl. No. 17/030,340, mailed on Dec. 2, 2022, 2 pages.
Advisory Action received for U.S. Appl. No. 17/381,570, mailed on May 23, 2023, 5 pages.
Applicant-Initiated Interview Summary received for U.S. Appl. No. 16/249,627, mailed on Aug. 1, 2023, 3 pages.
Applicant-Initiated Interview Summary received for U.S. Appl. No. 16/249,627, mailed on Mar. 1, 2023, 4 pages.
Applicant-Initiated Interview Summary received for U.S. Appl. No. 17/031,723, mailed on Jun. 22, 2023, 2 pages.
Applicant-Initiated Interview Summary received for U.S. Appl. No. 17/031,854, mailed on Apr. 6, 2023, 5 pages.
Applicant-Initiated Interview Summary received for U.S. Appl. No. 17/031,859, mailed on Aug. 1, 2023, 4 pages.
Applicant-Initiated Interview Summary received for U.S. Appl. No. 17/031,859, mailed on Mar. 3, 2023, 5 pages.
Applicant-Initiated Interview Summary received for U.S. Appl. No. 17/041,438, mailed on Jun. 23, 2023, 4 pages.
Applicant-Initiated Interview Summary received for U.S. Appl. No. 17/398,810, mailed on Jun. 28, 2023, 5 pages.
Applicant-Initiated Interview Summary received for U.S. Appl. No. 17/591,184, mailed on Feb. 27, 2023, 2 pages.
Applicant-Initiated Interview Summary received for U.S. Appl. No. 17/591,184, mailed on Jun. 28, 2023, 2 pages.
Applicant-Initiated Interview Summary received for U.S. Appl. No. 17/666,301, mailed on Mar. 28, 2023, 4 pages.
Applicant-Initiated Interview Summary received for U.S. Appl. No. 17/735,395, mailed on Apr. 28, 2023, 2 pages.
Applicant-Initiated Interview Summary received for U.S. Appl. No. 17/735,395, mailed on Aug. 1, 2023, 2 pages.
Applicant-Initiated Interview Summary received for U.S. Appl. No. 17/744,500, mailed on May 30, 2023, 4 pages.
Applicant-Initiated Interview Summary received for U.S. Appl. No. 17/892,534, mailed on Aug. 3, 2023, 3 pages.
Applicant-Initiated Interview Summary received for U.S. Appl. No. 17/951,875, mailed on Feb. 28, 2023, 2 pages.
Applicant-Initiated Interview Summary received for U.S. Appl. No. 17/951,875, mailed on Jun. 27, 2023, 2 pages.
Applicant-Initiated Interview Summary received for U.S. Appl. No. 17/952,027, mailed on May 30, 2023, 4 pages.
Applicant-Initiated Interview Summary received for U.S. Appl. No. 17/952,133, mailed on Jul. 3, 2023, 4 pages.
Applicant-Initiated Interview Summary received for U.S. Appl. No. 17/381,570, mailed on Apr. 6, 2023, 4 pages.
Brief Communication Regarding Oral Proceedings received for European Patent Application No. 18727543.3, mailed on Mar. 23, 2023, 1 page.
Corrected Notice of Allowance received for U.S. Appl. No. 16/820,383, mailed on Apr. 28, 2023, 2 pages.
Corrected Notice of Allowance received for U.S. Appl. No. 17/030,318, mailed on Jun. 1, 2023, 3 pages.
Corrected Notice of Allowance received for U.S. Appl. No. 17/031,779, mailed on Jun. 14, 2023, 2 pages.
Dabek et al., "A timeline-based framework for aggregating and summarizing electronic health records", IEEE Workshop on Visual Analytics in Healthcare (VAHC), available online at: https://www.researchgate.net/publication/325833364_A_timeline-based_framework_for_aggregating_and_summarizing_electronic_health_records, 2017, 7 pages.
Decision to Grant received for European Patent Application No. 20182116.2, mailed on Mar. 23, 2023, 3 pages.
Decision to Grant received for European Patent Application No. 20203526.7, mailed on Jun. 22, 2023, 4 pages.
DiCristina, John, "Fitness Monitoring Equipment Goes Wireless", Frontier Technology, China Academic journal Electronic Publishing House, Online Available at: http://www.cnki.net, Dec. 2012, pp. 44-45 (Official Copy Only). {See Communication under 37 CFR § 1.98(a) (3)}.
Extended European Search Report received for European Patent Application No. 23150297.2, mailed on Mar. 28, 2023, 8 pages.
Extended European Search Report received for European Patent Application No. 23153898.4, mailed on May 4, 2023, 11 pages.
Extended European Search Report received for European Patent Application No. 23153899.2, mailed on May 4, 2023, 10 pages.
Extended European Search Report received for European Patent Application No. 23153900.8, mailed on May 4, 2023, 10 pages.
Final Office Action received for U.S. Appl. No. 16/249,627, mailed on Jun. 30, 2023, 19 pages.
Final Office Action received for U.S. Appl. No. 17/031,854, mailed on Feb. 23, 2023, 19 pages.
Final Office Action received for U.S. Appl. No. 17/031,874, mailed on Mar. 17, 2023, 24 pages.
Final Office Action received for U.S. Appl. No. 17/735,395, mailed on May 17, 2023, 31 pages.
Final Office Action received for U.S. Appl. No. 17/951,875, mailed on May 30, 2023, 12 pages.
GPSCity, "Garmin Connect Mobile App iOS Overview with GPS City", Available on: https://www.youtube.com/watch?v=rD-KPOJpmOA, 2014, 9 pages.
Intention to Grant received for European Patent Application No. 16837432.0, mailed on Apr. 14, 2023, 8 pages.
Intention to Grant received for European Patent Application No. 18727543.3, mailed on Apr. 12, 2023, 9 pages.
Intention to Grant received for European Patent Application No. 19721883.7, mailed on May 11, 2023, 9 pages.
International Preliminary Report on Patentability received for PCT Patent Application No. PCT/US2021/045375, mailed on Feb. 23, 2023, 15 pages.
Nakasuji, Yoshito, "Apple Watch", First Edition 1st Printing, Japan, Incorporated Company Technical Hyoronsha, Jun. 15, 2015, 4 pages (Official copy only). {See Communication under 37 CFR § 1.98(a) (3)}.
Non-Final Office Action received for U.S. Appl. No. 17/031,723, mailed on Jun. 2, 2023, 23 pages.
Non-Final Office Action received for U.S. Appl. No. 17/031,859, mailed on Jul. 10, 2023, 15 pages.
Non-Final Office Action received for U.S. Appl. No. 17/041,438, mailed on May 25, 2023, 47 pages.
Non-Final Office Action received for U.S. Appl. No. 17/398,810, mailed on Jun. 2, 2023, 19 pages.
Non-Final Office Action received for U.S. Appl. No. 17/566,521, mailed on May 15, 2023, 12 pages.
Non-Final Office Action received for U.S. Appl. No. 17/591,184, mailed on Apr. 21, 2023, 15 pages.
Non-Final Office Action received for U.S. Appl. No. 17/744,500, mailed on Apr. 19, 2023, 30 pages.
Non-Final Office Action received for U.S. Appl. No. 17/892,534, mailed on May 10, 2023, 17 pages.
Non-Final Office Action received for U.S. Appl. No. 17/951,613, mailed on Aug. 2, 2023, 42 pages.
Non-Final Office Action received for U.S. Appl. No. 17/951,976, mailed on Aug. 3, 2023, 16 pages.
Non-Final Office Action received for U.S. Appl. No. 17/952,027, mailed on Apr. 28, 2023, 46 pages.
Non-Final Office Action received for U.S. Appl. No. 17/952,133, mailed on Jun. 2, 2023, 28 pages.
Non-Final Office Action received for U.S. Appl. No. 17/952,181, mailed on Aug. 7, 2023, 18 pages.
Notice of Acceptance received for Australian Patent Application No. 2021266294, mailed on Mar. 3, 2023, 3 pages.
Notice of Acceptance received for Australian Patent Application No. 2022201761, mailed on Jun. 15, 2023, 3 pages.
Notice of Acceptance received for Australian Patent Application No. 2022203508, mailed on Jun. 27, 2023, 3 pages.
Notice of Acceptance received for Australian Patent Application No. 2022204568, mailed on Jul. 27, 2023, 3 pages.
Notice of Acceptance received for Australian Patent Application No. 2022209277, mailed on Apr. 28, 2023, 3 pages.

(56) References Cited

OTHER PUBLICATIONS

Notice of Acceptance received for Australian Patent Application No. 2022235614, mailed on Jul. 6, 2023, 3 pages.
Notice of Allowance received for Chinese Patent Application No. 201911396643.1, mailed on Jun. 15, 2023, 8 pages (4 pages of English Translation and 4 pages of Official Copy).
Notice of Allowance received for Chinese Patent Application No. 201911401161.0, mailed on Apr. 24, 2023, 11 pages (5 pages of English Translation and 6 pages of Official Copy).
Notice of Allowance received for Japanese Patent Application No. 2021-131726, mailed on Mar. 17, 2023, 4 pages (1 page of English Translation and 3 pages of Official Copy).
Notice of Allowance received for Japanese Patent Application No. 2021-153558, mailed on Jun. 9, 2023, 4 pages (1 page of English Translation and 3 pages of Official Copy).
Notice of Allowance received for Japanese Patent Application No. 2021-192437, mailed on May 19, 2023, 4 pages (1 page of English Translation and 3 pages of Official Copy).
Notice of Allowance received for Japanese Patent Application No. 2021-571468, mailed on May 19, 2023, 4 pages (1 page of English Translation and 3 pages of Official Copy).
Notice of Allowance received for Japanese Patent Application No. 2022-076722, mailed on Jul. 28, 2023, 4 pages (1 page of English Translation and 3 pages of Official Copy).
Notice of Allowance received for Korean Patent Application No. 10-2020-0123821, mailed on Mar. 28, 2023, 8 pages (2 pages of English Translation and 6 pages of Official Copy).
Notice of Allowance received for Korean Patent Application No. 10-2020-0123840, mailed on May 26, 2023, 9 pages (2 pages of English Translation and 7 pages of Official Copy).
Notice of Allowance received for Korean Patent Application No. 10-2022-7031866, mailed on May 1, 2023, 7 pages (2 pages of English Translation and 5 pages of Official Copy).
Notice of Allowance received for Korean Patent Application No. 10-2022-7036381, mailed on Jul. 12, 2023, 7 pages (2 pages of English Translation and 5 pages of Official Copy).
Notice of Allowance received for Korean Patent Application No. 10-2023-0023706, mailed on Mar. 27, 2023, 8 pages (2 pages of English Translation and 6 pages of Official Copy).
Notice of Allowance received for U.S. Appl. No. 16/820,383, mailed on Aug. 2, 2023, 14 pages.
Notice of Allowance received for U.S. Appl. No. 16/820,383, mailed on Mar. 8, 2023, 13 pages.
Notice of Allowance received for U.S. Appl. No. 17/030,318, mailed on May 16, 2023, 5 pages.
Notice of Allowance received for U.S. Appl. No. 17/031,779, mailed on May 26, 2023, 9 pages.
Notice of Allowance received for U.S. Appl. No. 17/381,570, mailed on Jul. 26, 2023, 14 pages.
Notice of Allowance received for U.S. Appl. No. 17/516,537, mailed on Apr. 17, 2023, 8 pages.
Notice of Allowance received for U.S. Appl. No. 17/666,301, mailed on May 4, 2023, 10 pages.
Notice of Allowance received for U.S. Appl. No. 17/852,020, mailed on Jul. 12, 2023, 9 pages.
Notice of Allowance received for U.S. Appl. No. 17/951,875, mailed on Jul. 26, 2023, 7 pages.
Notice of Allowance received for U.S. Appl. No. 18/078,444, mailed on May 12, 2023, 9 pages.
Office Action received for Australian Patent Application No. 2020268150, mailed on May 8, 2023, 4 pages.
Office Action received for Australian Patent Application No. 2022201761, mailed on Feb. 28, 2023, 5 pages.
Office Action received for Australian Patent Application No. 2022201823, mailed on Jun. 26, 2023, 6 pages.
Office Action received for Australian Patent Application No. 2022201823, mailed on Mar. 9, 2023, 3 pages.
Office Action received for Australian Patent Application No. 2022202977, mailed on Jul. 21, 2023, 3 pages.
Office Action received for Australian Patent Application No. 2022202977, mailed on May 2, 2023, 5 pages.
Office Action received for Australian Patent Application No. 2022203508, mailed on May 19, 2023, 2 pages.
Office Action received for Australian Patent Application No. 2022204568, mailed on Mar. 11, 2023, 4 pages.
Office Action received for Australian Patent Application No. 2022204568, mailed on May 22, 2023, 4 pages.
Office Action received for Australian Patent Application No. 2022209277, mailed on Mar. 10, 2023, 6 pages.
Office Action received for Australian Patent Application No. 2022235614, mailed on May 9, 2023, 2 pages.
Office Action received for Chinese Patent Application No. 201811303556.2, mailed on May 19, 2023, 6 pages (3 pages of English Translation and 3 pages of Official Copy).
Office Action received for Chinese Patent Application No. 201880032190.1, mailed on May 31, 2023, 20 pages (12 pages of English Translation and 8 pages of Official Copy).
Office Action received for Chinese Patent Application No. 201911396643.1, mailed on Apr. 6, 2023, 26 pages (15 pages of English Translation and 11 pages of official copy).
Office Action received for Chinese Patent Application No. 201911396744.9, mailed on Apr. 6, 2023, 19 pages (7 pages of English Translation and 12 pages of Official Copy).
Office Action received for Chinese Patent Application No. 201911396819.3, mailed on Apr. 6, 2023, 21 pages (10 pages of English Translation and 11 pages of Official copy).
Office Action received for Chinese Patent Application No. 201911401375.8, mailed on Apr. 7, 2023, 10 pages (5 pages of English Translation and 5 pages of Official Copy).
Office Action received for German Patent Application No. 112015007285.3, mailed on Mar. 7, 2023, 15 pages (5 pages of English Translation and 10 pages of Official Copy).
Office Action received for Indian Patent Application No. 202215032692, mailed on Jun. 15, 2023, 3 pages.
Office Action received for Japanese Patent Application No. 2021-565912, mailed on Jun. 26, 2023, 3 pages (1 page of English Translation and 2 pages of Official Copy).
Office Action received for Japanese Patent Application No. 2022-022159, mailed on Feb. 20, 2023, 10 pages (5 pages of English Translation and 5 pages of Official Copy).
Office Action received for Japanese Patent Application No. 2022-076722, mailed on Mar. 13, 2023, 6 pages (3 pages of English Translation and 3 pages of Official Copy).
Office Action received for Japanese Patent Application No. 2022-078280, mailed on Jul. 24, 2023, 8 pages (4 pages of English Translation and 4 pages of Official Copy).
Office Action received for Korean Patent Application No. 10-2020-0124134, mailed on Jun. 23, 2023, 8 pages (4 pages of English Translation and 4 pages of Official Copy).
Office Action received for Korean Patent Application No. 10-2020-0124134, mailed on Mar. 28, 2023, 9 pages (4 pages of English Translation and 5 pages of Official Copy).
Office Action received for Korean Patent Application No. 10-2022-7036278, mailed on Jun. 30, 2023, 10 pages (4 pages of English Translation and 6 pages of Official Copy).
Result of Consultation received for European Patent Application No. 18727543.3, mailed on Mar. 15, 2023, 6 pages.
Summons to Attend Oral Proceedings received for European Patent Application No. 21165295.3, mailed on Jul. 25, 2023, 14 pages.
Summons to Attend Oral Proceedings received for European Patent Application No. 21168916.1, mailed on Jul. 14, 2023, 12 pages.
Supplemental Notice of Allowance received for U.S. Appl. No. 17/666,301, mailed on Jun. 5, 2023, 2 pages.
Supplemental Notice of Allowance received for U.S. Appl. No. 17/666,301, mailed on May 17, 2023, 2 pages.
Supplemental Notice of Allowance received for U.S. Appl. No. 17/852,020, mailed on Aug. 4, 2023, 2 pages.
Supplemental Notice of Allowance received for U.S. Appl. No. 18/078,444, mailed on Jun. 15, 2023, 2 pages.
Updated Notice of Allowance received for U.S. Appl. No. 17/030,318, mailed on Feb. 23, 2023, 3 pages.

(56) References Cited

OTHER PUBLICATIONS

Yuling et al., "Research on Motion Modeling of Virtual Gear Measuring Center", Tool Technology, vol. 43, No. 2, 2009, pp. 85-87 (Official Copy Only). {See Communication under 37 CFR § 1.98(a) (3)}.
Applicant-Initiated Interview Summary received for U.S. Appl. No. 17/951,976, mailed on Aug. 23, 2023, 2 pages.
Decision to Grant received for German Patent Application No. 112015007285.3, mailed on Jul. 25, 2023, 11 pages (1 page of English Translation and 10 pages of Official Copy).
Final Office Action received for U.S. Appl. No. 17/952,027, mailed on Aug. 21, 2023, 47 pages.
Notice of Allowance received for Chinese Patent Application No. 201811303556.2, mailed on Jul. 28, 2023, 2 pages (1 of English Translation and 1 page of Official Copy).
Notice of Allowance received for Chinese Patent Application No. 201911396744.9, mailed on Aug. 3, 2023, 5 pages (1 page of English Translation and 4 pages of Official Copy).
Notice of Allowance received for Japanese Patent Application No. 2022-022159, mailed on Aug. 10, 2023, 4 pages (1 page of English Translation and 3 pages of Official Copy).
Office Action received for European Patent Application No. 20760607.0, mailed on Aug. 17, 2023, 7 pages.
Supplemental Notice of Allowance received for U.S. Appl. No. 17/381,570, mailed on Aug. 11, 2023, 2 pages.
Applicant-Initiated Interview Summary received for U.S. Appl. No. 17/744,500, mailed on Oct. 17, 2023, 4 pages.
Applicant-Initiated Interview Summary received for U.S. Appl. No. 17/896,791, mailed on Oct. 12, 2023, 2 pages.
Notice of Allowance received for Chinese Patent Application No. 201880032190.1, mailed on Oct. 7, 2023, 4 pages (1 page of English Translation and 3 pages of Official Copy).
Office Action received for Japanese Patent Application No. 2022-130087, mailed on Oct. 2, 2023, 12 pages (6 pages of English Translation and 6 pages of Official Copy).
Supplemental Notice of Allowance received for U.S. Appl. No. 17/952,181, mailed on Oct. 6, 2023, 2 pages.
Supplemental Notice of Allowance received for U.S. Appl. No. 18/078,444, mailed on Oct. 16, 2023, 4 pages.
Decision to Grant received for European Patent Application No. 18727543.3, mailed on Aug. 18, 2023, 2 pages.
Decision to Grant received for European Patent Application No. 19721883.7, mailed on Aug. 31, 2023, 4 pages.
Examiner Interview Summary received for U.S. Appl. No. 17/896,791, mailed on Sep. 1, 2023, 2 pages.
Invitation to Pay Search Fees received for European Patent Application No. 21714460.9, mailed on Aug. 8, 2023, 3 pages.
Non-Final Office Action received for U.S. Appl. No. 17/896,791, mailed on Aug. 30, 2023, 11 pages.
Notice of Allowance received for Chinese Patent Application No. 201911396819.3, mailed on Aug. 3, 2023, 5 pages (1 page of English Translation and 4 pages of Official Copy).
Notice of Allowance received for U.S. Appl. No. 17/952,185, mailed on Aug. 30, 2023, 12 pages.
Notice of Allowance received for U.S. Appl. No. 18/078,444, mailed on Aug. 31, 2023, 6 pages.
Office Action received for Australian Patent Application No. 2020268150, mailed on Aug. 24, 2023, 5 pages.
Office Action received for Chinese Patent Application No. 201911396876.1, mailed on Apr. 7, 2023, 16 pages (9 pages of English Translation and 7 pages of Official Copy).
Supplemental Notice of Allowance received for U.S. Appl. No. 17/951,875, mailed on Aug. 25, 2023, 2 pages.
Chengcheng et al., "Platform of Development of Motion Control Systems Experimental Software", Experimental Technology and Management, vol. 30, No. 1, Jan. 2013, 3 pages (Official Copy Only). {See Communication under 37 CFR § 1.98(a) (3)}.
Corrected Notice of Allowance received for U.S. Appl. No. 17/041,438, mailed on Sep. 27, 2023, 3 pages.
Final Office Action received for U.S. Appl. No. 17/031,723, mailed on Oct. 4, 2023, 13 pages.
Final Office Action received for U.S. Appl. No. 17/398,810, mailed on Oct. 4, 2023, 17 pages.
Final Office Action received for U.S. Appl. No. 17/591,184, mailed on Sep. 22, 2023, 19 pages.
Final Office Action received for U.S. Appl. No. 17/952,133, mailed on Sep. 26, 2023, 20 pages.
Non-Final Office Action received for U.S. Appl. No. 17/210,920, mailed on Sep. 28, 2023, 22 pages.
Notice of Acceptance received for Australian Patent Application No. 2022201823, mailed on Sep. 26, 2023, 3 pages.
Notice of Acceptance received for Australian Patent Application No. 2022202977, mailed on Sep. 26, 2023, 3 pages.
Notice of Allowance received for Chinese Patent Application No. 201911396876.1, mailed on Sep. 6, 2023, 5 pages (1 page of English Translation and 4 pages of Official Copy).
Notice of Allowance received for U.S. Appl. No. 17/952,027, mailed on Oct. 4, 2023, 13 pages.
Notice of Allowance received for U.S. Appl. No. 17/952,181, mailed on Sep. 27, 2023, 9 pages.
Office Action received for Chinese Patent Application No. 202211193170.7, mailed on Jun. 30, 2023, 19 pages (9 pages of English Translation and 10 pages of Official Copy).
Office Action received for Japanese Patent Application No. 2022-131993, mailed on Sep. 15, 2023, 6 pages (3 pages of English Translation and 3 pages of Official Copy).
Office Action received for Korean Patent Application No. 10-2021-7036242, mailed on Sep. 19, 2023, 13 pages (6 pages of English Translation and 7 pages of Official Copy).
Supplemental Notice of Allowance received for U.S. Appl. No. 17/952,185, mailed on Oct. 2, 2023, 2 pages.
Advisory Action received for U.S. Appl. No. 17/952,133, mailed on Oct. 20, 2023, 7 pages.
Applicant-Initiated Interview Summary received for U.S. Appl. No. 17/031,723, mailed on Oct. 31, 2023, 4 pages.
Applicant-Initiated Interview Summary received for U.S. Appl. No. 17/591,184, mailed on Oct. 30, 2023, 2 pages.
Non-Final Office Action received for U.S. Appl. No. 16/249,627, mailed on Oct. 31, 2023, 23 pages.
Non-Final Office Action received for U.S. Appl. No. 17/031,854, mailed on Oct. 18, 2023, 22 pages.
Notice of Acceptance received for Australian Patent Application No. 2023203050, mailed on Oct. 24, 2023, 3 pages.
Notice of Allowance received for U.S. Appl. No. 17/041,438, mailed on Oct. 19, 2023, 2 pages.
Notice of Allowance received for U.S. Appl. No. 17/951,875, mailed on Oct. 20, 2023, 8 pages.
Office Action received for Australian Patent Application No. 2023237090, mailed on Oct. 18, 2023, 3 pages.
Office Action received for Chinese Patent Application No. 201911401375.8, mailed on Sep. 26, 2023, 13 pages (6 pages of English Translation and 7 pages of Official Copy).
Office Action received for European Patent Application No. 21714460.9, mailed on Oct. 24, 2023, 13 pages.
Supplemental Notice of Allowance received for U.S. Appl. No. 17/952,181, mailed on Oct. 27, 2023, 2 pages.
Prasad et al., "Understanding Sharing Preferences and Behavior for Mhealth Devices", Proceedings of the 2012 ACM workshop on Privacy in the electronic society, Available online at: https://dl.acm.org/doi/10.1145/2381966.2381983, Oct. 15, 2012, pp. 117-128.
Applicant-Initiated Interview Summary received for U.S. Appl. No. 17/951,613, mailed on Sep. 8, 2023, 5 pages.
Applicant-Initiated Interview Summary received for U.S. Appl. No. 17/952,027, mailed on Sep. 11, 2023, 3 pages.
Final Office Action received for U.S. Appl. No. 17/744,500, mailed on Sep. 19, 2023, 35 pages.
Intention to Grant received for European Patent Application No. 16837432.0, mailed on Sep. 7, 2023, 9 pages.
Non-Final Office Action received for U.S. Appl. No. 17/951,624, mailed on Sep. 19, 2023, 41 pages.
Non-Final Office Action received for U.S. Appl. No. 17/735,395, mailed on Sep. 20, 2023, 29 pages.

(56) References Cited

OTHER PUBLICATIONS

Notice of Allowance received for Japanese Patent Application No. 2022-078280, mailed on Sep. 4, 2023, 4 pages (1 page of English Translation and 3 pages of Official Copy).
Notice of Allowance received for Japanese Patent Application No. 2022-107903, mailed on Sep. 1, 2023, 4 pages (1 page of English Translation and 3 pages of Official Copy).
Notice of Allowance received for U.S. Appl. No. 17/041,438, mailed on Sep. 20, 2023, 11 pages.
Office Action received for Australian Patent Application No. 2023203050, mailed on Sep. 1, 2023, 3 pages.
Supplemental Notice of Allowance received for U.S. Appl. No. 17/381,570, mailed on Sep. 13, 2023, 2 pages.
Advisory Action received for U.S. Appl. No. 17/591,184, mailed on Nov. 14, 2023, 5 pages.
Advisory Action received for U.S. Appl. No. 17/744,500, mailed on Nov. 14, 2023, 5 pages.
Applicant-Initiated Interview Summary received for U.S. Appl. No. 16/249,627, mailed on Nov. 21, 2023, 5 pages.
Applicant-Initiated Interview Summary received for U.S. Appl. No. 17/951,624, mailed on Nov. 16, 2023, 3 pages.
Applicant-Initiated Interview Summary received for U.S. Appl. No. 17/735,395, mailed on Nov. 15, 2023, 2 pages.
Final Office Action received for U.S. Appl. No. 17/031,859, mailed on Nov. 13, 2023, 15 pages.
Final Office Action received for U.S. Appl. No. 17/892,534, mailed on Nov. 9, 2023, 17 pages.
Notice of Allowance received for U.S. Appl. No. 17/951,976, mailed on Nov. 17, 2023, 9 pages.
Office Action received for Australian Patent Application No. 2023203776, mailed on Nov. 7, 2023, 2 pages.
Office Action received for Japanese Patent Application No. 2023-110196, mailed on Nov. 6, 2023, 4 pages (2 pages of English Translation and 2 pages of Official Copy).
Office Action received for Korean Patent Application No. 10-2023-7034892, mailed on Nov. 8, 2023, 5 pages (2 pages of English Translation and 3 pages of Official Copy).
Pre-Appeal Review Report received for Japanese Patent Application No. 2021-565912, mailed on Oct. 12, 2023, 5 pages (2 pages of English Translation and 3 pages of Official Copy).
Advisory Action received for U.S. Appl. No. 17/398,810, mailed on Dec. 11, 2023, 4 pages.
Applicant-Initiated Interview Summary received for U.S. Appl. No. 17/031,854, mailed on Dec. 21, 2023, 5 pages.
Applicant-Initiated Interview Summary received for U.S. Appl. No. 17/210,920, mailed on Jan. 26, 2024, 3 pages.
Applicant-Initiated Interview Summary received for U.S. Appl. No. 17/735,395, mailed on Jan. 31, 2024, 2 pages.
Applicant-Initiated Interview Summary received for U.S. Appl. No. 17/892,534, mailed on Feb. 1, 2024, 4 pages.
Applicant-Initiated Interview Summary received for U.S. Appl. No. 17/952,233, mailed on May 24, 2023, 5 pages.
Applicant-Initiated Interview Summary received for U.S. Appl. No. 17/952,233, mailed on Sep. 7, 2023, 4 pages.
Applicant-Initiated Interview Summary received for U.S. Appl. No. 17/952,239, mailed on May 31, 2023, 2 pages.
Applicant-Initiated Interview Summary received for U.S. Appl. No. 18/135,056, mailed on Jan. 3, 2024, 2 pages.
Corrected Notice of Allowance received for U.S. Appl. No. 17/041,438, mailed on Dec. 1, 2023, 2 pages.
Corrected Notice of Allowance received for U.S. Appl. No. 17/744,500, mailed on Jan. 12, 2024, 3 pages.
Corrected Notice of Allowance received for U.S. Appl. No. 17/896,791, mailed on Jan. 2, 2024, 2 pages.
Corrected Notice of Allowance received for U.S. Appl. No. 17/951,613, mailed on Jan. 2, 2024, 2 pages.
Corrected Notice of Allowance received for U.S. Appl. No. 17/952,027, mailed on Jan. 22, 2024, 3 pages.
Corrected Notice of Allowance received for U.S. Appl. No. 17/952,239, mailed on Jul. 12, 2023, 2 pages.
Corrected Notice of Allowance received for U.S. Appl. No. 17/952,239, mailed on Nov. 15, 2023, 2 pages.
Decision on Appeal received for Korean Patent Application No. 10-2020-0124134, mailed on Oct. 20, 2023, 24 pages (4 pages of English Translation and 20 pages of Official Copy).
Decision to Grant received for European Patent Application No. 16837432.0, mailed on Dec. 21, 2023, 2 pages.
Extended European Search Report received for European Patent Application No. 23189089.8, mailed on Nov. 23, 2023, 11 pages.
Final Office Action received for U.S. Appl. No. 17/735,395, mailed on Dec. 7, 2023, 29 pages.
Final Office Action received for U.S. Appl. No. 17/951,624, mailed on Jan. 25, 2024, 48 pages.
Final Office Action received for U.S. Appl. No. 17/952,233, mailed on Jun. 26, 2023, 18 pages.
Intention to Grant received for European Patent Application No. 21714460.9, mailed on Feb. 8, 2024, 12 pages.
International Preliminary Report on Patentability received for PCT Patent Application No. PCT/US2022/029297, mailed on Nov. 30, 2023, 10 pages.
International Search Report and Written Opinion received for PCT Patent Application No. PCT/US2023/024104, mailed on Oct. 18, 2023, 18 pages.
International Search Report and Written Opinion received for PCT Patent Application No. PCT/US2023/024185, mailed on Sep. 18, 2023, 12 pages.
Minutes of the Oral Proceedings received for European Patent Application No. 21168916.1, mailed on Jan. 3, 2024, 5 pages.
Non-Final Office Action received for U.S. Appl. No. 17/952,075, mailed on Jan. 16, 2024, 27 pages.
Non-Final Office Action received for U.S. Appl. No. 17/952,233, mailed on Apr. 28, 2023, 21 pages.
Non-Final Office Action received for U.S. Appl. No. 17/952,233, mailed on Feb. 2, 2024, 18 pages.
Non-Final Office Action received for U.S. Appl. No. 17/952,239, mailed on Apr. 4, 2023, 45 pages.
Non-Final Office Action received for U.S. Appl. No. 18/135,056, mailed on Dec. 7, 2023, 16 pages.
Non-Final Office Action received for U.S. Appl. No. 18/204,217, mailed on Feb. 13, 2024, 21 pages.
Notice of Acceptance received for Australian Patent Application No. 2023203776, mailed on Dec. 12, 2023, 3 pages.
Notice of Allowance received for Chinese Patent Application No. 201911401375.8, mailed on Nov. 26, 2023, 2 pages (1 page of English Translation and 1 page of Official Copy).
Notice of Allowance received for Japanese Patent Application No. 2022-131993, mailed on Dec. 18, 2023, 4 pages (1 page of English Translation and 3 pages of Official Copy).
Notice of Allowance received for Korean Patent Application No. 10-2020-0124134, mailed on Nov. 21, 2023, 8 pages (2 pages of English Translation and 6 pages of Official Copy).
Notice of Allowance received for Korean Patent Application No. 10-2022-7036278, mailed on Jan. 30, 2024, 8 pages (2 pages of English Translation and 6 pages of Official Copy).
Notice of Allowance received for U.S. Appl. No. 16/820,383, mailed on Dec. 7, 2023, 13 pages.
Notice of Allowance received for U.S. Appl. No. 17/041,438, mailed on Jan. 22, 2024, 10 pages.
Notice of Allowance received for U.S. Appl. No. 17/591,184, mailed on Dec. 11, 2023, 9 pages.
Notice of Allowance received for U.S. Appl. No. 17/744,500, mailed on Dec. 22, 2023, 38 pages.
Notice of Allowance received for U.S. Appl. No. 17/896,791, mailed on Dec. 15, 2023, 9 pages.
Notice of Allowance received for U.S. Appl. No. 17/951,613, mailed on Dec. 8, 2023, 13 pages.
Notice of Allowance received for U.S. Appl. No. 17/951,613, mailed on Feb. 2, 2024, 5 pages.
Notice of Allowance received for U.S. Appl. No. 17/951,875, mailed on Dec. 26, 2023, 7 pages.
Notice of Allowance received for U.S. Appl. No. 17/952,027, mailed on Dec. 29, 2023, 6 pages.

(56) References Cited

OTHER PUBLICATIONS

Notice of Allowance received for U.S. Appl. No. 17/952,185, mailed on Dec. 13, 2023, 9 pages.
Notice of Allowance received for U.S. Appl. No. 17/952,239, mailed on Jun. 23, 2023, 5 pages.
Notice of Allowance received for U.S. Appl. No. 17/952,239, mailed on Oct. 20, 2023, 5 pages.
Office Action received for Chinese Patent Application No. 201980018078.7, mailed on Nov. 25, 2023, 20 pages (9 pages of English Translation and 11 pages of Official Copy).
Office Action received for European Patent Application No. 20733174.5, mailed on Dec. 18, 2023, 9 pages.
Office Action received for European Patent Application No. 20760607.0, mailed on Jan. 3, 2024, 7 pages.
Office Action received for Korean Patent Application No. 10-2023-7018399, mailed on Jan. 24, 2024, 11 pages (4 pages of English Translation and 7 pages of Official Copy).
Result of Consultation received for European Patent Application No. 21168916.1, mailed on Dec. 11, 2023, 25 pages.
Supplemental Notice of Allowance received for U.S. Appl. No. 17/952,181, mailed on Dec. 20, 2023, 2 pages.
Supplemental Notice of Allowance received for U.S. Appl. No. 17/952,185, mailed on Nov. 30, 2023, 2 pages.
Extended European Search Report received for European Patent Application No. 23192409.3, mailed on Feb. 20, 2024, 13 pages.
Non-Final Office Action received for U.S. Appl. No. 17/952,133, mailed on Feb. 28, 2024, 22 pages.
Notice of Acceptance received for Australian Patent Application No. 2023237090, mailed on Feb. 23, 2024, 3 pages.
Notice of Allowance received for Japanese Patent Application No. 2023-110196, mailed on Feb. 13, 2024, 4 pages (1 page of English Translation and 3 pages of Official Copy).
Notice of Allowance received for U.S. Appl. No. 17/892,534, mailed on Feb. 21, 2024, 7 pages.
Office Action received for Indian Patent Application No. 202315061713, mailed on Feb. 14, 2024, 8 pages.
Office Action received for Indian Patent Application No. 202315061718, mailed on Feb. 14, 2024, 8 pages.
Office Action received for Japanese Patent Application No. 2023-041035, mailed on Feb. 9, 2024, 13 pages (6 pages of English Translation and 7 pages of Official Copy).
Advisory Action received for U.S. Appl. No. 16/249,627, mailed on May 21, 2024, 3 pages.
Corrected Notice of Allowance received for U.S. Appl. No. 17/952,233, mailed on May 9, 2024, 2 pages.
Final Office Action received for U.S. Appl. No. 17/031,854, mailed on May 16, 2024, 21 pages.
Office Action received for Chinese Patent Application No. 202310774963.6, mailed on Apr. 21, 2024, 18 pages (11 pages of English Translation and 7 pages of Official Copy).
Office Action received for Korean Patent Application No. 10-2023-0114488, mailed on Apr. 30, 2024, 16 pages (6 pages of English Translation and 10 pages of Official Copy).
Corrected Notice of Allowance received for U.S. Appl. No. 16/820,383, mailed on Mar. 27, 2024, 2 pages.
Corrected Notice of Allowance received for U.S. Appl. No. 17/041,438, mailed on Mar. 28, 2024, 2 pages.
Corrected Notice of Allowance received for U.S. Appl. No. 17/952,185, mailed on Mar. 27, 2024, 2 pages.
Extended European Search Report received for European Patent Application No. 23217005.0, mailed on Mar. 13, 2024, 12 pages.
Non-Final Office Action received for U.S. Appl. No. 17/735,395, mailed on Mar. 19, 2024, 32 pages.
Notice of Allowance received for U.S. Appl. No. 18/204,217, mailed on Mar. 26, 2024, 7 pages.
Office Action received for Chinese Patent Application No. 202310775734.6, mailed on Mar. 2, 2024, 11 pages (5 pages of English Translation and 6 pages of Official Copy).
Office Action received for Chinese Patent Application No. 202310828052.7, mailed on Mar. 6, 2024, 16 pages (7 pages of English Translation and 9 pages of Official Copy).
Office Action received for Japanese Patent Application No. 2023-065859, mailed on Mar. 11, 2024, 8 pages (4 pages of English Translation and 4 pages of Official Copy).
Office Action received for Korean Patent Application No. 10-2023-7025320, mailed on Mar. 11, 2024, 9 pages (4 pages of English Translation and 5 pages of Official Copy).
Applicant-Initiated Interview Summary received for U.S. Appl. No. 17/952,233, mailed on Apr. 2, 2024, 4 pages.
Extended European Search Report received for European Patent Application No. 23218255.0, mailed on Mar. 27, 2024, 10 pages.
Final Office Action received for U.S. Appl. No. 16/249,627, mailed on Apr. 3, 2024, 23 pages.
Notice of Allowance received for Chinese Patent Application No. 201980018078.7, mailed on Mar. 28, 2024, 2 pages (1 page of English Translation and 1 page of Official Copy).
Office Action received for Australian Patent Application No. 2023214377, mailed on Mar. 27, 2024, 3 pages.
Office Action received for Chinese Patent Application No. 202310774963.6, mailed on Feb. 8, 2024, 11 pages (5 pages of English Translation and 6 pages of Official Copy).
Applicant-Initiated Interview Summary received for U.S. Appl. No. 17/952,133, mailed on Apr. 23, 2024, 3 pages.
Office Action received for Chinese Patent Application No. 202311059240.4, mailed on Mar. 19, 2024, 11 pages (5 pages of English Translation and 6 pages of Official Copy).
Result of Consultation received for European Patent Application No. 21165295.3, mailed on Apr. 18, 2024, 3 pages.
Applicant-Initiated Interview Summary received for U.S. Appl. No. 16/249,627, mailed on May 2, 2024, 5 pages.
Decision to Refuse received for European Patent Application No. 21165295.3, mailed on Apr. 29, 2024, 14 pages.
Extended European Search Report received for European Patent Application No. 24152191.3, mailed on Apr. 15, 2024, 11 pages.
Final Office Action received for U.S. Appl. No. 17/210,920, mailed on May 6, 2024, 27 pages.
Final Office Action received for U.S. Appl. No. 18/135,056, mailed on May 2, 2024, 18 pages.
Minutes of Oral Proceedings received for European Patent Application No. 21165295.3. mailed on Apr. 26, 2024, 6 pages.
Notice of Allowance received for Chinese Patent Application No. 202310775734.6, mailed on Apr. 18, 2024, 4 pages (1 page of English Translation and 3 pages of Official Copy).
Notice of Allowance received for U.S. Appl. No. 17/952,233, mailed on May 1, 2024, 9 pages.
Office Action received for Chinese Patent Application No. 202080039364.4, mailed on Apr. 9, 2024, 15 pages (7 pages of English Translation and 8 pages of Official Copy).
Brief Communication Regarding Oral Proceedings received for European Patent Application No. 21165295.3, mailed on Feb. 27, 2024, 1 page.
International Search Report and Written Opinion received for PCT Patent Application No. PCT/US2023/030718, mailed on Jan. 9, 2024, 12 pages.
Notice of Allowance received for U.S. Appl. No. 17/896,791, mailed on Mar. 13, 2024, 8 pages.
Notice of Allowance received for U.S. Appl. No. 17/951,976, mailed on Mar. 12, 2024, 5 pages.
Office Action received for Chinese Patent Application No. 202211193170.7, mailed on Jan. 6, 2024, 13 pages (6 pages of English Translation and 7 pages of Official Copy).
Applicant-Initiated Interview Summary received for U.S. Appl. No. 17/735,395, mailed on May 30, 2024, 2 pages.
Corrected Notice of Allowance received for U.S. Appl. No. 17/892,534, mailed on Jun. 5, 2024, 6 pages,.
Corrected Notice of Allowance received for U.S. Appl. No. 17/896,791, mailed on Jun. 7, 2024, 2 pages.
Decision to Refuse received for Japanese Patent Application No. 2022-130087, mailed on Apr. 30, 2024, 6 pages (3 pages of English Translation and 3 pages of Official Copy).

(56) References Cited

OTHER PUBLICATIONS

Notice of Allowance received for Chinese Patent Application No. 202311059240.4, mailed on May 23, 2024, 2 pages (1 page of English Translation and 1 page of Official Copy).
Office Action received for Australian Patent Application No. 2023214377, mailed on Jun. 5, 2024, 4 pages.

* cited by examiner

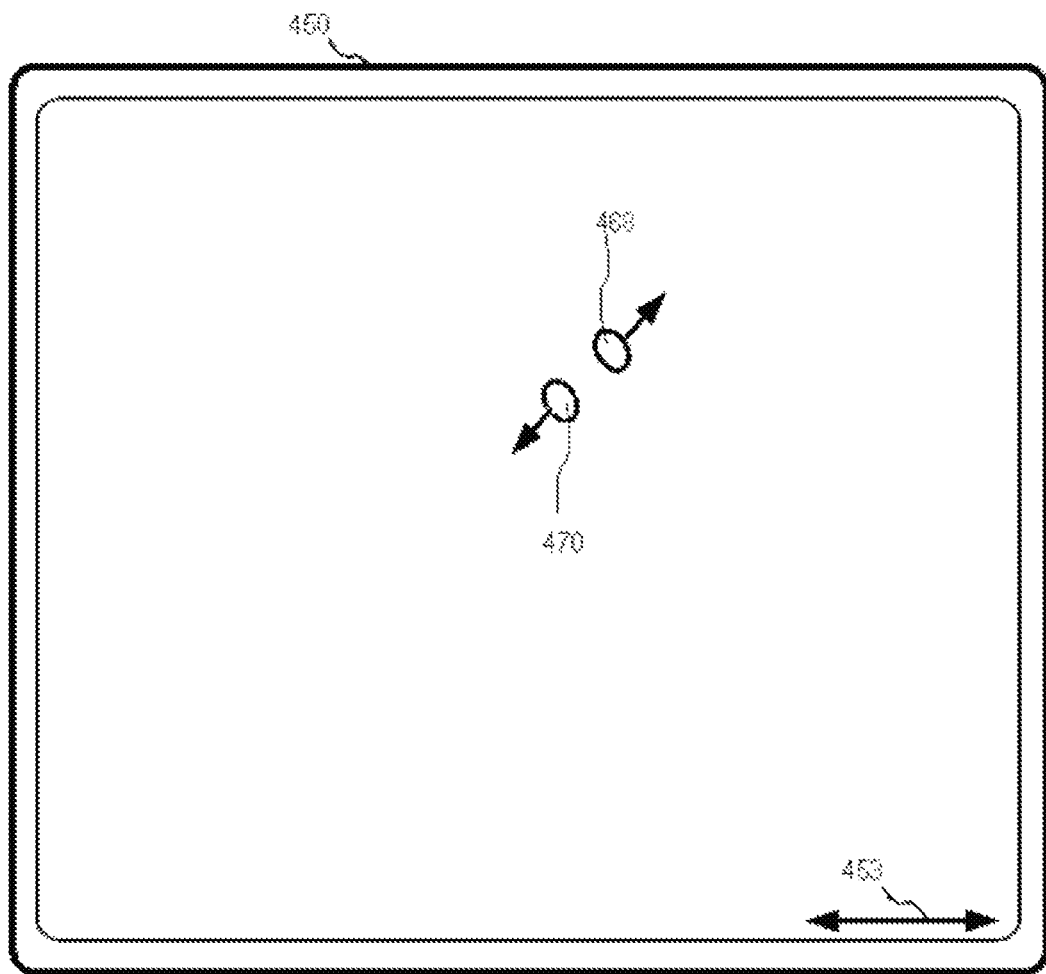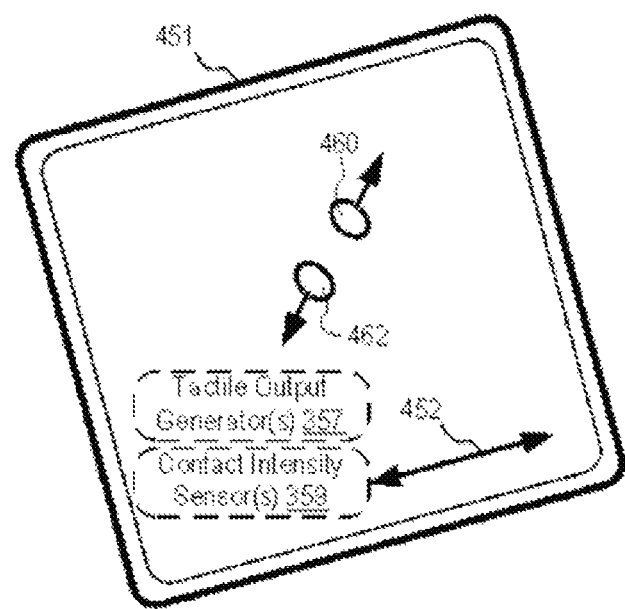
FIG. 4B

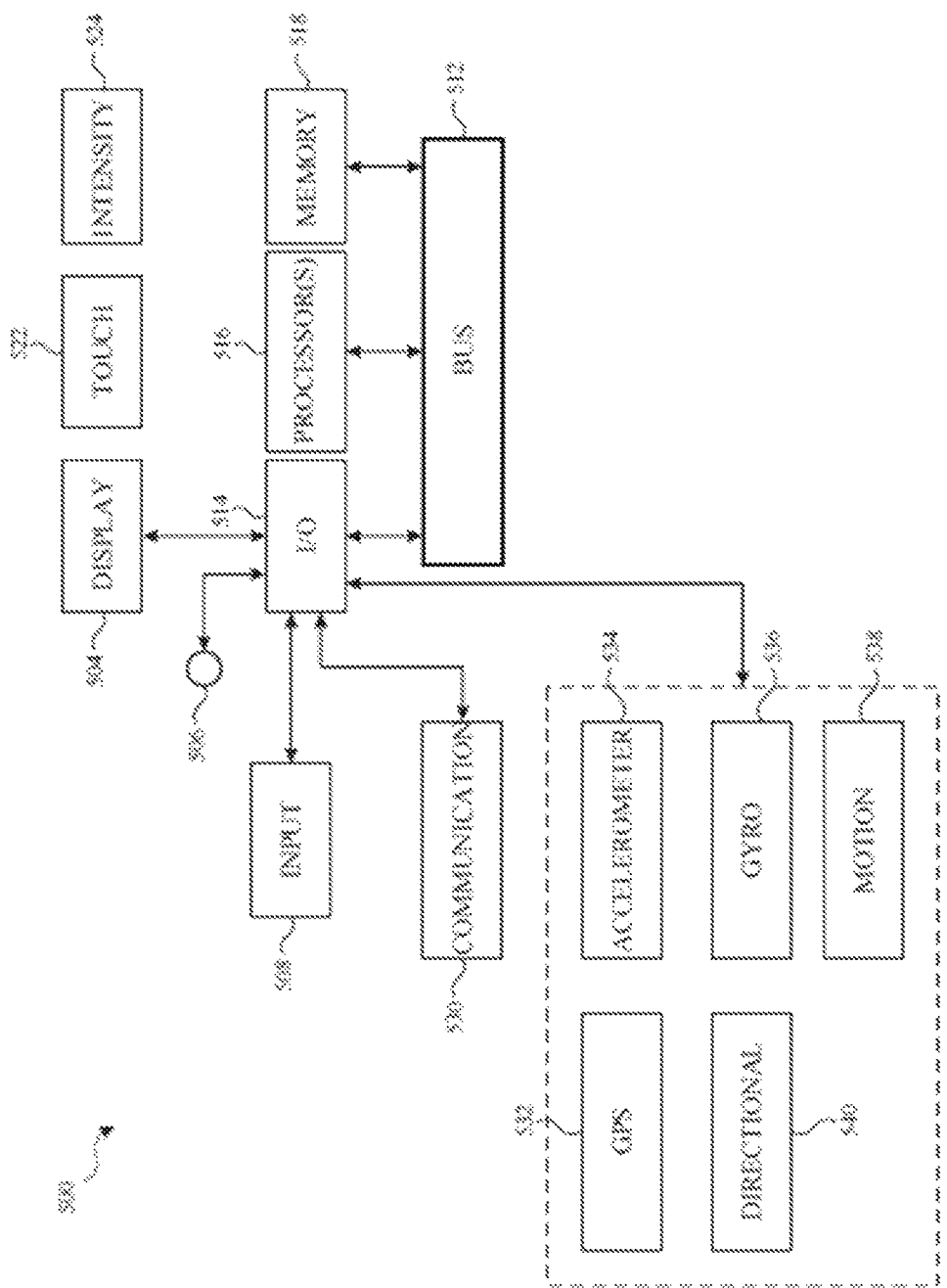

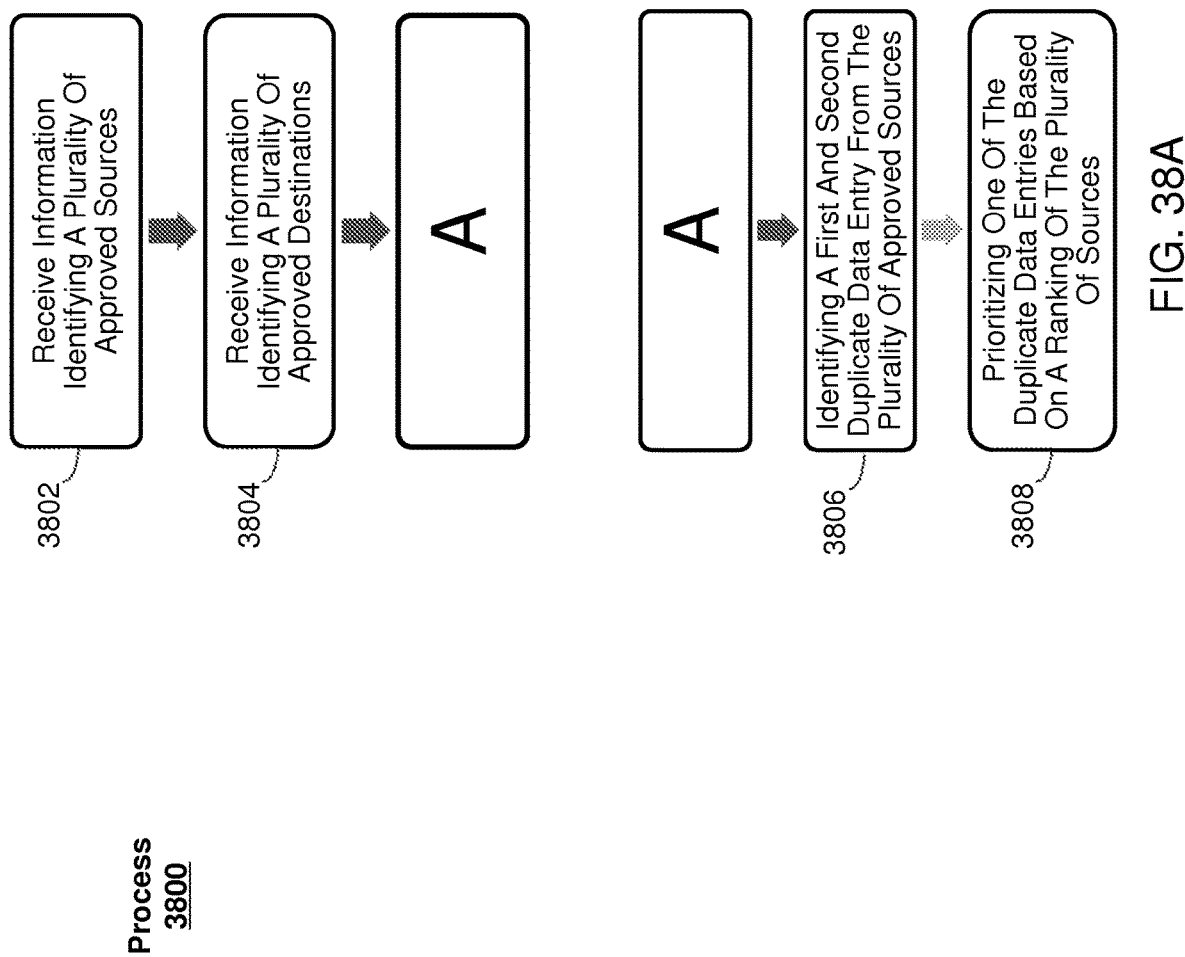

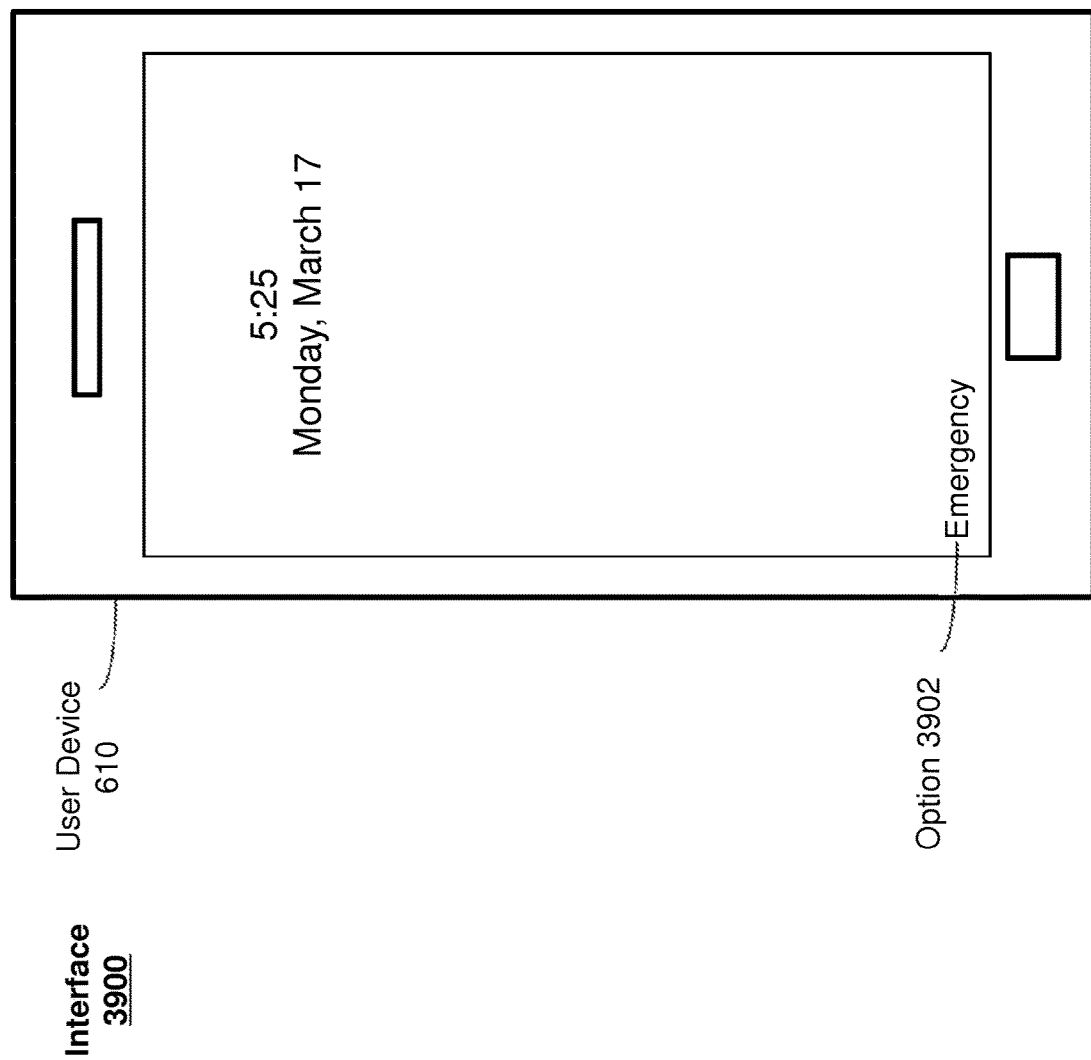

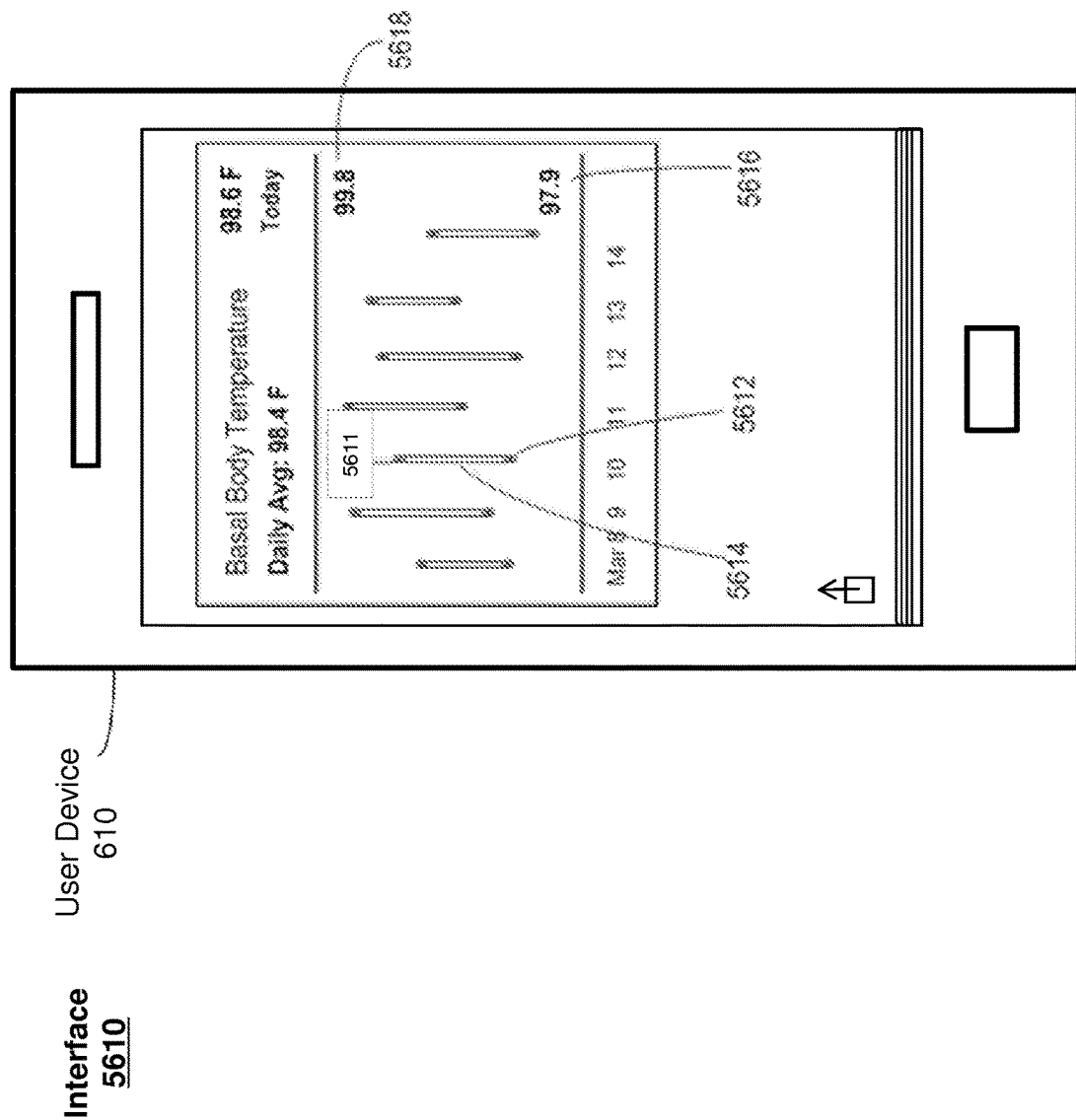

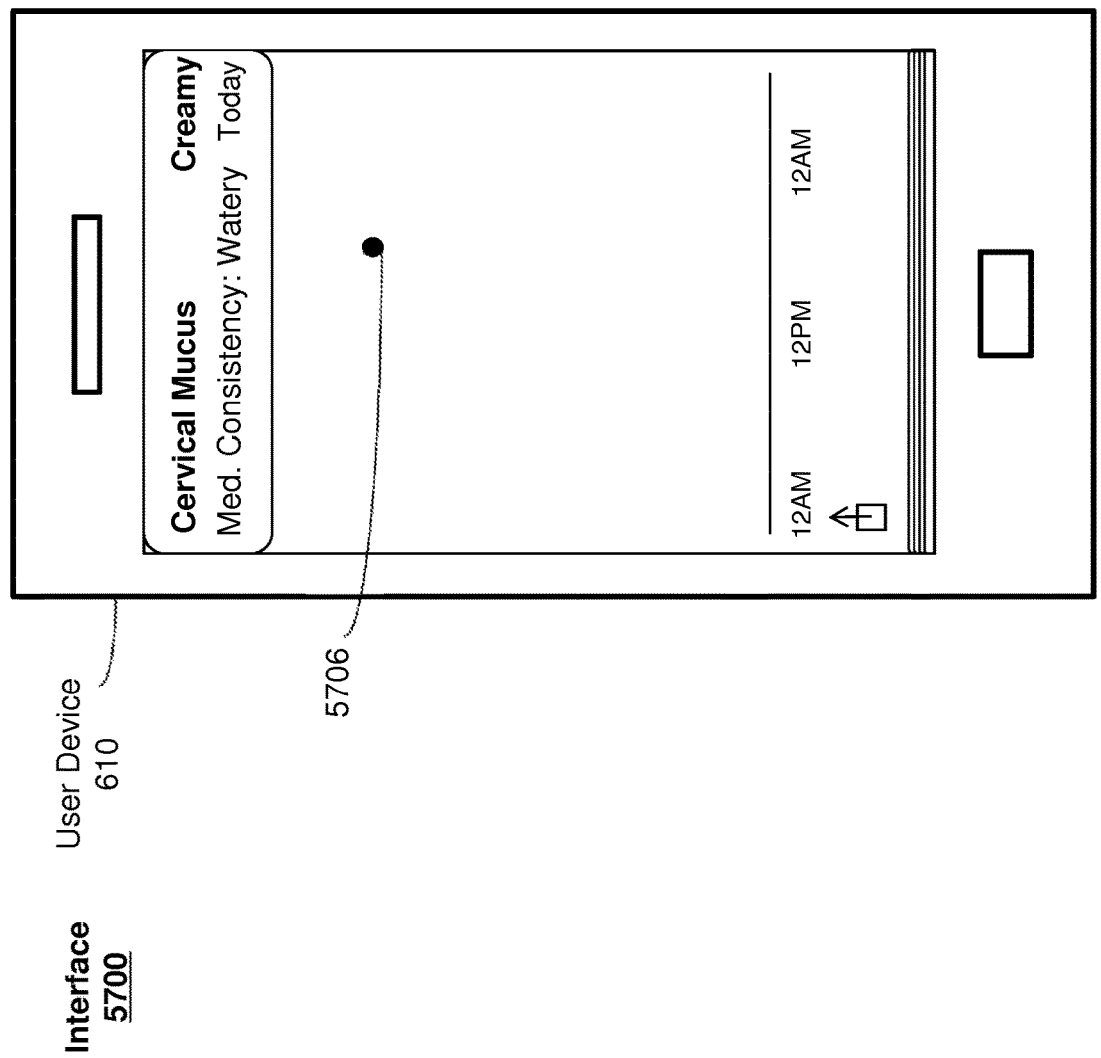

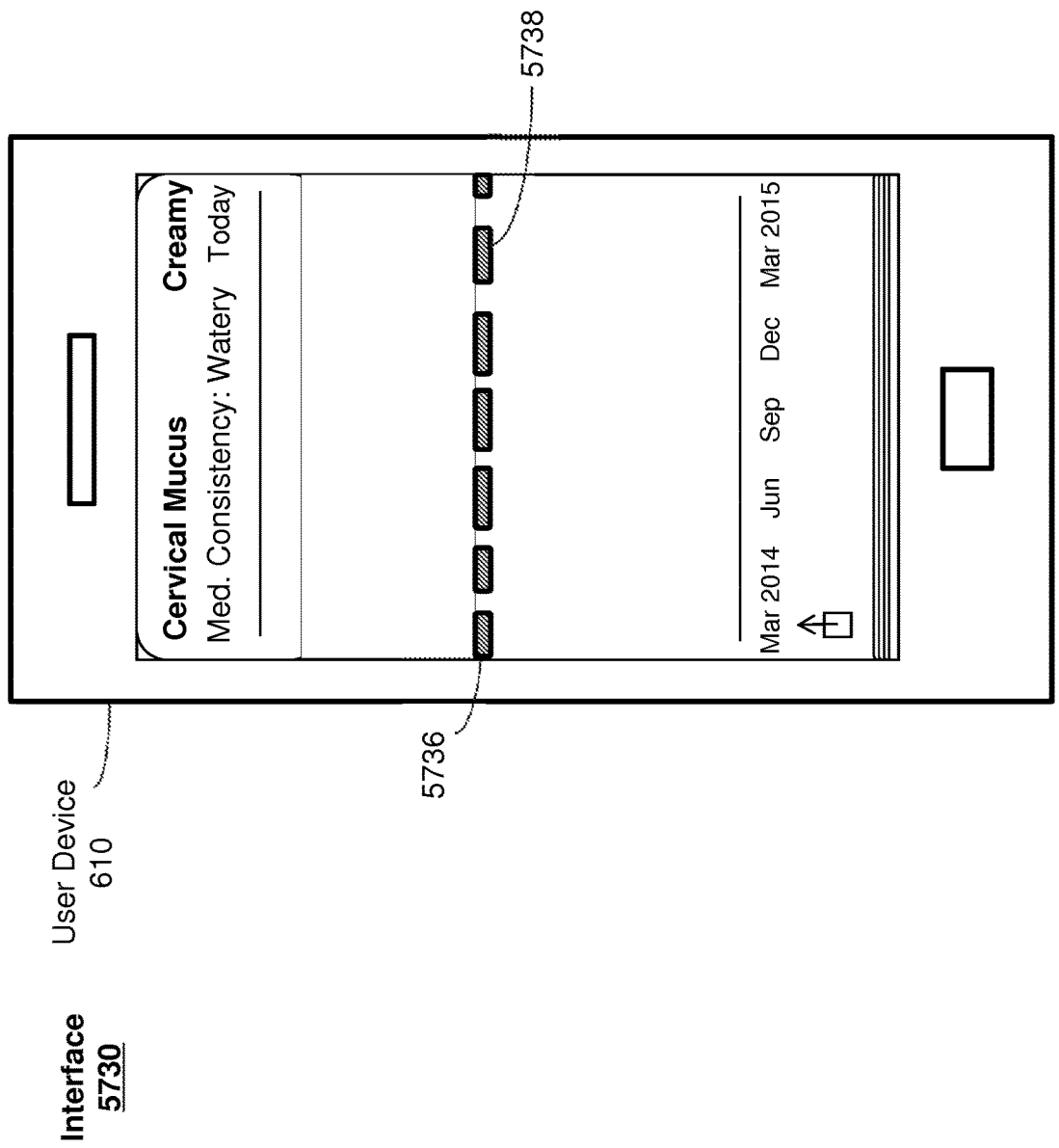

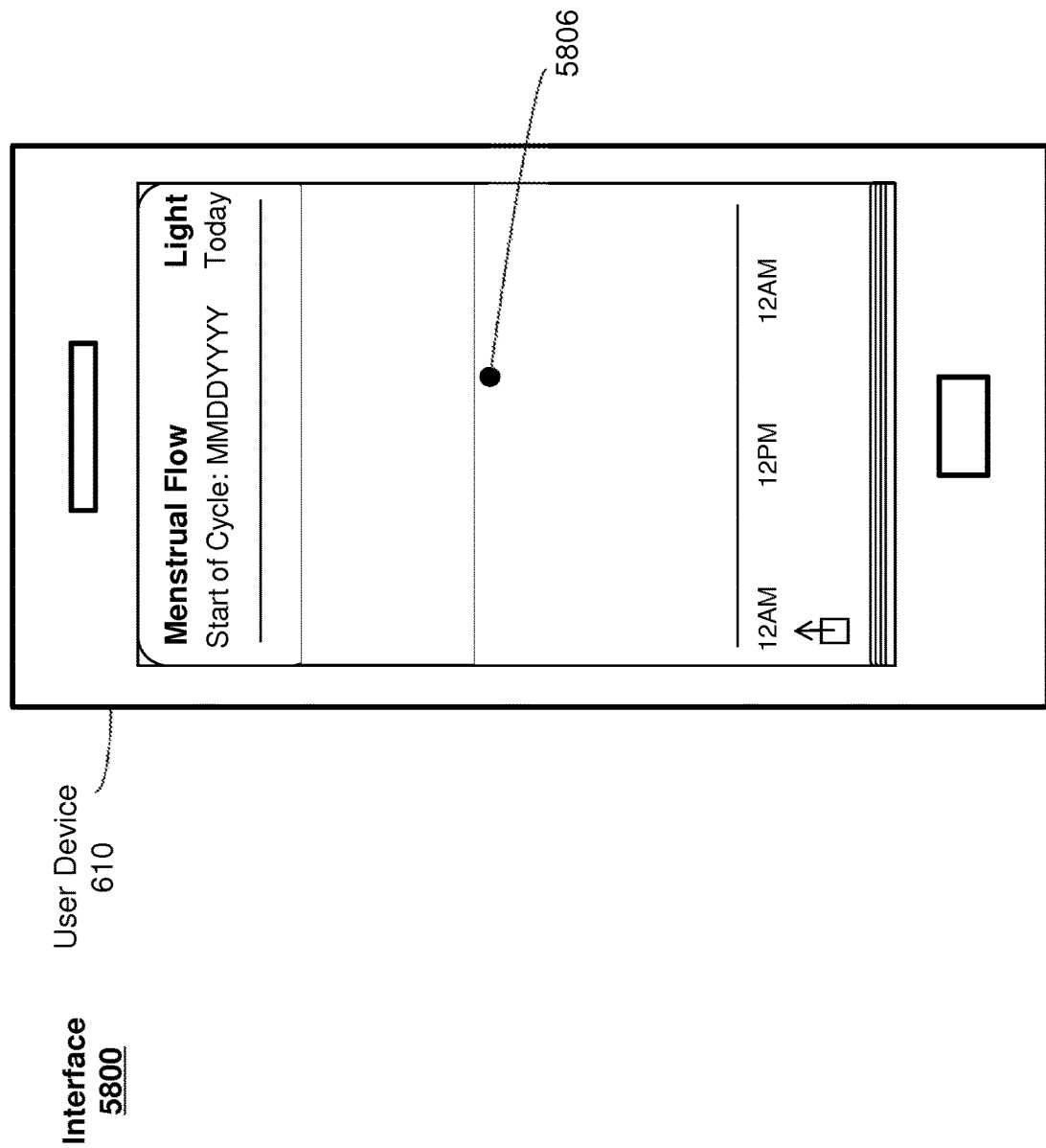

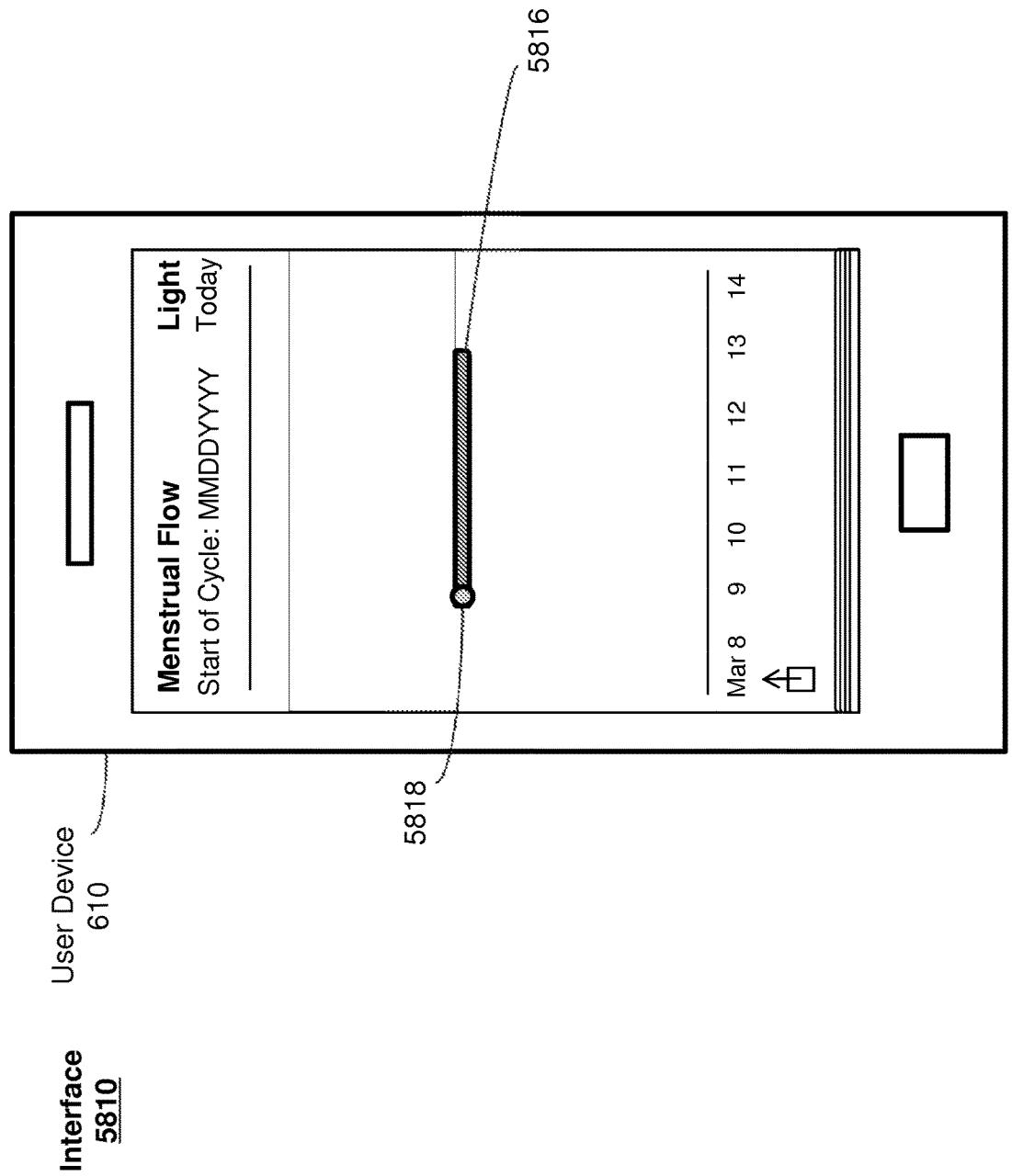

WELLNESS AGGREGATOR

CROSS-REFERENCE TO RELATED APPLICATIONS

This application is a continuation of U.S. non-provisional patent application Ser. No. 17/735,395, entitled "WELLNESS AGGREGATOR," filed May 3, 2022, which is a continuation of U.S. non-provisional patent application Ser. No. 16/820,383, entitled "WELLNESS AGGREGATOR," filed Mar. 16, 2020, which is a continuation of U.S. non-provisional patent application Ser. No. 14/732,773, entitled "WELLNESS AGGREGATOR", filed Jun. 7, 2015, which is a continuation-in-part of International Application PCT/US2013/073195, entitled "WELLNESS AGGREGATOR", filed Dec. 4, 2013, and a continuation-in-part of International Application PCT/US2015/032474, entitled "WELLNESS AGGREGATOR", filed May 26, 2015, which claims priority to U.S. Provisional Patent Application Ser. No. 62/129,945, entitled "WELLNESS AGGREGATOR", filed Mar. 8, 2015, and U.S. Provisional Patent Application Ser. No. 62/006,032, entitled "WELLNESS AGGREGATOR", filed May 30, 2014. This application is a continuation-in-part of U.S. non-provisional patent application Ser. No. 14/599,424, entitled "WELLNESS AGGREGATOR", filed Jan. 16, 2015, which claims priority to U.S. Provisional Patent Application Ser. No. 62/006,032, entitled "WELLNESS AGGREGATOR", filed May 30, 2014. The content of these applications is hereby incorporated by reference herein.

This application relates to U.S. Provisional Patent Application Ser. No. 62/006,031, entitled "MANAGING USER INFORMATION," filed May 30, 2014, the content of which is hereby incorporated by reference herein.

FIELD

The following disclosure relates generally to data management and, more specifically, to aggregating and sharing wellness data.

BACKGROUND

Approximately 133 million Americans currently suffer from at least one chronic condition. This number is expected to rise to approximately 165 million by the year 2020. As a result, the cost of healthcare in the United States is expected to increase dramatically. Attempts have been made to improve the health of individuals by providing them with tools to monitor and, track their wellness data. Wellness data can generally include any type of data associated with a person's health, such as their weight, heart rate, blood pressure, blood glucose level, medication compliance, activity level, or the like. Users can monitor their wellness using devices, such as blood pressure cuffs, blood glucose monitors, electrocardiograms, step counters, and the like. Software applications (e.g., Apps) associated with each of these devices have also been developed to allow users to track their wellness data over time. While each application can be used to view useful information about a user's health, current applications are limited in their ability to allow users to store, view, and share wellness data collected by different devices.

SUMMARY

The present disclosure relates to processes for aggregating and sharing wellness data. One example process can include causing a display of an aggregated view of a plurality of types of wellness data, wherein the aggregated view comprises a plurality of partitions, each partition of the plurality of partitions associated with a type of the plurality of types of wellness data; receiving a selection of a partition of the plurality of partitions; and causing a display of an expanded view of the selected partition of the plurality of partitions.

An example process can include display, on the display screen, a graph comprising: a first data-set representation of a first data set in which a first dependent variable varies as an independent variable changes and a second data-set representation of a second data set in which a second dependent variable varies as the independent variable changes, wherein the first data-set representation comprises a plurality of indicators corresponding to values of the dependent variables of the first data-set representation, wherein the second data-set representation is associated with a range of vertical positions within the graph, wherein the dependent variables of the first data set are chosen from a set of discrete values; detect, at a respective location on the display screen, a user input; in response to detecting the user input: in accordance with a determination that the respective location corresponds to an indicator of the plurality of indicators, display, on the display screen, an indication that the first data-set representation has been selected; and in accordance with a determination that the respective location is within the range of vertical positions associated with the second data-set representation, but away from the plurality of indicators, display, on the display screen, an indication that the second data-set representation has been selected.

Devices and non-transitory computer-readable storage media for performing these processes are also provided.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIG. 5B is a block diagram illustrating a personal electronic device in accordance with some embodiments.

FIGS. 38A and 38B illustrate an example process for managing and displaying wellness or non-wellness data according to various examples.

FIG. 39 illustrates example interfaces for displaying emergency medical information according to various examples.

FIGS. 56A-56D illustrate exemplary interfaces for displaying wellness or non-wellness data according to various examples.

FIGS. 57A-57D illustrate exemplary interfaces for displaying wellness or non-wellness data according to various examples.

FIGS. 58A-58D illustrate exemplary interfaces for displaying wellness or non-wellness data according to various examples.

DESCRIPTION OF EMBODIMENTS

Figure 1A:
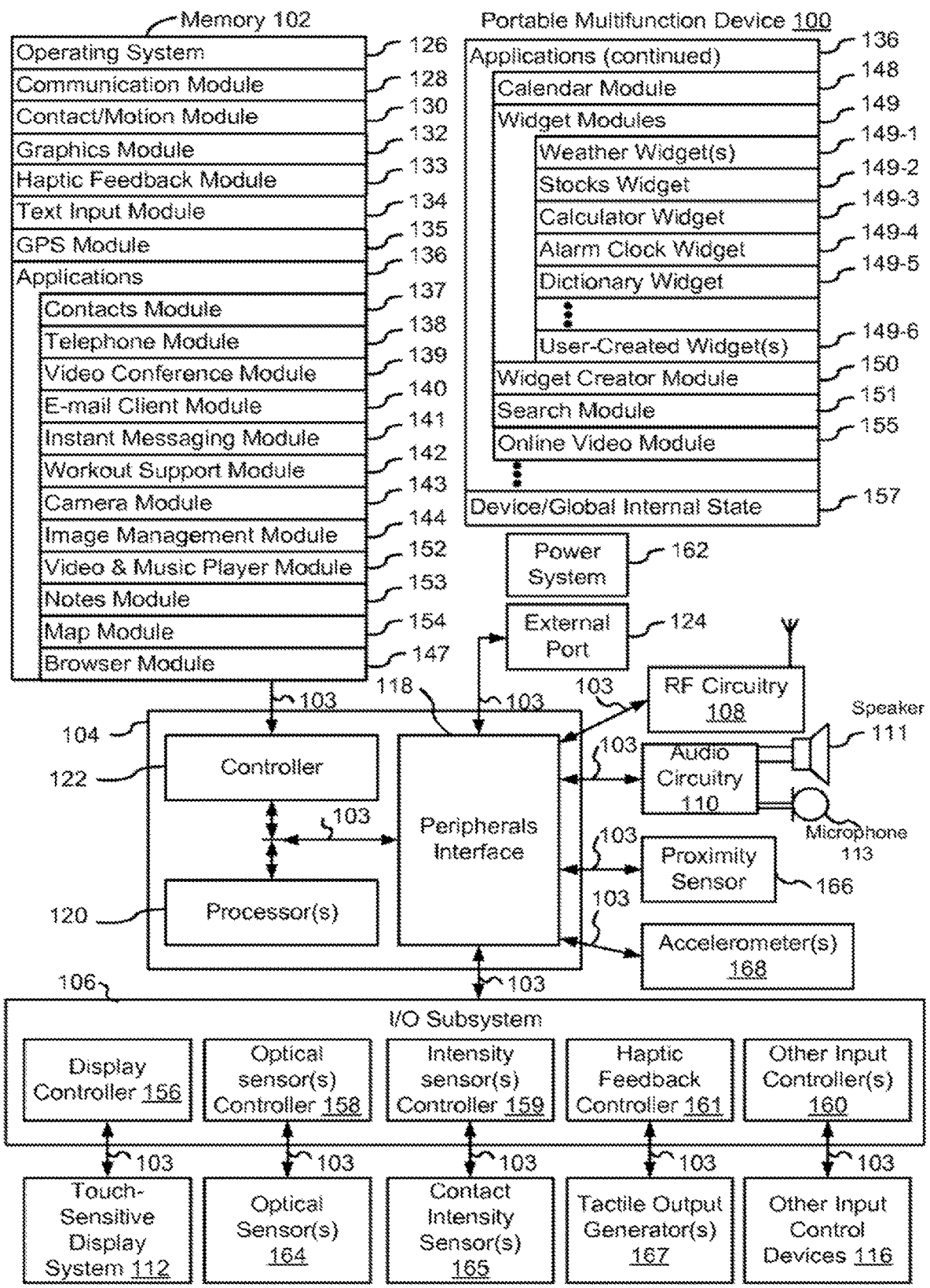
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

The present disclosure relates to aggregating and sharing wellness data. The wellness data can be received by a user device from any number of sensors external or internal to the user device, from a user manually entering the wellness data, or from other users or entities. The user device can securely store the wellness data on the user device and transmit the wellness data to be stored on a remote database. A user of the device can share some or all of the wellness data with friends, relatives, caregivers, healthcare providers, or the like. The user device can further display a user's wellness data in an aggregated view of different types of wellness data. For example, the aggregated view can include a set of partitions, where each partition corresponds to a different type of wellness data. Wellness data of other users can also be viewed if authorizations from those users have been received. In some examples, the partitions can be displayed as having the appearance and associated animations of a stack of cards, where each card corresponds to a different partition (and thus, a different type of wellness data). In this view of stacked cards, each card can display a partial view of a portion of its corresponding wellness data. When the user selects one of the cards, a first expanded view of the selected card including at least one of first reconfigured data, additional data, or an expanded view of the original data can be displayed. A second expanded view of the selected card can be displayed in response to a change in the orientation of the user device. The second expanded view can include at least one of second reconfigured data, additional data, or an expanded view of the original data can be displayed. In one example, the second expanded view can include a graph of the wellness data over time.

Below, FIGS. 1A-1B, 2, 3, 4A-4B, and 5A-5B provide a description of exemplary devices for performing the techniques for sharing wellness data. FIGS. 10-15, 17, 19-20, 22-26, 28-37, 39-44, and 55-66 illustrate exemplary user interfaces for sharing wellness data. The user interfaces in the figures are also used to illustrate the processes described below, including the processes in FIGS. 8, 9, 16, 18, 21, 27, 38A-B, and 45.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device may support a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 may include one or more computer-readable storage mediums. The computer-readable storage mediums may be tangible and non-transitory. Memory 102 may include high-speed random access memory and may also include non-volatile memory, such as one or more magnetic disk storage devices, flash memory devices, or other non-volatile solid-state memory devices. Memory controller 122 may control access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 may be implemented on a single chip, such as chip 104. In some other embodiments, they may be implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data may be retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button may disengage a lock of touch screen 112 or begin a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) may turn power to device 100 on or off. The user may be able to customize a functionality of one or more of the buttons. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output may include graphics, text, icons, video, and any combination thereof (collectively termed "graphics"). In some embodiments, some or all of the visual output may correspond to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 may use LCD (liquid crystal display) technology, LPD (light emitting polymer display) technology, or LED (light emitting diode) technology, although other display technologies may be used in other embodiments. Touch screen 112 and display controller 156 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 may be analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 may have a video resolution in excess of 100 dpi. In some embodiments, the touch screen has a video resolution of approximately 160 dpi. The user may make contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from touch screen 112 or an extension of the touch-sensitive surface formed by the touch screen.

Device 100 also includes power system 162 for powering the various components. Power system 162 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 may also include one or more optical sensors 164. FIG. 1A shows an optical sensor coupled to optical sensor controller 158 in I/O subsystem 106. Optical sensor 164 may include charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 may capture still images or video. In some embodiments, an optical sensor is located on the back of device 100, opposite touch screen display 112 on the front of the device so that the touch screen display may be used as a viewfinder for still and/or video image acquisition. In some embodiments, an optical sensor is located on the front of the device so that the user's image may be obtained for video conferencing while the user views the other video conference participants on the touch screen display. In some embodiments, the position of optical sensor 164 can be changed by the user (e.g., by rotating the lens and the sensor in the device housing) so that a single optical sensor 164 may be used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 may also include one or more proximity sensors 166. FIG. 1A shows proximity sensor 166 coupled to peripherals interface 118. Alternately, proximity sensor 166 may be coupled to input controller 160 in I/O subsystem 106. Proximity sensor 166 may perform as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 may also include one or more accelerometers 168. FIG. 1A shows accelerometer 168 coupled to peripherals interface 118. Alternately, accelerometer 168 may be coupled to an input controller 160 in I/O subsystem 106. Accelerometer 168 may perform as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
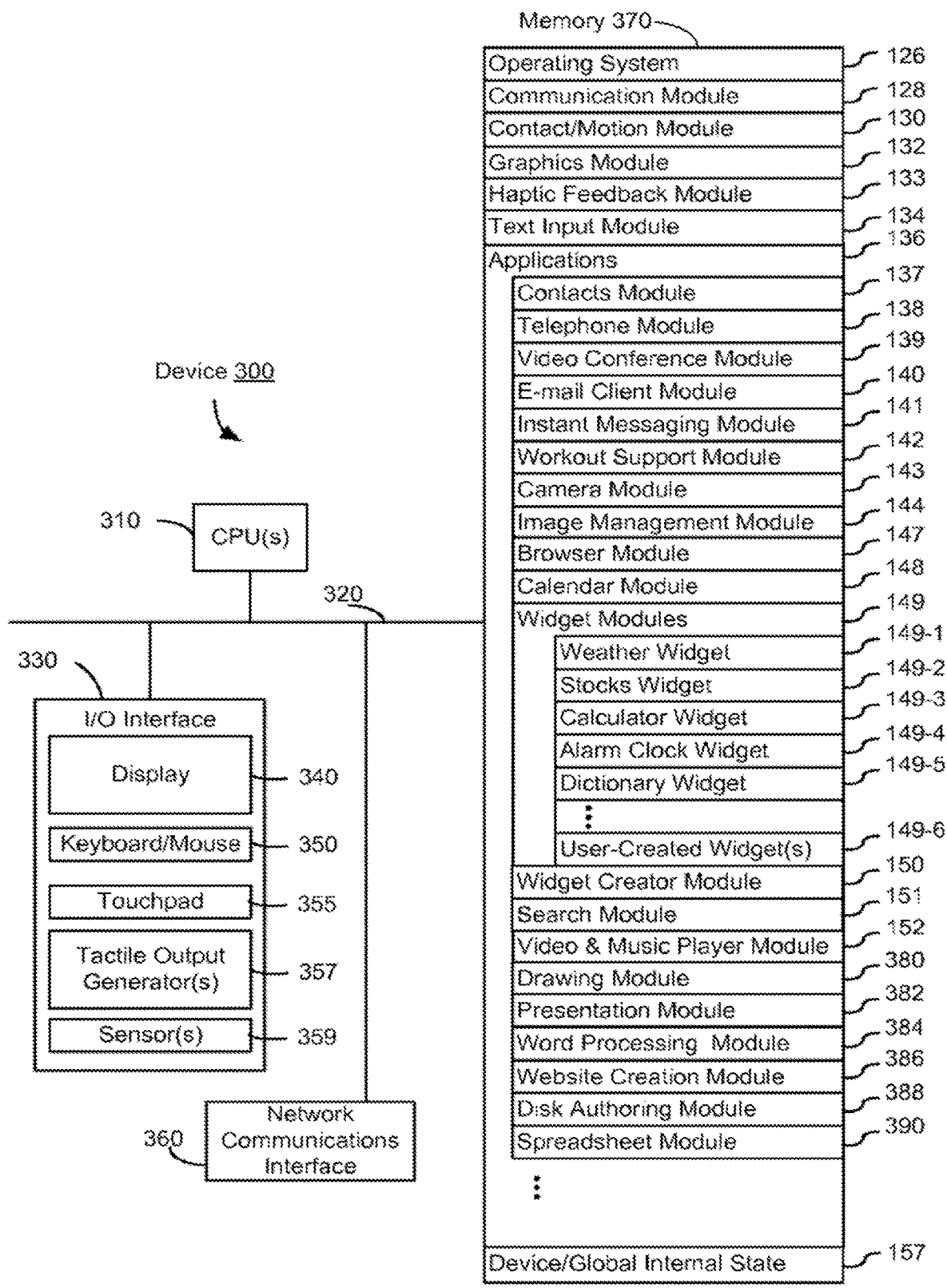
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which may be a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 may include the following modules (or sets of instructions), or a subset or superset thereof:
- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which may include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that may be stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 may be used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 may be used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication may use any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages may include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that may be downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 may be used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 may be used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules may be combined or otherwise rearranged in various embodiments. For example, video player module may be combined with music player module into a single module (e.g., video and music player module 152, FIG. 1A). In some embodiments, memory 102 may store a subset of the modules and data structures identified above. Furthermore, memory 102 may store additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 may be reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
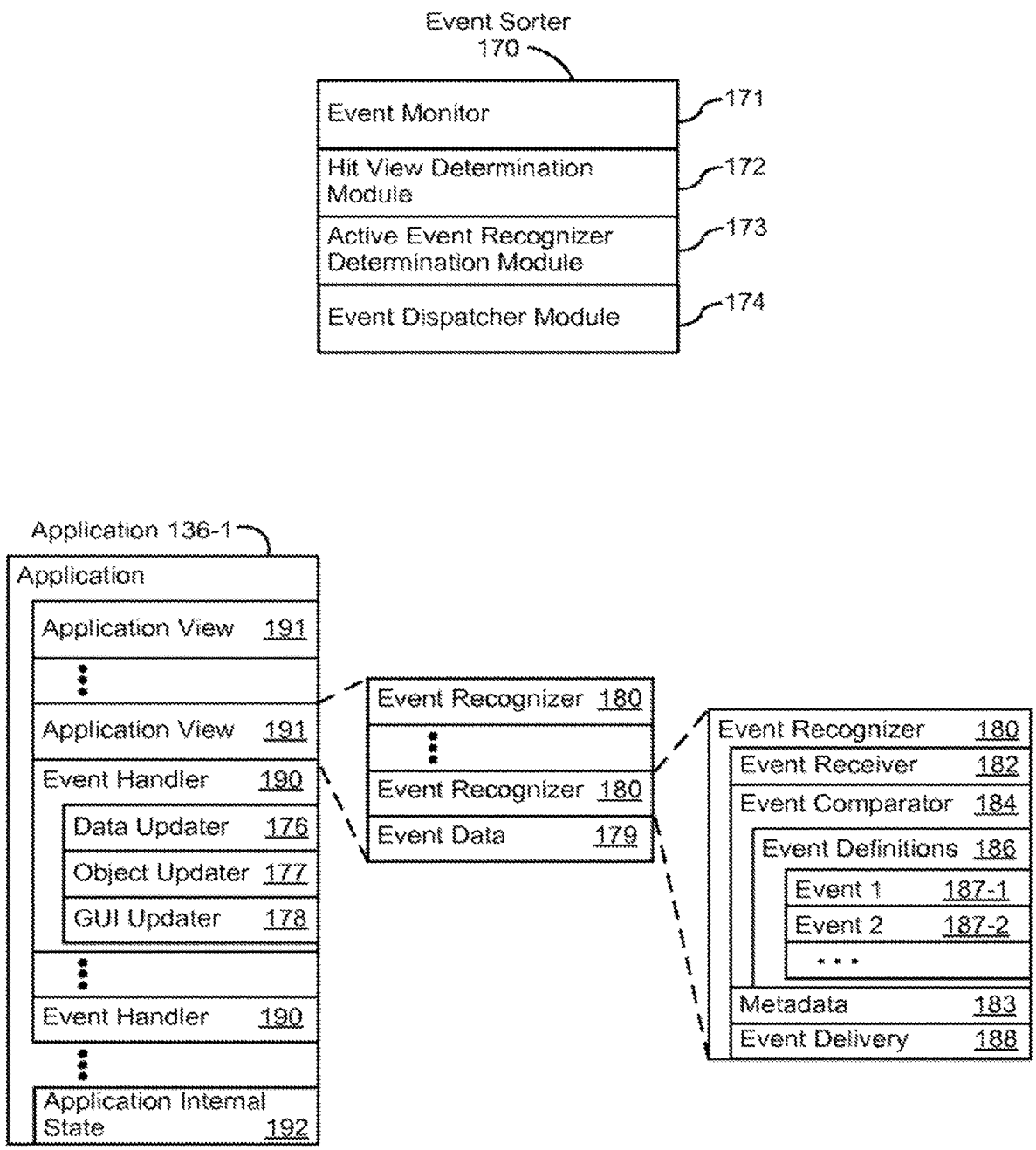
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected may correspond to programmatic levels within a programmatic or view hierarchy of the application. For example, the lowest level view in which a touch is detected may be called the hit view, and the set of events that are recognized as proper inputs may be determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 may utilize or call data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which may include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information may also include speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers may interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
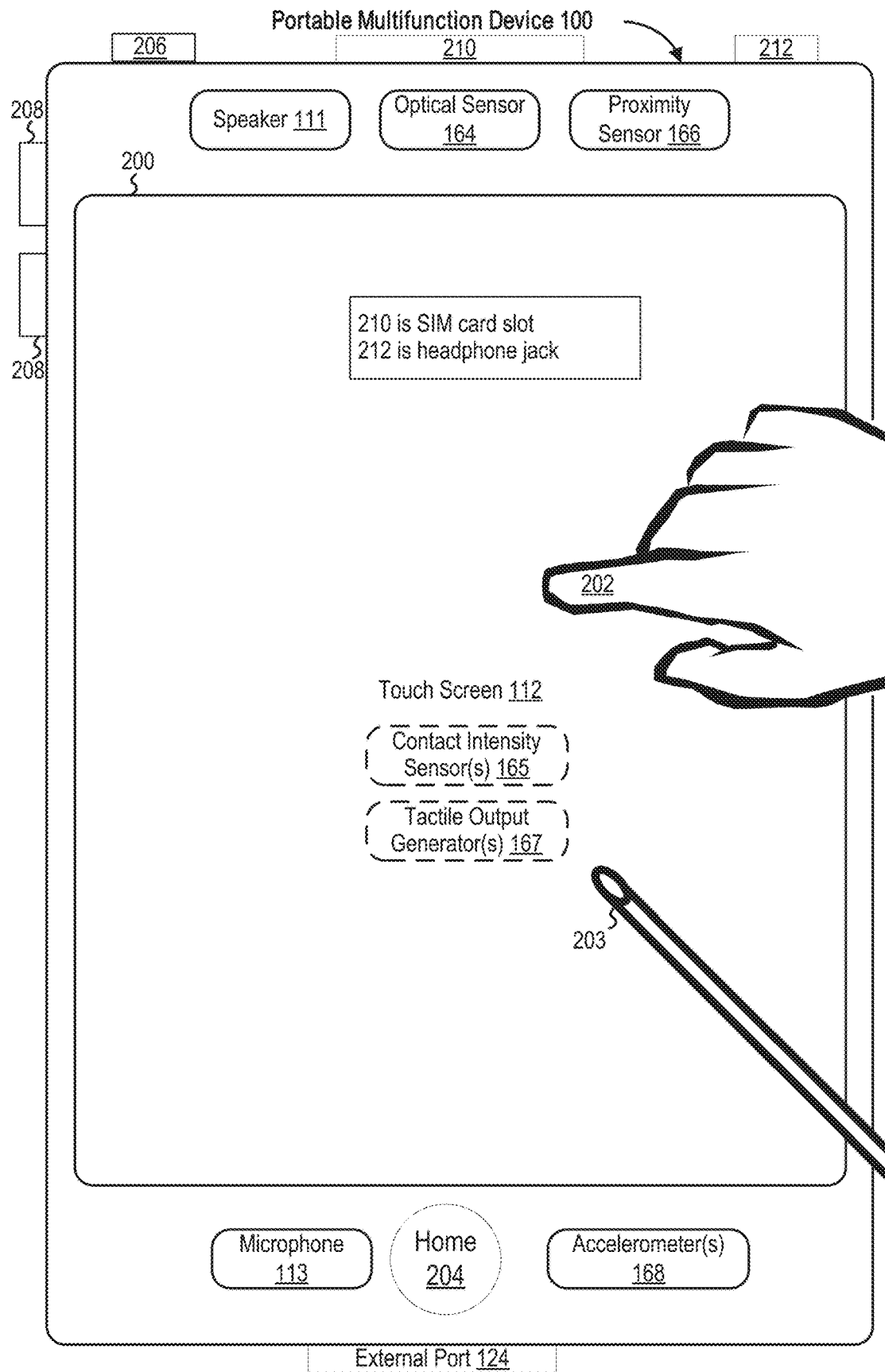
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 may also include one or more physical buttons, such as "home" or menu button 204. As described previously, menu button 204 may be used to navigate to any application 136 in a set of applications that may be executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 may be stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules may be combined or otherwise rearranged in various embodiments. In some embodiments, memory 370 may store a subset of the modules and data structures identified above. Furthermore, memory 370 may store additional modules and data structures not described above.

Attention is now directed towards embodiments of user interfaces that may be implemented on, for example, portable multifunction device 100.

Figure 4A:
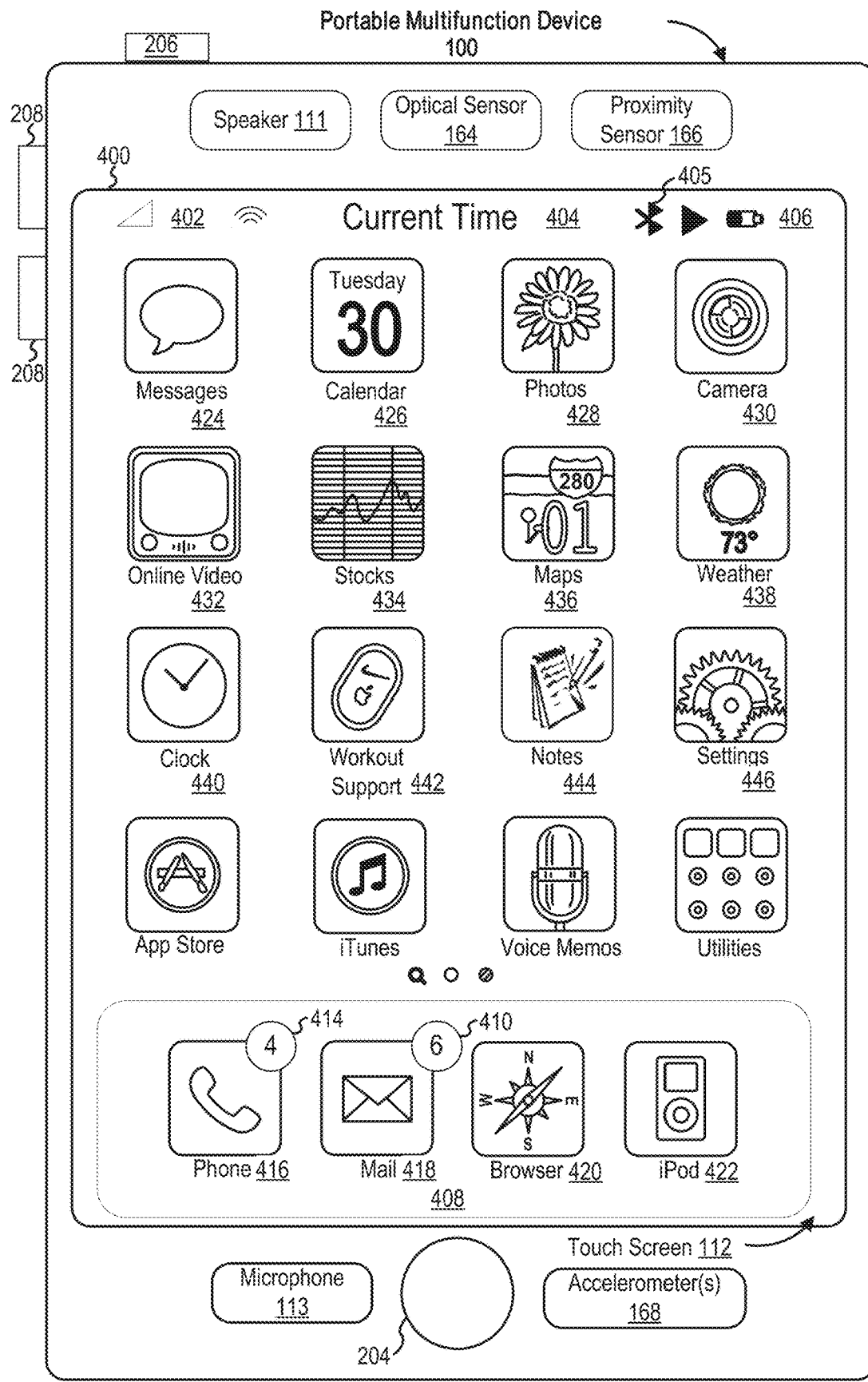
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces may be implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
 Icon 416 for telephone module 138, labeled "Phone," which optionally includes an indicator 414 of the number of missed calls or voicemail messages;
 Icon 418 for e-mail client module 140, labeled "Mail," which optionally includes an indicator 410 of the number of unread e-mails;
 Icon 420 for browser module 147, labeled "Browser;" and
 Icon 422 for video and music player module 152, also referred to as iPod (trademark of Apple Inc.) module 152, labeled "iPod;" and
Icons for other applications, such as:
 Icon 424 for IM module 141, labeled "Messages;"
 Icon 426 for calendar module 148, labeled "Calendar;"

Icon 428 for image management module 144, labeled "Photos;"

Icon 430 for camera module 143, labeled "Camera;"

Icon 432 for online video module 155, labeled "Online Video;"

Icon 434 for stocks widget 149-2, labeled "Stocks;"

Icon 436 for map module 154, labeled "Maps;"

Icon 438 for weather widget 149-1, labeled "Weather;"

Icon 440 for alarm clock widget 149-4, labeled "Clock;"

Icon 442 for workout support module 142, labeled "Workout Support;"

Icon 444 for notes module 153, labeled "Notes;" and

Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 may optionally be labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 357) for detecting intensity of contacts on touch-sensitive surface 451 and/or one or more tactile output generators 359 for generating tactile outputs for a user of device 300.

Although some of the examples which follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
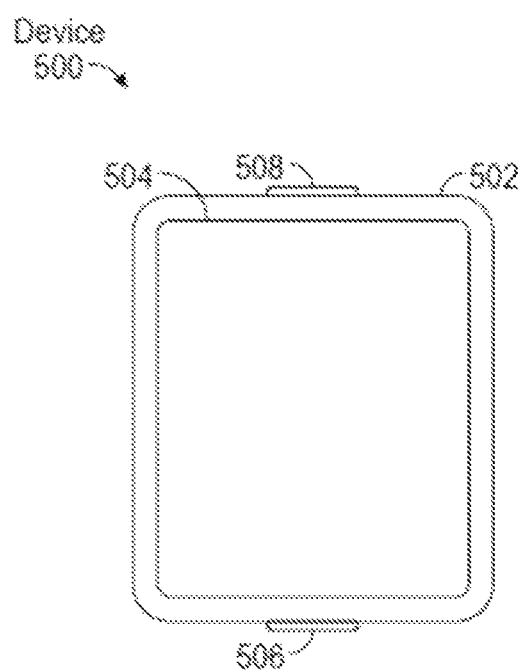
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) may have one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Techniques for detecting and processing touch intensity may be found, for example, in related applications: International Patent Application Serial No. PCT/US2013/040061, titled "Device, Method, and Graphical User Interface for Displaying User Interface Objects Corresponding to an Application," filed May 8, 2013, and International Patent Application Serial No. PCT/US2013/069483, titled "Device, Method, and Graphical User Interface for Transitioning Between Touch Input to Display Output Relationships," filed Nov. 11, 2013, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms may permit device 500 to be worn by a user.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, touch-intensity sensitive component 524. In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 may be a rotatable input device or a depressible and rotatable input device, for example. Input mechanism 508 may be a button, in some examples.

Input mechanism 508 may be a microphone, in some examples. Personal electronic device 500 can include various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can be a non-transitory computer-readable storage medium, for storing computer-executable instructions, which, when executed by one or more computer processors 516, for example, can cause the computer processors to perform the techniques described above, including processes 800, 900, 1600, 1800, 2100, 2700, 3800, and 4500 (FIGS. 8, 9, 16, 18, 21, 27, 38A-B, and 45, respectively). The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that may be displayed on the display screen of devices 100, 300, and/or 500 (FIGS. 1, 3, and 5). For example, an image (e.g., icon), a button, and text (e.g., hyperlink) may each constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds may include a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation) rather than being used to determine whether to perform a first operation or a second operation.

In some embodiments, a portion of a gesture is identified for purposes of determining a characteristic intensity. For example, a touch-sensitive surface may receive a continuous swipe contact transitioning from a start location and reaching an end location, at which point the intensity of the contact increases. In this example, the characteristic intensity of the contact at the end location may be based on only a portion of the continuous swipe contact, and not the entire swipe contact (e.g., only the portion of the swipe contact at the end location). In some embodiments, a smoothing algorithm may be applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface may be characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

System Overview

Figure 6:
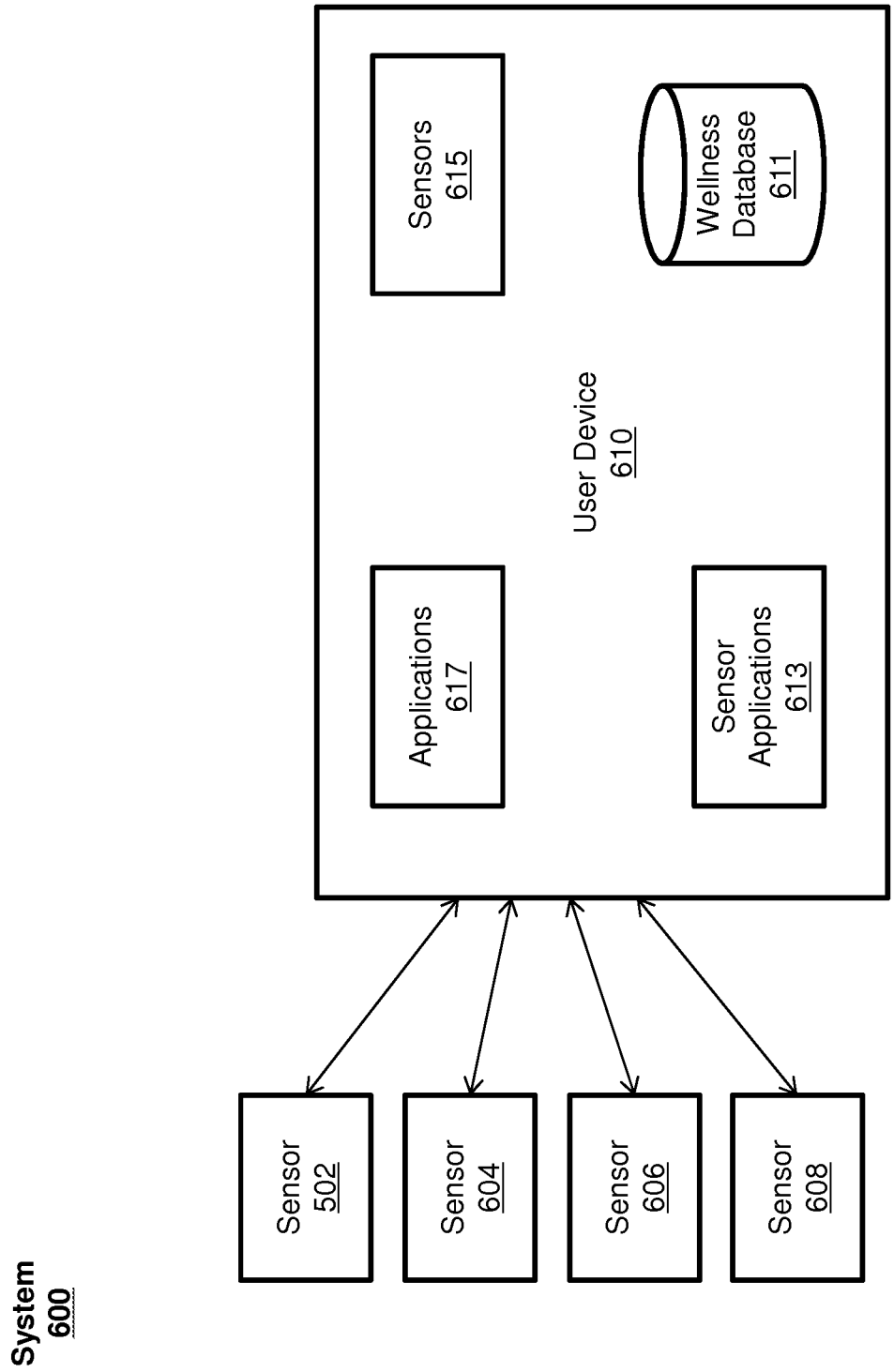
FIG. 6 illustrates a block diagram of an example system for aggregating wellness data according to various examples.

FIG. 6 illustrates an example system 600 for aggregating and sharing wellness data. As mentioned above, wellness data can include, but is not limited to, any type of data associated with a person's health, such as their weight, heart rate, blood pressure, blood glucose level, medication compliance, activity level, or the like. System 600 can be used to collect wellness data associated with a user, store the wellness data, present the wellness data to the user in useful ways, and selectively share the user's wellness data with other users or entities based on permissions set by the user. In addition, in some examples, system 600 can further be used to collect non-wellness data along with wellness data, correlate the non-wellness data with the wellness data, and display the non-wellness data with the wellness data.

System 600 can include one or more user devices 610 including any electronic device, such as a mobile phone, tablet computer, desktop computer, laptop computer, PDA, or the like. In some examples, user device 610 can include a device similar or identical to those shown in FIGS. 1A and 3 and described above. For example, user device 610 can include an operating system and a wellness database 611 for securely storing wellness or non-wellness data along with associated metadata, such as the time the data was recorded, type of data, device used to record the data, user associated with the data, and the like. User device 610 can further include application programming interfaces (APIs) with access controls for storing data in the wellness database 611 and for accessing data stored in the wellness database 611.

User device 610 can be configured to receive wellness or non-wellness data from various sources and can store the received data in the wellness database 611. For example, user device 610 can be configured to receive wellness or non-wellness data from sensors 602, 604, 606, and 608. These sensors can include any type of sensor capable of obtaining wellness data, such as a biometric sensor, activity tracker, or the like. For example, sensors 602, 604, 606, and 608 can include, but are not limited to, a scale, blood pressure cuff, blood glucose monitor, electrocardiogram, step counter, gyroscope, accelerometer, SpO2 sensor, respiration sensor, posture sensor, stress sensor, photoplethysmogram, galvanic skin response sensor, temperature sensor, asthma inhaler, or the like. Sensors 602, 604, 606, and 608 can also include other types of sensors, such as audio sensors, ambient light sensors, electromagnetic sensors, touch sensors, capacitive sensors, and the like, for obtaining non-wellness data, such as situational data, temporal data, personal data, contact data, and the like data. In some examples, each sensor can be a separate device, while, in other examples, any combination of two or more of the sensors can be included within a single device. For example, the gyroscope, accelerometer, photoplethysmogram, galvanic skin response sensor, and temperature sensor can be included within a wearable electronic device, such as a smart watch, while the scale, blood pressure cuff, blood glucose monitor, SpO2 sensor, respiration sensor, posture sensor, stress sensor, and asthma inhaler can each be separate devices. While specific examples are provided, it should be appreciated that other sensors can be used and other combinations of sensors can be combined into a single device.

Sensors 602, 604, 606, and 608 can be used to measure wellness or non-wellness data continuously, intermittently, periodically, or at any other desired frequency or interval of time. For example, sensors 602, 604, 606, and 608 can be used to obtain a single measurement or multiple measurements over a length of time. Sensors 602, 604, 606, and 608 can be configured to measure wellness or non-wellness data at the same intervals of time, or can be configured to measure wellness or non-wellness data at different intervals of time. These intervals may be set by a user or may be a default setting for each sensor. Additionally, sensors 602, 604, 606, 608 can be used to measure wellness or non-wellness data at any time or location desired by the user. Moreover, sensors 602, 604, 606, and 608 can be used with or without the supervision of a healthcare provider. For example, a user can use sensors 602, 604, 606, and 608 to obtain sensor measurements at home without the supervision of a medical professional.

In some examples, user device 610 can include software sensor applications 613 (e.g., third party applications) associated with each of sensors 602, 604, 606, and 608 for interfacing with the sensors to allow user device 610 to receive the wellness or non-wellness data. In these examples, the applications 613 can use the device's APIs to store the wellness or non-wellness data in the wellness database 611 of user device 610. In some examples, the software sensor applications 613 can be Apps and device 610 can be a smart phone, tablet computer, or the like. It should be understood that "third party" can correspond to an entity different than the manufacturer of device 610 and/or the entity that created and/or maintains the operating system of device 610. In these instances, third party applications and their corresponding sensors can communicate and function within the operating system of device 610 according to a predefined device protocol associated with device 610.

The applications 613 can similarly use the device's APIs to access data stored in the wellness database 611. In other examples, user device 610 can be configured to share one or more communication formats with sensors 602, 604, 606, and 608 to allow user device 610 to receive and interpret the wellness or non-wellness data from the sensors. The received data can then be stored in the wellness database 611 of user device 610.

User device 610 can further receive wellness or non-wellness data from its own wellness or non-wellness data sensors 615, such as a GPS sensor, clock, gyroscope, accelerometer, or the like, from a user interacting with user device 610, from another entity, such as a physician, or from other non-sensor sources. For example, using the device's APIs, wellness or non-wellness data can be received from applications 617 on user device 610, such as a clock application, a calendaring application, a gaming application, an application from a healthcare provider, a messaging application, or the like. The wellness or non-wellness data from the applications 617 can originate from a user interacting with the applications, a remote database (e.g., database for a medical website), a healthcare provider institution (e.g., via the institution's App), or the like. In these examples, the usage of the application 617 (e.g., how long you play a video game application, when you play the video game, number of times interacting with a stock application, number of times interacting with a social networking application, length of time interacting with a social networking application, etc.), usage of user device 610 (e.g., length of time on the phone or number of text messages sent as determined from a phone payment application, time spent browsing the Internet as determined from the device's browser, etc.), time spent listening to music as determined from a music or streaming radio application, time spent using a remote application for controlling a television, amount of time or money spent on shopping websites, time spent on pornographic websites (e.g., to identify addictions), weather data from a weather application (e.g., to determine how weather affects a user's health), type of events occurring in the user's life as determined from a calendar (e.g., meetings, birthdays, holidays, etc.), interactions with certain people as determined from a contact list and/or calendar application and/or a messaging application and/or phone of user device 610, or the like, can be received by user device 610 and stored in the wellness database 611.

In some examples, default or user-selected settings can be provided to restrict the access that at least one application (e.g., at least one of applications 613 and 617) on user device 610 has to the wellness database 611 of user device 610 (for both storage and retrieval purposes) and to the sensor data generated by sensors 615 within user device 610 and/or sensor data generated by sensors 602, 604, 606, and 608. For example, an application for tracking a user's running sessions can be granted access to the data generated by the GPS sensor of user device 610, but can be prevented from accessing the user's blood pressure data stored in the wellness database 611. In some examples, an entity other than the owner of user device 610 can set the authorization settings for various applications on user device 610. For example, the manufacturer of user device 610 and/or the entity that created and/or maintains the operating system of user device 610 can evaluate the applications to determine if they should be given access to the user's wellness data and/or sensor data generated or received by user device 610. In some examples, these settings can be overridden by the user.

User device 610 can further include a display for displaying the stored wellness data or non-wellness data. A more detailed description of the interface of the display of user device 610 is described below with respect to FIGS. 10-15, 17, 19-20, 22-26, 28-37, 39-44, 55-62, and 64-66.

Figure 7:
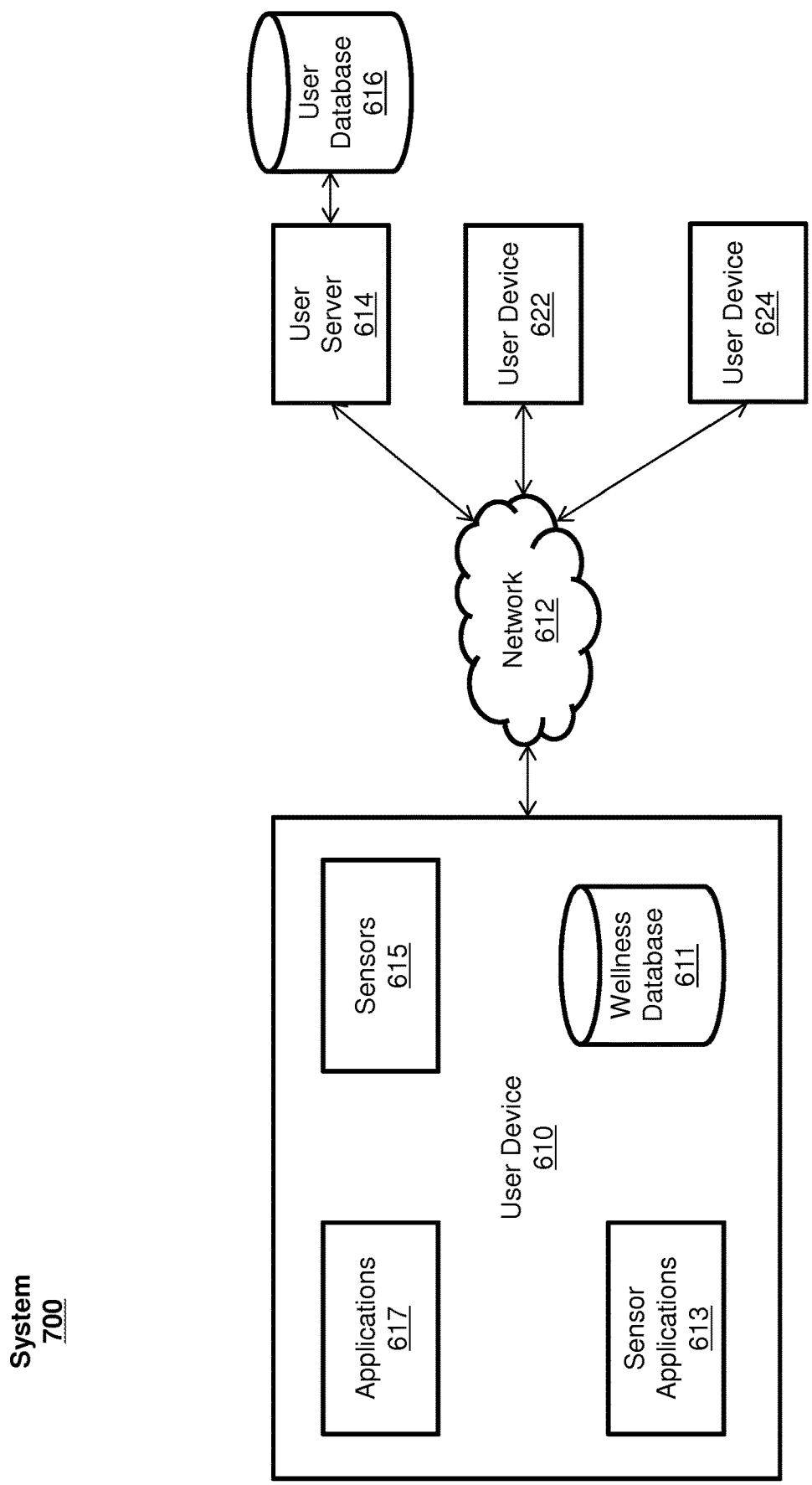
FIG. 7 illustrates a block diagram of an example system for sharing wellness data according to various examples.

FIG. 7 illustrates system 700 for sharing user wellness data. Referring to FIG. 7, user server 614 can be communicatively coupled to user device 610 via network 612, which can include the Internet, an intranet, or any other wired or wireless public or private network. User device 610 can be configured to securely transmit the aggregated wellness or non-wellness data and associated metadata stored on the device to user server 614 for storage in user database 616. In some examples, the wellness or non-wellness data and associated metadata can be transmitted to user server 614 for storage in user database 616 in response to an explicit request for such a transfer by the user of device 610, while, in other examples, the wellness or non-wellness data can be synced with the data in user database 616 continuously, periodically, intermittently, or at any desired frequency. In yet other examples, the user's wellness or non-wellness data can be stored only on user device 610 and may not be stored in an external database.

In some examples, user server 614 and user database 616 can be configured to securely store a user's wellness or non-wellness data using a public/private key system that only allows the owner of the wellness or non-wellness data to decrypt the data. Additionally, the wellness or non-wellness data stored in user database 616 can be stored anonymously (e.g., without identifying and/or personal information about the user, such as a legal name, username, time and location data, or the like). In this way, other users, hackers, and the owner/operator of user database 616 cannot determine the identity of the user associated with the data stored in database 616. In some examples, a user can access their wellness or non-wellness data stored in user database 616 from a user device that is different than the one used to upload the wellness or non-wellness data to user server 614. In these instances, the user can be required to provide login credentials to access their wellness or non-wellness data. User server 614 can be configured to perform the authorization process to restrict access to the data within user database 616.

System 700 can further include any number of other user devices 622 and 624 coupled to network 612. In some examples, user devices 622 and 624 can be operated by the same user as user device 610. In these instances, the user can access their wellness or non-wellness data stored in user database 616 by providing user server 614 with the appropriate credentials. In some examples, wellness and non-wellness data can be synced between user database 616 and one or more of user device 610, 622, and 624. In other examples, the user of user devices 622 and 624 can be a person that is different than the user of user device 610. In these examples, the users of devices 622 and 624 cannot access the wellness or non-wellness data of the user of user device 610 without the authorization of the user of user device 610. If authorization is given, wellness or non-wellness data can be shared with the users of user devices 622 and 624. The sharing of this data will be discussed in greater detail below with respect to FIGS. 7-8.

In some examples, any of the above described sources of wellness or non-wellness data can be configured to measure, generate, or receive wellness or non-wellness data continuously, intermittently, periodically, or at any other desired frequency or interval of time. As such, the wellness or non-wellness data can similarly be stored or updated in wellness database 611 or user database 616 continuously, intermittently, periodically, or at any other desired frequency or interval of time. The frequencies and intervals of time used for measuring, generating, receiving, or storing wellness or non-wellness can be the same or they can be different. Additionally, these frequencies and intervals can be default values or they can be set by a user to provide the user with wellness or non-wellness data that has been updated within a desired length of time.

While not shown, it should be appreciated that many other user devices can be coupled to user server 614 through network 612 to collect and store wellness or non-wellness data for other users in a manner similar to that described above.

User Database

As discussed above, a user's wellness or non-wellness data can be stored in user database 616 and can be shared with other users with the owning user's authorization. The other users can be any type of user, such as a friend, family member, caregiver, physician, social media provider, or the like. Different types and levels of authorization can be granted for the wellness or non-wellness data contained in wellness database 616.

Figure 8:
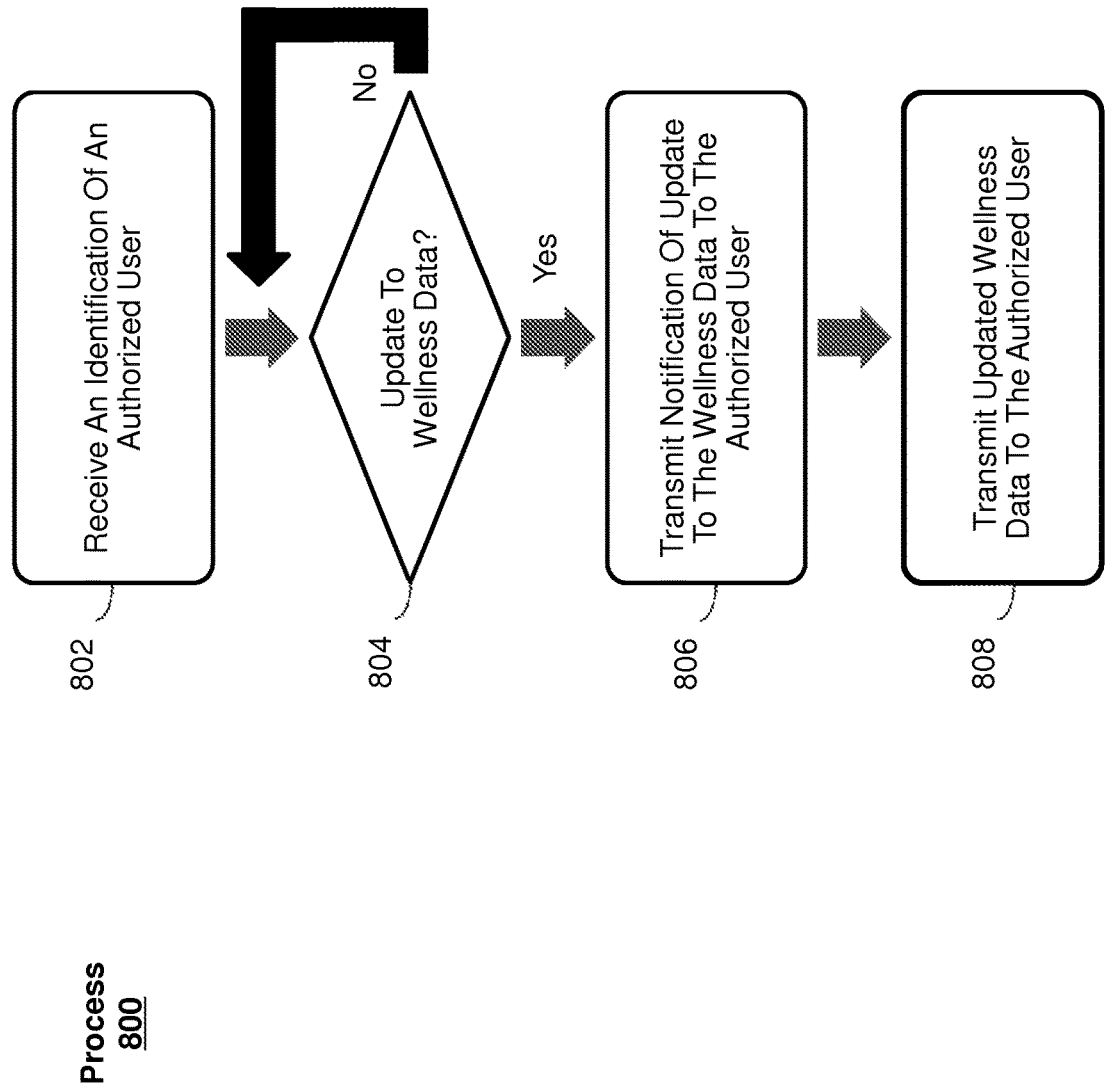
FIG. 8 illustrates an example process for authorizing and pushing wellness data to authorized other users according to various examples.

In some examples, the shared wellness or non-wellness data can be pushed to the user device (e.g., user device 622 or 624) of the authorized other user. FIG. 8 illustrates an example process 800 for authorizing and pushing wellness or non-wellness data to authorized other users. At block 802, an identification of an authorized other user can be received. This can be received by a user device (e.g., user device 610) from the user associated with the shared wellness or non-wellness data. The identification can include a username, legal name, contact information, or any other identifier or credential for the other user, along with a level of access, such as access to all of the wellness or non-wellness data or a subset of the wellness or non-wellness data. In some examples, the authorized other user can be grouped into categories of users (e.g., family, friends, other, etc.), where each category is associated with a particular set of wellness data types that those authorized other users are allowed to view. For example, users in the family category can be allowed to view all types of wellness data, while users in the friend category can only view activity data.

At block 804, the user's wellness or non-wellness data can be monitored by the user's device to determine if any updates to the data have been made. If no update has been made, the process can repeat block 804. If, however, an addition or change to the user's wellness or non-wellness data has been identified, the process can proceed to block 806. In some examples, any change to the user's wellness or non-wellness data can cause process 800 to proceed to block 806, while, in other examples, only changes to certain types of the user's wellness or non-wellness data can cause process 800 to proceed to block 806.

At block 806, a notification can be transmitted to one or more authorized other users. For example, a notification can be transmitted from the user's device (e.g., user device 610) to the device of the authorized other user (e.g., user device 622 or 624). The notification can include a message indicating that an update has been made to the user's wellness or non-wellness data. The process can then proceed to block 808.

At block 808, the updated wellness or non-wellness data can be transmitted to the authorized other user. For example, the updated wellness or non-wellness data can be transmitted from the user's device (e.g., user device 610) to the device of the authorized other user (e.g., user device 622 or 624). In some examples, this data can only be transmitted if the authorized other user indicated a desire to view the updated wellness or non-wellness data, while, in other examples, the updated wellness or non-wellness data can be transmitted to the user device of the authorized other user without receiving a request from the authorized other user to view the data.

The pushing of wellness or non-wellness data performed using process 800 can be useful in situations in which a user wants to keep a caregiver or family member (or other user) updated with his/her wellness or non-wellness data. For instance, an elderly parent can grant authorization to push his/her wellness or non-wellness data to a child to allow the child to easily monitor the elderly user's health or medication compliance without having to constantly request this information from the parent.

Figure 9:
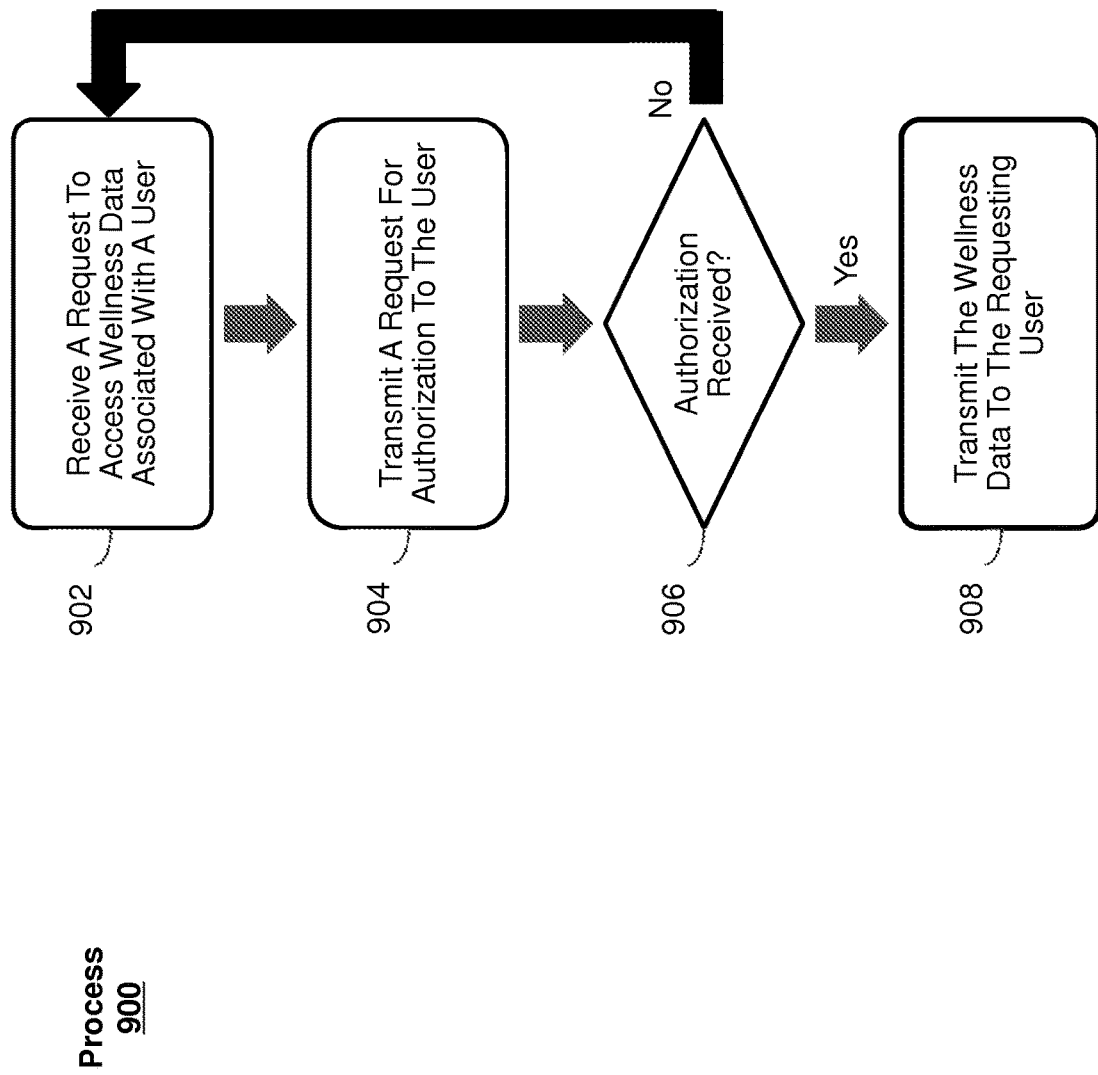
FIG. 9 illustrates an example process for authorizing users to pull wellness data according to various examples.

In other examples, a user's wellness or non-wellness data can be shared with other users by allowing other users to pull the wellness or non-wellness data. FIG. 9 illustrates an example process 900 for authorizing other users to pull wellness or non-wellness data. At block 902, a request to access a particular user's wellness or non-wellness data can be received. The request can identify the user associated with the requested wellness or non-wellness data and, optionally, the portion of the wellness or non-wellness data to be accessed. The identification can include a username, legal name, contact information, or any other identifier or credential for the user. The request can be received by a user device (e.g., user device 610) of the user associated with the requested data from a user device (e.g., user device 622 or 624) of the requesting user.

At block 904, a request for authorization can be transmitted to the user associated with the requested wellness or non-wellness data. In some examples, the request can be transmitted from the user device (e.g., user device 622 or 624) of the requesting user to the user device (e.g., user device 610) of the user associated with the requested data. The request can then be displayed to the user associated with the requested data by the user's device (e.g., user device 610).

At block 906, it can be determined if an authorization has been received from the user associated with the requested wellness or non-wellness data. The authorization can be received in any manner. For example, a prompt can be displayed to the user associated with the requested data on their user device 610. If authorization is denied, the process can return to block 902. If, however, authorization is granted, the process can proceed to block 908.

At block 908, the requested wellness or non-wellness data can be transmitted to the entity that requested access to the wellness or non-wellness data at block 902. The requested wellness or non-wellness data can be transmitted from the user's device (e.g., user device 610) to the requesting entity's device (e.g., user device 622 or 624).

In some examples, if authorization to access a user's wellness or non-wellness data is granted before a request is made at block 902, process 900 can proceed from block 902 to block 908 without performing blocks 904 or 906. For example, if a parent grants access to their wellness or non-wellness data to their child, a request by the child for the parent's wellness or non-wellness data can be received at block 902 and the requested wellness or non-wellness data can be transmitted to the child at block 908 without any intervening action by the parent.

The pulling of wellness or non-wellness data using process 900 can be useful in situations where an authorized other user does not want to be constantly updated with updates to a user's wellness or non-wellness data, but would like occasional access to the data. For example, a physician may want access to a patient's medical records and wellness or non-wellness data just prior to meeting with the patient. In this situation, the physician can request the patient's wellness or non-wellness data and can either receive the requested data or cause a request to be sent to the user device 610 of the patient. In response to receiving an authorization from the patient, the requested data can be sent from user device 610 to the physician's computing device (e.g., user device 622 or 624). In some examples, the received wellness or non-wellness data can be added to an electronic medical record (EMR) associated with the user.

In some examples, whether using a push or pull sharing model, the wellness or non-wellness data of a user may not be permanently stored on the user device of authorized other users. In this way, authorization to these other users can be revoked, causing the user's wellness data to be inaccessible by the formerly authorized other users. Additionally, in some examples, reports detailing or summarizing a user's wellness or non-wellness data can be generated. These reports can then be transmitted via email, secure transfer, or the like, to any desired recipient. In yet other examples, user device 610 can be configured to communicate some or all of the user's wellness or non-wellness data, such as medical insurance information, blood type, medical history, etc., to medical personnel using near field communication or another communication protocol. This can be useful when checking in to a hospital or during medical emergencies when relevant medical data is needed.

Aggregated Data View

As discussed above, user device 610 can be configured to aggregate wellness or non-wellness data associated with a user that was received from the user, from one or more sensors 602, 604, 606, and 608, or from a non-sensor source. User device 610 can also be configured to display the user's aggregated wellness or non-wellness data in various ways using various interfaces.

Figure 10:
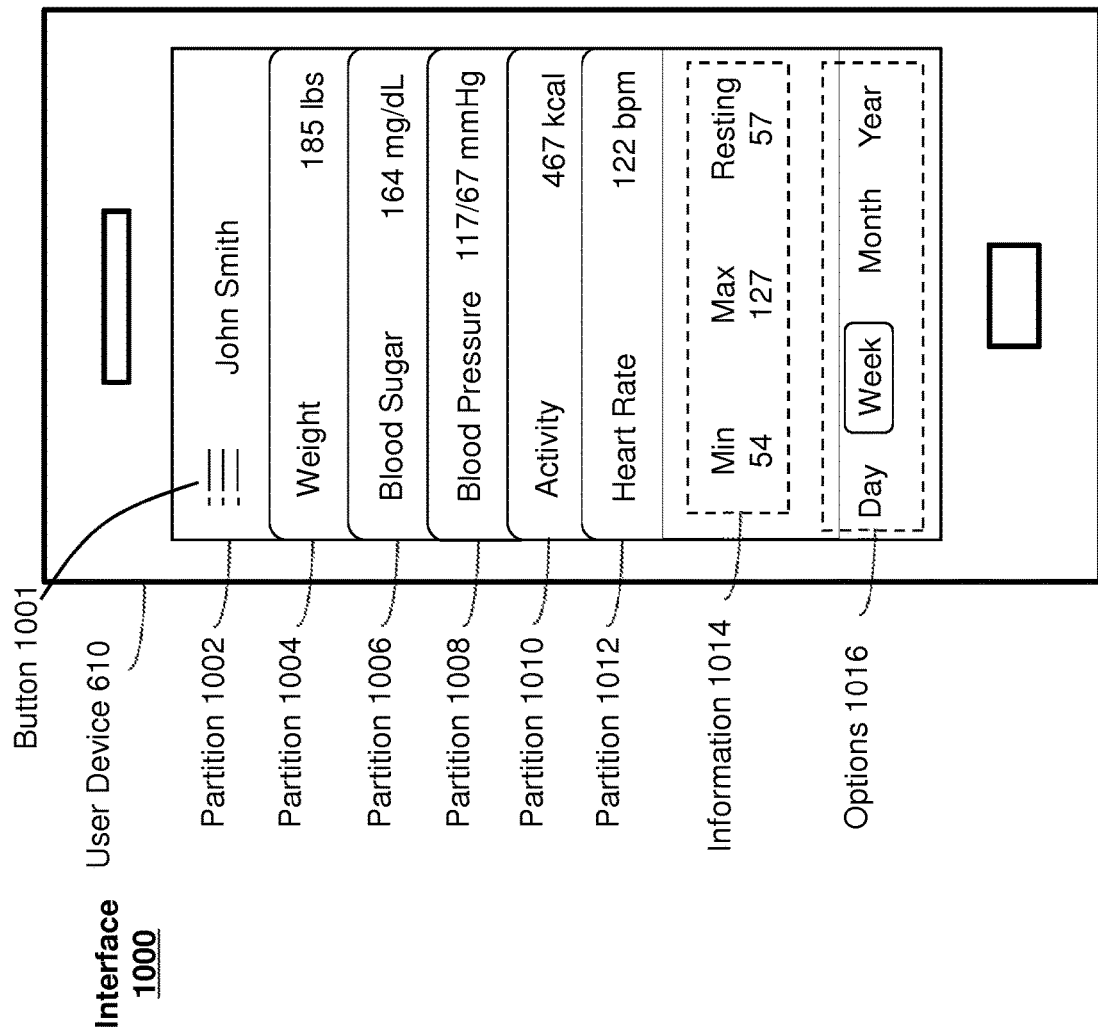
FIG. 10 illustrate example interfaces for displaying aggregated wellness data according to various examples.

FIG. 10 illustrates one example interface 1000 that can be used by user device 610 to display a user's aggregated wellness or non-wellness data. Interface 1000 can include any number of partitions 1002, 1004, 1006, 1008, 1010, and 1012, each containing a different type of wellness data associated with the user. In the aggregated view of FIG. 10, the partitions can be used to display a partial view of a portion of the different types of wellness data. In the examples shown in FIGS. 10-15, 17, and 19-20, the partitions are illustrated as having the appearance and associated animations of a stack of cards, where each card corresponds to a different partition (and thus, a different type of wellness data). It should be appreciated, however, that the partitions can be displayed in any other desired manner.

Interface 1000 can include a first partition 1002 displayed at the top of the interface that can include an identifier (e.g., name) of the user. As shown, the name "John Smith" of the user of user device 610 is displayed on partition 1002. Interface 1000 can further include button 1001 for viewing wellness data associated with other users. This feature is described in greater detail below with respect to FIGS. 15 and 16.

Interface 1000 can further include another partition 1004 displayed adjacent to partition 1002 such that it appears to be overlapping partition 1002 like a stacked card. This partition can include an indication of the type of wellness data contained on the partition as well as a partial view (e.g., summary, example, or the like) of a portion the partition's wellness data. Specifically, partition 1004 includes the word "Weight" to indicate that the partition contains weight data associated with the user "John Smith." Partition 1004 can further include the most recent weight "185 lbs" of "John Smith."

Interface 1000 can further include another partition 1006 displayed adjacent to partition 1004 such that it appears to be overlapping partition 1004 like a stacked card. This partition can include an indication of the type of wellness data contained on the partition as well as a partial view (e.g., summary, example, or the like) of a portion the partition's wellness data. Specifically, partition 1006 includes the words "Blood Sugar" to indicate that the partition contains blood sugar data associated with the user "John Smith." Partition 1006 can further include the most recent blood sugar level "164 mg/dL" of "John Smith."

Interface 1000 can further include another partition 1008 displayed adjacent to partition 1006 such that it appears to be overlapping partition 1006 like a stacked card. This partition can include an indication of the type of wellness data contained on the partition as well as a partial view (e.g., summary, example, or the like) of a portion the partition's wellness data. Specifically, partition 1008 includes the words "Blood Pressure" to indicate that the partition contains blood pressure data associated with the user "John Smith." Partition 1008 can further include the most recent blood pressure measurement "117/67 mmHg" of "John Smith."

Interface 1000 can further include another partition 1010 displayed adjacent to partition 1008 such that it appears to be overlapping partition 1008 like a stacked card. This partition can include an indication of the type of wellness data contained on the partition as well as a partial view (e.g., summary, example, or the like) of a portion of the partition's wellness data. Specifically, partition 1010 includes the word "Activity" to indicate that the partition contains activity data (e.g., calories burned) associated with the user "John Smith." Partition 1010 can further include the current daily number of calories burned "467 kcal" by "John Smith."

Interface 1000 can further include another partition 1012 displayed adjacent to partition 1010 such that it appears to be overlapping partition 1010 like a stacked card. This partition can include an indication of the type of wellness data contained on the partition as well as a partial view (e.g., summary, example, or the like) of a portion of the partition's wellness data. Specifically, partition 1012 includes the words "Heart Rate" to indicate that the partition contains heart rate data associated with the user "John Smith." Partition 1012 can further include the most recent heart rate measurement "122 bpm" of "John Smith." Additionally, since partition 1012 is at the top of the stack of partitions, additional information 1014 and/or options 1016 can be displayed on the face of the partition. In the illustrated example, the additional information includes the minimum, maximum, and resting heart rate of "John Smith" over the span of a week, which was selected using options 1016.

The ordering of some or all of the partitions can be static or dynamic. For example, partition 1002 containing the user's name can remain at the top of the display, while the remaining partitions can be ordered based on the time of day, how recently the wellness data associated with the partition is updated, the frequency that the wellness data associated with the partition is updated, whether a notable event is approaching (e.g., medication that should be taken, a sensor measurement that should be performed, etc.), or the like. The ordering can also be manually changed by the user. If interface 1000 includes more partitions than can be displayed on a single screen, a vertical scrolling can be performed to display the remaining partitions. Alternatively, a 3D scrolling of the partitions may be performed to give the appearance of flipping through a stack of cards.

While specific example partition types have been provided above, it should be appreciated that partitions containing different types of wellness data can be included within interface 1000. Additionally, users can generate customized partitions that can be used to display any desired type of user-entered data. For example, a partition can be created to track the medication compliance of a user. The user can enter the time, amount, and type of medicine taken and this data can be displayed on the created partition. Other custom partitions for different wellness data types, such as nutrition, sleep, smoking, or the like can also be generated.

Additionally, while specific examples of partial views (e.g., summary, example, or the like) of a portion of the partitions' wellness data have been provided above, it should be appreciated that the partial views can summarize or provide examples of the wellness data in different ways. For example, rather than display the most recent value of a particular wellness data type, a mean, mode, median, another single data point, or the like of the wellness data over all or a portion of time (e.g., a week, month, year, etc.) can be displayed on the partitions in the aggregated view. Alternatively, in other examples, a current and average value can be displayed on the partitions in the aggregated view. In yet other examples, the partitions in the aggregated view can include a display of a current value and a goal value for the type of wellness data.

The partitions 1002, 1004, 1006, 1008, 1010, and 1012 can be selected to display an expanded view of the partition containing reconfigured data, additional data, or an enlarged view of the original data contained on the partition. For example, a user can select a partition by tapping on the desired partition displayed on a touch sensitive display, can highlight and click on the partition using a mouse or other input device, or select the desired partition using any other input means. In response to a selection of a partition, user device 610 can hide the contents of the other partitions and display the selected partition on all or most of the display of user device 610.

Figure 11:
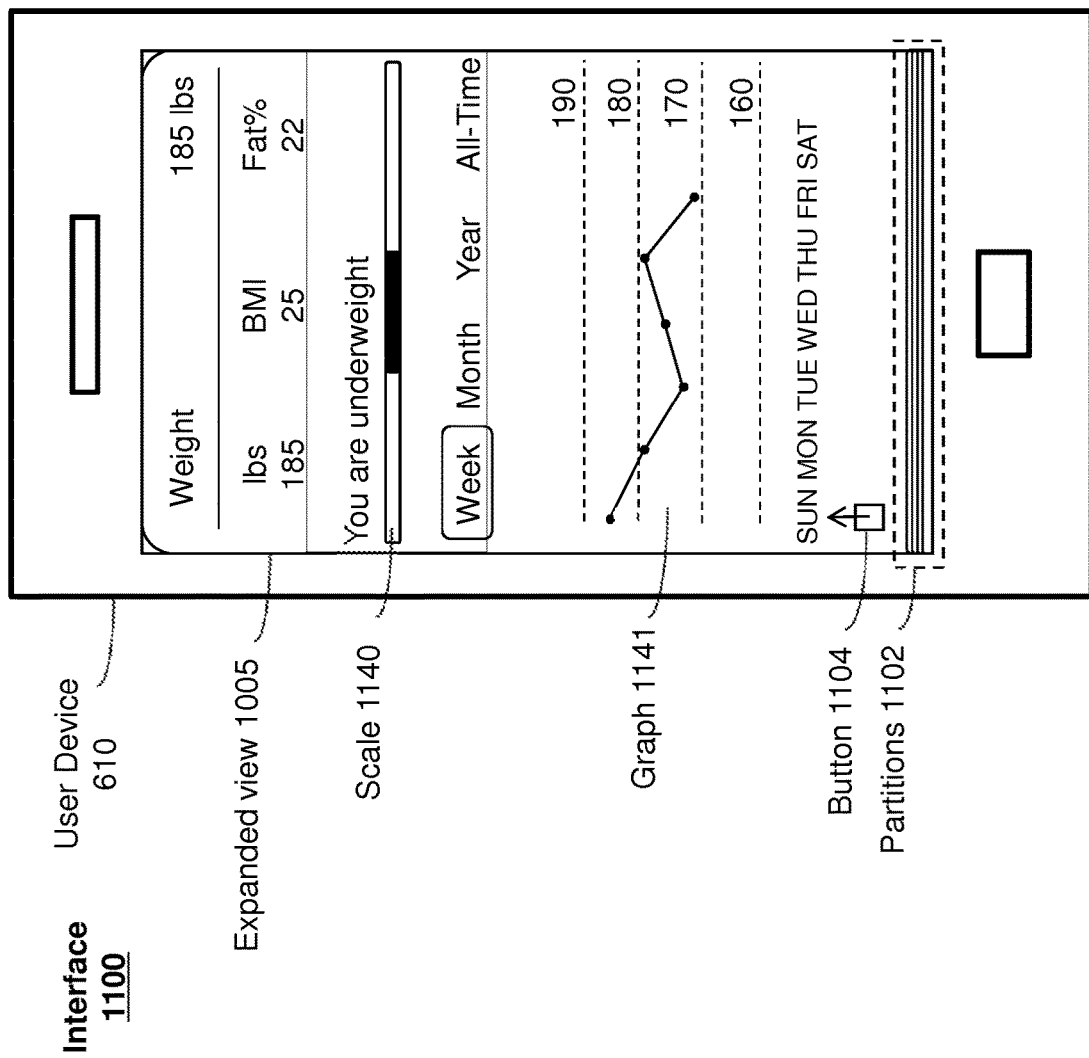
FIG. 11 illustrates example interfaces for displaying aggregated wellness data according to various examples.

For example, FIG. 11 illustrates an example interface 1100 that can be displayed in response to a user selecting partition 1004 in interface 1000. In interface 1100, expanded view 1005 of partition 1004 can be displayed prominently within the display of user device 610, while the remaining partitions can be animated as being collapsed off the display into the stack of partitions 1102 displayed at the bottom of the display. In the illustrated example, expanded view 1005 can include additional weight-related data, such as the user's weight, body mass index (BMI), and fat percentage, that were not shown in interface 1000. Expanded view 1005 can further include summaries of the user's weight data, such as a sliding scale 1140 indicating the user's weight relative to a range of weights and a graph 1141 tracking the user's weight throughout the day, week, month, or year. Interface 1100 can further include button 1104 that can cause user device 610 to display options for sharing some or all of their wellness data using any desired communication medium, such as text message, email, social media provider, or the like. In these examples, the wellness data can be encrypted and sent from the user device 610 directly to the user device of the recipient (rather than from user server 614), where the wellness data can be decrypted. To return to the aggregated view of partitions shown in interface 1000, the user can select (e.g., tap, click, or otherwise select) the stack of partitions 1102. It should be appreciated that the contents of interface 1100 and expanded view 1005 are provided as examples, and that expanded view 1005 can instead include any type or summary of weight-related data.

Figure 12:
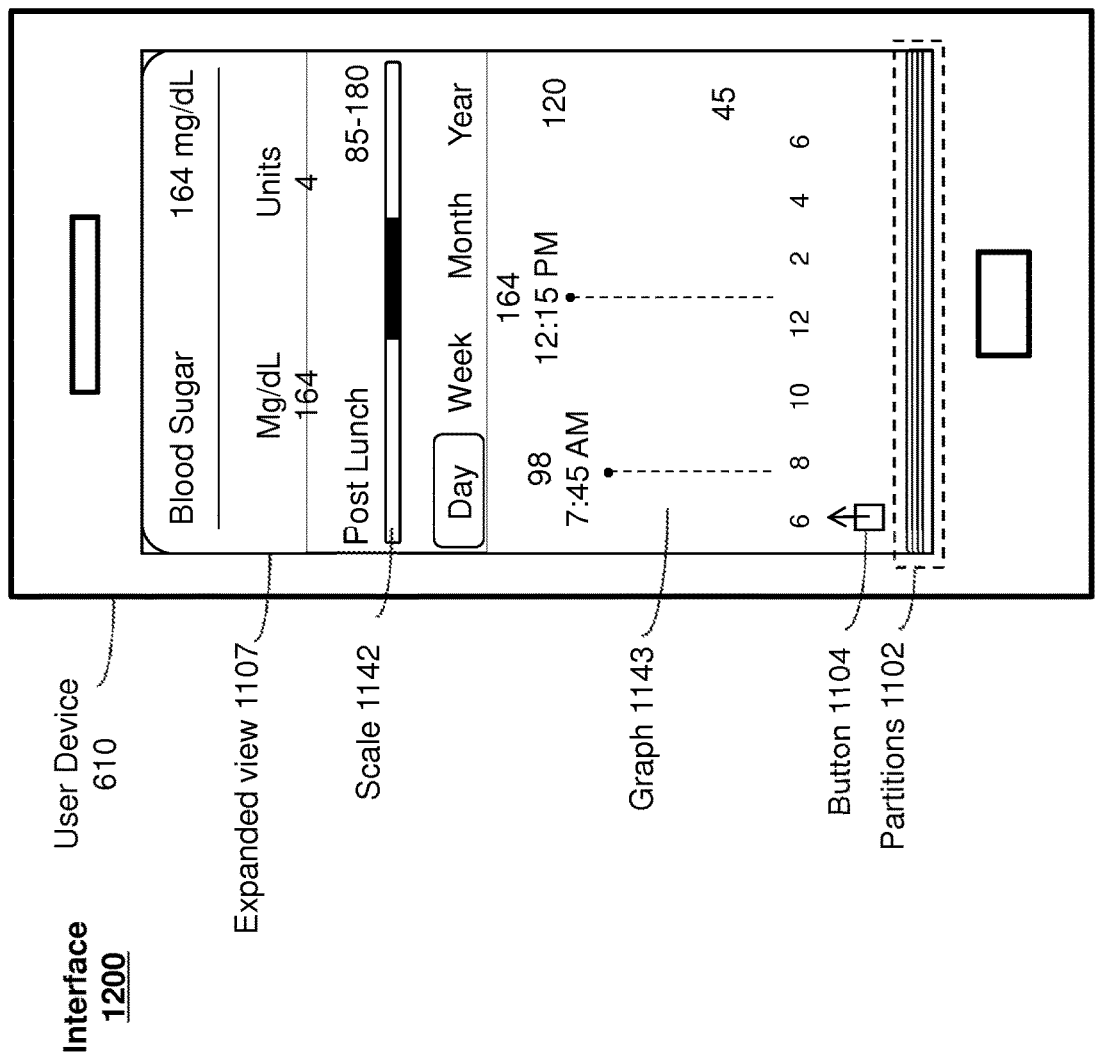
FIG. 12 illustrates example interfaces for displaying aggregated wellness data according to various examples.

FIG. 12 illustrates an example interface 1200 that can be displayed in response to a user selecting partition 1006 in interface 1000. In interface 1200, expanded view 1007 of partition 1006 can be displayed prominently within the display of user device 610, while the remaining partitions can be animated as being collapsed off the display into the stack of partitions 1102 displayed at the bottom of the display. In the illustrated example, expanded view 1007 can include additional blood sugar-related data, such as the user's blood sugar and units that were not shown in interface 1000. Expanded view 1007 can further include summaries of the user's blood sugar data, such as a sliding scale 1142 indicating the user's blood sugar after a meal relative to a range of typical blood sugar level and a graph 1143 tracking the user's blood sugar throughout the day, week, month, or year. Interface 1200 can also include button 1104, described above. To return to the aggregated view of partitions shown in interface 1000, the user can select (e.g., tap, click, or otherwise select) the stack of partitions 1102. It should be appreciated that the contents of interface 1200 and expanded view 1007 are provided as examples, and that expanded view 1007 can instead include any type or summary of blood sugar-related data.

Figure 13:
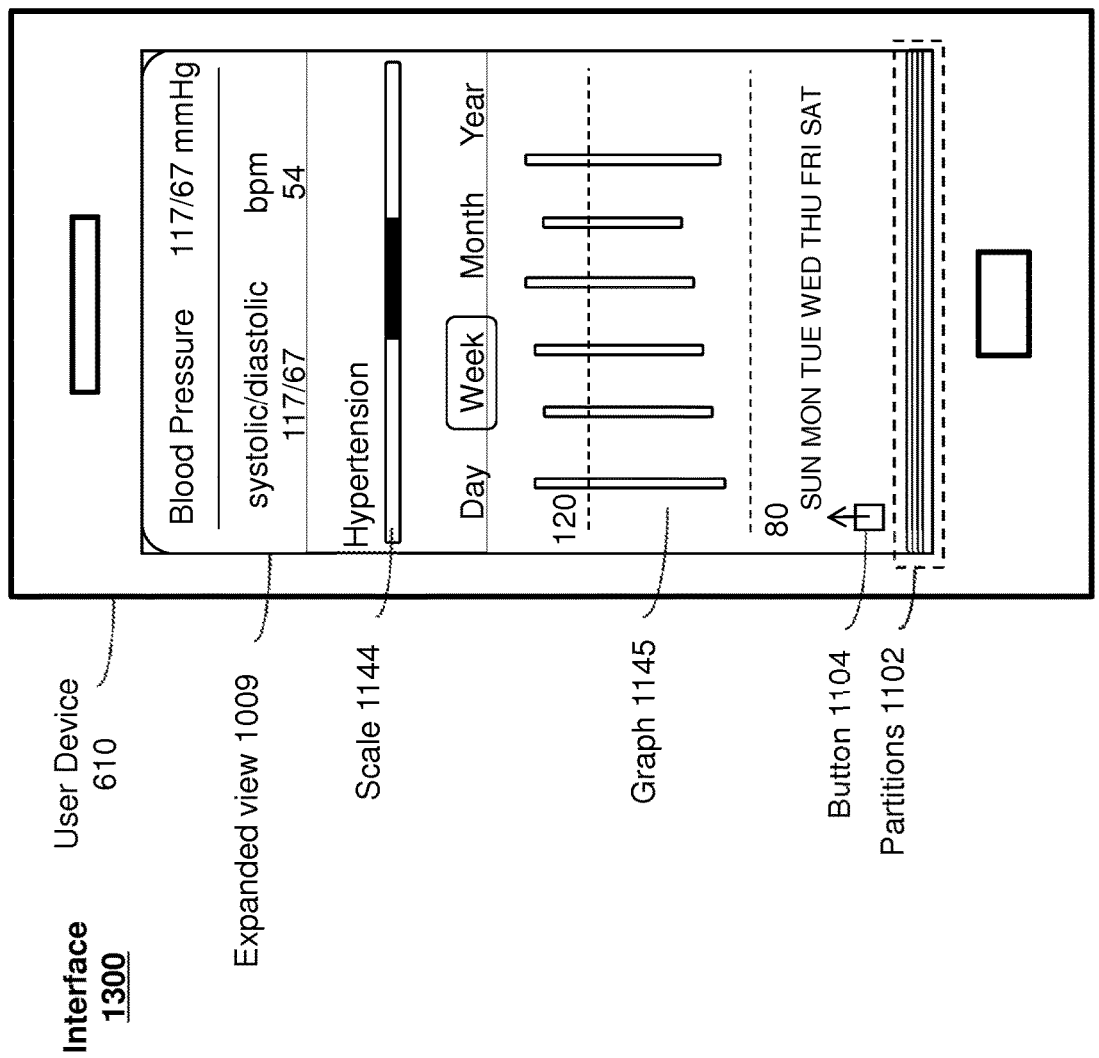
FIG. 13 illustrates example interfaces for displaying aggregated wellness data according to various examples.

FIG. 13 illustrates an example interface 1300 that can be displayed in response to a user selecting partition 1008 in interface 1000. In interface 1300, expanded view 1009 of partition 1008 can be displayed prominently within the display of user device 610, while the remaining partitions can be animated as being collapsed off the display into the stack of partitions 1002 displayed at the bottom of the display. In the illustrated example, expanded view 1009 can include additional blood pressure-related data, such as the user's blood pressure and beats per minute (bpm) that were not shown in interface 1000. Expanded view 1009 can further include summaries of the user's blood pressure data, such as a sliding scale 1044 indicating the user's blood pressure relative to typical blood pressure values and a graph 1045 tracking the user's blood pressure throughout the day, week, month, or year. Interface 1300 can also include button 1004, described above. To return to the aggregated view of partitions shown in interface 1000, the user can select (e.g., tap, click, or otherwise select) the stack of partitions 1002. It should be appreciated that the contents of interface 1300 and expanded view 1009 are provided as examples, and that expanded view 1009 can instead include any type or summary of blood pressure-related data.

Figure 14:
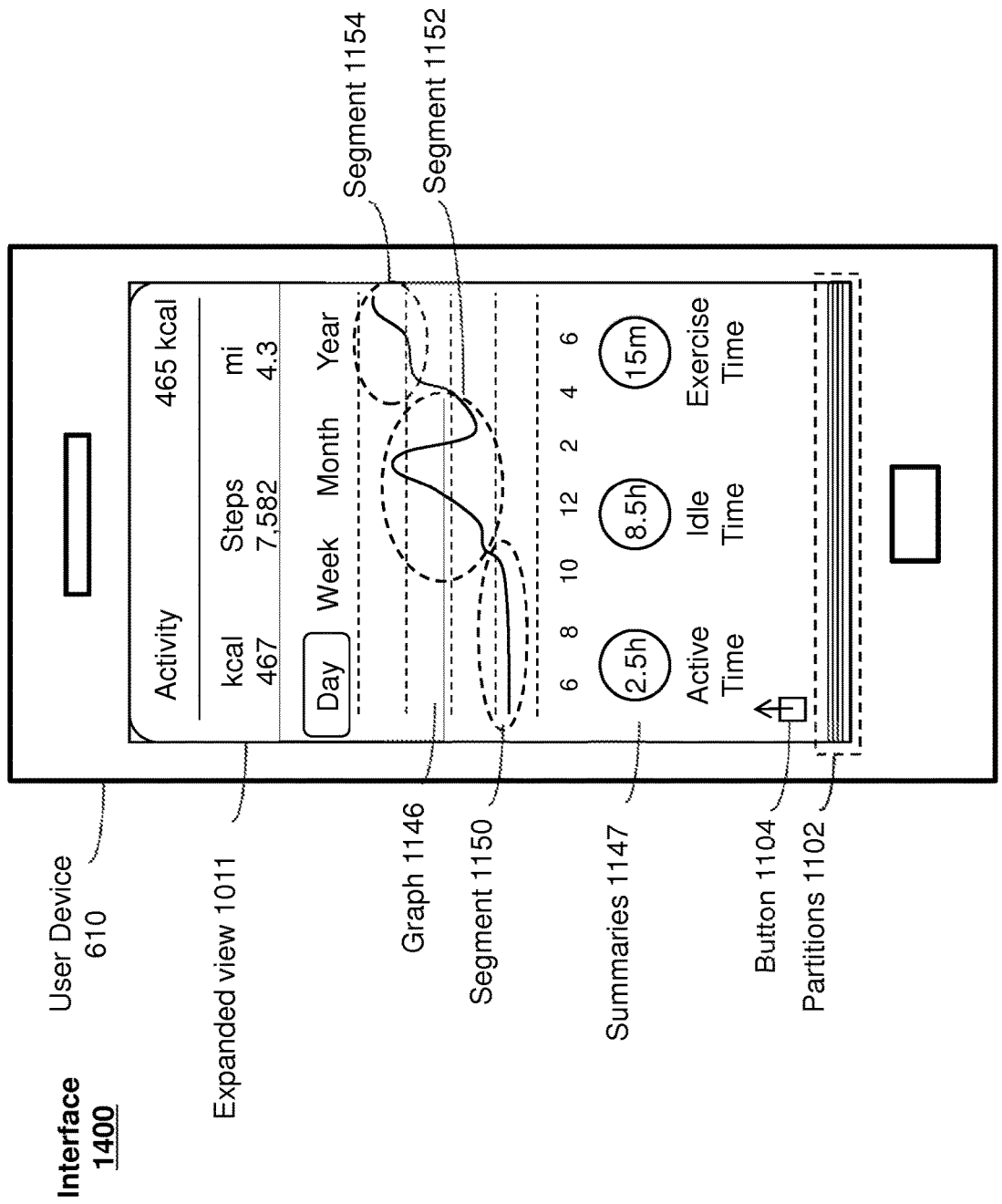
FIG. 14 illustrates example interfaces for displaying aggregated wellness data according to various examples.

FIG. 14 illustrates an example interface 1400 that can be displayed in response to a user selecting partition 1010 in interface 1000. In interface 1400, expanded view 1011 of partition 1010 can be displayed prominently within the display of user device 610, while the remaining partitions can be animated as being collapsed off the display into the stack of partitions 1102 displayed at the bottom of the display. In the illustrated example, expanded view 1011 can include additional activity-related data, such as the calories burned, steps taken, and miles traveled by the user that were not shown in interface 1000. Expanded view 1011 can further include summaries of the user's blood pressure data, such as a graph 1146 tracking the intensity of their activity throughout the day, week, month, or year, and summaries 1147 showing the total time spent active, idle, and exercising. Interface 1400 can also include button 1104, described above. To return to the aggregated view of partitions shown in interface 1000, the user can select (e.g., tap, click, or otherwise select) the stack of partitions 1102. It should be appreciated that the contents of interface 1400 and expanded view 1011 are provided as examples, and that expanded view 1011 can instead include any type or summary of activity-related data.

Figure 15:
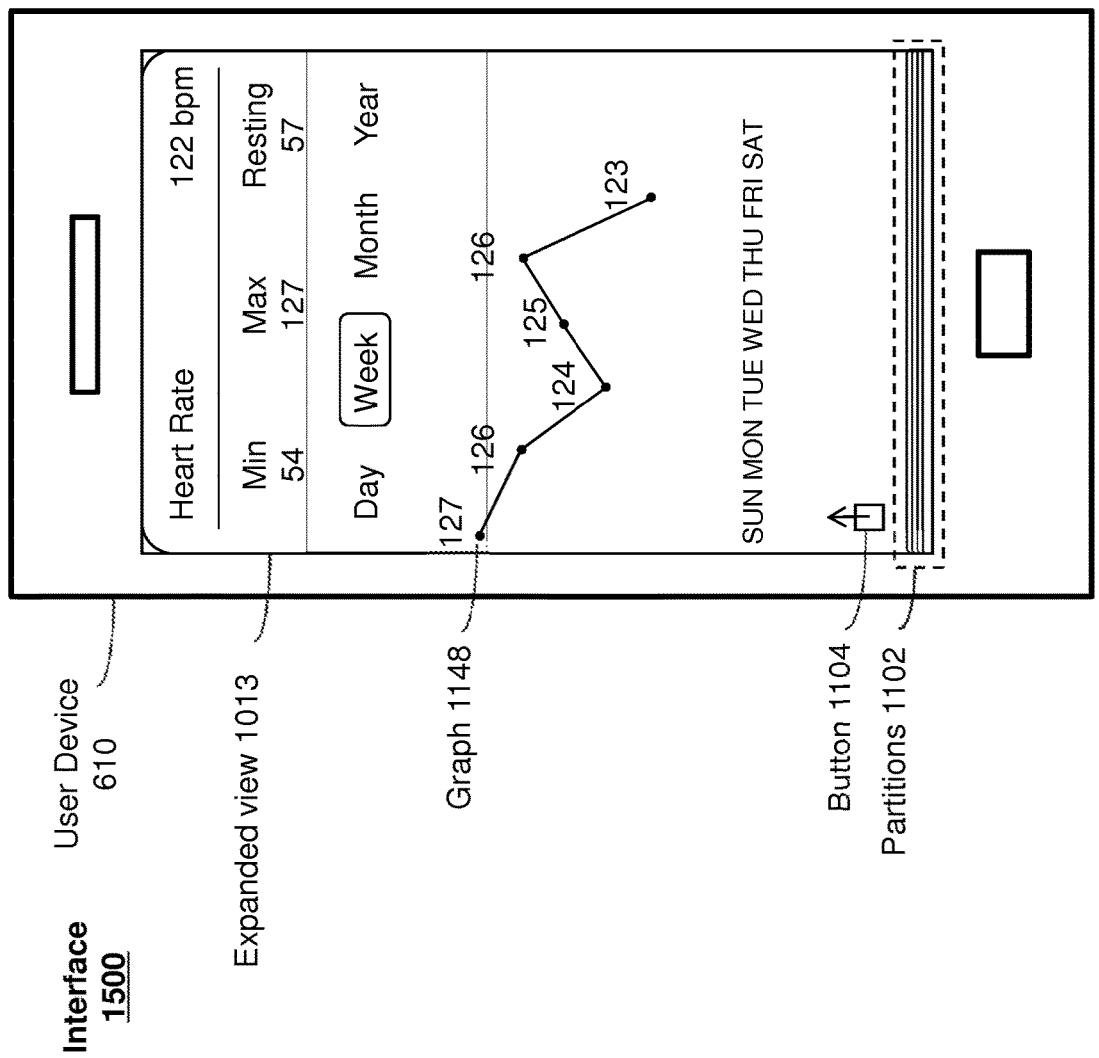
FIG. 15 illustrates example interfaces for displaying aggregated wellness data according to various examples.

FIG. 15 illustrates an example interface 1500 that can be displayed in response to a user selecting partition 1012 in interface 1000. In interface 1500, expanded view 1013 of partition 1012 can be displayed prominently within the display of user device 610, while the remaining partitions can be animated as being collapsed off the display into the stack of partitions 1102 displayed at the bottom of the display. In the illustrated example, expanded view 1013 can include additional heart rate-related data, such as minimum, maximum, and resting heart rate of the user over a day, week, month, or year. However, unlike partitions 1004, 1006, 1008, and 1010, this data was previously displayed within interface 1000 since partition 1012 was displayed in the aggregated view as being located at the top of the stack of partitions. Expanded view 1013 can further include a summary of the user's heart rate data, such as a graph 1148 tracking the user's heart rate throughout the day, week, month, or year. Interface 1500 can also include button 1104, described above. To return to the aggregated view of partitions shown in interface 1000, the user can select (e.g., tap, click, or otherwise select) the stack of partitions 1102. It should be appreciated that the contents of interface 1500 and expanded view 1013 are provided as examples, and that expanded view 1013 can instead include any type or summary of heart rate-related data.

In some examples, a user's wellness data used to generate the interfaces shown in FIGS. 10-15 and 55 may have been received from one or more sensor devices and/or applications. In these examples, the wellness data of the same type from different devices may be combined and displayed on a single partition. For example, the weight data shown in interface 1100 in FIG. 11 can be obtained from repeated measurements taken using the same scale. Alternatively, some of the measurements could have been obtained from one scale, while the remaining measurements could have been obtained from one or more different scales. As a result, some points in graph 1141 could have been generated using weight data from one scale, while other points in graph 1141 could have been generated using weight data from one or more other scales. In another example, the activity data shown in interface 1400 in FIG. 14 may have been obtained from a single step counting device. Alternatively, the data may be aggregated from a step counting device, a first GPS-enabled watch used to record a user's running session, and a second GPS-enabled watch used to record a user's rowing session. In these examples, graph 1146 showing the intensity of the user's activity can be a segmented graph generated from a combination of the data obtained from the step tracking device and the first and second GPS-enabled watches, with each segment coming from one of the devices. In particular, graph 1146 can include a first segment 1150 generated from data from the step counting device, a second segment 1152 generated from data from the first GPS-enabled watch, and a third segment 1154 generated from data from the second GPS-enabled watch. Aggregating data in this way advantageously allows a user to record and view wellness data in a manner that does not directly tie the wellness data to a particular device or application (e.g., smartphone applications). While three segments are shown in FIG. 14, it should be appreciated that the segmented graph can include any number of segments corresponding to different sensors and/or applications.

Figure 16:
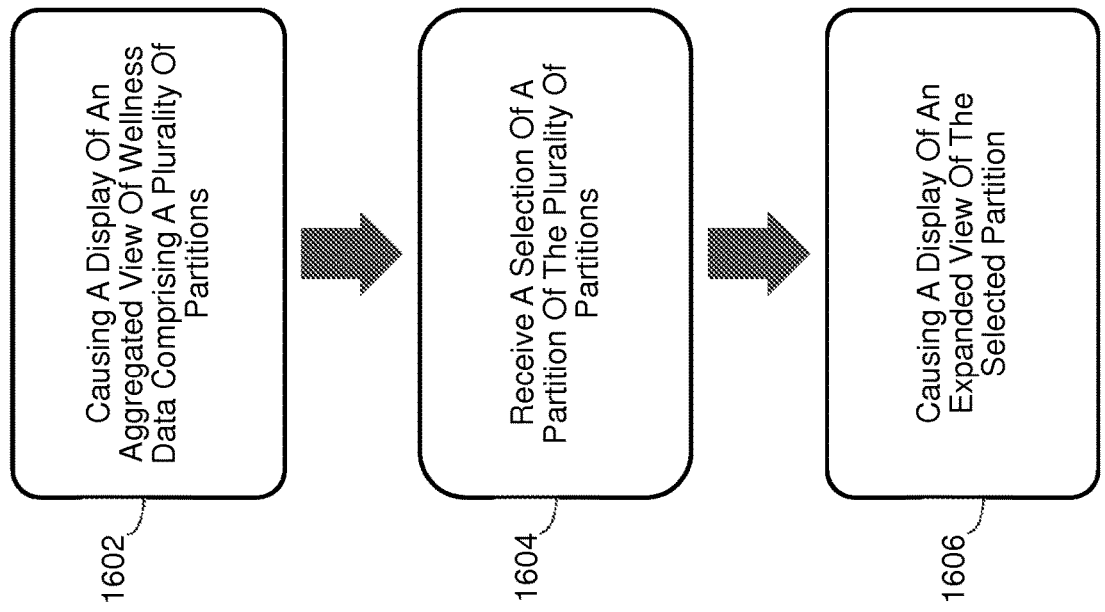
FIG. 16 illustrates an example process for displaying aggregated wellness data according to various examples.

FIG. 16 illustrates an example process 1600 for displaying wellness data according to various examples. At block 1602, an aggregated view of wellness data containing a plurality of partitions similar or identical to partitions 1002, 1004, 1006, 1008, 1010, and 1012 can be displayed on a user device similar or identical to user device 610. The partitions can include an identifier for the type of wellness data displayed on the partition and a partial view (e.g., summary, example, or the like) of a portion of the type of wellness data associated with the partition. For example, an interface similar or identical to interface 1000 can be displayed containing various wellness data partitions 1002, 1004, 1006, 1008, 1010, and 1012.

At block 1604, a selection of one of the displayed partitions can be received. The selection can be received by the user device, and can be in the form of a mouse click, tap on a touch sensitive display, or the like. In response to a selection of the partition, an expanded view of the selected partition can be displayed at block 1606. The expanded view can include a view showing a larger portion of the selected partition and at least one of reconfigured wellness data (e.g., a rearranged view of the wellness data displayed on the selected partition in the aggregated view displayed at block 1602), additional wellness data (e.g., wellness data that was not previously displayed on the selected partition in the aggregated view displayed at block 1602), or an enlarged view of the wellness data displayed in the aggregated view displayed at block 1602 (e.g., a larger view of the same wellness data displayed on the selected partition in the aggregated view displayed at block 1602). Additionally, partitions that were not selected can be reduced in size or removed from the display. For example, any of interfaces 1100, 1200, 1300, 1400, or 1500 can be displayed in response to a selection of partition 1004, 1006, 1008, 1010, or 1012 of interface 1000, respectively.

In some examples, the display presented at block 1606 can include a selectable option (e.g., button 1204) to share wellness data. In other examples, the display presented at block 1606 can further include a selectable option (e.g., partitions 1202) to cause the aggregated view containing partitions displayed at block 1602 to again be displayed. The process can then return to block 1604, where a selection of another partition can be received.

Figure 17:
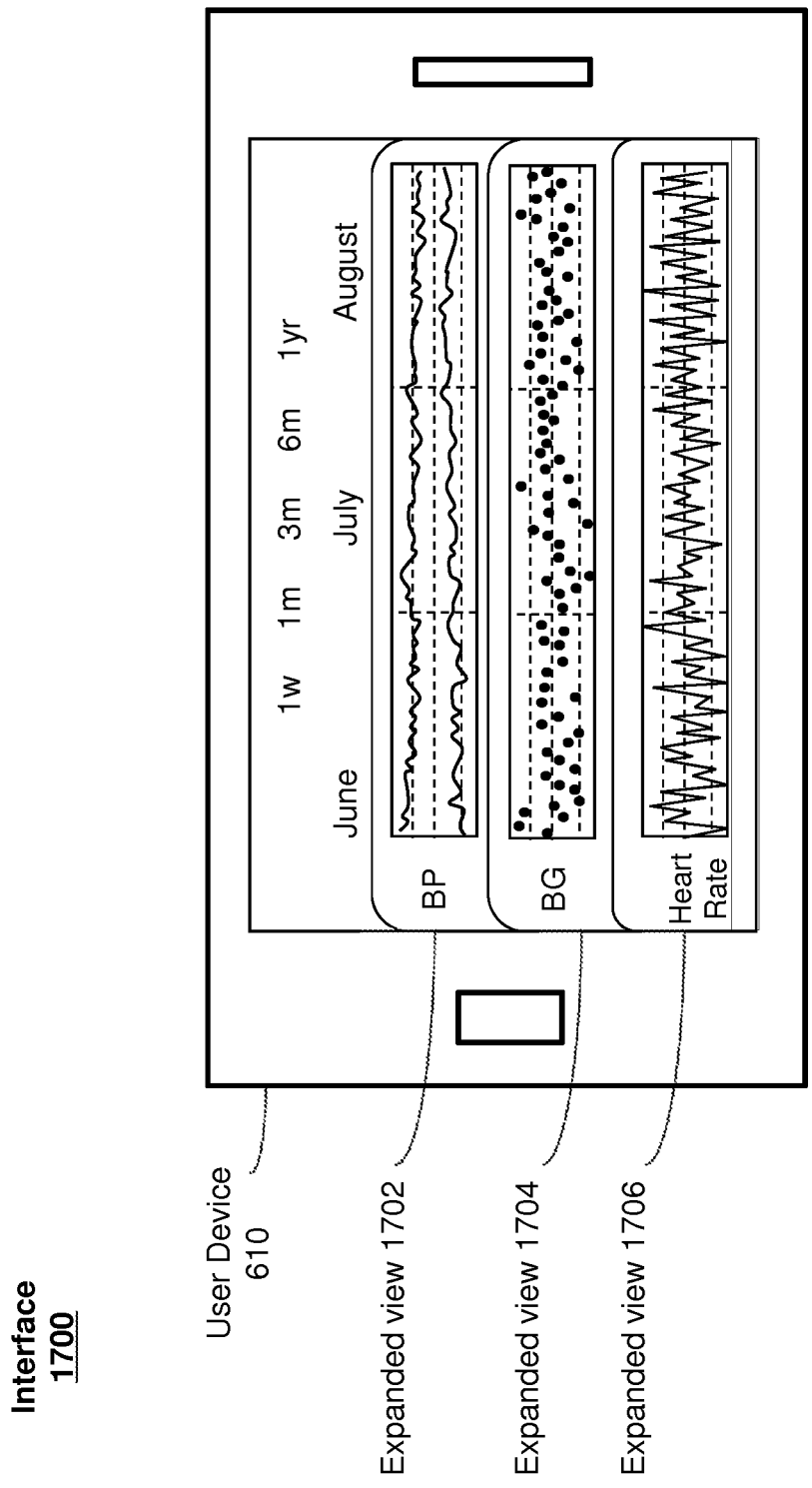
FIG. 17 illustrates an example interface for displaying aggregated wellness data according to various examples.

FIG. 17 illustrates an example interface 1700 that can be displayed in response to a user rotating user device 610 to a landscape view. In this orientation, user device 610 can display expanded views of a smaller subset of partitions than displayed in the aggregated view of interface 1000. For example, interface 1700 can include expanded view 1702 of partition 1008, expanded view 1704 of partition 1006, and expanded view 1706 of partition 1012. In the illustrated example, the expanded views of the partitions can include graph representations of the wellness data over various lengths of time. This can allow a user to view the displayed types of wellness data and see how they change relative to each other over time and to evaluate how a change in one type of wellness data relates to a change (or lack thereof) in another type of wellness data. For example, one type of wellness data that can be displayed can include medications taken over time. This data can be compared to a user's blood pressure and heart rate to determine if the medication is having a beneficial or detrimental effect. In some examples, user device 610 can select the types of wellness data to be displayed when user device 610 is rotated into landscape orientation. The selection can be made based on predetermined combinations of wellness data types that are often associated with each other or can be made based on an analysis of the various types of wellness data. In the latter example, wellness data types that are identified as potentially being correlated can be displayed. Wellness data types not shown in the initial display of interface 1700 can be viewed by scrolling through the partitions. Additionally, the partitions can be selected to display more detailed information in the same way as performed in interface 1000.

Figure 18:
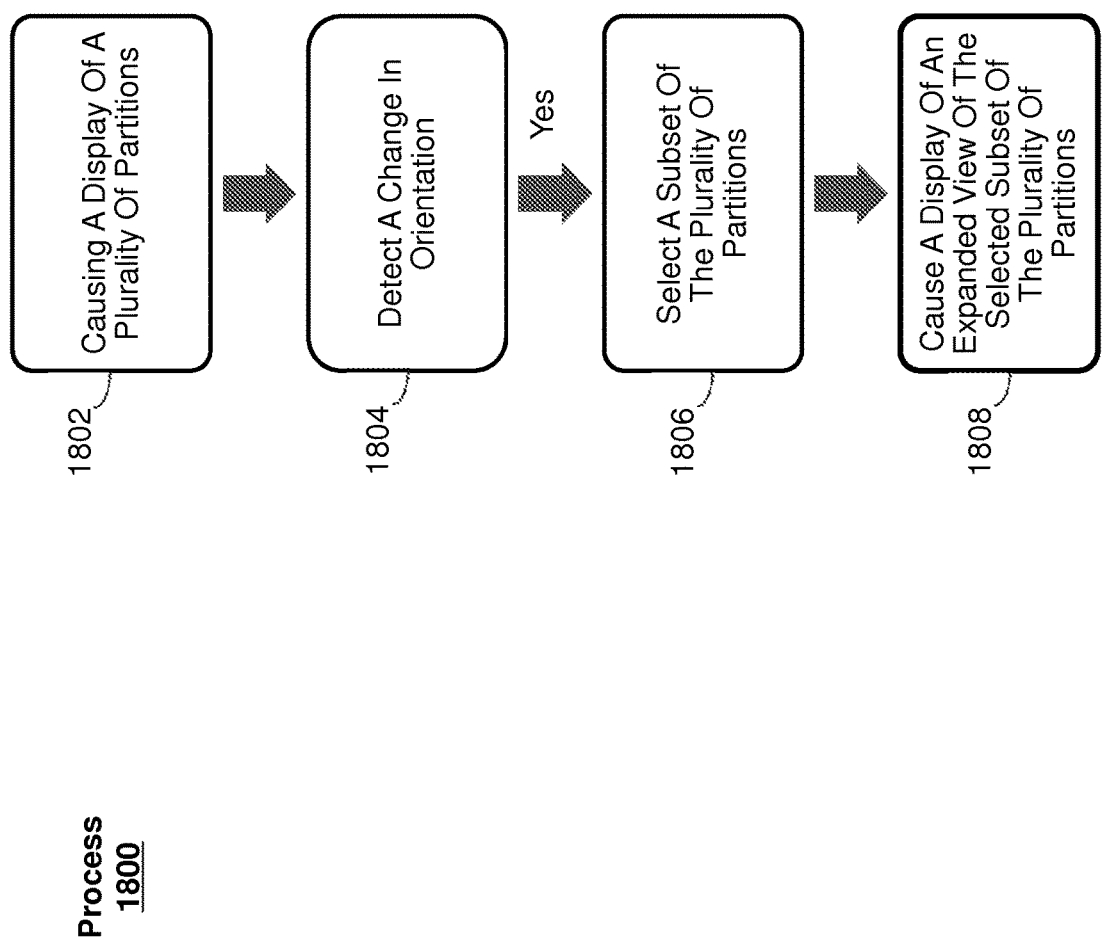
FIG. 18 illustrates an example process for displaying aggregated wellness data according to various examples.

FIG. 18 illustrates an example process 1800 for displaying wellness data based on an orientation of the device according to various examples. At block 1802, an aggregated view containing a plurality of partitions similar or identical to partitions 1002, 1004, 1006, 1008, 1010, and 1012 can be displayed by a user device similar or identical to user device 610. The partitions can include an identifier for the type of wellness data displayed on the partition and a partial view (e.g., summary, example, or the like) of a portion the type of wellness data associated with the partition. For example, an interface similar or identical to interface 1000 can be displayed containing various wellness data partitions 1002, 1004, 1006, 1008, 1010, and 1012.

At block 1804, a change in orientation of the user device can be detected. For example, a gyroscope and/or an accelerometer within the user device can indicate that the orientation of the device has been changed from portrait to landscape. In response to a detected change in orientation by a threshold amount, the process can proceed to block 1806.

At block 1806, a subset of the plurality of partitions displayed at block 1802 can be selected for display. In some examples, the subset can be a predetermined subset of the plurality of partitions. In other examples, the subset can be selected based on user-defined preferences for display. In yet other examples, the subset of the plurality of partitions can be selected based on an analysis of the wellness data sets associated with each partition to determine if any of the types of wellness data are potentially correlated. If a potential correlation is identified, the partitions associated with the potentially correlated data can be selected at block 1806.

At block 1808, expanded views of the subset of partitions selected at block 1806 can be displayed. In some examples, the identifier for the type of wellness data displayed on the expanded view of the partition and/or the summary, example, or other view of the type of wellness data associated with the partition can be different than that shown on the partitions at block 1802. For example, the summary or example data on each expanded view can be replaced with a graph representation of the wellness data over time, as shown in FIG. 17. In this way, relationships between the displayed types of wellness data can be observed. In some examples, in response to detecting a change in the orientation of the user device to a portrait orientation, the process can return to block 1802.

Figure 19:
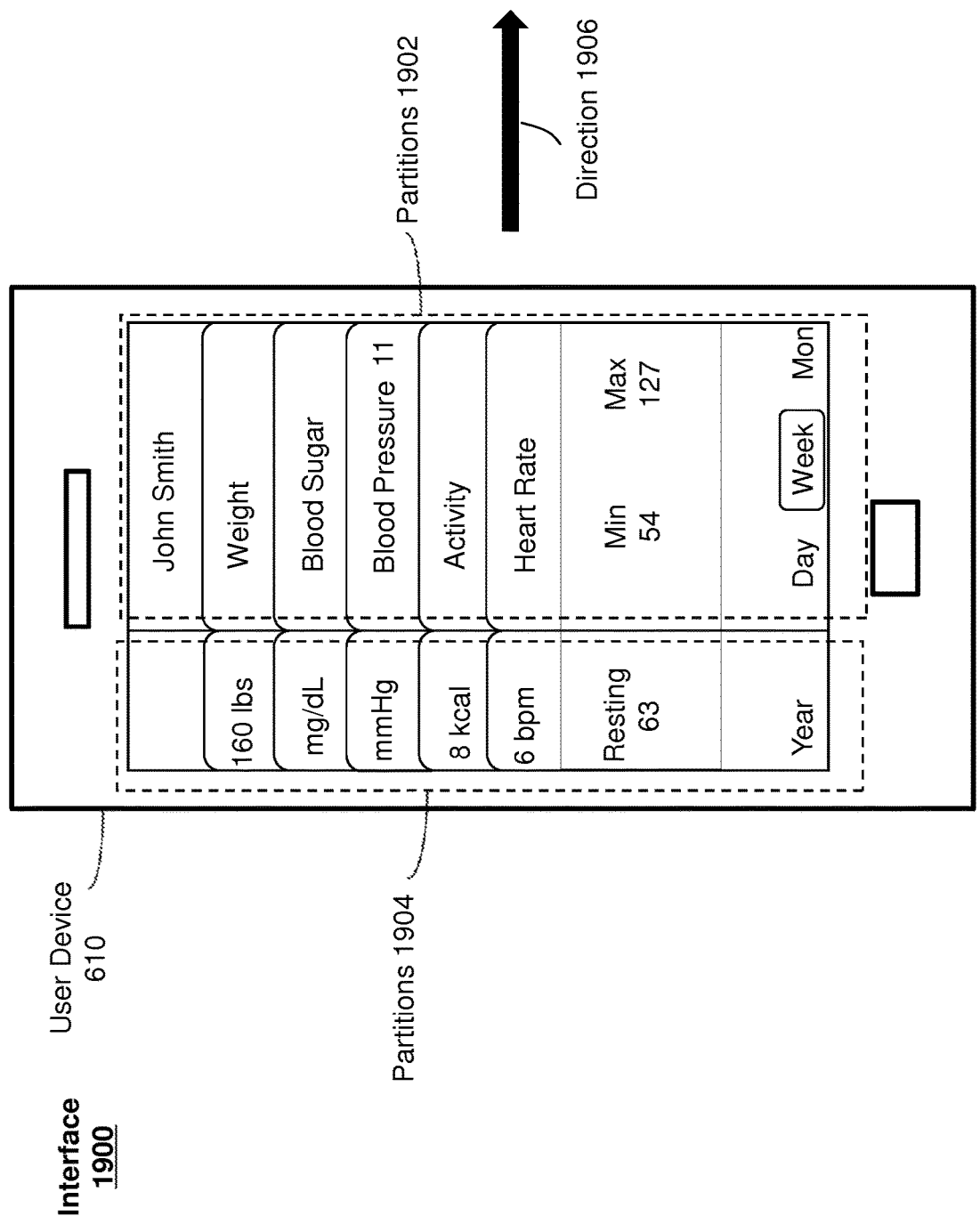
FIG. 19 illustrates an example interface for displaying aggregated wellness data of other users according to various examples.

As discussed above, in some examples, the user of user device 610 can be granted access to the wellness data of other users. In these examples, user device 610 can allow the user to view the wellness data of other users in a similar format as discussed above with respect to FIGS. 10-18. For example, as shown by interface 1900 in FIG. 19, to view the wellness data of other users, the user can laterally scroll the contents of the interface in direction 1906 to cause a first set of partitions 1904 from a first user to be displayed in place of the second set of partitions 1902 from a second user. In particular, the second set of partitions 1902 for the second user can be translated off the display in the direction 1906 of the scroll, while the first plurality of partitions 1904 can be translated onto the display in the same direction 1906 but from the opposite side of the display. It should be appreciated that FIG. 19 illustrates a transitional state in which partitions 1902 are being removed from the display and partitions 1904 are being scrolled in direction 1906 onto the display. As such, only the left side of partitions 1902 and the right side of partitions 1904 are visible. As partitions 1902 and 1904 continue to be scrolled in direction 1906, a smaller portion of partitions 1902 may be visible while a larger portion of partitions 1904 may be visible until partitions 1902 are completely removed from the display and partitions 1904 occupy all or most of the display. While not shown, the top partition of partitions 1904 can include the first user's name and can be displayed as the screen continues to be scrolled in direction 1906. This scrolling operation can be performed any number of times (and in any direction) to scroll through the partitions for all users that the user of device 610 is authorized to access.

Figure 20:
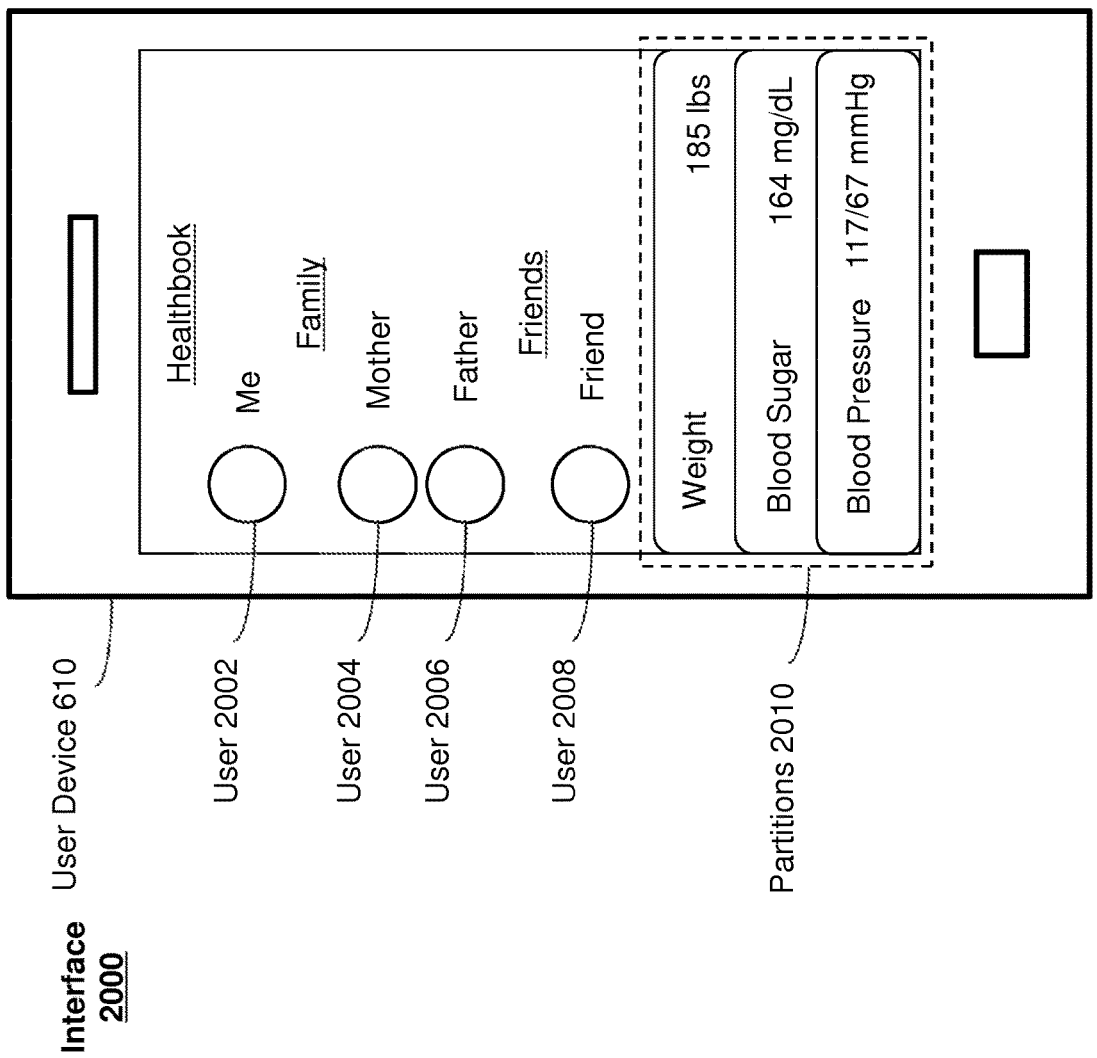
FIG. 20 illustrates another example interface for displaying aggregated wellness data of other users according to various examples.

FIG. 20 illustrates another example interface 2000 for viewing the wellness data of other users. In some examples, interface 2000 can be displayed in response to a selection of button 1001 of interface 1000. As shown, interface 2000 can include a list of users 2002, 2004, 2006, and 2008 that have authorized the user of user device 610 to access their wellness data. In some examples, the circles next to each user's name can be replaced with an image associated with the user. These images can be the same image as used in device 610's contact list or can include another image. In the illustrated example, users 2002, 2004, 2006, and 2008 have been grouped into different categories (e.g., self, family, and friends). The categories can be used to logically group users together or, as discussed above, can indicate a level of authorization to view the wellness data of the other users. For example, users in the "family" category may have authorized a larger set of their wellness data to be viewed, while users in the "friend" category may have authorized a smaller set of their wellness data to be viewed. In response to a selection of one of users 2002, 2004, 2006, and 2008, partitions 2010 can be updated to reflect the wellness data of the selected user. This can include updating the types of wellness data displayed on the partitions (e.g., based on the types of wellness data the other user has authorized the user of user device 610 to view) as well as the associated partial views (e.g., summary, example, or the like) of portions the wellness data. In other examples, the list of users 2002, 2004, 2006, and 2008 can be displayed in response to vertically scrolling interface 1000 up or down to expose the list of users.

Figure 21:
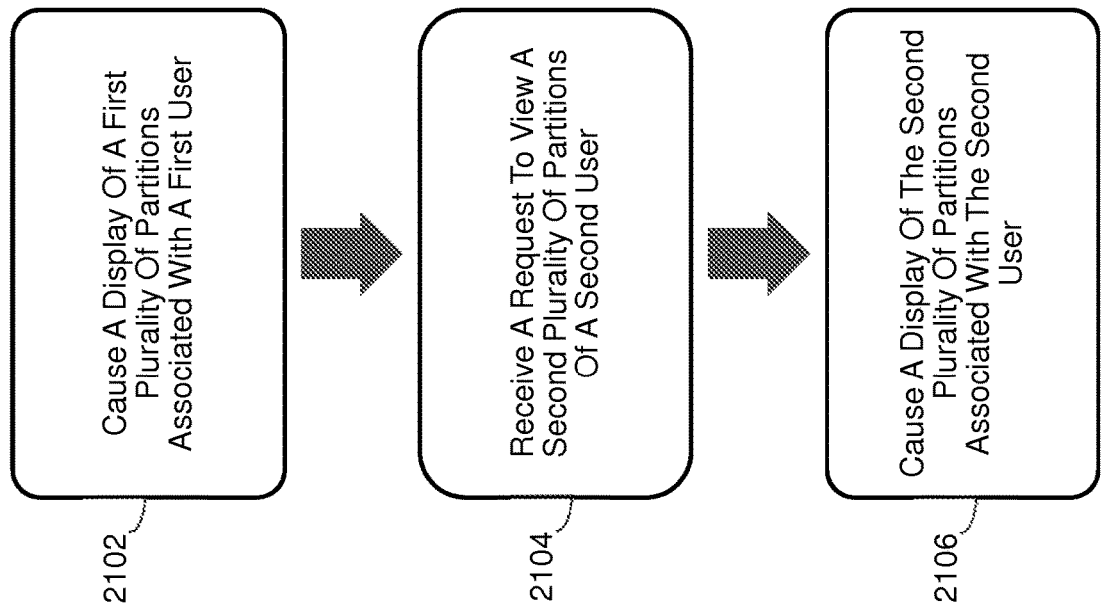
FIG. 21 illustrates an example process for displaying aggregated wellness data of other users according to various examples.

FIG. 21 illustrates an exemplary process 2100 for displaying wellness data associated with two or more users according to various examples. At block 2102, a display of a first plurality of partitions associated with a first user can be displayed. The partitions can be similar or identical to partitions 1002, 1004, 1006, 1008, 1010, and 1012 and can be displayed by a user device similar or identical to user device 610. The partitions can include an identifier for the type of wellness data displayed on the partition and a partial view (e.g., summary, example, or the like) of a portion the type of wellness data associated with the partition. For example, an interface similar or identical to interface 1000 can be displayed containing various wellness data partitions 1002, 1004, 1006, 1008, 1010, and 1012.

At block 2104, a request to view a second plurality of partitions of a second user can be received. The second user can be a user that has authorized the first user to view their wellness data as described above. In some examples, the request can include a user input to scroll the display of the first plurality of partitions displayed at block 2102 and can be received by the user device in the form of rotation of a mouse wheel, an arrow key on a keyboard, a touch and/or swipe on a touch sensitive display, or the like. Similar to the example shown in FIG. 19, the scroll direction can be in a horizontal direction relative to the contents of the display and can be perpendicular to a scroll direction that causes additional partitions associated with the first user to be displayed. However, it should be appreciated that other scroll directions can be used. In other examples, the request to view the second plurality of partitions can be received in the form of a selection of the second user from a list of users. For example, the second user can be selected from a list of users similar to that shown in FIG. 20. The list can be displayed in response to a selection of a button (e.g., button 1001) or other selection mechanism, such as vertically scrolling the first plurality of partitions displayed at block 2102 to expose the list of users. In response to receiving the request to view the second plurality of partitions at block 2104, the process can proceed to block 2106.

At block 2106, a display of the second plurality of partitions associated with the second user can be displayed. In some examples, when the request to view the second plurality of partitions received at block 2104 included a request to scroll the display of the first plurality of partitions, the first plurality of partitions can be translated off the display in the direction of the scroll, while the second plurality of partitions can be translated onto the display in the same direction but from the opposite side of the display, as shown in FIG. 19. In other examples, when the request to view the second plurality of partitions received at block 2104 included a selection of the second user from a list of users, the first plurality of partitions can be replaced with a display of the second plurality of partitions, as shown in FIG. 20. Additional requests to view wellness data partitions of other users can be received and blocks 2104 and 2106 can be repeated to display some or all of the sets of partitions associated with users that have authorized the user of device 610 to view their wellness data.

It should be appreciated that the processes described above can be combined. For example, process 1800 can be combined with process 1600 such that after the plurality of partitions are displayed at block 1502, a change in orientation of the user device can cause blocks 1804, 1806, and 1808 to be performed. Similarly, process 2100 can be combined with process 1500 such that after the plurality of partitions are displayed at block 1602, the receipt of a request to view partitions associated with other users can cause blocks 2104 and 2106 to be performed to display a plurality of partitions associated with another user.

As mentioned above, systems 600 and 700 can be configured to measure, generate, receive, or store wellness or non-wellness data continuously, intermittently, periodically, or at any other desired frequency or interval of time. Processes 1600, 1800, and 2100 can similarly be performed to update the display of wellness or non-wellness data continuously, intermittently, periodically, or at any other desired frequency or interval of time. For example, the device performing process 1600, 1800, or 2100 can receive updated wellness or non-wellness data from wellness database 611 or user database 616 continuously, intermittently, periodically, or at any other desired frequency or interval of time. In some examples, the device performing process 1600, 1800, or 2100 can receive updates to all wellness or non-wellness data at the same frequency or interval of time. In other examples, the device performing process 1600, 1800, or 2100 can be configured to receive updates to different types of data at different frequencies or intervals of time. For example, heart rate data can be updated every second, while weight data and menstrual flow data can be updated daily. These intervals and frequencies can be default values or can be selected by the user.

Dashboard View

Figure 22:
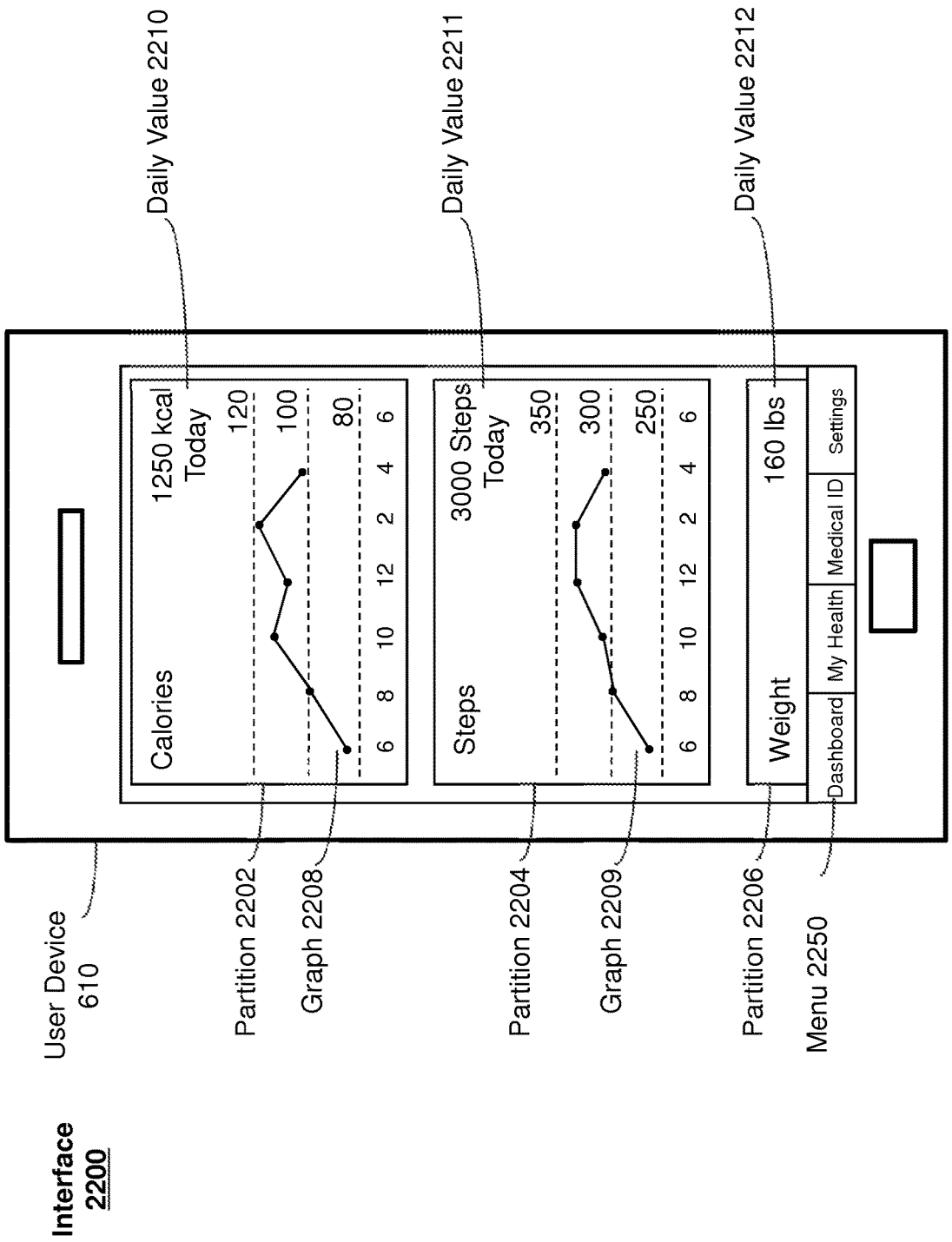
FIG. 22 illustrates example interfaces for displaying wellness or non-wellness data according to various examples.

FIG. 22 illustrates one example interface 2200 that can be displayed by user device 610 to display a detailed view of a user's wellness or non-wellness data. Interface 2200 can include any number of partitions 2202, 2204, and 2206, each representing a different type of wellness or non-wellness data associated with the user (e.g., data stored in wellness database 611). In some examples, the partitions can be displayed in a color based on the type of wellness or non-wellness data that it represents. For example, a partition representing nutrition data can be displayed in one color, and a partition representing of fitness data can be displayed in another.

In some examples, a partition can include an identification of the type of wellness or non-wellness data that the partition represents (e.g., calories, steps, weight, or the like), a numerical daily value of the represented type of wellness or non-wellness data, and a graph representation of the represented type of wellness or non-wellness data. For example, partition 2202 can include the text "Calories" to indicate that it represents Calorie data, a current daily value 2210 of 1250 Calories burned, and a graph representation 2208 of the Calorie data over time throughout the day. Similarly, partition 2204 can include the text "Steps" to indicate that it represents step data, a current daily value 2211 of 3100 steps, and a graph representation 2209 of the step data over time throughout the day. Interface 2200 can further include a partial view of partition 2206 showing the text "Weight" to indicate that it represents weight data, as well as a daily value 2212 of 160 lbs. In the illustrated example, the graphs of each partition are non-overlapping with each other.

In some examples, the detailed view of the user's wellness or non-wellness data can include partitions not shown in interface 2200. In these examples, a user can initiate a scroll request by swiping up or down on a touch sensitive display, by clicking and dragging on a display using a mouse or other input device, by manipulating a scroll-wheel, by performing a swiping gesture on a touch pad, or the like. In response to detecting the scroll request, user device 610 can scroll the view of interface 2200 to display other partitions that were not previously displayed (or were partially displayed, such as partition 2206).

Figure 23:
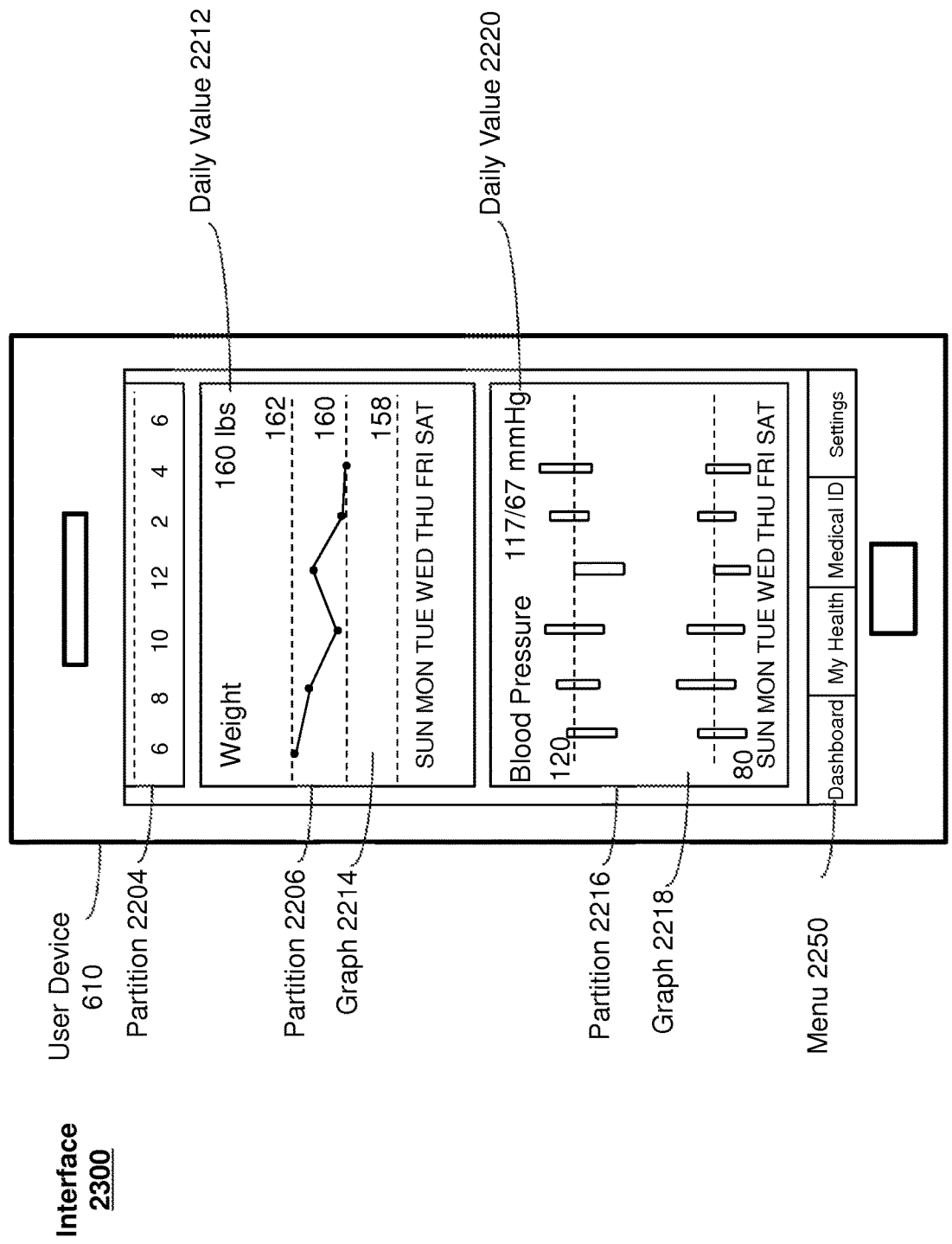
FIG. 23 illustrates example interfaces for displaying wellness or non-wellness data according to various examples.

For example, FIG. 23 illustrates an example interface 2300 that can be displayed in response to a user initiating a scroll request to scroll the view of interface 2200 in an upward direction. In interface 2300, the remainder of partition 2206 can be displayed to show a graph representation 2214 of the weight data over time throughout the week. Another partition 2216 can also be displayed below partition 2206 in interface 2300. Partition 2316 can include the text "Blood Pressure" to indicate that it represents blood pressure data, a current daily value 2210 of 117/67 mmHg, and a graph representation 2218 of the blood pressure data over time throughout the week. In the example shown in FIG. 23, graph 2218 includes two vertical bars for each day. The top and bottom of the upper vertical bar for each day can represent the high and low diastolic blood pressure values, respectively, for the day. Similarly, the top and bottom of the lower vertical bar for each day can represent the high and low systolic blood pressure values, respectively, for that day.

In some examples, the order of partitions within interface 2200 or 2300 can be changed in response to detecting a user request to reorder the partitions. In some examples, the request to reorder can include a selecting and holding of one of the partitions for greater than a threshold length of time. After detecting that the threshold length of time has elapsed, user device 610 can animate the partitions in a way that indicates that the partitions can be reordered. In some examples, the partitions can be reordered by dragging a selected partition to a desired location. However, in other examples, the partitions can be reordered in any other desired manner.

While only four partitions 2202, 2204, 2206, and 2216 are shown in the detailed view illustrated by interfaces 2200 and 2300, it should be appreciated that the detailed view can include additional partitions representing any number and any type of wellness or non-wellness data. Similar to partitions 2202, 2204, 2206, and 2216, these additional partitions can include identifications of the type of wellness or non-wellness data that the partitions represent, numerical daily values of the represented types of wellness or non-wellness data, and graph representations of the represented types of wellness or non-wellness data.

Figure 24:
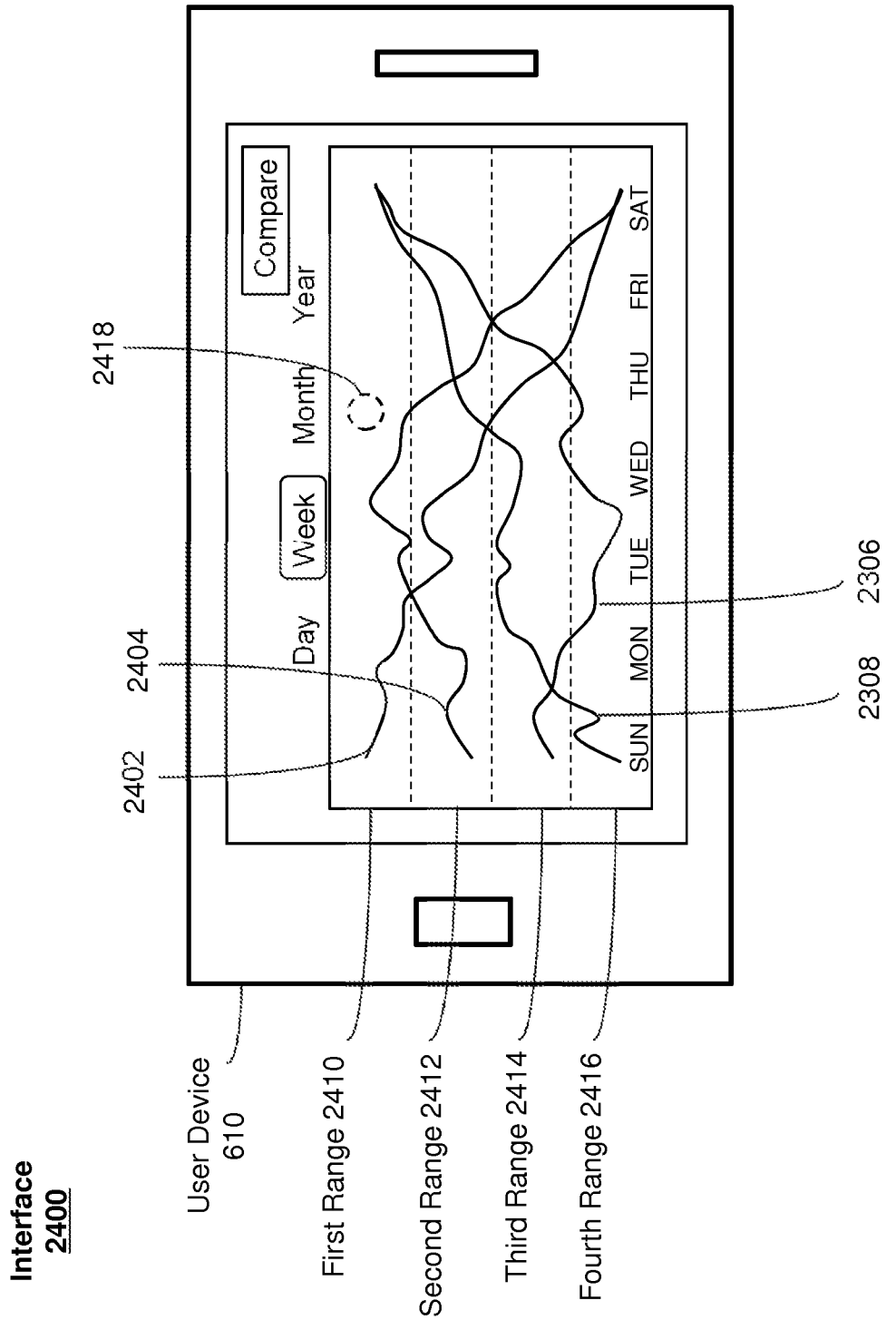
FIG. 24 illustrates example interfaces for displaying wellness or non-wellness data according to various examples.

In some examples, a graph view of some or all of the wellness or non-wellness data displayed in the detailed view can be displayed in response to a graph-view input. In some examples, the graph-view input can include a detected change in orientation of user device 610. For example, FIG. 24 illustrates an example interface 2400 that can be displayed in response detecting a rotation of user device 610 to a landscape view. The graph view of interface 2400 can include data-set representations 2402, 2404, 2406, and 2408, each representing a different set of wellness or non-wellness data. In the illustrated example, the y-axis of the graph can represent a dependent variable of the various data sets, and the x-axis of the graph can represent an independent variable. For example, if data-set representation 2402 represents a set of Calorie data, then the y-axis dependent variable can be Calories, and the x-axis independent variable can be time. Similarly, if data-set representation 2404 represents step data, then the y-axis dependent variable can be a number of steps, and the x-axis independent variable can be time.

In some examples, the data-set representations can be displayed in a color based on the type of wellness or non-wellness data that it represents. For example, a data-set representation representing nutrition data can be displayed in one color, and a data-set representation of fitness data can be displayed in another. In some examples, the colors used for the different types of wellness or non-wellness data can correspond to the colors used to display the partitions in the detailed views of interfaces 2200 and 2300. For example, a partition representing a set of nutrition data can be displayed in the same color as a data-set representation representing the same set of nutrition data.

In some examples, the independent variable of the x-axis can be the same for all data-set representations shown in the graph view. For example, the time represented by the x-axis can be the same for each data-set representation.

In some examples, the dependent variable of the y-axis can be measured or reported in a different unit for some or all of the data-set representations. For example, the dependent variable for data-set representation 2402 can be expressed in Calories, the dependent variable for data-set representation 2404 can be expressed in a number of steps, the dependent variable for data-set representation 2406 can be expressed in pounds (representing weight data), and the dependent variable for data-set representation 2408 can be expressed in mmHg (representing blood pressure data). Since these data-set representations having different units of measurement can be shown overlaid on the same display, a different vertical y-axis scaling can be used to display the various data-set representations. In some examples, to determine a vertical scale for one of the data-set representations, the minimum and maximum value of the represented data set that are to be displayed within the graph can be determined. For example, to determine the scaling factor for data-set representation 2402 representing Calorie data, the maximum and minimum values of the Calorie data can be determined over the span of time represented by the x-axis of the display. In the example shown in FIG. 24, this can include determining the maximum and minimum values of the Calorie data over a week. The determined maximum value can be multiplied by a first scaling factor that can have any value (e.g., a value greater than or equal to 1, such as 1.1), and the determined minimum value can be multiplied by a second scaling factor that can be the same or different from the first scaling factor (e.g., a value less than or equal to 1, such as 0.9). The products of the maximum and minimum values multiplied by the first and second scaling factors can be assigned to the maximum vertical position (e.g., highest position on the y-axis) and the minimum vertical position within the graph (e.g., lowest position on the y-axis), respectively. This allows the data-set representation to be fully displayed within the graph. For example, if the maximum and minimum values of the Calorie data represented by data-set representation 2402 is 1000 Calories and 300 Calories, respectively, and if a first scaling factor of 1.1 and a second scaling factor of 0.9 are used, then the maximum vertical position of the y-axis can represent 1100 Calories and the minimum vertical position of the y-axis can represent 270 Calories for data-set representation 2402. This process can be repeated for each of the displayed data-set representations, resulting in a different scale for each of the data-set representations. This advantageously allows the data-set representations to be clearly displayed overlaid on the same graph. For example, if the same scaling factor were instead used for all sets of data, it is possible that the values for one data-set representation can be substantially larger than another, causing the other data-set representation to appear as a flat line.

In some examples, one or more of the displayed data-set representations can be selected to display additional data associated with the selected data-set representation. In some examples, for the purpose of selecting a particular data-set representation by a user, the data-set representations of the graph view shown in interface 2400 can be associated with a range (e.g., a unique range) of vertical positions within the graph. For example, the graph shown in interface 2400 can be divided into four ranges of vertical positions 2410, 2412, 2414, and 2416 separated by the dashed lines. In this example, data-set representation 2402 can be associated with first range of vertical positions 2410, data-set representation 2404 can be associated with second range of vertical positions 2412, data-set representation 2406 can be associated with third range of vertical positions 2414, and data-set representation 2408 can be associated with fourth range of vertical positions 2416.

A selection of one of the data-set representations can be made by entering a user input within a range of vertical positions corresponding to the desired data-set representation, regardless of the horizontal position of the user input. For example, to select data-set representation 2402, a user input in the form of a touch event by a finger or other device on a touch sensitive display, a click of a mouse or other device, a touch event on a touch pad, or the like, can be made at location 2418 having a vertical position located within the first range of vertical positions 2410.

Figure 25A:
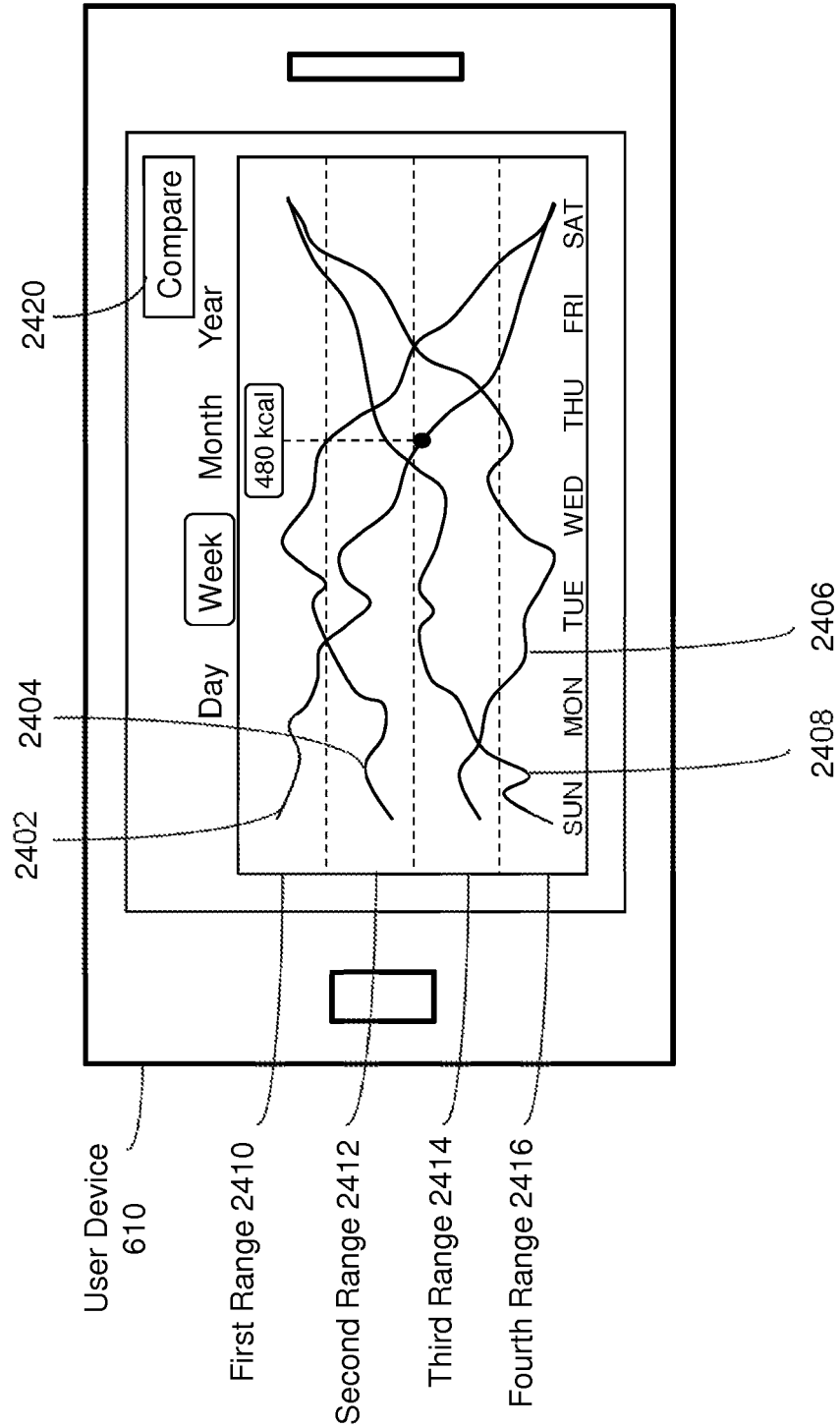
FIGS. 25A and 25B illustrate example interfaces for displaying wellness or non-wellness data according to various examples.

In response to detecting the user input at location 2418 having a vertical position within first range 2410, user device 610 can display an indication that data-set representation 2402 was selected. For example, FIG. 25A shows interface 2500 that can be displayed in response to detecting the input received at location 2418 in interface 2400. As shown, a circle marker can be displayed overlaid on data-set representation 2410 at a horizontal position corresponding to the horizontal position of location 2418. Additionally, a numerical value of 480 kcal can be displayed, indicating that the value of the data set represented by data-set representation 2402 has a value of 480 at the horizontal position of the user input (e.g., horizontal position of location 2418). As shown, data-set representation 2402 can be selected by a user input at location 2418 even though the line of data-set representation 2402 is not located near location 2418. This can advantageously allow a user to select a desired data-set representation without having to select a particular portion of the data-set representation, which can be difficult at locations where multiple data-set representations overlap. In some examples, one of the data-set representations 2402, 2404, 2406, or 2408 can represent blood pressure data. In these examples, for purposes of generating the line of the data-set representation, the dependent variable for the blood pressure data can include an average of the diastolic and the systolic blood pressure. However, the numerical value displayed in response to a selection of the data-set representation for blood pressure data can include a high value for diastolic blood pressure, a low value for diastolic blood pressure, a high value for systolic blood pressure, and a low value for systolic blood pressure associated with the time corresponding to the horizontal position of the user input.

In some examples, one of the data-set representations 2402, 2404, 2406, or 2408 can represent heart rate data. In these examples, the numerical value displayed in response to a selection of the data-set representation for heart rate data can include a high value for heart rate and a low value for heart rate associated with the time corresponding to the horizontal position of the user input.

Figure 25B:
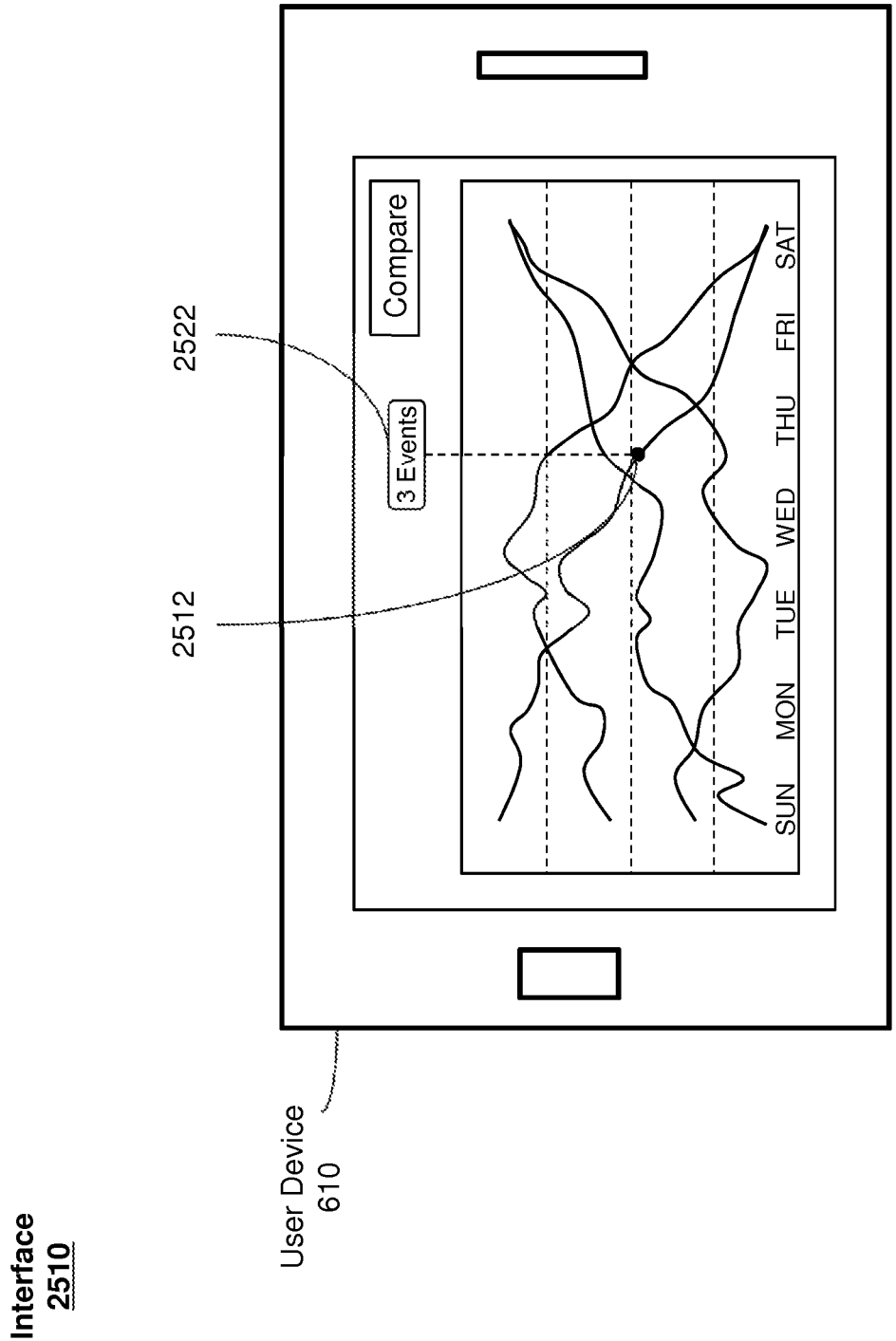

In some examples, the indication of a selection displayed in response to detecting a user input can further include highlighting an area below the line of the selected data-set representation, as shown in FIG. 25B. For example, the area below the line of the selected data-set representation can be darkened, brightened, displayed with a different color, or otherwise highlighted relative to other portions of the graph to change the line graph into an area graph of the selected data set. In addition, as is the case in FIG. 25B, indicator 2522 can provide a read-out of the value of a dependent variable (e.g., sexual activity events) corresponding to an independent variable corresponding to location 2512. In some examples, the data-set representations that are not currently selected can be removed from the display, greyed out, or otherwise made less visible within the graph.

In some examples, a user input can be continuously applied to the displayed graph and moved in a horizontal direction within one of the range of vertical positions to scrub through values of the selected data-set representation. For example, in response to detecting that the user input received at location 2418 is moved in the left direction, the circle marker displayed over data-set representation 2402 can be animated such that it appears to move along the line of data-set representation 2402 at horizontal positions corresponding to the current horizontal position of the user input. Similarly, the displayed value can change to reflect the value of the data set represented by data-set representation 2402 at the horizontal position of the user input.

In some examples, the vertical ranges of values within the graph associated with the data-set representations can be static. In other examples, the vertical ranges of values within the graph associated with the data-set representations can change. For example, in response to detecting a user input at a location within first range 2410, the size of first range 2410 can expand based on a length of time that the detected user input remains within first range 2410. As a result, the other vertical ranges can contract, or decrease in size. In some examples, the size of first range 2410 can expand to cover the entire graph. In other examples, the size of first range 2410 can expand to a predefined limit. Expanding the size of a selected range of vertical positions advantageously provides the user with a greater tolerance for vertical deviation as the user moves their user input in a horizontal direction to select different portions of a data-set representation.

Figure 26:
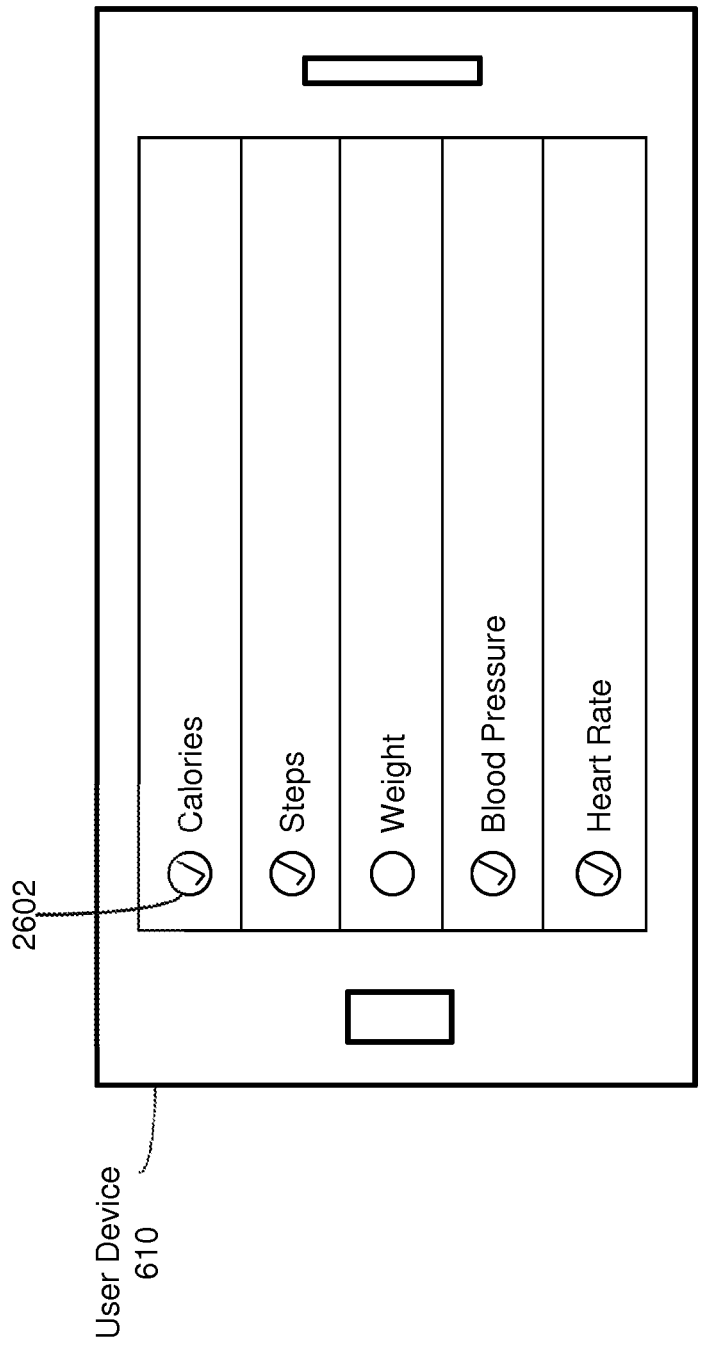
FIG. 26 illustrates example interfaces for displaying wellness or non-wellness data according to various examples.

In some examples, interface 2400 or 2500 can include a compare option 2420 to select the sets of wellness or non-wellness data that are to be displayed within the graph view. For example, FIG. 26 illustrates an example interface 2600 that can be displayed in response to a user selection of compare option 2420 in interface 2400 or 2500. As shown, interface 2600 includes a list of types of wellness or non-wellness data that can be displayed within the graph view. Each type of wellness or non-wellness data can be associated with a selectable option, such as option 2602, to allow the user to add or remove the associated type of wellness or non-wellness data from the graph view. In the illustrated example, the data sets corresponding to Calorie data, step data, blood pressure data, and heart rate data are selected to be displayed within the graph view, while weight data is not. In some examples, the list of wellness or non-wellness data displayed within interface 2600 can include the types of wellness or non-wellness represented by the partitions of interfaces 2200 and 2300.

Figure 64A:
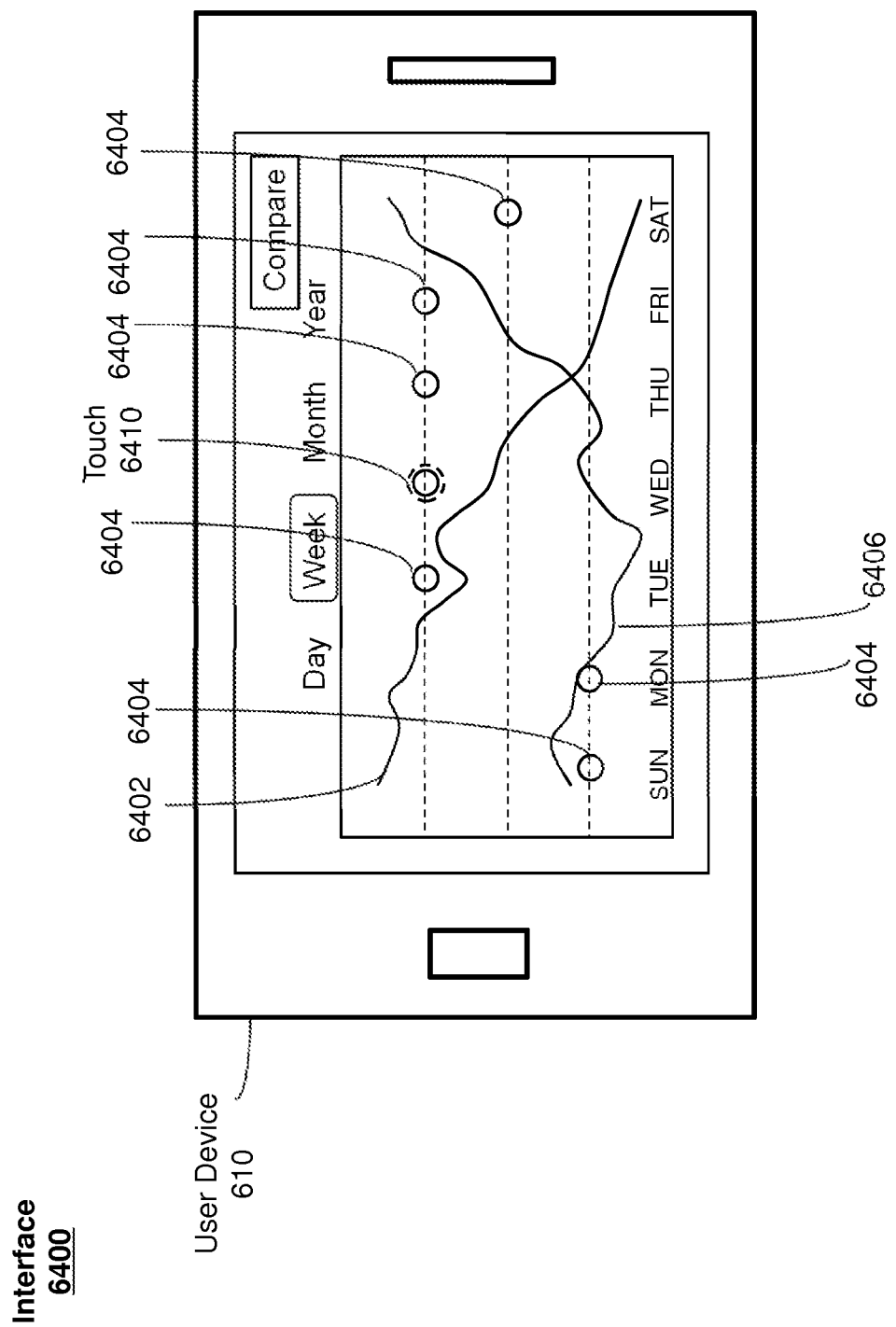
FIG. 64A-64F illustrate exemplary interfaces for displaying wellness or non-wellness data according to various examples.

As another example, FIG. 64A illustrates exemplary user interface 6400 that can be displayed in response detecting a rotation of user device 610 to a landscape view. The graph view of interface 6400 can include data-set representations 6402, 6404, and 6406, each representing a different set of wellness or non-wellness data. In the illustrated example, the y-axis of the graph can represent a dependent variable of the various data sets, and the x-axis of the graph can represent an independent variable. For example, if data-set representation 6402 represents a set of Calorie data, then the y-axis dependent variable can be Calories, and the x-axis independent variable can be time.

Data-set representation 6404, which is shown with discrete dependent variable values, can represent various wellness or non-wellness information. Examples of underlying data represented by data-set representation 6404 are discussed with reference to FIGS. 64B-64F.

Figure 64B:
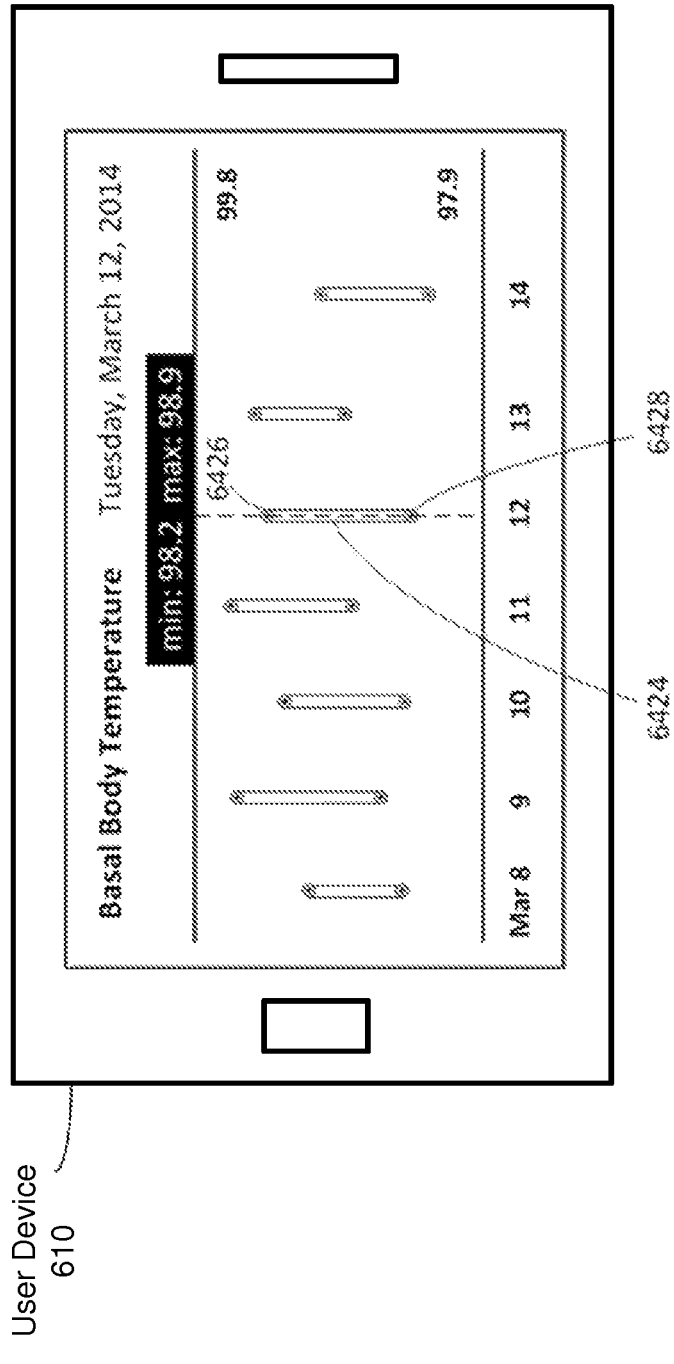

Turning to FIG. 64B, data-set representation 6404 can represent the wellness information of basal temperature in some examples. As can be seen, user interface 6410 in user interface 6400 is displayed responsive to touch input 6410 on an indicator of data-set representation 6404 in user interface 6400 (FIG. 64A). User interface 6410 provides basal body temperature range 6424 corresponding to the location of touch input 6410. Range 6424 has a high value as indicated by marker 6426 and a low value as indicated by marker 6428, which are also provided in text read-out 6422.

Figure 64C:
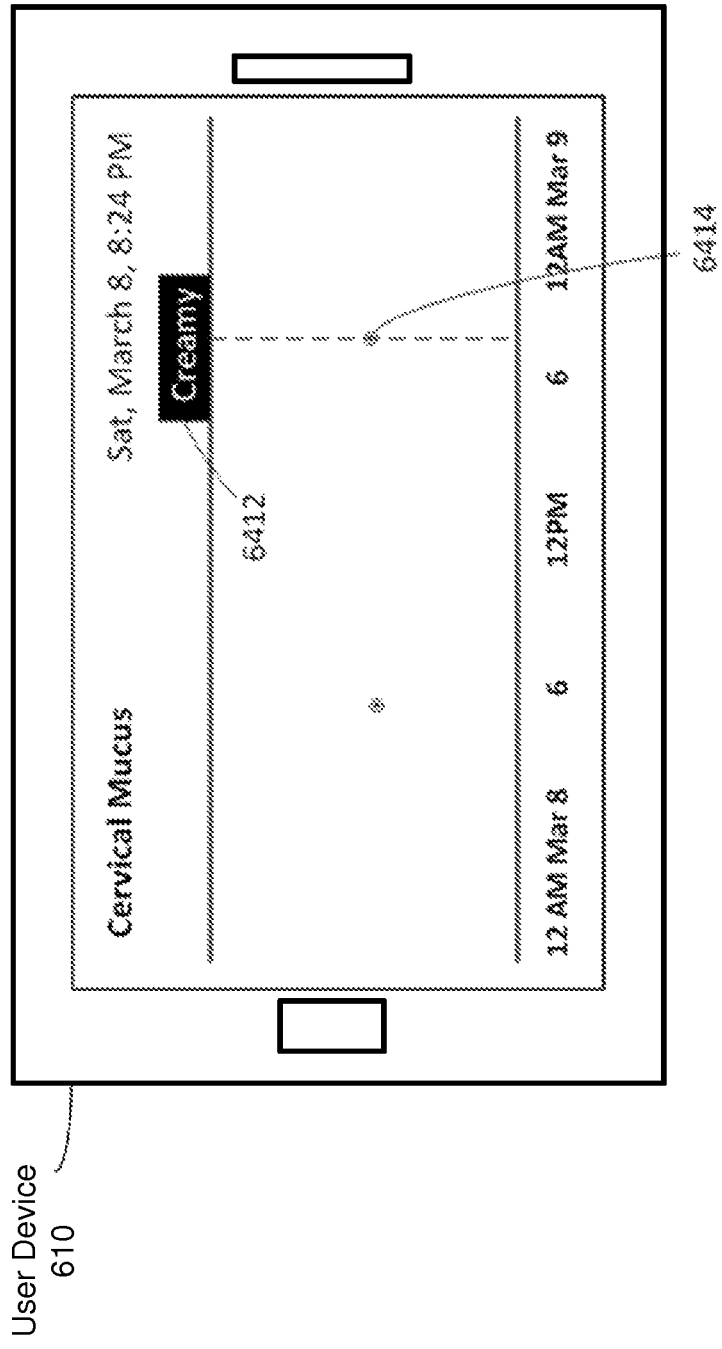

Turning to FIG. 64C, data-set representation 6404 can represent the wellness information of cervical mucus information in some examples. As can be seen, user interface 6420 is displayed responsive to touch input 6410 on an indicator of data-representation 6404 in user interface 6400 (FIG. 64A). User interface 6420 provides cervical mucus information, which can take on discrete values such as "dry", "watery," or "creamy," for example. As shown, indicator 6414 corresponding to touch input 6410 shows a text read-out 6412 of "creamy".

Figure 64D:
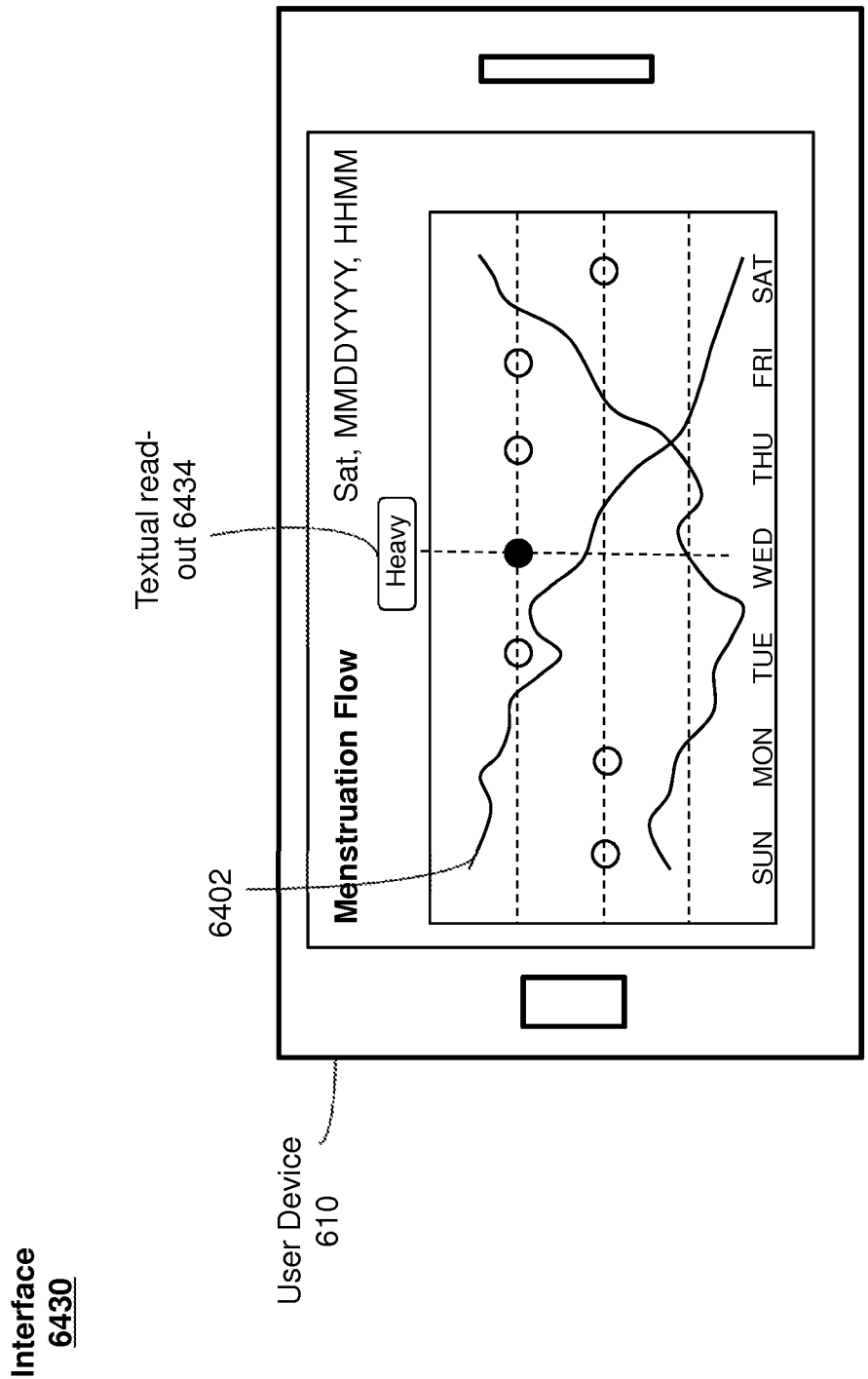

Turning to FIG. 64D, data-set representation 6404 can represent the wellness information of menstrual flow in some examples. As can be seen, user interface 6430 is displayed responsive to touch input 6410 on an indicator of data-representation 6404 in user interface 6400 (FIG. 64A). User interface 6420 provides menstrual flow information, which can take on discrete values such as "light," "medium," or "heavy," for example. As shown, indicator 6434 corresponding to touch input 6410 shows a text read-out 6434 of "heavy".

Figure 64E:
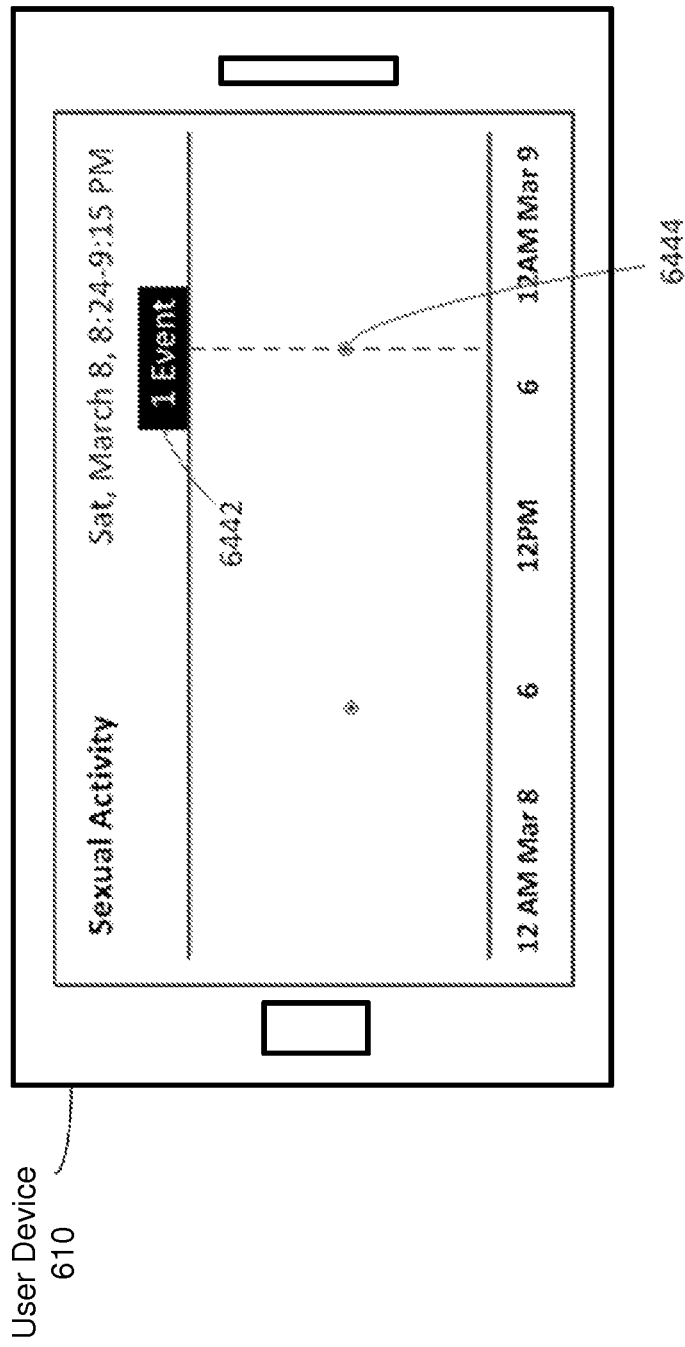

Turning to FIG. 64E, data-set representation 6404 can represent the wellness information of sexual activity in some examples. As can be seen, user interface 6440 is displayed responsive to touch input 6410 on an indicator of data-representation 6404 in user interface 6400 (FIG. 64A). User interface 6440 provides sexual activity information, such as the number of sexual activity events at a given time interval. As shown, indicator 6444 corresponding to touch input 6410 shows a text read-out 6442 that one sexual activity event has occurred at the time corresponding to the horizontal location of touch input 6410.

Figure 64F:
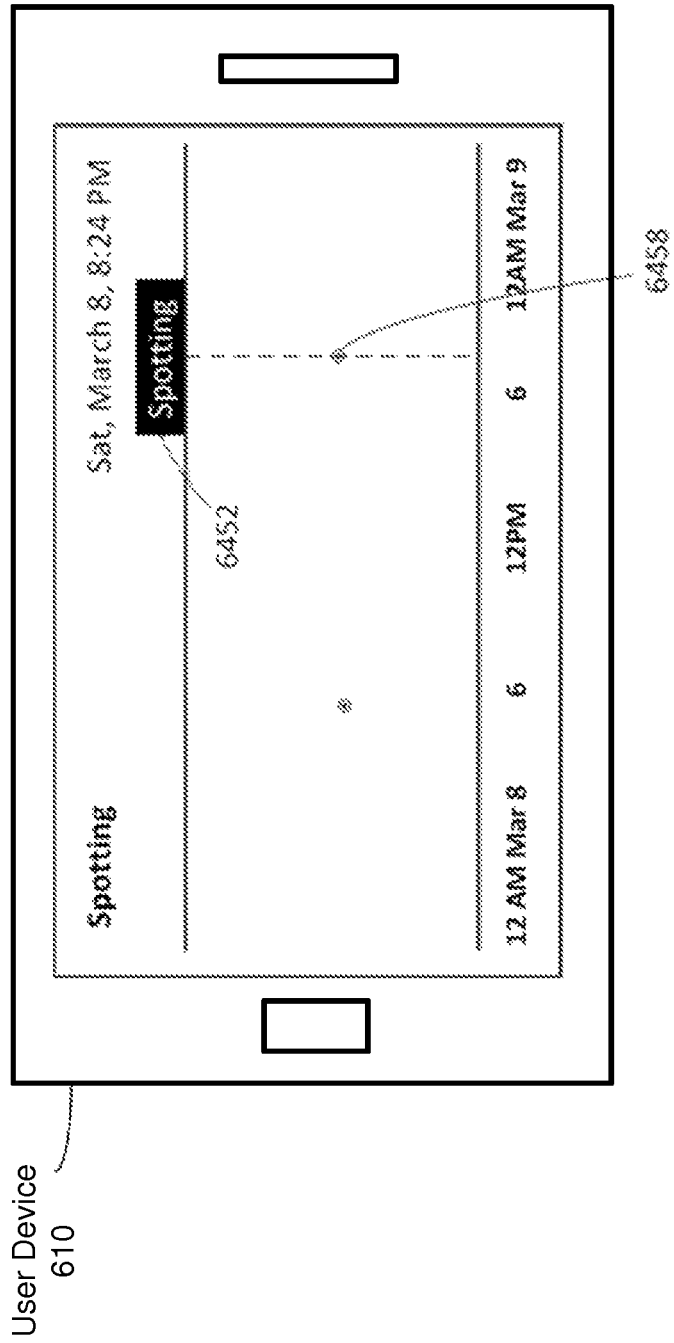

Turning to FIG. 64F, data-set representation 6404 can represent the wellness information of menstrual spotting in some examples. As can be seen, user interface 6450 is displayed responsive to touch input 6410 on an indicator of data-representation 6404 in user interface 6400 (FIG. 64A). User interface 6450 provides menstrual spotting information, such as the occurrence of spotting at a given time interval. As shown, indicator 6458 corresponding to touch input 6410 shows a text read-out 6452 indicating menstrual spotting at the time corresponding to the horizontal location of touch input 6410.

Figure 65A:
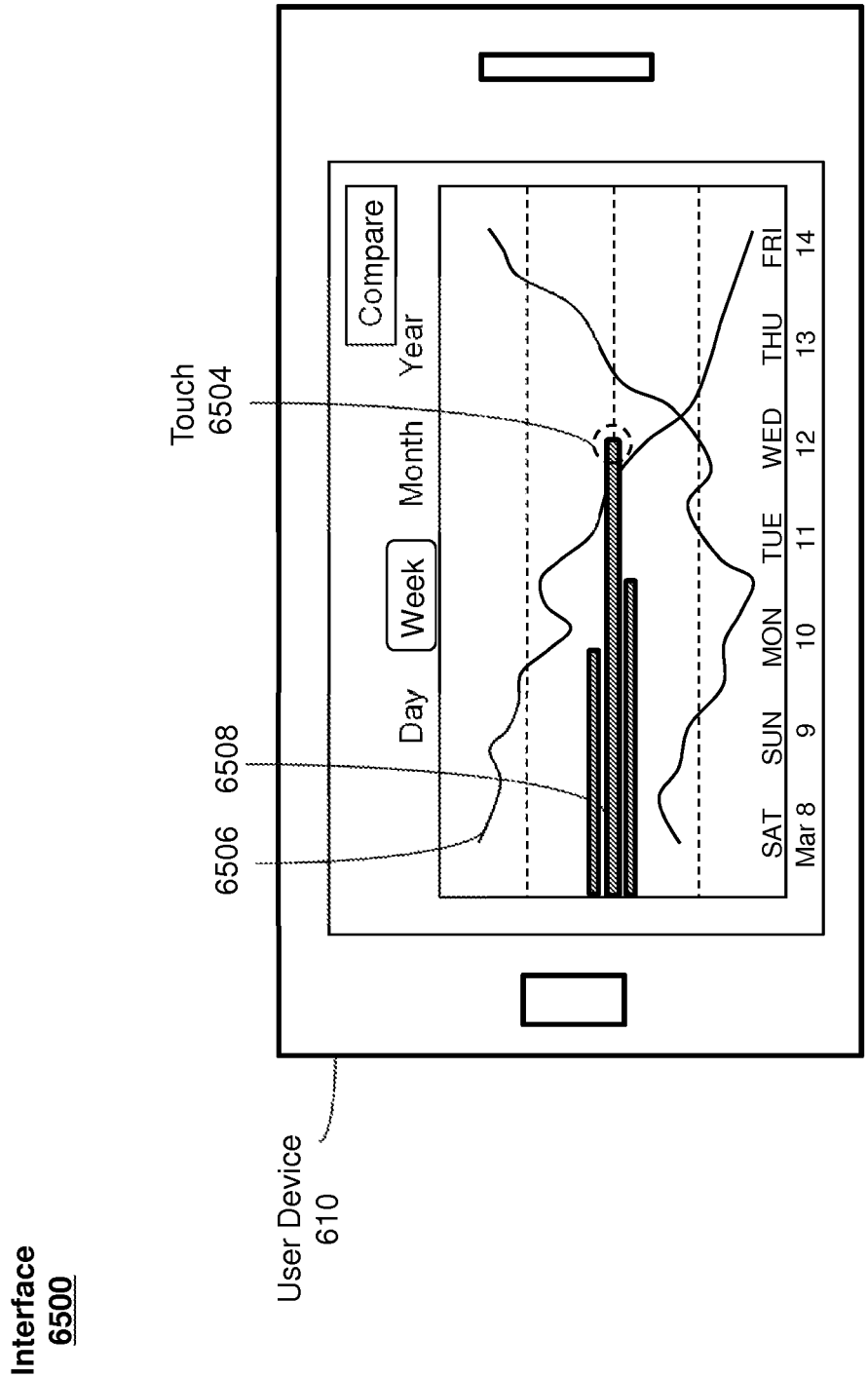
FIGS. 65A-65C illustrate exemplary interfaces for displaying wellness or non-wellness data according to various examples.

As another example, FIG. 65A illustrates exemplary user interface 6500 that can be displayed in response detecting a rotation of user device 610 to a landscape view. The graph view of interface 6500 can include, among others, data-set representations 6506 and 6508 each representing a different set of wellness or non-wellness data. In the illustrated example, the y-axis of the graph can represent a dependent variable of the various data sets, and the x-axis of the graph can represent an independent variable. For example, if data-set representation 6506 represents a set of Calorie data, then the y-axis dependent variable can be Calories, and the x-axis independent variable can be time.

Data-set representation 6508, which is shown as horizontal bar(s), can represent various wellness or non-wellness information. Examples of underlying data represented by data-set representation 6504 are discussed with reference to FIGS. 65B-65C.

Figure 65B:
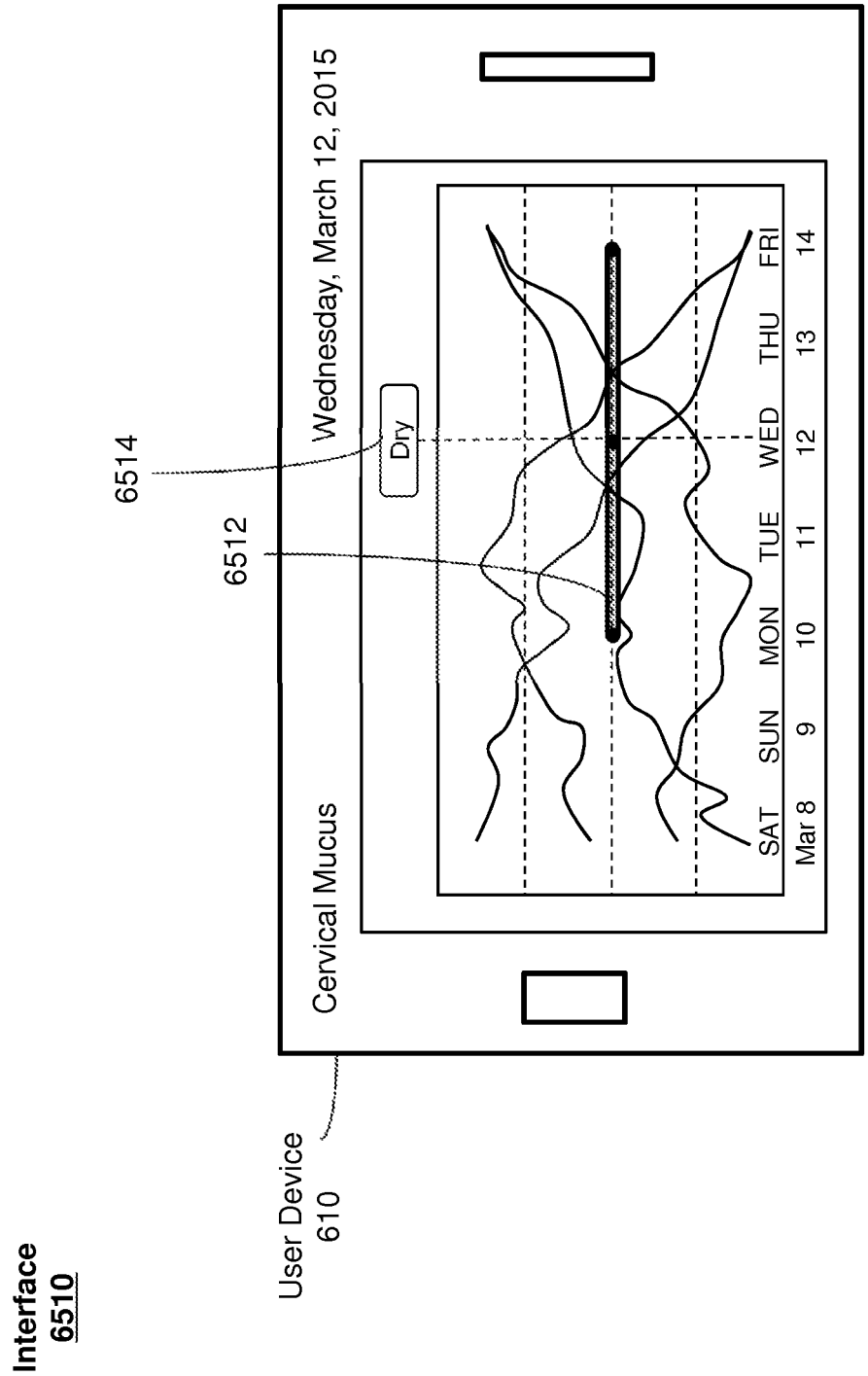

Turning to FIG. 65B, data-set representation 6508 can represent the wellness information of cervical mucus information in some examples. As can be seen, user interface 6510 is displayed responsive to touch input 6504 on an indicator of data-representation 6508 in user interface 6500 (FIG. 65A). User interface 6510 provides cervical mucus information, which can take on discrete values such as "dry," "watery," or "creamy," for example. As shown, range 6512 corresponding to touch input 6504 shows a text read-out 6514 of "creamy". In this example, the dependent variable of data-set representation 6508 takes on values from a set of discrete values (e.g., "dry", "watery", and "creamy"). In some examples, range 6512 covers the weekdays corresponding to the location of touch input 6510.

Figure 65C:
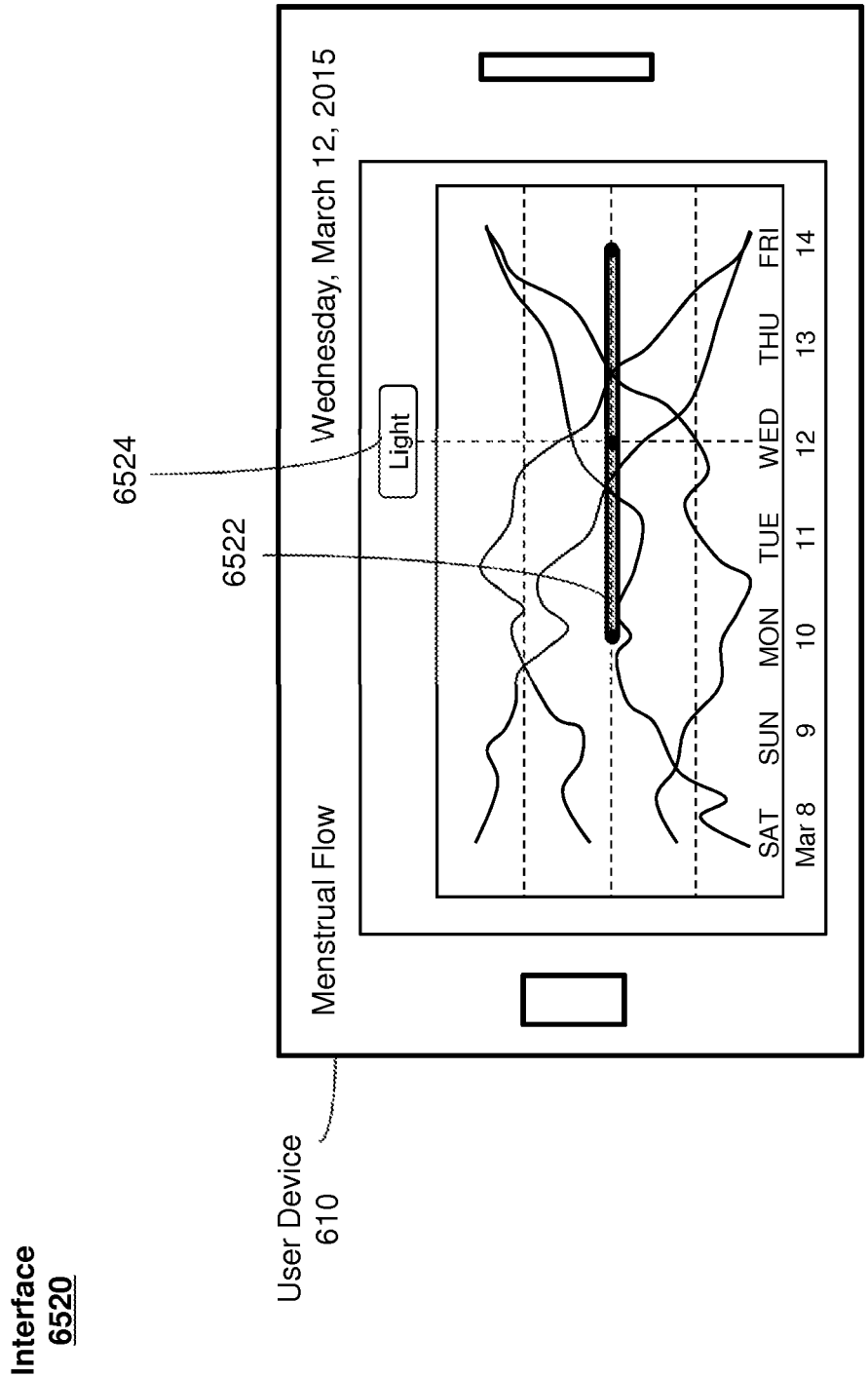

Turning to FIG. 65C, data-set representation 6508 can represent the wellness information of menstrual flow in some examples. As can be seen, user interface 6520 is displayed responsive to touch input 6504 on an indicator of data-representation 6508 in user interface 6500 (FIG. 65A). User interface 6520 provides menstrual flow information, which can take on discrete values such as "light," "medium," or "heavy," for example. As shown, range 6522 corresponding to touch input 6504 shows a text read-out 6524 of "light". In this example, the dependent variable of data-set representation 6508 takes on values from a set of discrete values (e.g., "light," "medium," and "heavy"). In some examples, range 6522 covers the weekdays corresponding to the location of touch input 6510.

Figure 66A:
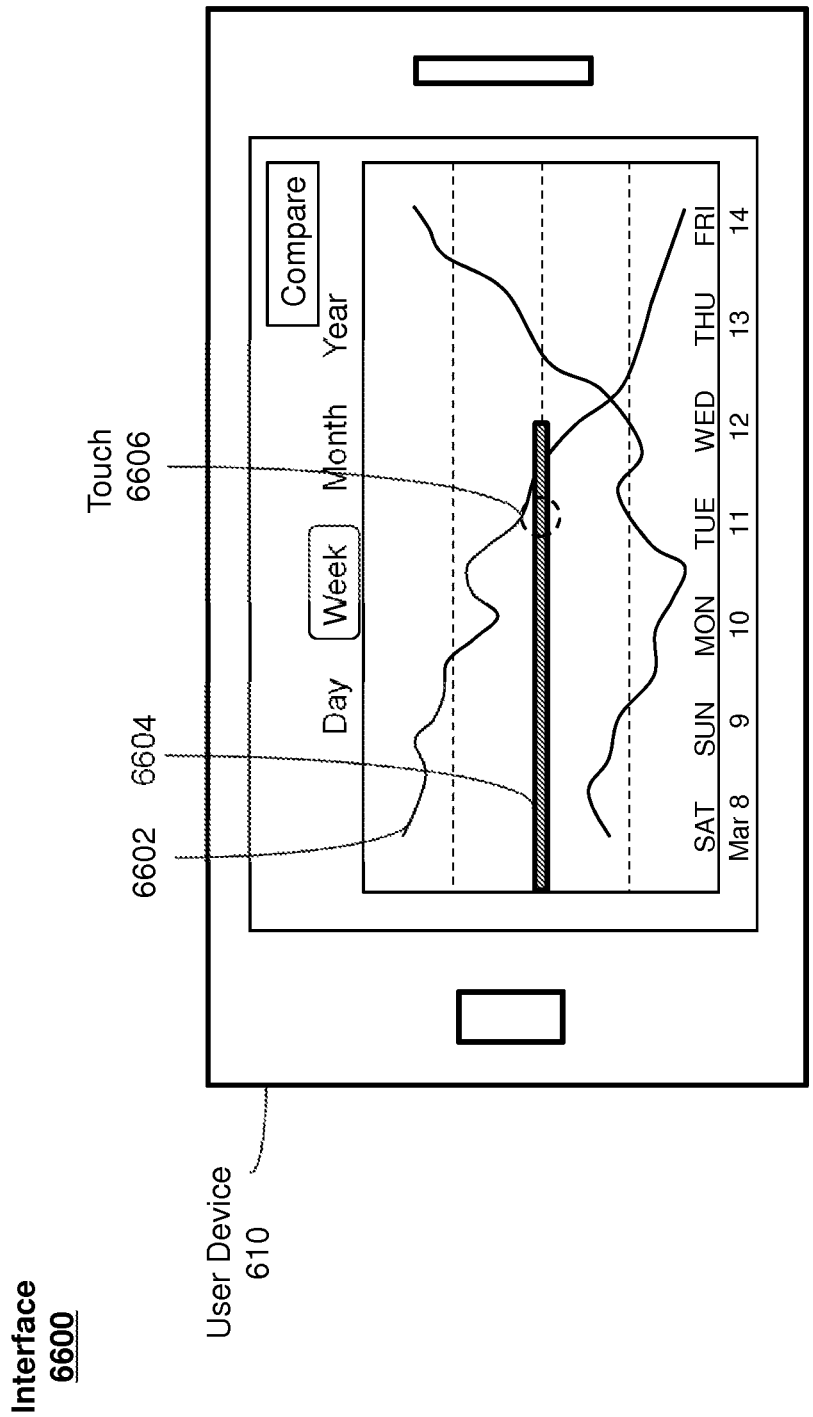
FIGS. 66A and 66B illustrate exemplary interfaces for displaying wellness or nonwellness data according to various examples.

As another example, FIG. 66A illustrates exemplary user interface 6600 that can be displayed in response detecting a rotation of user device 610 to a landscape view. The graph view of interface 6600 can include, among others, data-set representations 6602 and 6604 each representing a different set of wellness or non-wellness data. In the illustrated example, the y-axis of the graph can represent a dependent variable of the various data sets, and the x-axis of the graph can represent an independent variable. For example, if data-set representation 6602 represents a set of Calorie data, then the y-axis dependent variable can be Calories, and the x-axis independent variable can be time.

Figure 66B:
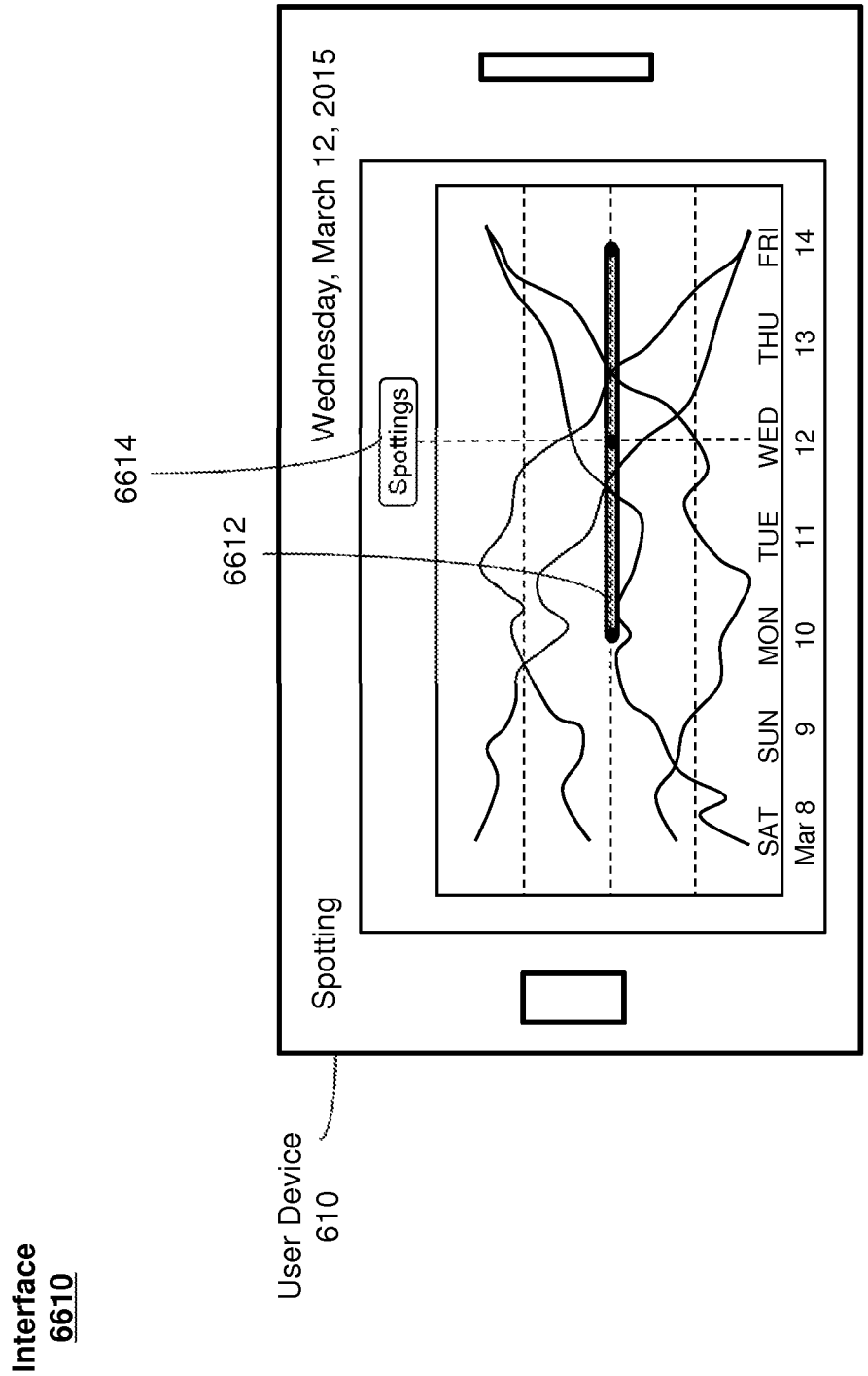

Data-set representation 6604, which is shown as a horizontal bar, can represent wellness or non-wellness information. Examples of underlying data represented by data-set representation 6604 are discussed with reference to FIG. 66B. As can be seen in FIG. 66B, data-set representation 6604 can represent the wellness information of menstrual spotting in some examples. User interface 6610 provides menstrual spotting information, such as the occurrence of spotting at a given time interval. As shown, range 6612 shows a text read-out 6614 indicating menstrual spotting at the time corresponding to the horizontal location of touch input 6606. In this example, the dependent variable of data-set representation 6604 takes on values from a set of discrete values (e.g., Boolean values of "positive" or "negative"). In some examples, range 6612 covers the weekdays corresponding to the location of touch input 6606.

In some examples, the detailed view of the wellness or non-wellness data can be displayed in response to a detailed-view input received while any of interfaces 2400, 2500, 2510, 6400, 6410, 6420, 6430, 6440, 6500, 6510, 6520, 6600, or 6610 (FIGS. 24, 25, and 64-66) are being displayed. In some examples, the detailed-view input can include a detected change in orientation of user device 610. For example, interface 2200, 2300, 5600, 5610, 5620, 5630, 5700, 5710, 5720, 5730, 5800, 5810, 5820, 5830, 5900, 5910, 5920, 5930, 6000, 6010, 6020, 6030, 6100, 6110, 6120, or 6130 (FIGS. 22, 23, and 56-61) can be displayed in response to detecting a rotation of user device 610 to a portrait view.

While the graph view shown in interfaces 2400, 2500, 6400, 6500, or 6660 (FIGS. 24, 25, 64, 65, and 66) include three or four data-set representations, it should be appreciated that the graph can include any number of data-set representations. Additionally, the number of ranges of vertical positions can change based on the number of displayed data-set representations (e.g., to be equal to the number of displayed data-set representations). For example, if six data-set representations are displayed within the graph, then six discrete ranges of vertical positions can be associated with the data-set representations to allow a user to select the desired data-set representation.

Figure 27:
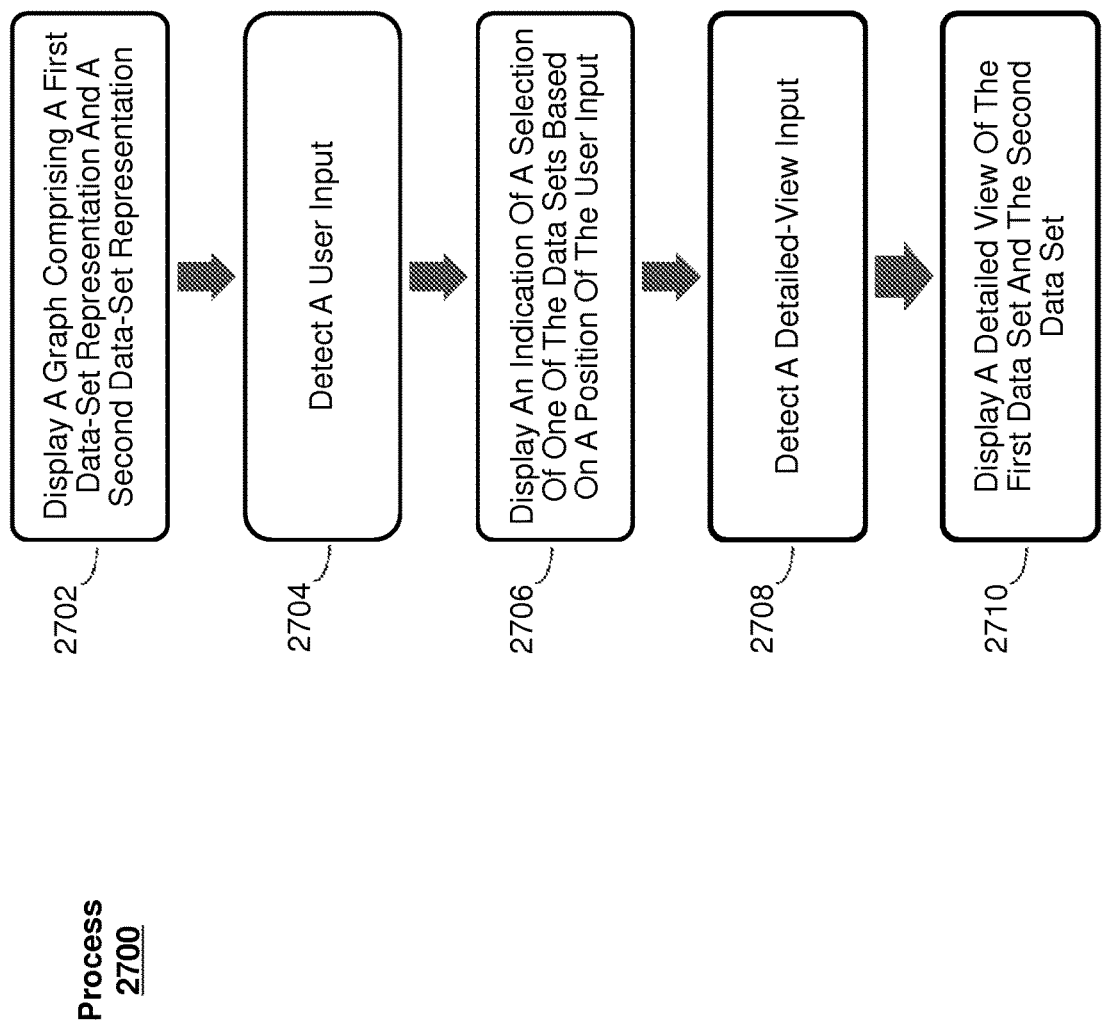
FIG. 27 illustrates an example process for displaying wellness or non-wellness data according to various examples.

FIG. 27 illustrates an example process 2700 for displaying continuous and/or discrete wellness or non-wellness data according to various examples. Process 2700 can be performed at an electronic device (e.g., device 610) with a display. In some examples, the display can include a touch-sensitive display. In other examples, the display can be separate from a touch-sensitive surface. Some blocks of process 2700 can be combined and/or the order of some blocks can be changed.

As described below, process 2700 provides an intuitive way to select overlapping data-set representations in a graph view. At block 2702, a graph view of wellness or non-wellness data can be displayed on a display of a user device (e.g., user device 610). For example, an interface similar or identical to interface 2400, 2500, 6400, 6500, or 6660 (FIGS. 24, 25, 64, 65, and 66) can be displayed. The graph view can include a first data-set representation (e.g., data set representation 2402) of a first data set in which a first dependent variable varies as an independent variable changes and a second data-set representation (e.g., data set representation 2404) of a second data set in which a second dependent variable varies as the independent variable changes.

In some examples, the first data set can include a first set of wellness data, and the second data set can include a second set of wellness data.

In some examples, the first data-set representation can be associated with a first range of vertical positions within the graph (e.g., first range 2410) and the second data-set representation can be associated with a second range of vertical positions within the graph (e.g., second range 2412).

In some examples, the first data-set representation can be displayed in the graph overlapping the second data-set representation. For example, in FIGS. 24 and 25, data-set representations 2402, 2404, 2406, and 2408 are shown as overlapping in interfaces 2400 and 2500. As another example, FIG. 64, data-set representations 6402, 6404, and 6406 are shown as overlapping. In some examples, the first data-set representation and the second data-set representation can be colored-coded based on a type of data that they represent.

In some examples, the first range of vertical positions can be uniquely associated with the first data-set representation, and the second range of vertical positions can be uniquely associated with the second data-set representation. For example, first range 2410 is uniquely associated with data-set representation 2402 and second range 2412 is uniquely associated with data-set representation 2404 in interfaces 2400 and 2500.

In some examples, a vertical scale for displaying the first data-set representation can be different from a vertical scale for displaying the second data-set representation. In these examples, displaying the graph can include determining a vertical scale for the first data-set representation based on the maximum and minimum values of the first dependent variable of the first data-set representation that are to be displayed in the graph. Displaying the graph can further include determining a vertical scale for the second data-set representation based on the maximum and minimum values of the second dependent variable of the second data-set representation that are to be displayed in the graph. In some examples, the vertical scale for the first data-set representation can be defined by a maximum vertical position within the graph corresponding to a first multiplying factor multiplied by the maximum value of the first dependent variable of the first data-set representation that are to be displayed in the graph, and a minimum vertical position within the graph corresponding to a second multiplying factor multiplied by the minimum value of the first dependent variable of the first data-set representation that are to be displayed in the graph. In some examples, the vertical scale for the second data-set representation can be defined by a maximum vertical position within the graph corresponding to a third multiplying factor multiplied by the maximum value of the second dependent variable of the second data-set representation that are to be displayed in the graph, and a minimum vertical position within the graph corresponding to a fourth multiplying factor multiplied by the minimum value of the second dependent variable of the second data-set representation that are to be displayed in the graph. In some examples, the dependent variable for the first data set can be measured or reported in different units from the dependent variable for the second data set.

In some examples, the first data set has dependent variables that represent discrete data values, and the second data set has dependent variables that represent values along a continuous range of possible values. As used here, the word "discrete" value refers to distinct, non-continuous values, such as the category values of "heavy," "medium," and "light". A (first) data-set where dependent variables are aligned with discrete elements stands in contrast to a (second) data-set where dependent variables can take on any value along a given range, such as a temperature range, in that dependent variables of the first data set can take on values drawn from a finite set of discrete values, but dependent variables of the second data set can take on an infinite number of value along the applicable range. For example, body temperature can be represented using the discrete values (e.g., categories) of "hot," "normal," and "cold," as well as be represented using data points along a continuous range, such as the value 97.4 degrees along the range of 90 to 110 degrees.

At block 2704, a user input can be detected at a location on the display. Detecting the user input can include detecting a touch or hover event by a finger or other device on a touch sensitive display, a click of a mouse or other device, a touch or hover event on a touch pad, or the like.

At block 2706, a location of the user input can be determined. For example, the vertical and horizontal positions (e.g., y and x-axis coordinates) of the user input can be determined. In some examples, an indication of a selection of the first data-set representation can be displayed, in response to determining that the location of the user input on the display detected at block 2704 has a vertical position associated with the first range of vertical positions. Alternatively, in response to determining that the location of the user input on the display detected at block 2704 has a vertical position associated with the second range of vertical positions, an indication of a selection of the second data-set representation can be displayed. In some examples, an indication of a selection of the first data-set representation can be displayed, in response to determine that the location of the user input on the display detected at block 2704 is located at an indicator representing the value of a discrete dependent variable.

In some examples, displaying the indication of a selection can include displaying a marker overlaid on the selected data-set representation at a horizontal position corresponding to the horizontal position of the location of the user input. For example, a circle marker can be displayed over data-set representation 2402 in interface 2500 of FIG. 25 in response to detecting a user input at location 2418 in interface 2400. In another example, a filled circle marker can be displayed at over an indicator of data-set representation 6404 corresponding to touch input 6410 as shown in FIG. 64D.

In some examples, displaying the indication of a selection can include displaying a numerical and/or textual representation of a data entry of the data set represented by the selected data-set representation. The data entry can be associated with a category value corresponding to the horizontal position of the location of the detected user input. For example, a numerical value of 480 kcal can be displayed in response to receiving a user input at location 2418, as can been seen in FIGS. 24 and 25. In another example, a textual representation 6434 of "Heavy" can be displayed in response to receiving a user input at location 6410 as shown in FIG. 61D.

In some examples, the first data set or the second data set can include blood pressure data. In these examples, the displayed numerical value of the data entry can include a high value for diastolic blood pressure, a low value for diastolic blood pressure, a high value for systolic blood pressure, and a low value for systolic blood pressure. In some examples, the dependent variable of the first data-set representation or the second data-set representation can include average of blood pressure values.

In other examples, the first data set or the second data set can include heart rate data. In these examples, the displayed numerical value of the data entry can include a high value for heart rate and a low value for heart rate.

In some examples, the first data set or second data set can include reproductive health data, such as cervical mucus data, basal body temperature, or menstrual flow data. In these examples, the textual representation displayed in response to a selection of the data-set representation for cervical mucus can include "Creamy," "Dry," or "Egg white" associated with the time corresponding to the horizontal position of the user input. The textual representation displayed in response to a selection of the data-set representation for basal body temperature can include a temperature reading associated with the time corresponding to the horizontal position of the user input. The textual representation displayed in response to a selection of the data-set representation for menstrual flow can include "Heavy," "Medium," or "Light" associated with the time corresponding to the horizontal position of the user input.

In some examples, the first data-set representation can include a first line in the graph. In these examples, displaying the indication that the first data-set representation has been selected can include highlighting an area below the first line. For example, the area below the line of the selected data-set representation can be darkened, brightened, displayed with a different color, or otherwise highlighted relative to other portions of the graph to change the line graph into an area graph of the selected data set. In some examples, the data-set representations that are not currently selected can be removed from the display, greyed out, or otherwise made less visible within the graph.

In some examples, when a given data-set representation is selected, other data-set representations provide an indication that they are not selected, for example, by greying out.

In some examples, the first range of vertical positions within the graph can expand based on a length of time that the user input is detected while a vertical position of the location of the user input is within the first range of vertical positions. In other examples, the second range of vertical positions within the graph can expand based on a length of time that the user input is detected while the vertical position of the location of the user input is within the second range of vertical positions.

At block 2708, a detailed-view input can be detected at the electronic device. In some examples, detecting the detailed-view input can include detecting a change in orientation of the electronic device while displaying the graph. For example, detecting the detailed-view input can include detecting a change in orientation of the electronic device from a landscape view (e.g., shown in FIGS. 24-26) to a portrait view (e.g., shown in FIGS. 22-23). In other examples, the detailed-view input can include other types of inputs.

At block 2710, in response to detecting the detailed-view input, a detailed view of the first data set and the second data set can be displayed. For example, a detailed view similar or identical to those shown in interfaces 2200 and 2300 can be displayed. The detailed view can include a first partition associated with the first data set (e.g., partition 2202) and a second partition associated with the second data set (e.g., partition 2204).

In some examples, the first partition can include a first graph representation of the first data set (e.g., graph 2208), and the second partition can include a second graph representation of the second data set (e.g., graph 2210). In some examples, unlike the first and second data-set representation of the graph view, the first graph representation can be non-overlapping with the second graph representation in the detailed view.

In some examples, the first partition can be displayed in a color matching a color of the first data-set representation, and the second partition can be displayed in a color matching a color of the second data-set representation. For example, partition 2202 can be displayed in a color matching a color of data-set representation 2402, and partition 2204 can be displayed in a color matching a color of data-set representation 2404.

In some examples, process 2700 can further include detecting a request to scroll the detailed view and, in response to detecting the request to scroll the detailed view, scrolling the detailed view. For example, the detailed view shown in interface 2200 can be scrolled in the upward direction to display interface 2300 containing other partitions that were not previously displayed.

In some examples, process 2700 can further include detecting a request to reorder the first partition and the second partition and, in response to detecting the request to reorder the first partition and the second partition, reordering the first partition and the second partition within the detailed view. In some examples, detecting the request to reorder can include detecting a selection of one of the partitions for greater than a threshold length of time. After detecting the selection for the threshold length of time, user device 610 can animate the partitions in a way that indicates that the partitions can be reordered. The partitions can be displayed reordered in response to detecting that a selected partition is dragged to a new location within the detailed view.

In some examples, process 2700 can further include detecting a graph-view input at the electronic device and, in response to detecting the graph-view input, displaying the graph comprising the first data-set representation of the first data set and the second data-set representation of the second data set. In some examples, detecting the graph-view input can include detecting a change in orientation of the electronic device. For example, interface 2400 can be displayed in response to detecting a change in orientation of the electronic device from a portrait view to a landscape view.

It should be understood that the particular order in which the operations in FIG. 27 have been described is merely exemplary and is not intended to indicate that the described order is the only order in which the operations could be performed. One of ordinary skill in the art would recognize various ways to reorder the operations described herein. Additionally, it should be noted that details of other processes described herein with respect to other processes described herein (e.g., processes 900, 1600, 1800, 2100, 2700, 3800, or 4500) are also applicable in an analogous manner to process 2700 described above with respect to FIG. 27. For brevity, these details are not repeated here.

Input and Output of Heath Data with Granularity

Figure 28:
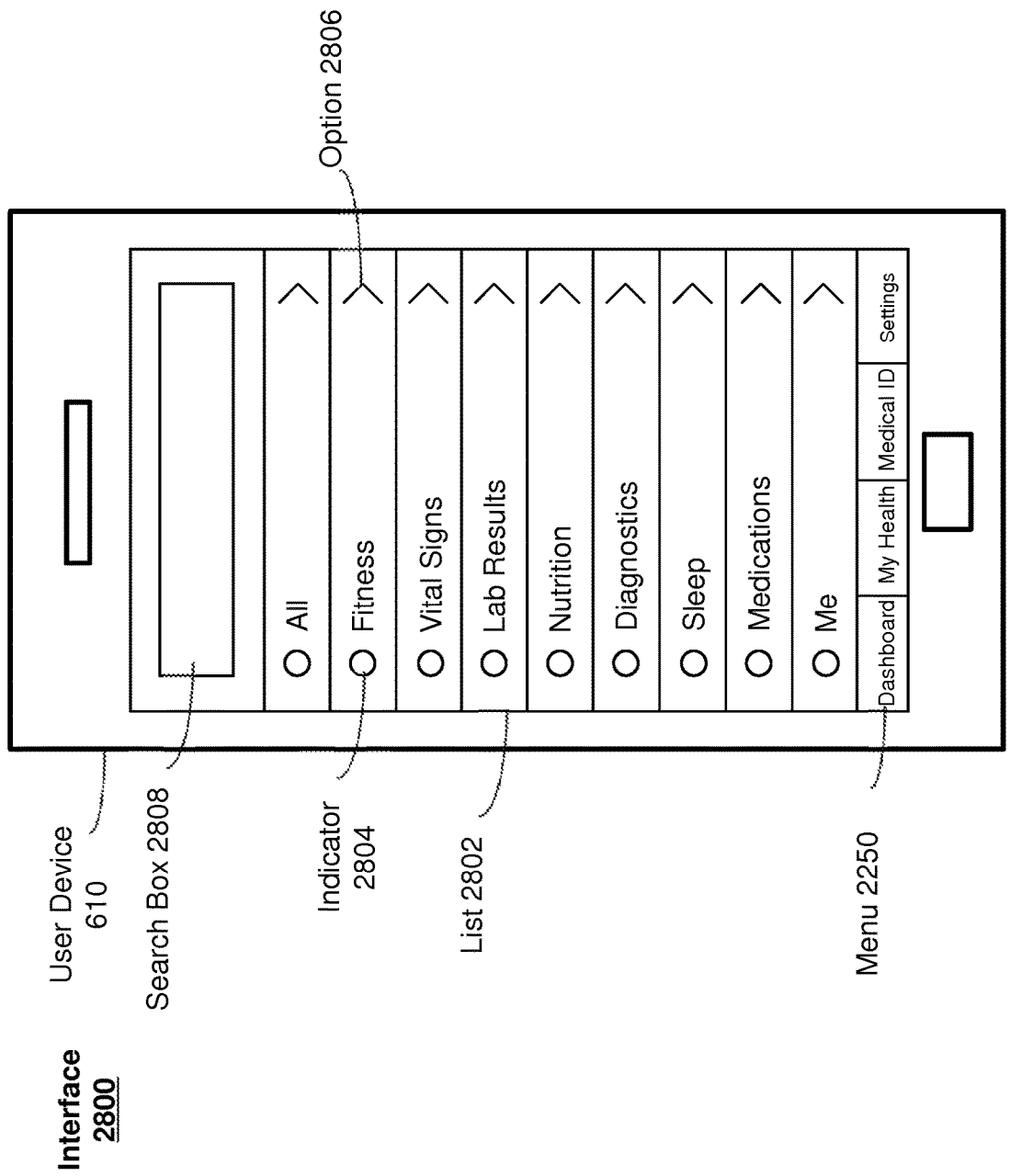
FIG. 28 illustrates example interfaces for displaying wellness or non-wellness data according to various examples.

FIG. 28 illustrates one example interface 2800 that can be displayed by user device 610 to display a user's wellness or non-wellness data. Interface 2800 can include a list 2802 of categories of wellness or non-wellness data. The categories can include one or more sub-categories of wellness or non-wellness data. The sub-categories can further include any number of additional sub-categories. For example, the category "Fitness" can include sub-categories "Body Mass Index," "Body Fat Percentage," "Height," "Body Mass," "Lean Body Mass," "Steps," "Distance," "Calories Burned," "Active Hours," and "Flights of Stairs." The category "Vital Signs" can include sub-categories "Heart Rate," "Systolic Blood Pressure," "Diastolic Blood Pressure," "Oxygen Saturation," "Respiratory Rate," and "Body Temperature." The category "Lab Results" can include sub-categories "Blood Glucose" and "Blood Alcohol Content." The category "Nutrition" can include sub-categories "Total Fat," "Polyunsaturated Fat," "Monounsaturated Fat," "Saturated Fat," "Cholesterol," "Sodium," "Potassium," "Carbohydrates from Sugar," "Dietary Fiber," "Sugars," "Dietary Calories," "Calories from Fat," "Protein," "Vitamin A," "Vitamin B6," "Vitamin B12," "Vitamin C," "Vitamin D," "Vitamin E," "Vitamin K," "Calcium," "Iron," "Thiamin," "Riboflavin," "Niacin," "Folic Acid," "Biotin," "Pantothenic Acid," "Phosphorus," "Iodine," "Magnesium," "Zinc," "Selenium," "Copper," "Manganese," "Chromium," "Molybdenum," and "Chloride." The category "Diagnostics" can include sub-categories "Number of Time Fallen," "Galvanic Skin Response," and "Body Heat Flux." The category "Medications" can include sub-category "Inhaler Use." The category "Sleep" can include subcategories "Hours Slept." The category "Me" can include sub-categories "Name," "Birthdate," "Gender," "Blood Type." It should be appreciated that the lists above are provided only as examples, and that additional or fewer categories can be included within interface 2800. Additionally, it should be appreciated that the categories of interface 2800 can include additional or fewer sub-categories.

In some examples, each item in list 2802 can include an indicator 2804 that can be color-coded based on the type of wellness or non-wellness data of the associated item in list 2802. For example, the indicator 2804 associated with "Fitness" can have a different color than the indicator 2804 associated with "Vital Signs." In some examples, the items in list 2802 can further include a selectable option 2806 that can be used to expand the associated category.

Figure 29:
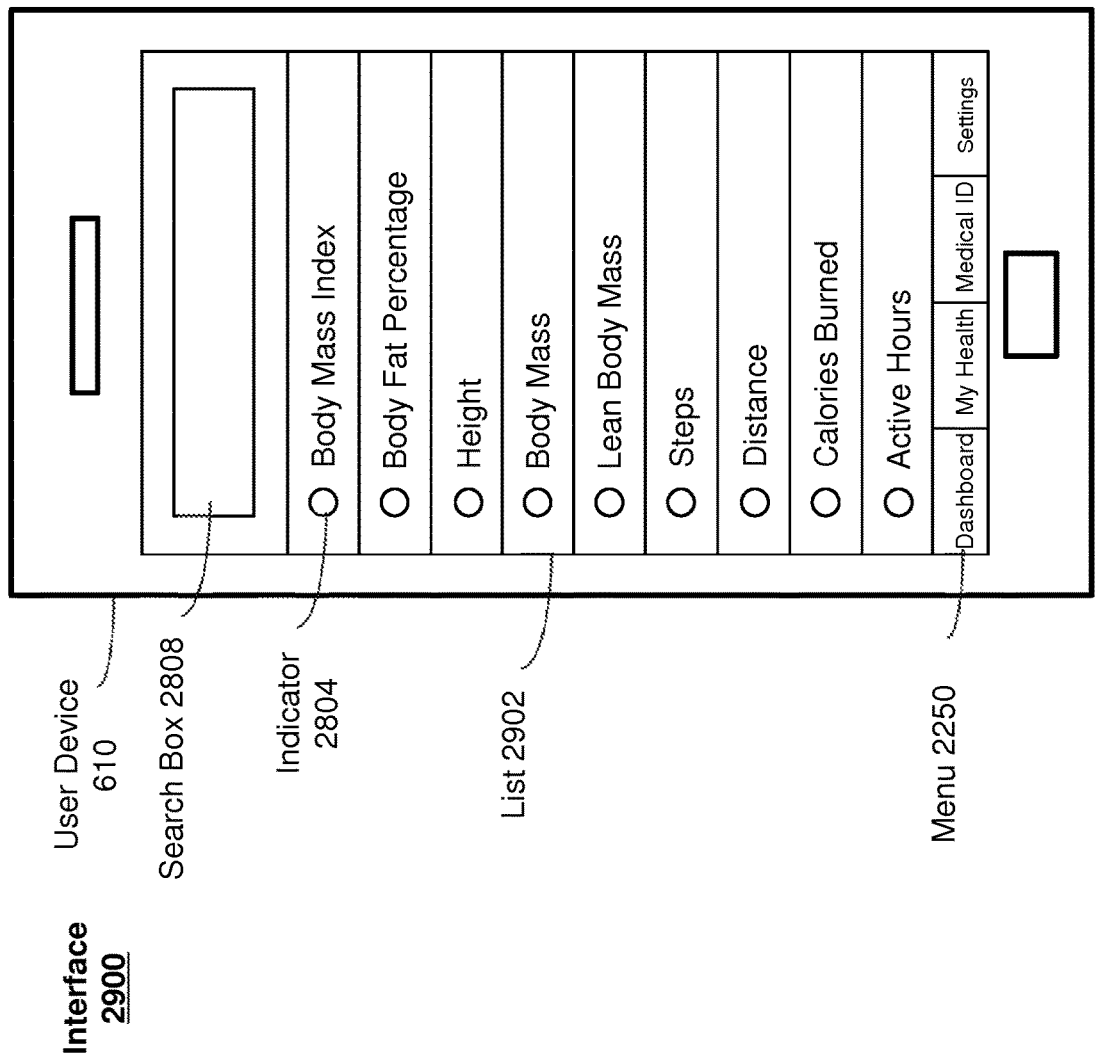
FIG. 29 illustrates example interfaces for displaying wellness or non-wellness data according to various examples.

For example, FIG. 29 illustrates interface 2900 that can be displayed in response to a selection of option 2806 associated with "Fitness." As shown, interface 2900 can include a list 2902 of sub-categories that fall under the broader category of "Fitness" that was selected in interface 2800. The list 2902 of sub-categories can be displayed in place of the previously displayed list 2802. Similar to list 2802, the items in list 2902 can include an indicator 2904 that can be color-cored based on the type of wellness or non-wellness data of the associated item in list 2902. In this example, since all of the sub-categories displayed within list 2902 fall under the same category or type of wellness or non-wellness data, the indicators 2904 associated with each item can be the same color. In some examples, the color of indicators 2904 associated with the items in list 2902 can be the same color as indicator 2804 associated with "Fitness." In other examples, the color of indicators 2904 associated with the items in list 2902 can be a different shade of the color of indicator 2804 associated with "Fitness." For example, indicators 2904 can be light green, while indicator 2804 associated with "Fitness" can be dark green.

Figure 30:
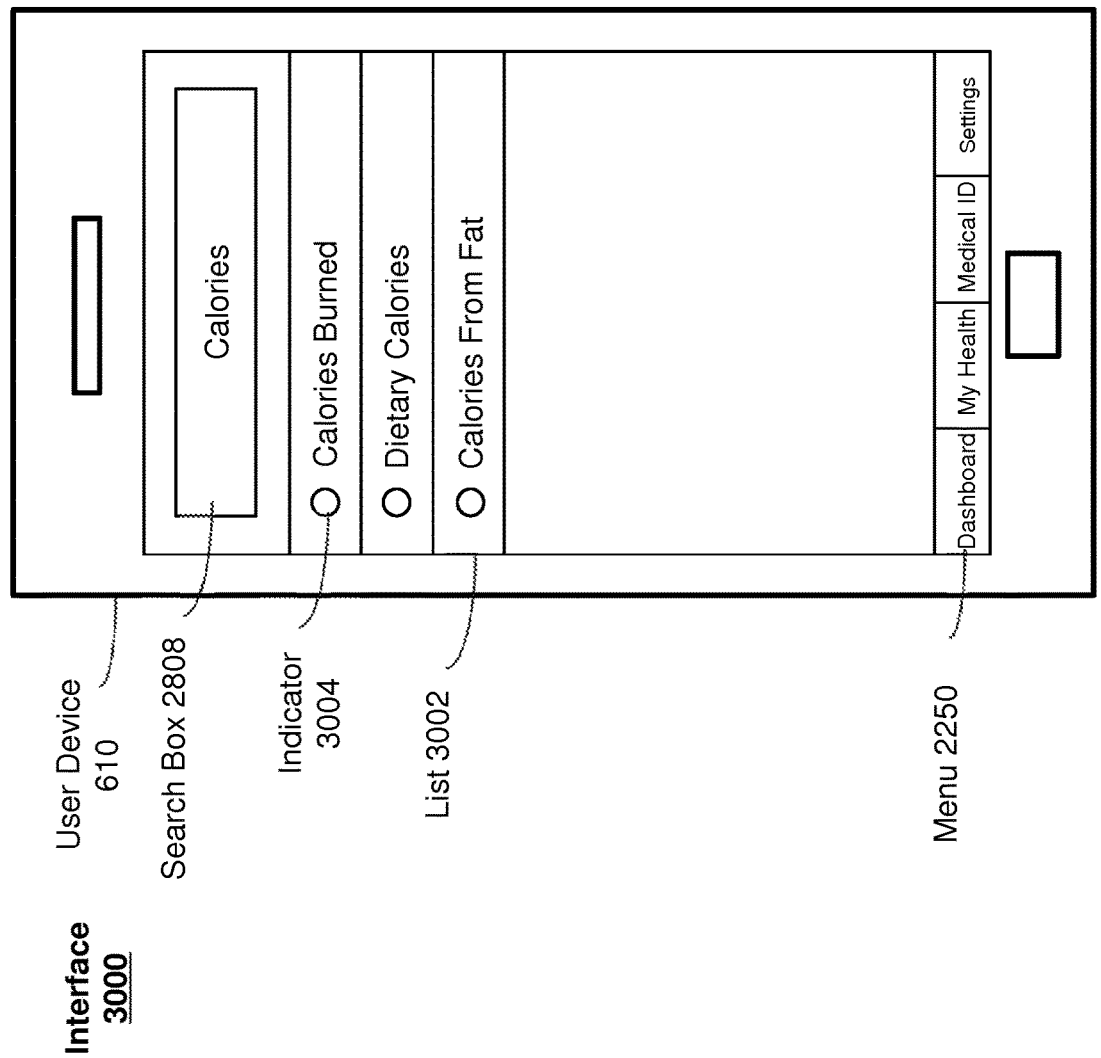
FIG. 30 illustrates example interfaces for displaying wellness or non-wellness data according to various examples.

Referring back to FIG. 28, interface 2800 (and interface 2900) can further include search box 2808 for performing keyword searches within the categories listed in list 2802. For example, FIG. 30 illustrates interface 3000 that can be displayed in response to a user entering the search query "Calories" in search box 2808. As shown, interface 3000 can include a list 3002 of sub-categories that match the search query "Calories." The sub-categories can be sub-categories of any of the categories of list 2802. For "Calories Burned" can be a sub-category of "Fitness," "Dietary Calories" can be a sub-category of "Nutrition," and "Calories From Fat" can be a sub-category of "Nutrition." Interface 3000 can further include indicators 3004 associated with the items in list 3002. Similar to indicators 2804 and 2904, indicators 3004 can be color-coded based on the type of wellness or non-wellness data of the associated item in list 3002. In this example, indicator 3004 of "Dietary Calories" can be the same color as indicator 3004 of "Calories From Fat" since they both fall within the broader category of "Nutrition." In some examples, the color of indicators 3004 of "Dietary Calories" and "Calories From Fat" can be the same color as indicator 2804 for "Nutrition." In other examples, the color of indicators 3004 of "Dietary Calories" and "Calories From Fat" can be a different shade of the color of indicator 2804 for "Nutrition." The indicator 3004 for "Calories Burned" can be a different color from indicators 3004 of "Dietary Calories" and "Calories From Fat" since "Calories Burned" falls within a different category (e.g., "Fitness"). In some examples, the color of indicator 3004 of "Calories Burned" can be the same color as indicator 2804 for "Fitness." In other examples, the color of indicator 3004 of "Calories Burned" can be a different shade of the color of indicator 2804 for "Fitness."

Figure 31:
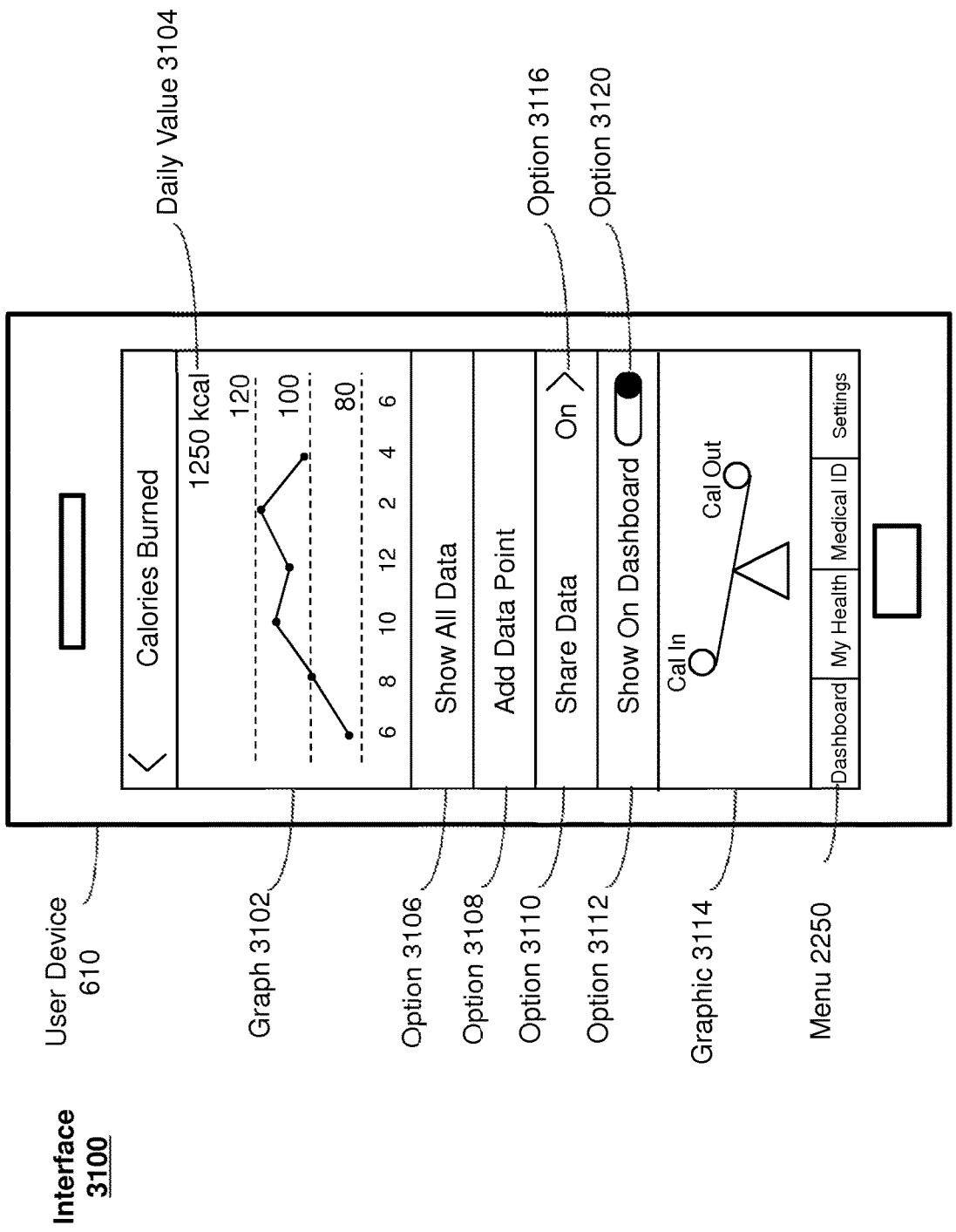
FIG. 31 illustrates example interfaces for displaying wellness or non-wellness data according to various examples.

In some examples, any of the sub-categories shown in interfaces 2900 and 3000 can be selected to display a detailed view of the sub-category. For example, FIG. 31 illustrates an example interface 3100 that can be displayed in response to a selection of "Calories Burned" from either interface 2900 or 3000. As shown, interface 3100 can include a text indication of the type of wellness or non-wellness data being displayed in the detailed view. For example, interface 3100 include the text "Calories Burned" to indicate that the information displayed within interface 3100 represents information associated with Calories burned.

Figure 33:
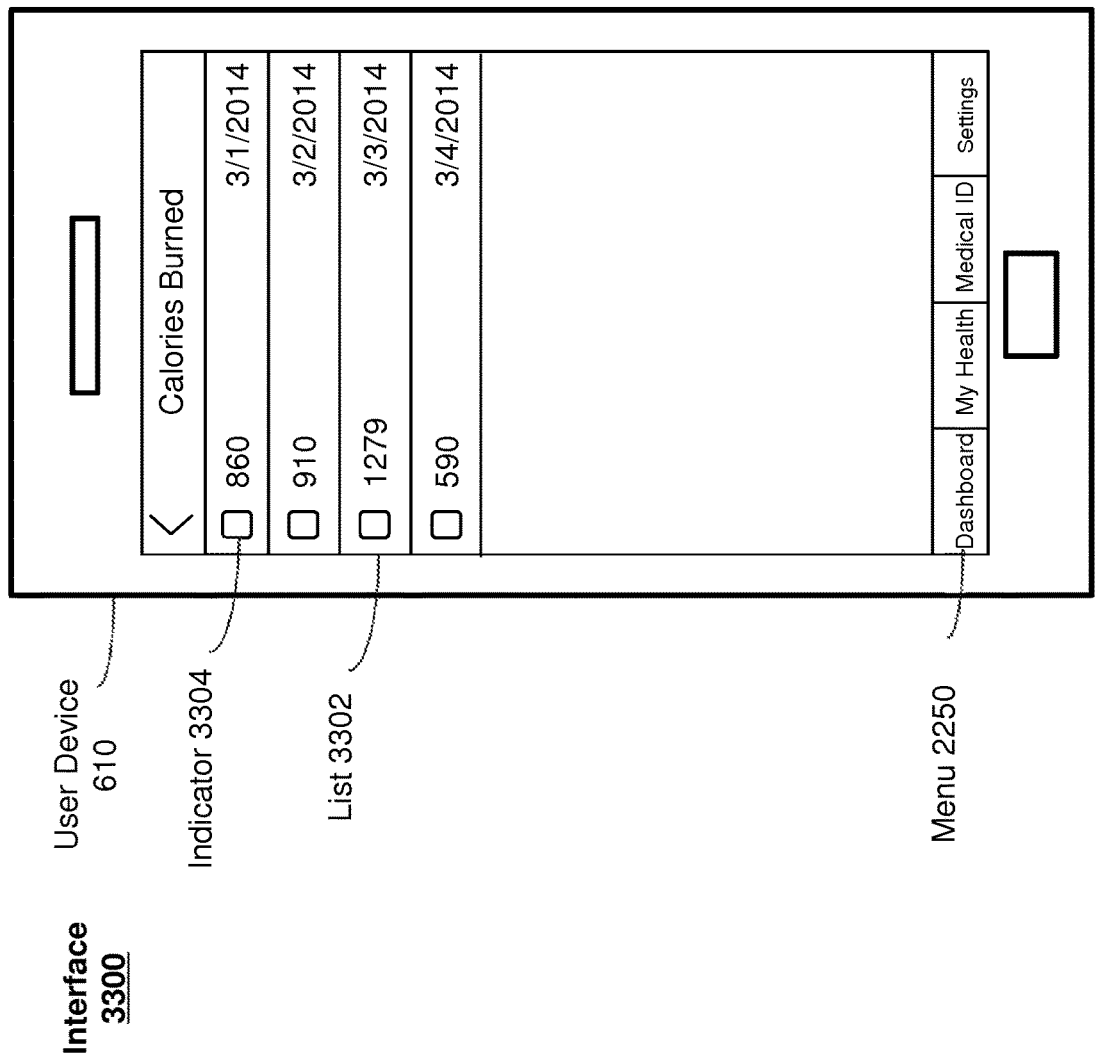
FIG. 33 illustrates example interfaces for displaying wellness or non-wellness data according to various examples.

In some examples, interface 3100 can further include a current daily value 3104 of 1250 kcal and a graph representation 3102 showing the number of Calories burned over time throughout the day. Interface 3100 can further include "Show All Data" option 3106 that can be used to display all data that falls within the sub-category of "Calories Burned." For example, FIG. 33 illustrates an example interface 3300 that can be displayed in response to a selection of option 3106 in interface 3100. As shown, interface 3300 can include a list 3302 of all data entries that represent calories burned (e.g., stored in wellness database 611). As shown, the data entries in list 3302 can include a numerical value of the data entry and an associated date (and can also include a time) that the corresponding data entry was recorded. For example, the first data entry in list 3302 can include the number 860 associated with date Mar. 1, 2014, indicating that 860 Calories were burned on Mar. 1, 2014. The data entries in list 3302 can further include an indicator 3304. Indicator 3304 can include a graphic, text, or other image that represents the source of the data entry. For example, if the first data entry was obtained from a wearable electronic Device 1, indicator 3304 associated with that data entry can include an image of the logo of the company that manufactured Device 1 or some other image associated with Device 1. Similarly, if the second data entry in list 3302 was obtained from a software application App 1, indicator 3304 associated with the second data entry can include an image associated with a logo of the company that created App 1 or some other image associated with App 1.

While shown for Calories burned, it should be appreciated that a list of data entries associated with any type of sub-category of wellness or non-wellness data can be displayed in a similar manner.

Figure 34:
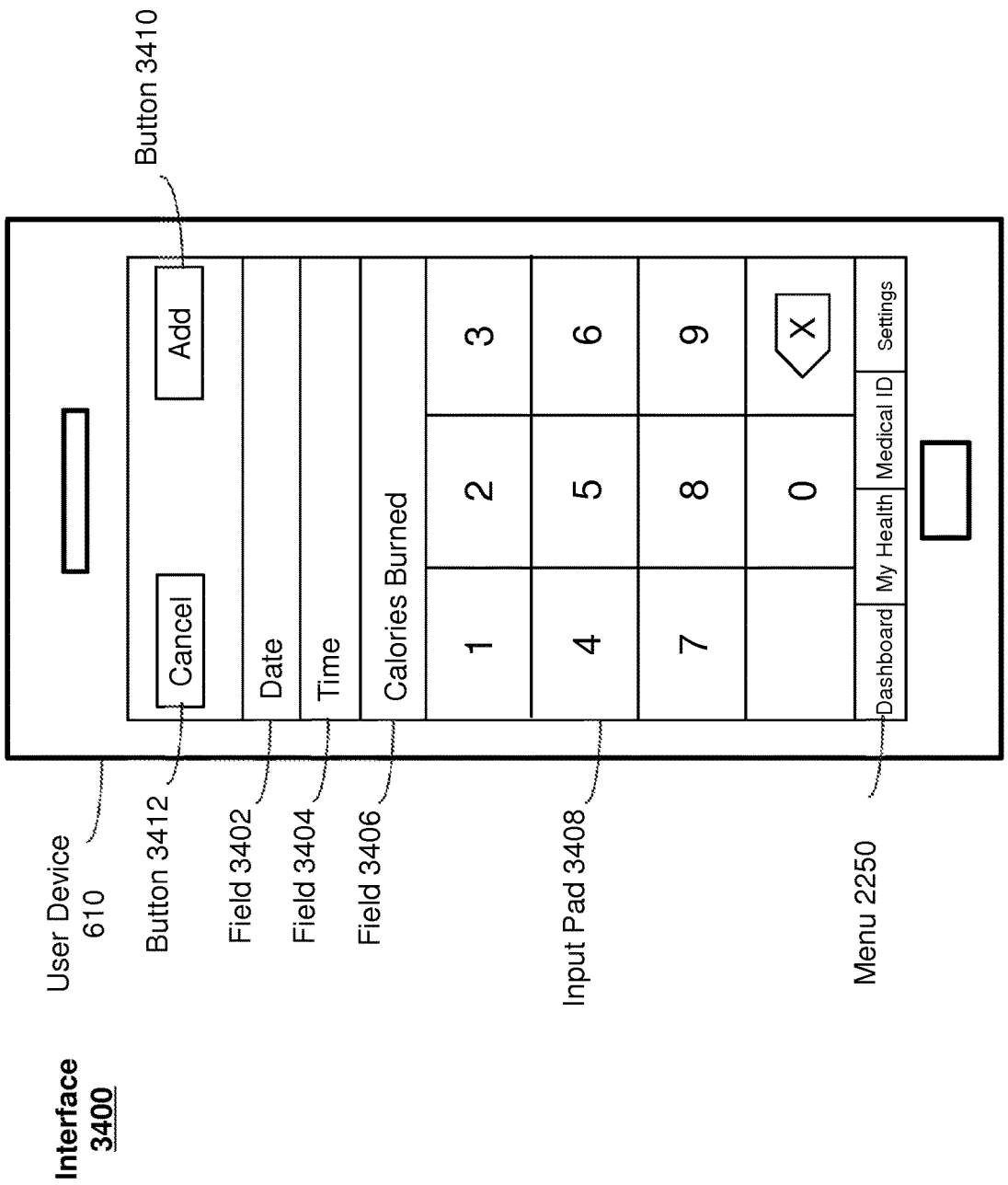
FIG. 34 illustrates example interfaces for displaying wellness or non-wellness data according to various examples.

Referring back to FIG. 31, interface 3100 can further include "Add Data Point" option 3108 that can be used to display an interface for manually entering a data entry within the sub-category of "Calories Burned." For example, FIG. 34 illustrates an example interface 3400 that can be displayed in response to a selection of option 3108 in interface 3100. As shown, interface 3400 can include fields 3402, 3404, and 3406 for entering the date, time, and number of Calories burned, respectively, for the data entry being input. Interface 3400 can further include numerical input pad 3408 for populating fields 3402, 3404, and 3406. Interface 3400 can further include "Add" button 3410 that can be selected to add the information contained in interface 3400 as a data entry within the Calories burned sub-category (e.g., to be stored in wellness database 611). Interface 3400 can further include "Cancel" button 3412 for canceling entry of the data entry.

Referring back to FIG. 31, interface 3100 (and interface 3200) can further include "Show On Dashboard" option 3112 having option 3120 for selectively causing the associated sub-category of data (e.g., Calories Burned) to be displayed in the detailed view of interfaces 2200 and 2300. When the switch of option 3120 is placed in the on position, the associated sub-category of data can be included within the detailed view of interfaces 2200 and 2300. However, when the switch of option 3120 is placed in the off position, the associated sub-category of data may not be included within the detailed view of interfaces 2200 and 2300.

As shown in FIG. 31, interface 3100 can further include graphic 3114. Graphic 3114 can include any image or other graphical representation of the wellness or non-wellness data represented displayed in interface 3100. For example, graphic 3114 can include a balance showing the relative values of Calories consumed and Calories expended by the user. However, it should be appreciated that any other graphic or image can be shown.

In some examples, the detailed view of the sub-category can further include additional information not shown in interface 3100. In these examples, a user can initiate a scroll request by swiping up or down on a touch sensitive display, by clicking and dragging on a display using a mouse or other input device, by manipulating a scroll-wheel, by performing a swiping gesture on a touch pad, or the like. In response to detecting the scroll request, user device 610 can scroll the view of interface 3100 to display information that was not previously displayed (or was partially displayed).

Figure 32:
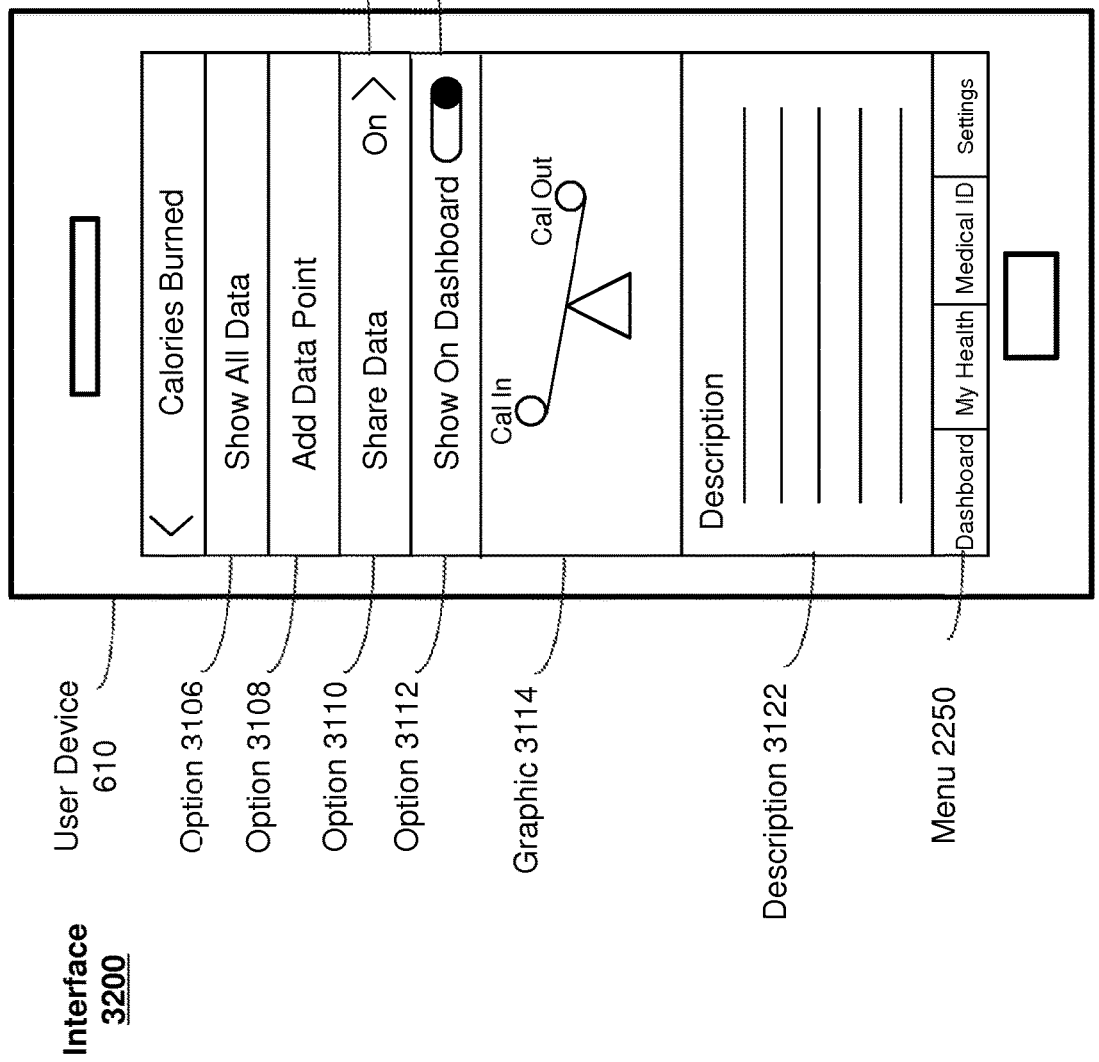
FIG. 32 illustrates example interfaces for displaying wellness or non-wellness data according to various examples.

For example, FIG. 32 illustrates an example interface 3200 that can be displayed in response to a user initiating a scroll request to scroll the view of interface 3100 in an upward direction. In interface 3200, graphic 3114 and options 3106, 3108, 3110, and 3112 can still be displayed, but can be located closer to the top of the display. Interface 3200 can further include text description 3122 below graphic 3114. Text description 3122 can include a text describing what the wellness or non-wellness data shown in interface 3200 represents. For example, text description 3122 can provide an explanation about what "Calories Burned" represents, such as how it is calculated, what an average daily value is for a typical person, how to increase the amount of Calories burned, or the like.

Figure 35:
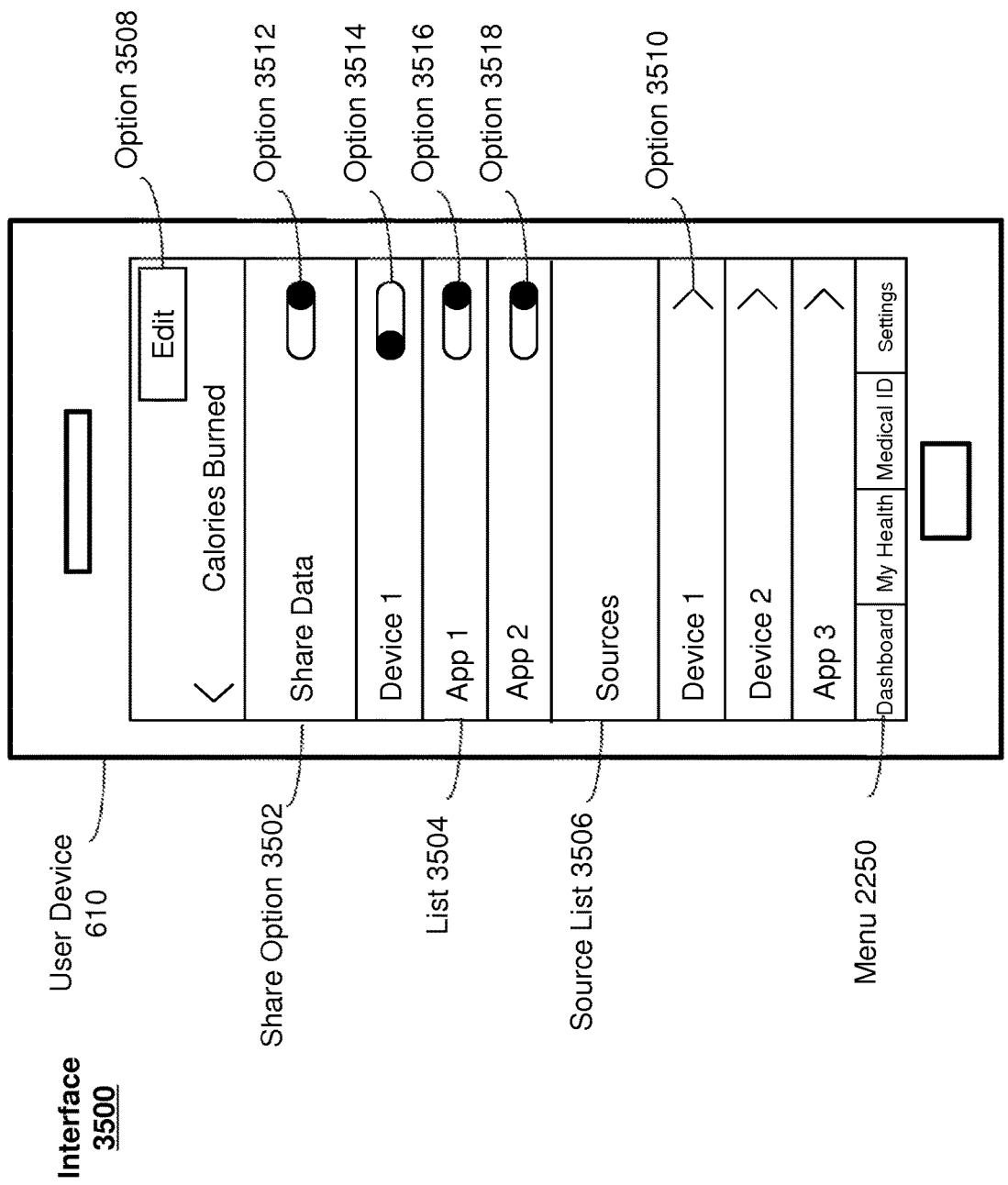
FIG. 35 illustrates example interfaces for displaying wellness or non-wellness data according to various examples.

Referring back to FIG. 31, interface 3100 can further include "Share Data" option 3110 having option 3116 for turning data sharing on or off. Data sharing can represent the ability for other devices or applications to access a user's wellness or non-wellness data (e.g., stored in wellness database 611). For example, FIG. 35 illustrates an example interface 3500 that can be displayed in response to a selection of option 3110 in interface 3100. As shown, interface 3500 can include share option 3502 having selectable option 3512. The position of the switch of option 3512 can be used to turn data sharing on or off. For example, when moved to the right, as shown in FIG. 35, the switch of option 3512 can turn on sharing option 3502. However, when moved to the left, the switch of option 3512 can turn off sharing option 3502.

Interface 3500 can further include a list 3504 of known possible destinations of wellness or non-wellness data. This list can include known devices or software applications that can potentially receive a user's wellness or non-wellness data (e.g., stored in wellness database 611). When option 3512 of share option 3502 is moved to the off position, data sharing for all listed devices and applications can be turned off. As such, selectable options 3514, 3516, and 3518 can be removed from interface 3500 or otherwise made inactive.

When option 3512 of share option 3502 is moved to the on position, selectable options 3514, 3516, and 3518 associated with the destinations in list 3504 can be displayed or made selectable. Similar to option 3512, the position of the switches of options 3514, 3516, and 3518 can be changed to turn data sharing on or off for the associated destination. For example, option 3514 for Device 1 is in the off position, indicating that data sharing is not turned on for Device 1. Options 3516 and 3518, however, are in the on position, indicating that data sharing is turned on for App 1 and App 2. When data sharing is turned on, the associated device or application can access the user's wellness or non-wellness data (e.g., stored in wellness database 611). For example, App 1, which can represent a weight tracking application, can access a user's fitness and nutrition data to track the user's caloric intake and outtake. When data sharing is turned off, the associated device or application may be prevented from accessing the user's wellness or non-wellness data (e.g., stored in wellness database 611). For example, Device 1 may be unable to access data stored in wellness database 611.

Interface 3500 can further include source list 3506 containing a list of known devices and applications that can potentially provide wellness or non-wellness data (e.g., to be stored in wellness database 611). The devices and applications in source list 3506 can be arranged in an order based on their priority. For example, as shown, Device 1 has priority over Device 2, which has priority over App 3. These relative priorities can be used to de-duplicate wellness or non-wellness data generated by two or more of the sources. For example, if Device 1 represents a fitness-tracking watch, and Device 2 represents a mobile phone, it is possible that both devices can provide step data associated with the user. Thus, by prioritizing the different sources, data from a higher ranked source can be used in place of data from a lower ranked source, or otherwise prioritized over data from the lower ranked source. This can be advantageous when one device is more likely to produce more accurate results than another. In some examples, duplicate data entries can be detected by identifying two or more data entries having metadata indicating that they are of the same type (e.g., step data, Calories burned, etc.) and having an associated timestamp that is within a threshold length of time from each other.

In some examples, interface 3500 can further include edit option 3508 for changing the order of the sources of source list 3506. For example, in response to a selection of option 3508, each item in source list 3506 can be moved (e.g., by clicking and dragging, etc.) relative to each other. The new order of sources within source list 3506 can define a new prioritization between sources.

Figure 36:
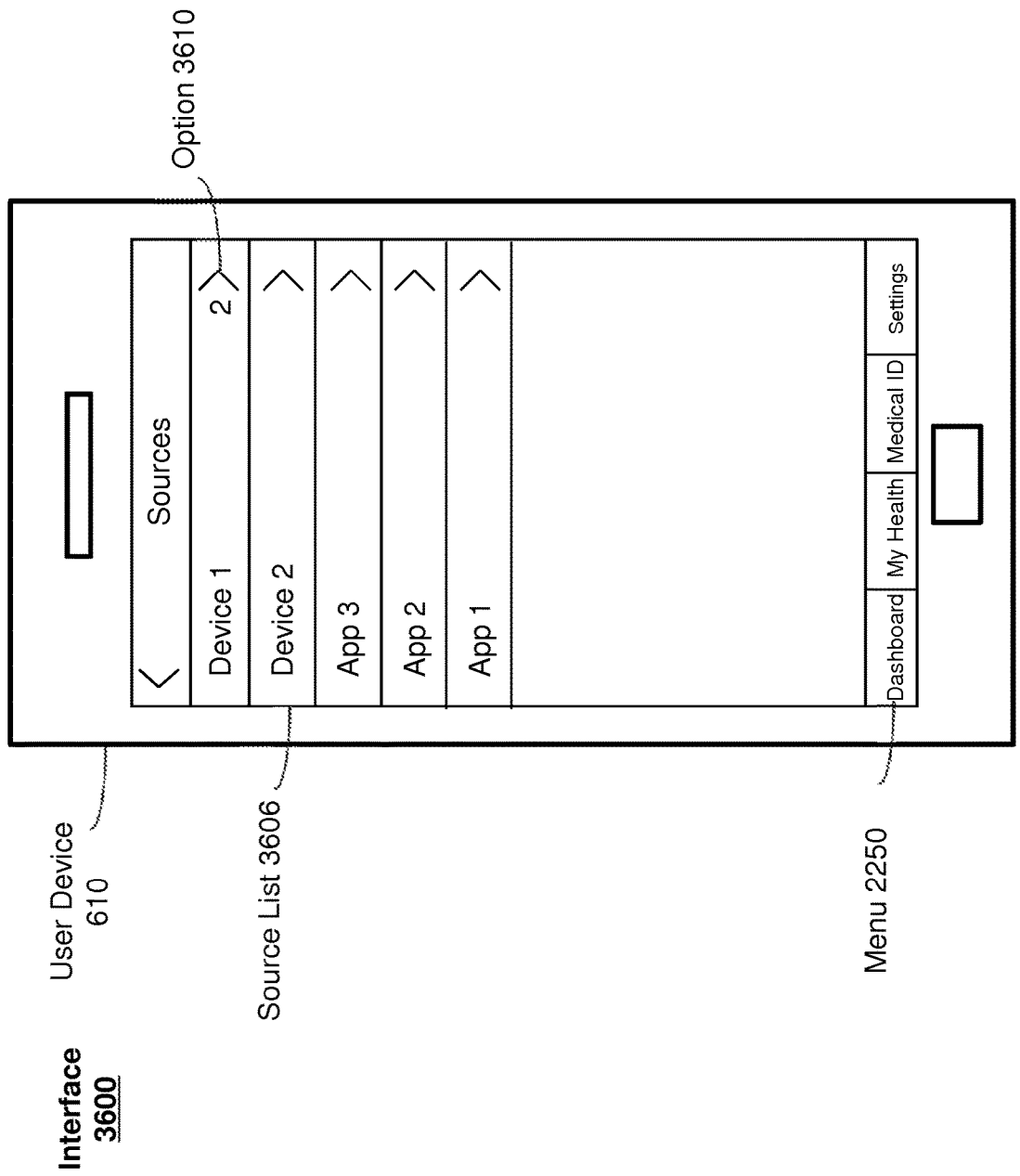
FIG. 36 illustrates example interfaces for displaying wellness or non-wellness data according to various examples.

In some examples, the "Sources" option of source list 3506 can be selected to display a more detailed view of the sources. For example, FIG. 36 illustrates an example interface 3600 that can be displayed in response to a selection of the "Sources" option of source list 3506. As shown, interface 3600 can include a source list 3606 similar to source list 3506. However, source list 3606 can further include sources App 2 and App 1, which were not displayed within interface 3500 because they were unable to be fit within the display. Interface 3600 can further include a numerical indicator associated with a source (e.g., Device 1) that indicates a number of new types of wellness or non-wellness data that the associated source can provide. For example, since the last time the user viewed interface 3600, Device 1 is now able to provide two new types of data (e.g., Calories burned and flights of stairs climbed). Interface 3600 can further include option 3610 associated with the sources in source list 3606 to provide more detailed control over the types of data that each source can provide.

Figure 37:
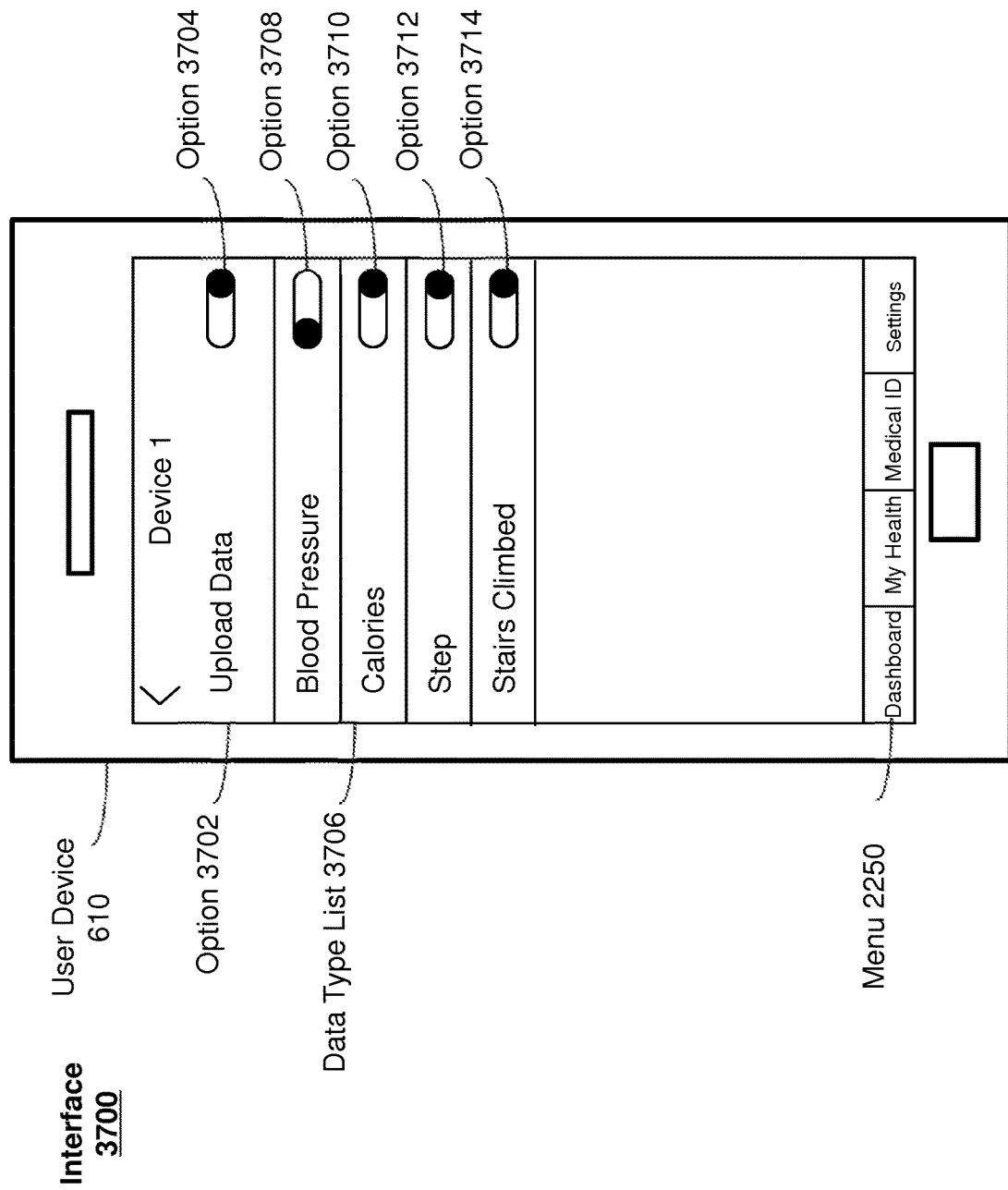
FIG. 37 illustrates example interfaces for displaying wellness or non-wellness data according to various examples.

For example, FIG. 37 illustrates an example interface 3700 that can be displayed in response to a selection of option 3610 in interface 3600 or option 3510 in interface 3500 associated with Device 1. As shown, interface 3700 can include upload option 3702 having selectable option 3704. The position of the switch of option 3704 can be used to turn data uploading from the device or application on or off (e.g., to be stored in wellness data base 611). For example, when moved to the right, as shown in FIG. 37, the switch of option 3704 can turn on data uploading by Device 1. However, when moved to the left, the switch of option 3704 can turn off data uploading by Device 1.

Interface 3700 can further include a list 3706 of data types that can be provided by Device 1. When option 3512 of share option 3704 is moved in the off position, data uploading for all listed types of data can be turned off. As such, selectable options 3708, 3710, 3712, and 3714 can be removed from interface 3700 or otherwise made inactive. When option 3704 of upload data option 3702 is moved to the on position, selectable options 3708, 3710, 3712, and 3714 associated with the list 3706 of data types can be displayed or made selectable. Similar to option 3704, the position of the switches of options 3708, 3710, 3712, and 3714 can be changed to turn data uploading on or off for the associated types of data. For example, option 3708 for Blood Pressure is in the off position, indicating that data uploading is not turned on for Blood Pressure data from Device 1. Options 3710, 3712, and 3714, however, are in the on position, indicating that data uploading is turned on for Calorie, Step, and Stairs Climbed data. When data uploading is turned on, the associated type of data can be provided by the device or application to be stored by user device 610 (e.g., in wellness database 611). For example, Calorie data generated by Device 1 can be received by user device 610 from Device 1 and stored in wellness database 611. When data uploading is turned off, the associated type of data may not be provided by the device or application to be stored by user device 610 (e.g., in wellness database 611). For example, blood pressure data generated by Device 1 may not be received by user device 610 from Device 1 and stored in wellness database 611. The options of interface 3700 advantageously allow a user to specifically define what types of data can be provided by a particular device or application.

While the examples shown in FIGS. 30-34 were for Calories burned, it should be appreciated that similar interfaces can also be displayed for other types of wellness or non-wellness data.

Figure 55A:
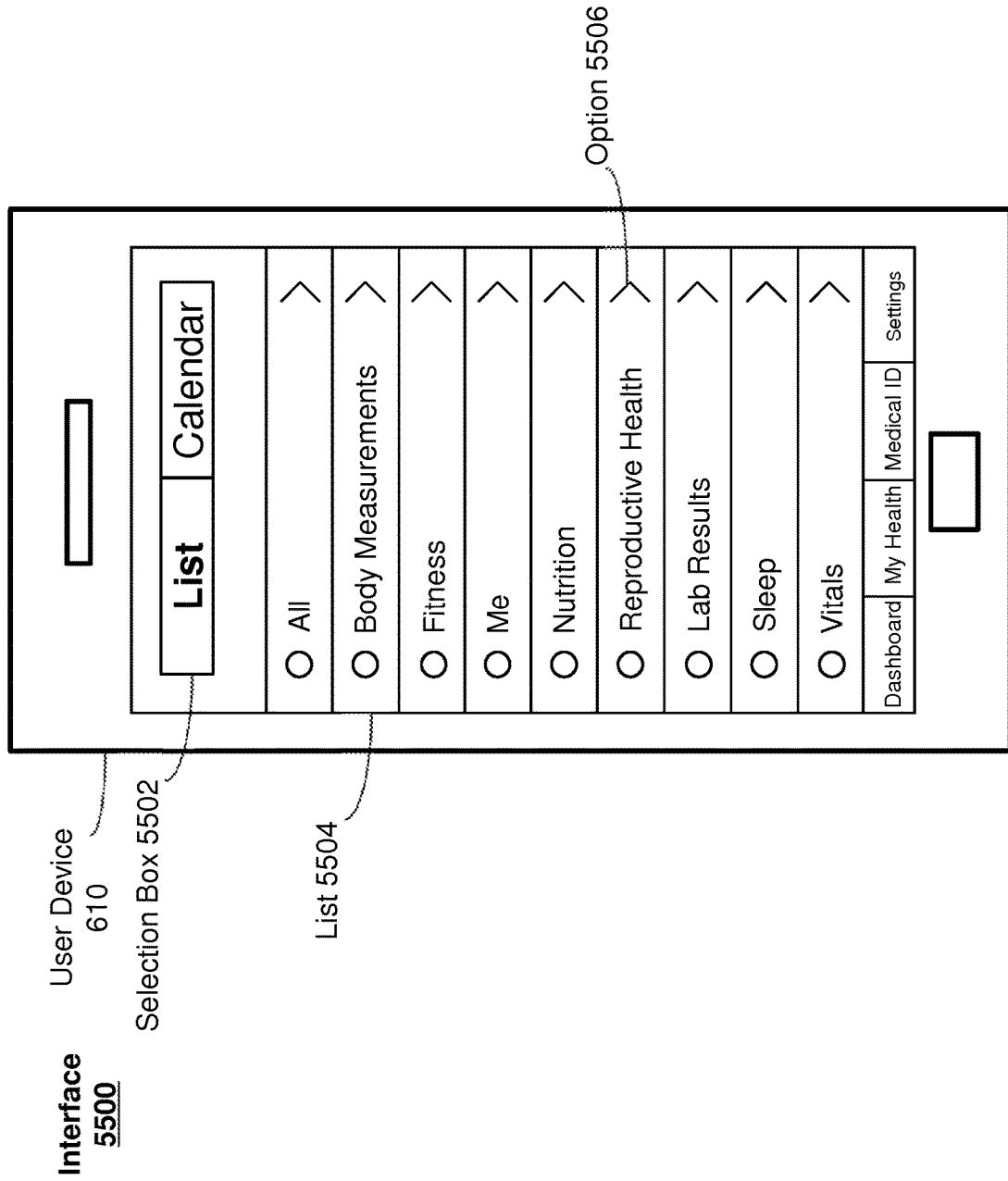
FIGS. 55A and 55B illustrate exemplary interfaces for displaying wellness or non-wellness data according to various examples.
Figure 55B:
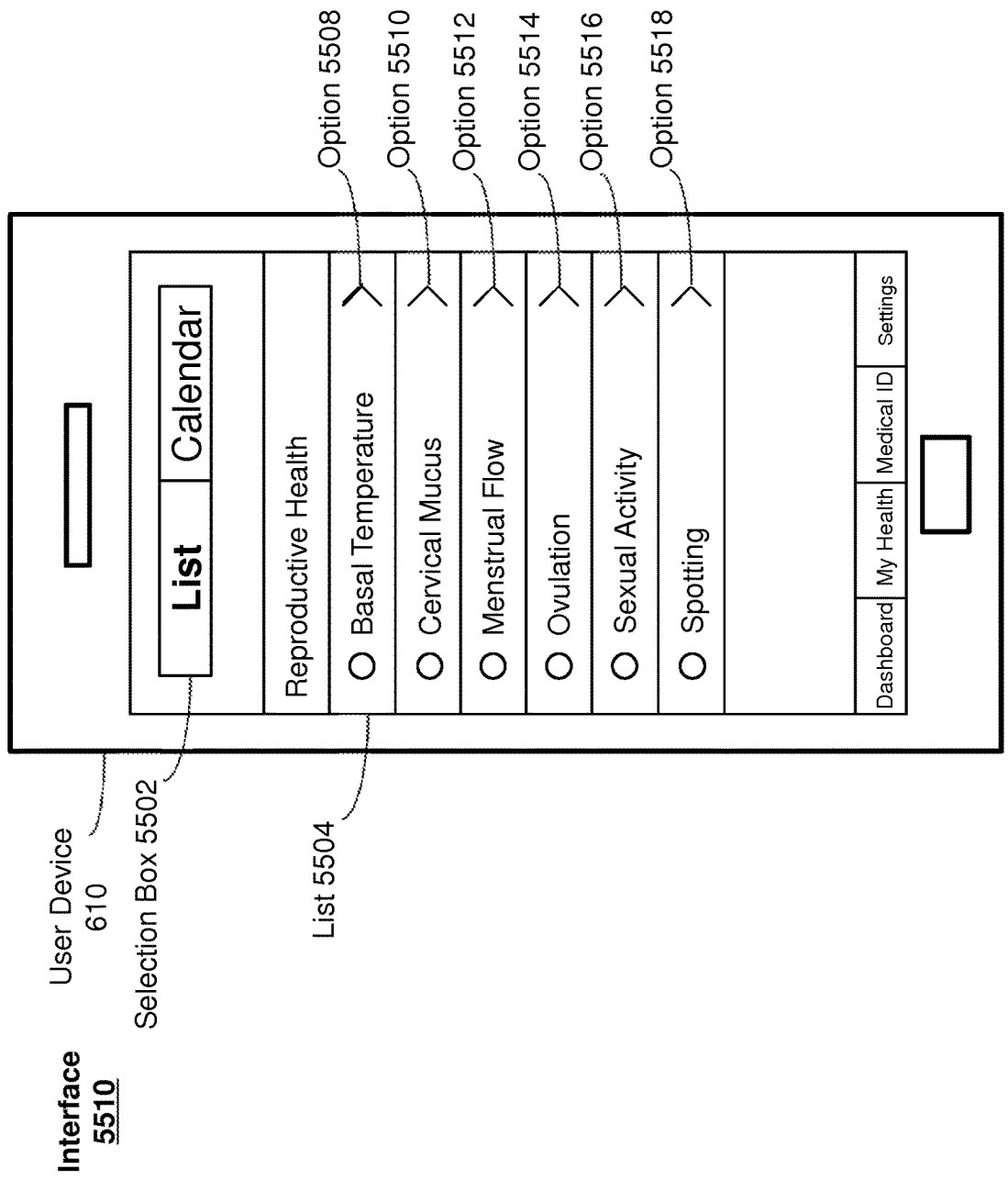

FIGS. 55A-55B illustrate other exemplary interfaces that can be displayed by user device 610 to display a user's wellness or non-wellness data. As seen in FIG. 55A, interface 5500 can include Selection Box 5502 that allows a user to select whether to view the data in a list view or calendar view. When the list view is selected, as depicted in FIG. 55, interface 5500 shows a list 5504 of categories of wellness or non-wellness data. Responsive to selection of option 5506 (reproductive health), device 610 displays interface 5510 which shows the sub-categories of wellness information associated with option 5506. These sub-categories of wellness information is described with respect to FIGS. 56-61.

Figure 56A:
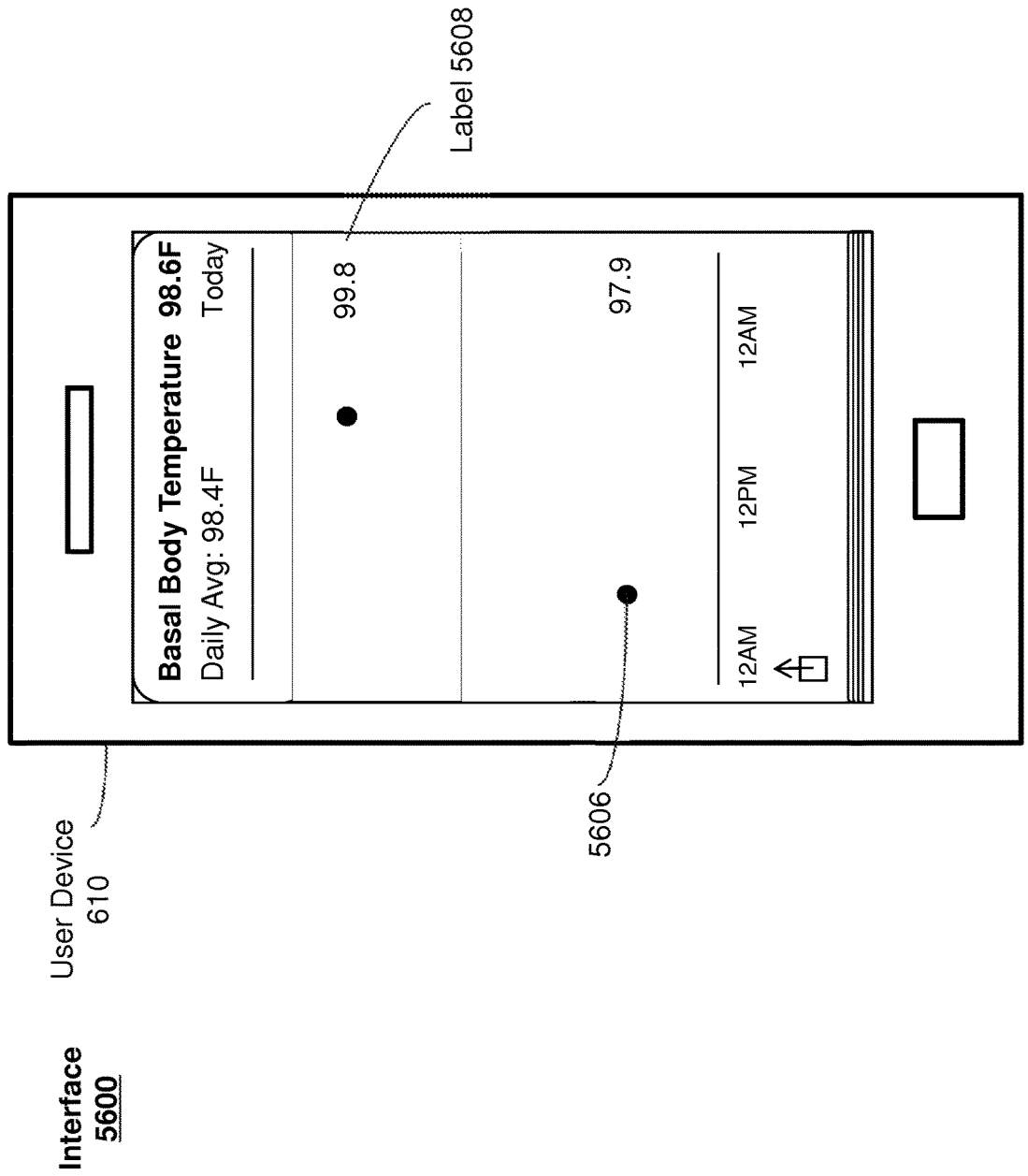
Figure 56C:
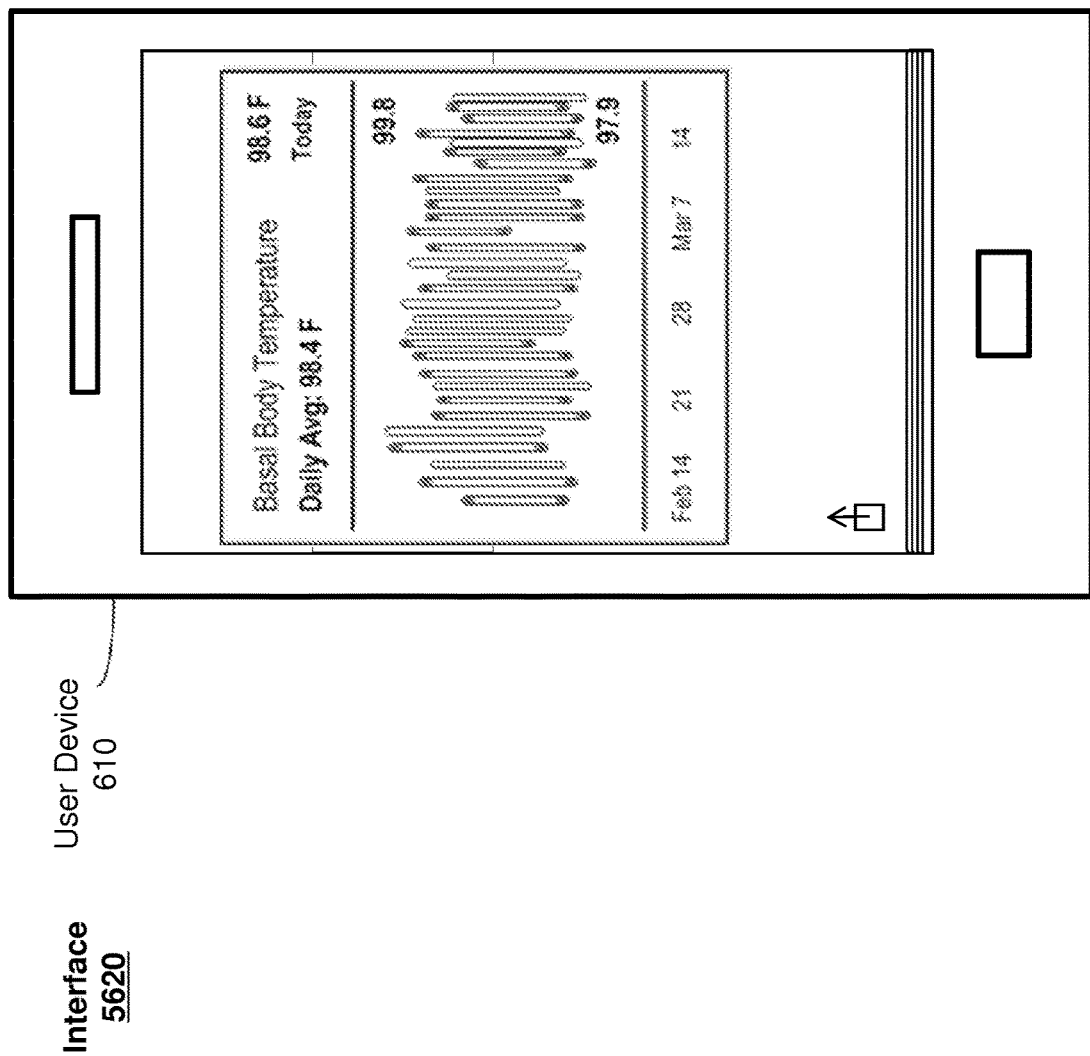
Figure 56D:
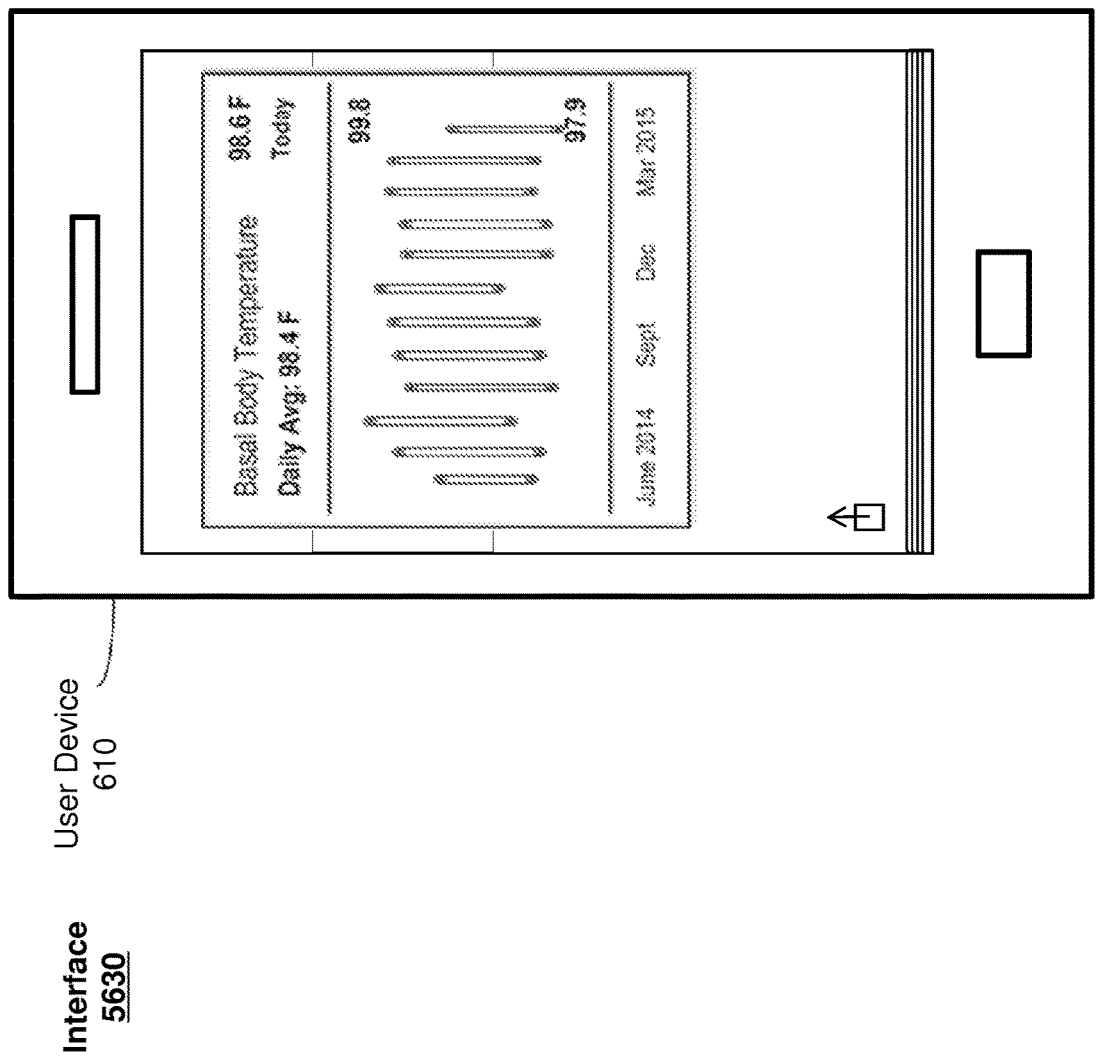

Turning to FIGS. 56A-56D, responsive to selection of option 5508 (FIG. 55B), one of interfaces 5600, 5610, 5620, or 5630 (FIGS. 56A-56D) is displayed, in some examples. As can be seen in FIG. 56A, interface 5600 depicts basal body temperature information at the hourly level of detail for a given day. Interface 5600 includes temperature label 5608, and indicator 5606 indicating temperature (e.g., dependent variable) for a given time (e.g., independent variable). Turning to FIG. 56B, interface 5610 depicts basal body temperature information at the daily level of detail for a given week. Notably, indicator 5611 depicts the high basal body temperature for a given day, indicator 5612 depicts the low basal body temperature for a given day, and range 5614 depicts the range of basal body temperatures for a given day. In addition, category label 5616 takes on the lowest basal body temperature for the week, while category label 5618 takes on the highest basal body temperature for the week. Similarly, interface 5620 depicted in FIG. 56C depicts basal body temperatures for a given month, and interface 5630 depicted in FIG. 56D depicts basal body temperatures for a given year. In some embodiments, a user navigates between user interfaces 5600, 5610, 5620, and 5630 (FIGS. 56A-56D) by pinching or de-pinching touch input on device 610.

Figure 57B:
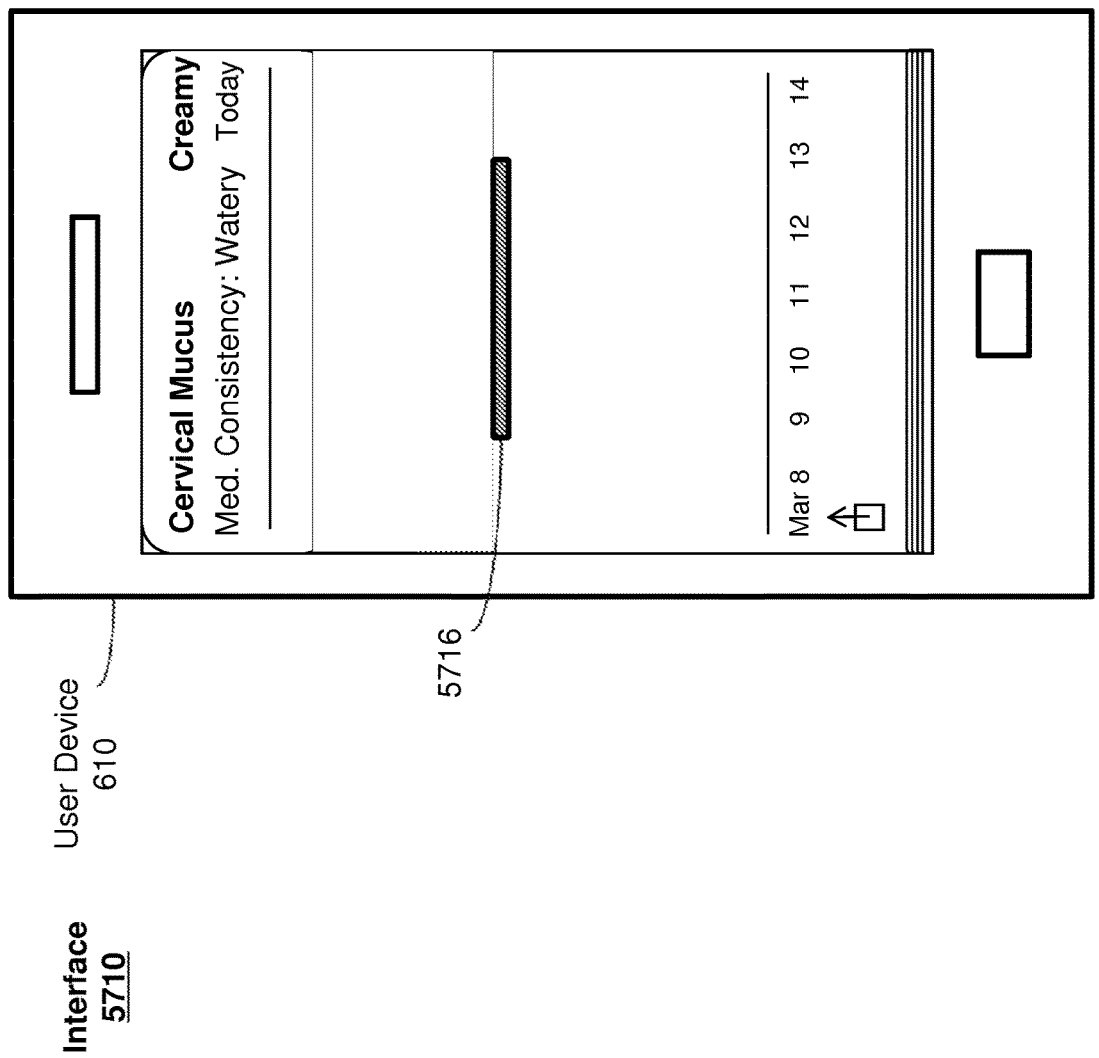
Figure 57C:
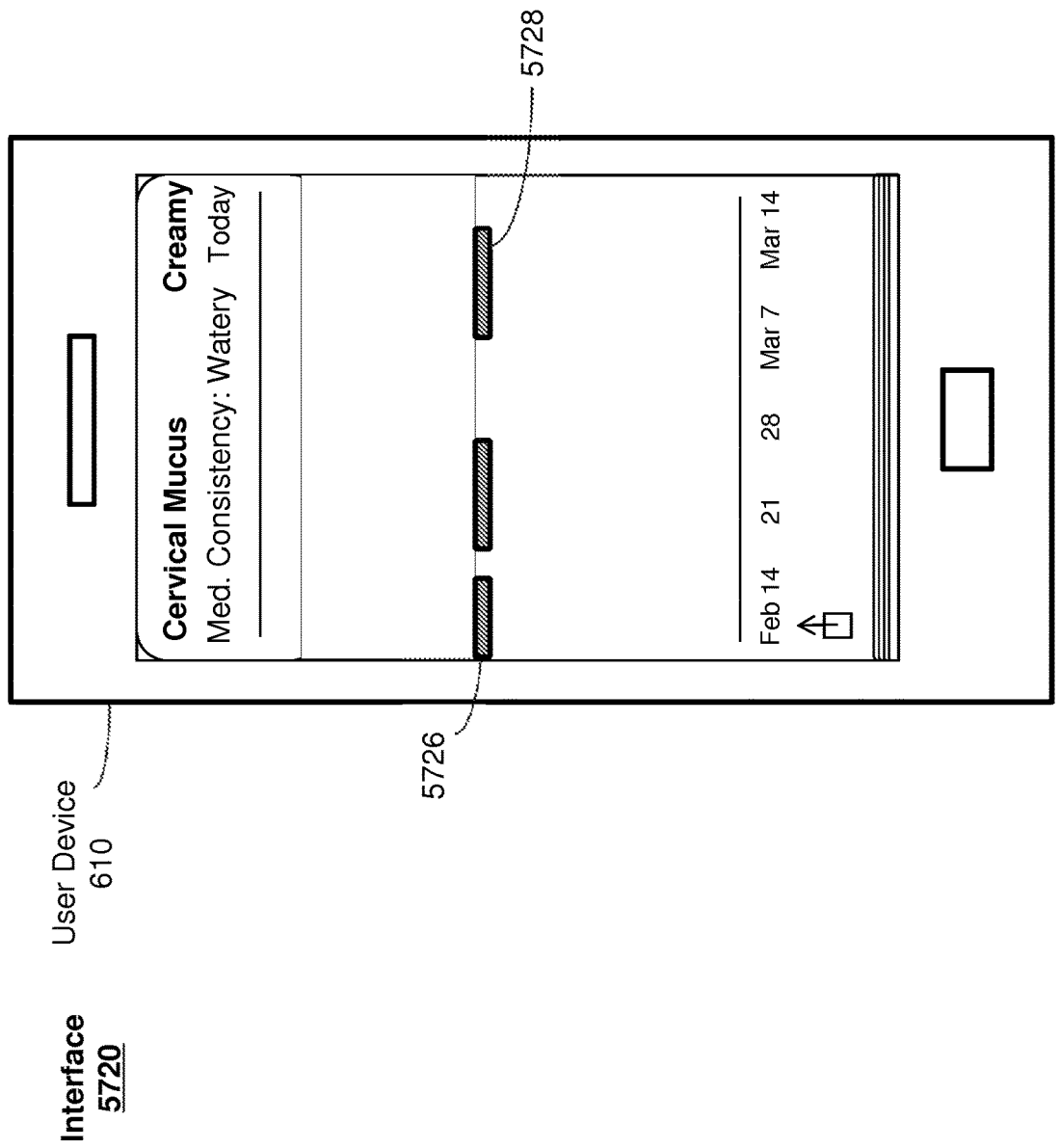

Turning to FIGS. 57A-57D, responsive to selection of option 5510 (FIG. 55B), one of interfaces 5700, 5710, 5720, or 5730 (FIGS. 57A-57D) is displayed, in some examples. As can be seen in FIG. 57A, interface 5700 depicts cervical mucus information at the hourly level of detail for a given day. Interface 5700 includes indicator 5706 whose horizontal position corresponds to an independent variable (e.g. time of day) of the data set, and whose vertical position corresponds to a dependent variable (e.g., mucus consistency) of the data set. Turning to FIG. 57B, interface 5710 depicts cervical mucus information at the daily level of detail for a given week. Notably, range indicator 5716 depicts the median consistency of cervical mucus for a period during which cervical mucus is observed. Similarly, interface 5720 depicted of FIG. 57C depicts median cervical mucus consistency across different periods 5726 and 5728 during which cervical discharge is observed, across the timeframe of a month. Similarly, interface 5730 depicted of FIG. 57D depicts median cervical mucus consistency across different periods 5736 and 5738 during which cervical discharge is observed, across the timeframe of a year. In some embodiments, a user navigates between user interfaces 5700, 5710, 5720, and 5730 (FIGS. 57A-57D) by pinching or de-pinching to zoom touch input on device 610.

Figure 58C:
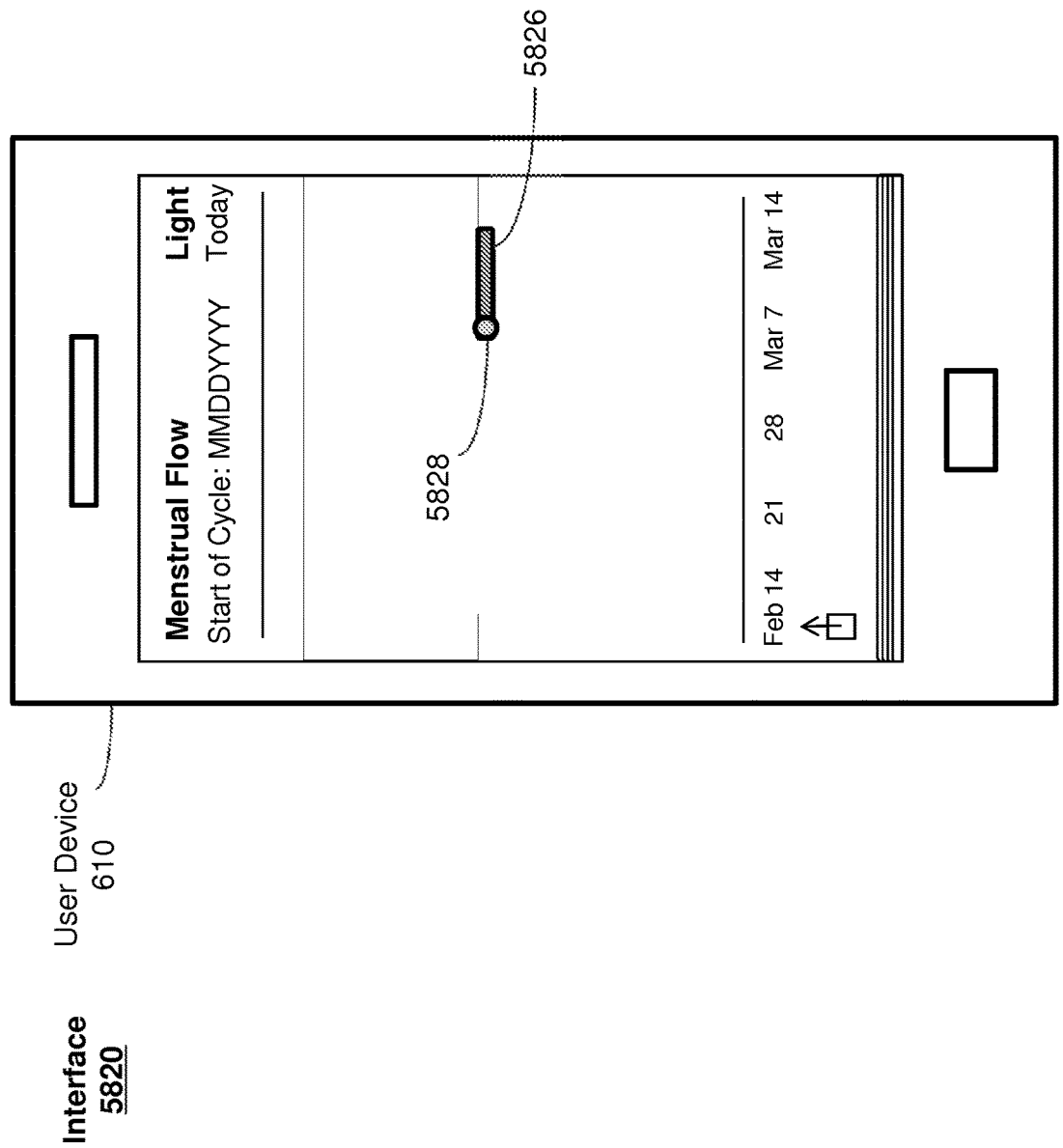
Figure 58D:
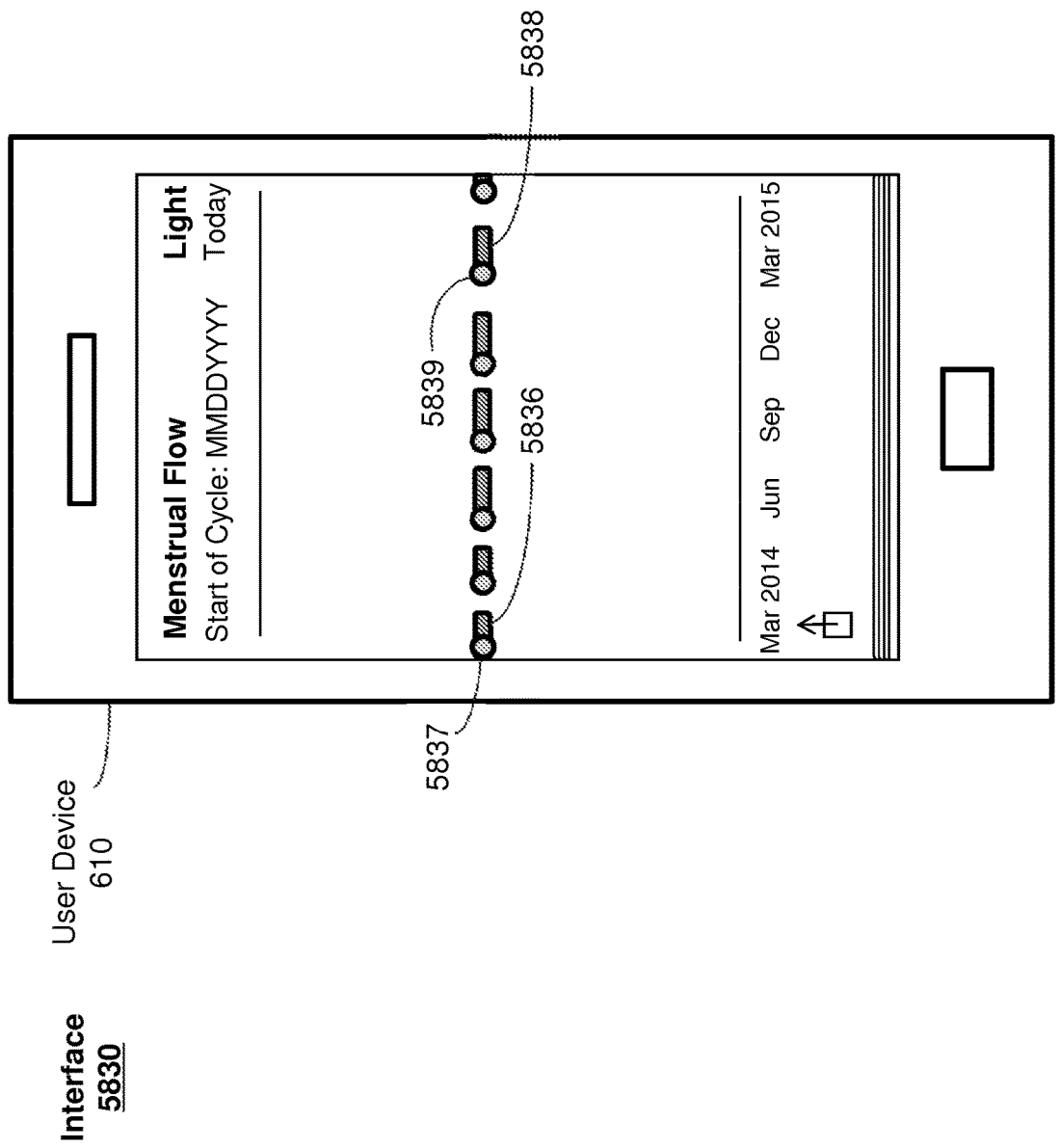

Turning to FIGS. 58A-58D, responsive to selection of option 5512 (FIG. 55B), one of interfaces 5800, 5810, 5820, or 5830 (FIGS. 58A-58D) is displayed, in some examples. As can be seen in FIG. 58A, interface 5800 depicts menstrual flow information at the hourly level of detail for a given day. Interface 5800 includes indicator 5806 whose horizontal position corresponds to an independent variable (e.g. time of day) of the data set, and whose vertical position corresponds to a dependent variable (e.g., menstrual flow) of the data set. Turning to FIG. 58B, interface 5810 depicts menstrual flow information at the daily level of detail for a given week. Notably, indicator 5818 marks the beginning of a period of menstrual flow as indicated by range 5816. Similarly, interface 5820 of FIG. 58C depicts menstrual flow for a month, with indicator 5828 marking the beginning of a period of menstrual flow as indicated by range 5826. Similarly, interface 5830 of FIG. 58D depicts menstrual flow for a year. Exemplary range indicators include 5836 and 5838. Exemplary beginning-of-cycle indicators include 5837 and 5839. In some embodiments, a user navigates between user interfaces 5800, 5810, 5820, and 5830 (FIGS. 58A-58D) by pinching or de-pinching to zoom touch input on device 610.

Figure 59A:
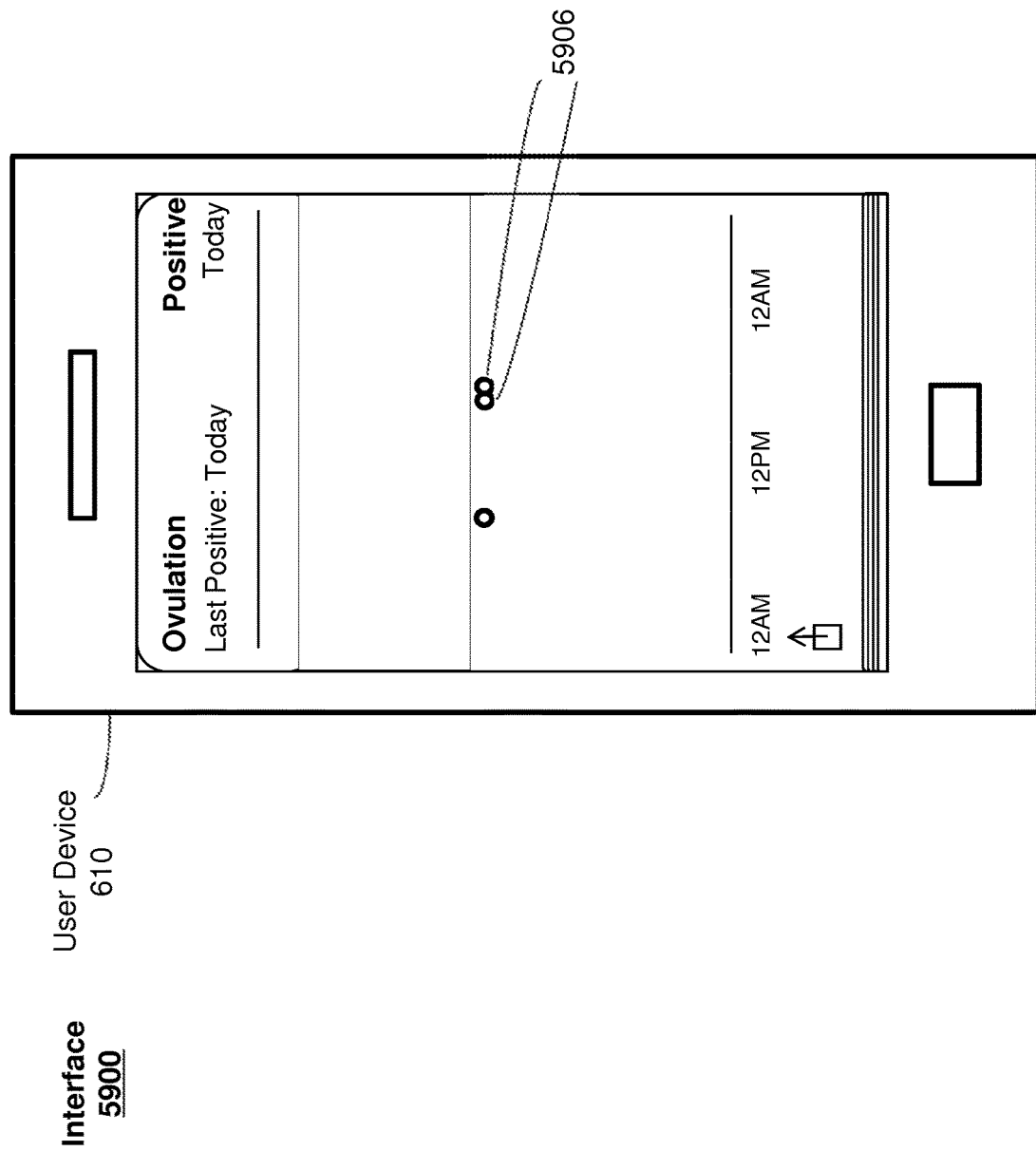
FIGS. 59A-59D illustrate exemplary interfaces for displaying wellness or non-wellness data according to various examples.
Figure 59B:
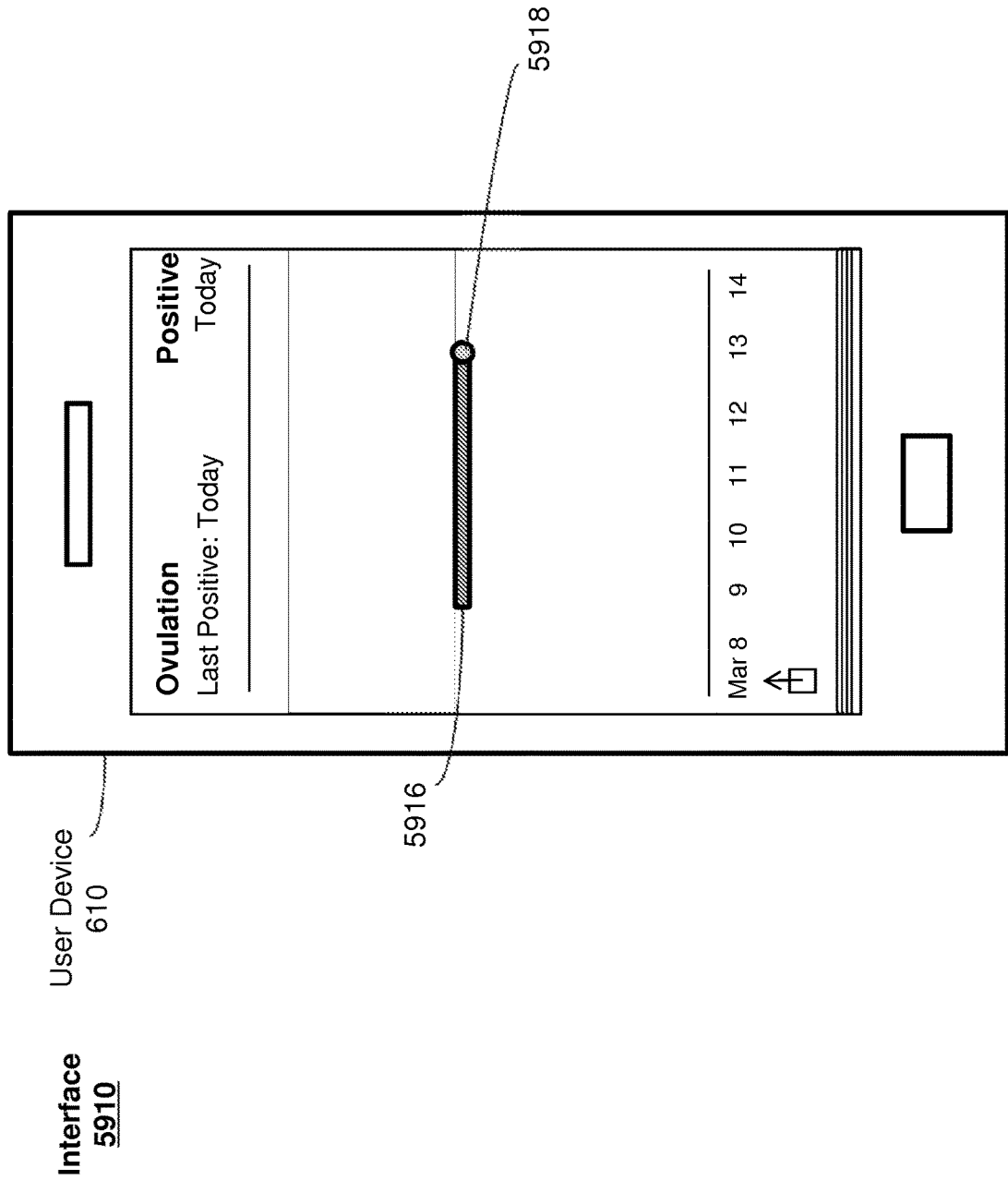
Figure 59C:
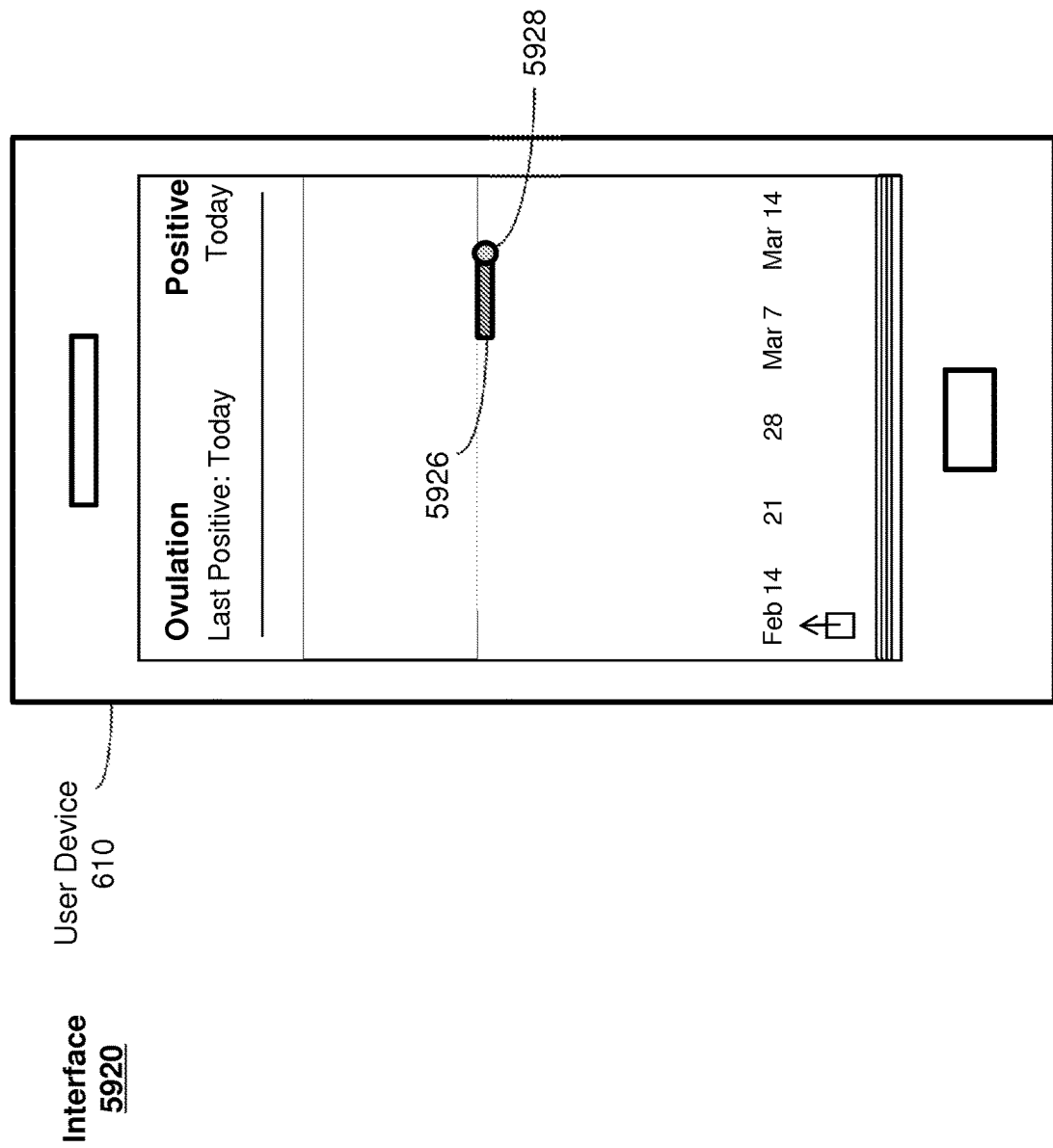
Figure 59D:
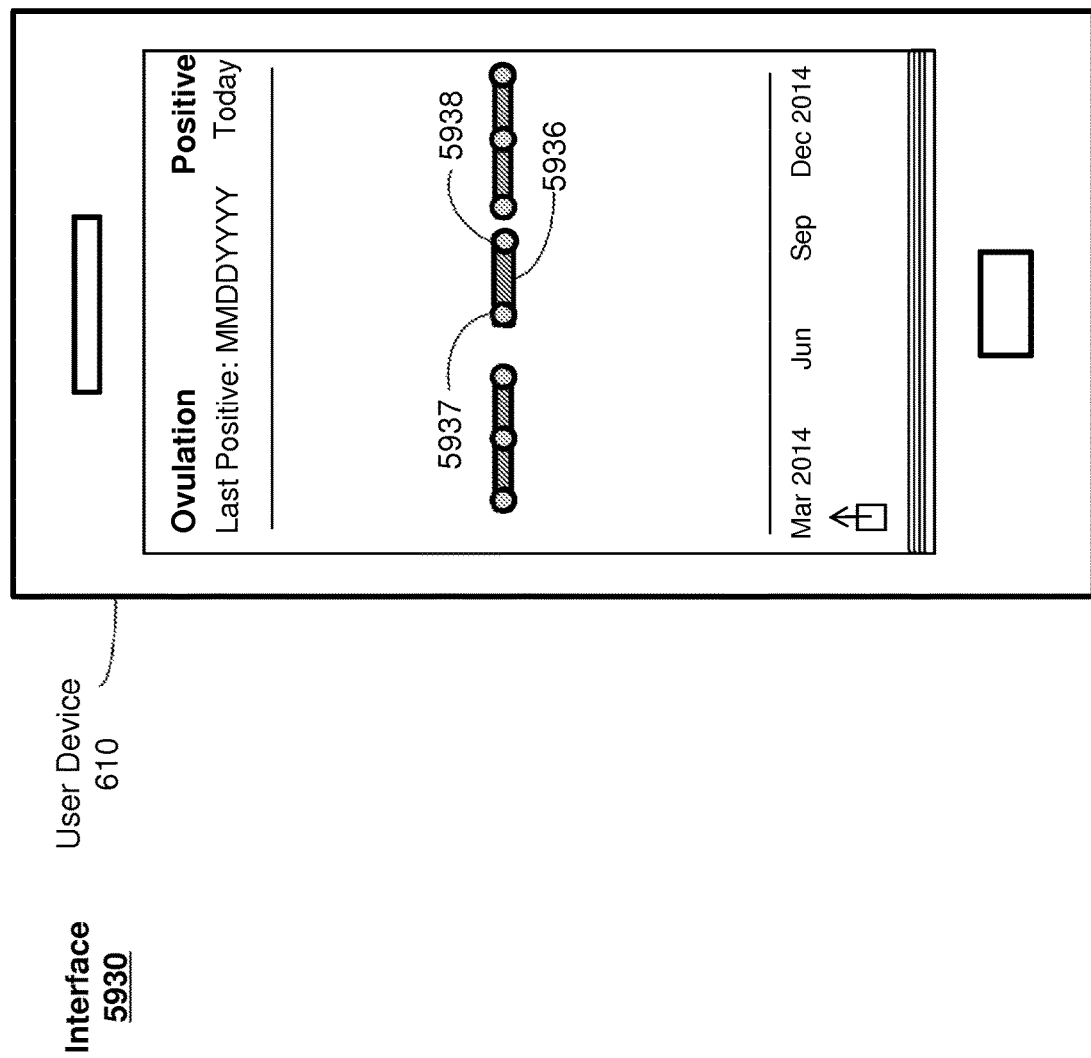

Turning to FIGS. 59A-59D, responsive to selection of option 5514 (FIG. 55B), one of interfaces 5900, 5910, 5920, or 5930 (FIGS. 59A-59D) is displayed, in some examples. As can be seen in FIG. 59A, interface 5900 depicts ovulation information at the hourly level of detail for a given day. Interface 5900 includes indicators 5906 whose horizontal positions correspond to independent variables (e.g. times of day) of the data set, and whose vertical positions correspond to dependent variables (e.g., ovulation levels) of the data set. Turning to FIG. 59B, interface 5910 depicts ovulation information at the daily level of detail for a given week. Notably, indicator 5918 marks the end of a period of ovulation as indicated by range 5916. Similarly, interface 5920 depicted of FIG. 59C depicts ovulation information for a month, while interface 5930 (FIG. 59D) depicts ovulation information for a year. In interface 5920, the end of range indicator 5926 is marked by indicator 5926 to indicate the end of an ovulation cycle. In interface 5930, range indicator 5936 includes indicator 5937 indicating positive ovulation and end-of-ovulation indicator 5938 indicating the end of an ovulation cycle. In some embodiments, a user navigates between user interfaces 5900, 5910, 5920, and 5930 (FIGS. 59A-59D) by pinching or de-pinching to zoom touch input on device 610.

Figure 60A:
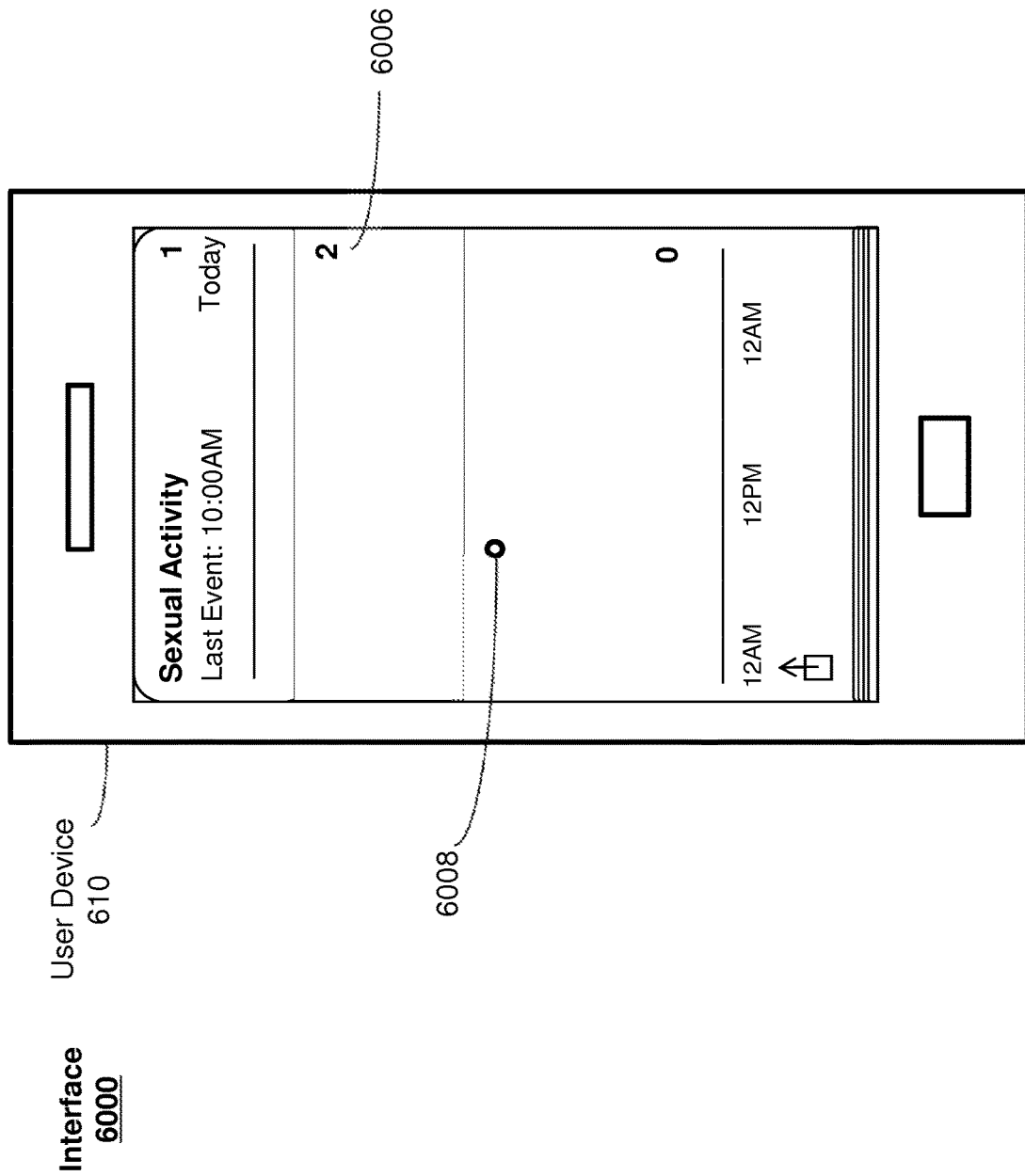
FIGS. 60A-60D illustrate exemplary interfaces for displaying wellness or non-wellness data according to various examples.
Figure 60B:
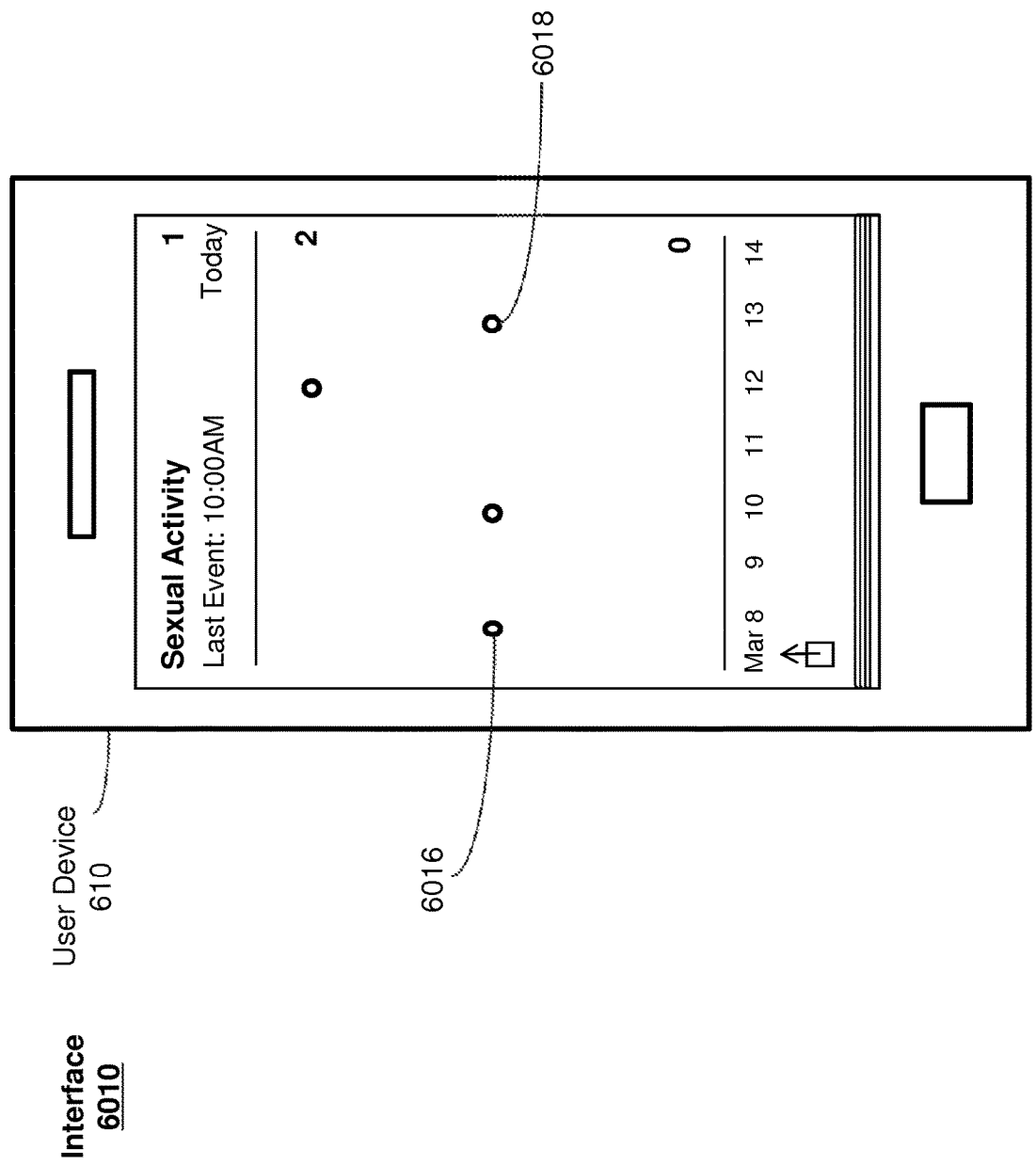
Figure 60C:
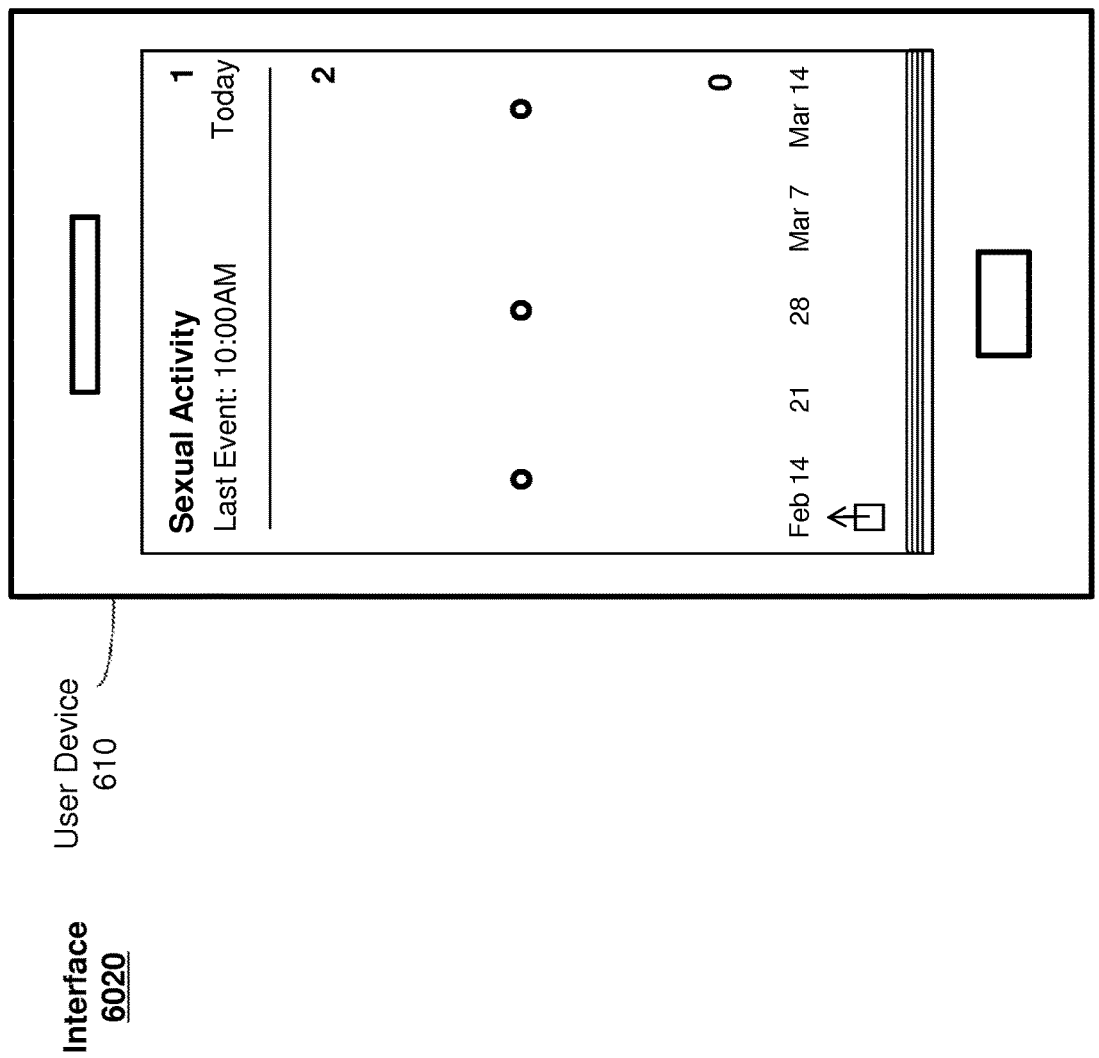
Figure 60D:
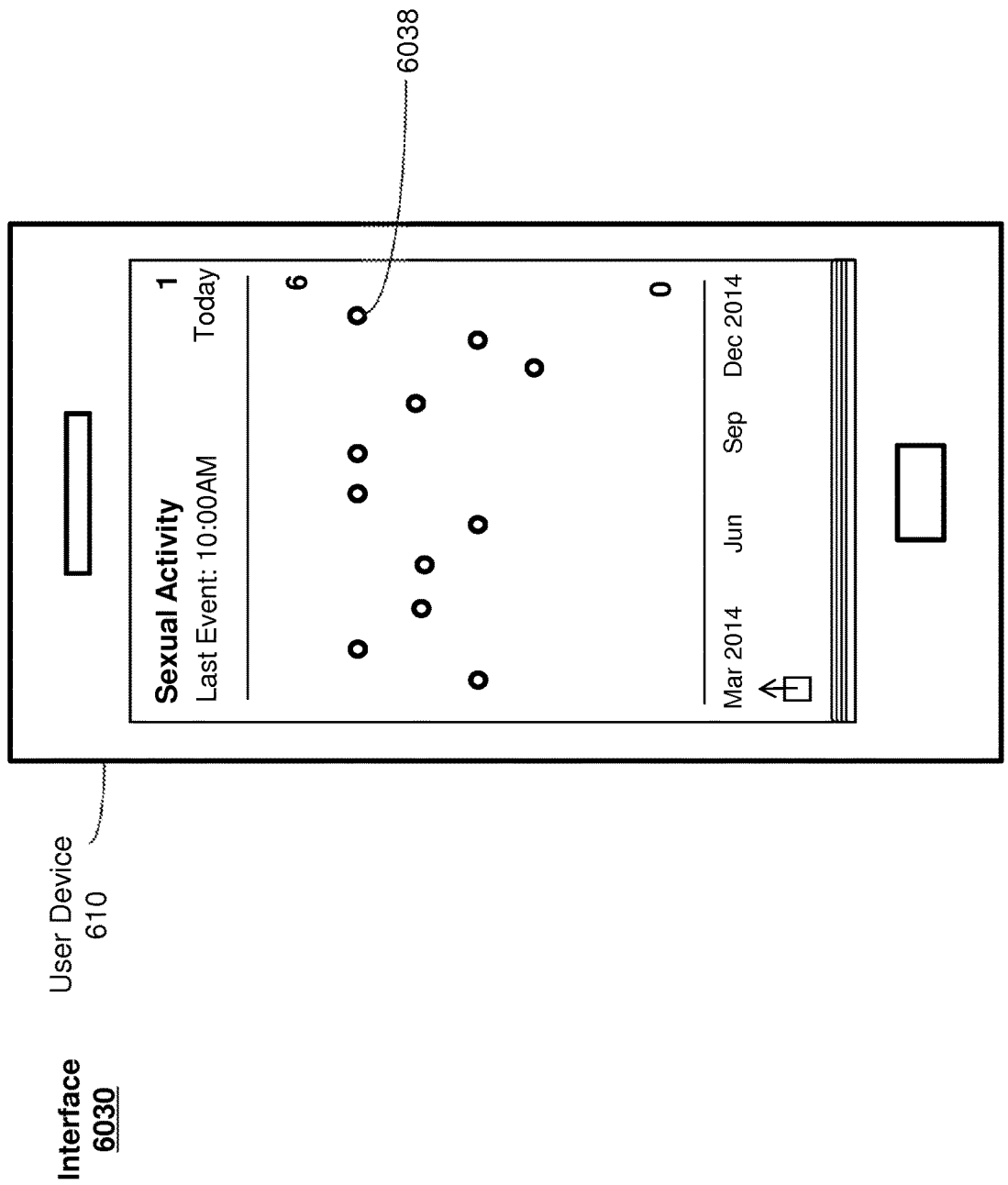

Turning to FIGS. 60A-60D, responsive to selection of option 5516 (FIG. 55B), one of interfaces 6000, 6010, 6020, or 6030 (FIGS. 60A-60D) is displayed, in some examples. As can be seen in FIG. 60A, interface 6000 depicts sexual activity information at the hourly level of detail for a given day. Category label 6006 is provided to indicate that the vertical location of indicator 6008 corresponds to one sexual activity event. Turning to FIG. 60B, interface 6010 depicts sexual activity information at the daily level of detail for a given week, with indicators 6016 and 6018 showing activity levels for different days of the week. Similarly, interface 6020 depicted of FIG. 60C depicts sexual activity information for a month, while interface 6030 (FIG. 60D) depicts sexual activity information at the monthly level of detail for a year. For example, indicator 6038 in interface 6030 indicates five sexual events have occurred in December 2014. In some embodiments, a user navigates between user interfaces 6000, 6010, 6020, and 6030 (FIGS. 60A-60D) by pinching or de-pinching to zoom touch input on device 610.

Figure 61A:
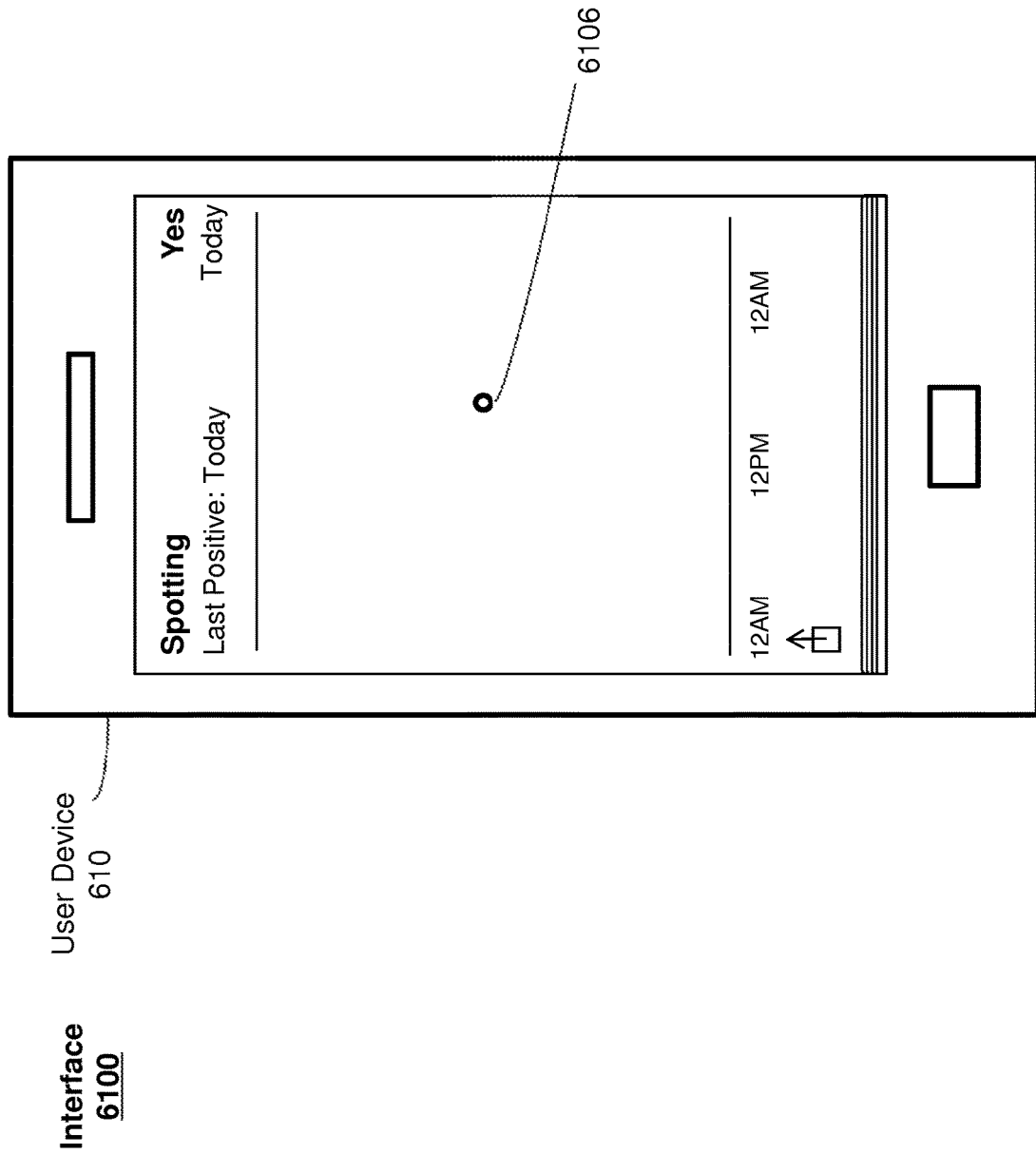
FIGS. 61A-61D illustrate exemplary interfaces for displaying wellness or nonwellness data according to various examples.
Figure 61B:
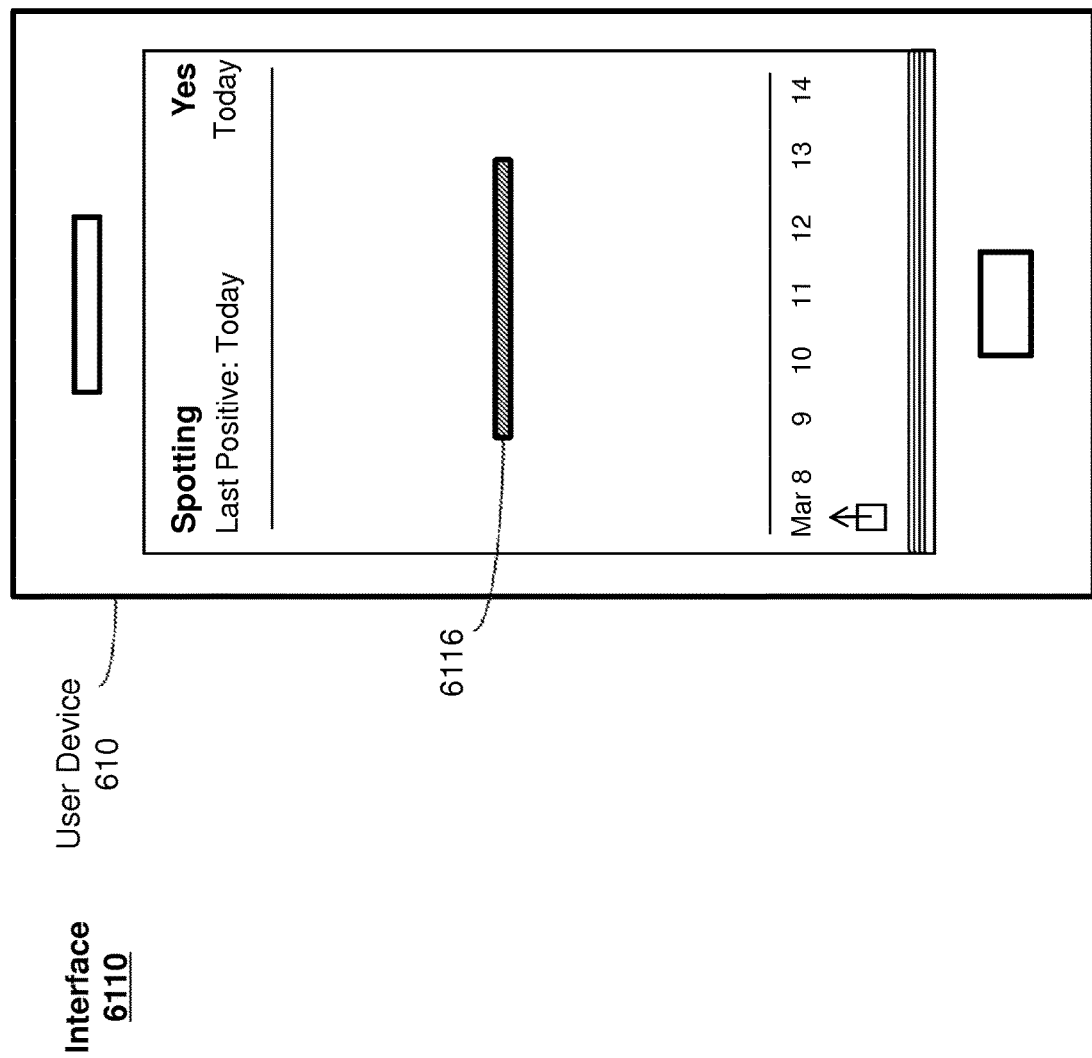
Figure 61C:
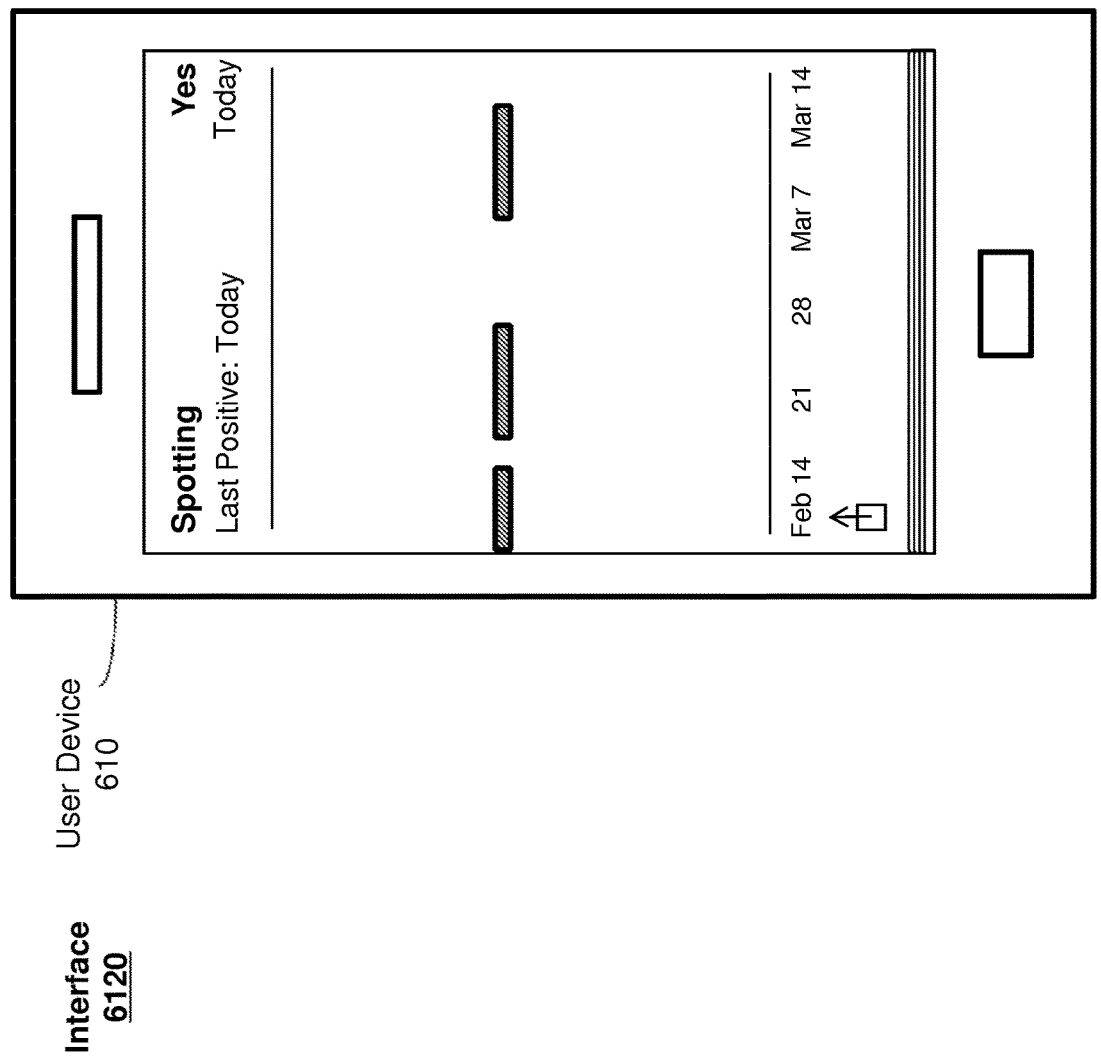
Figure 61D:
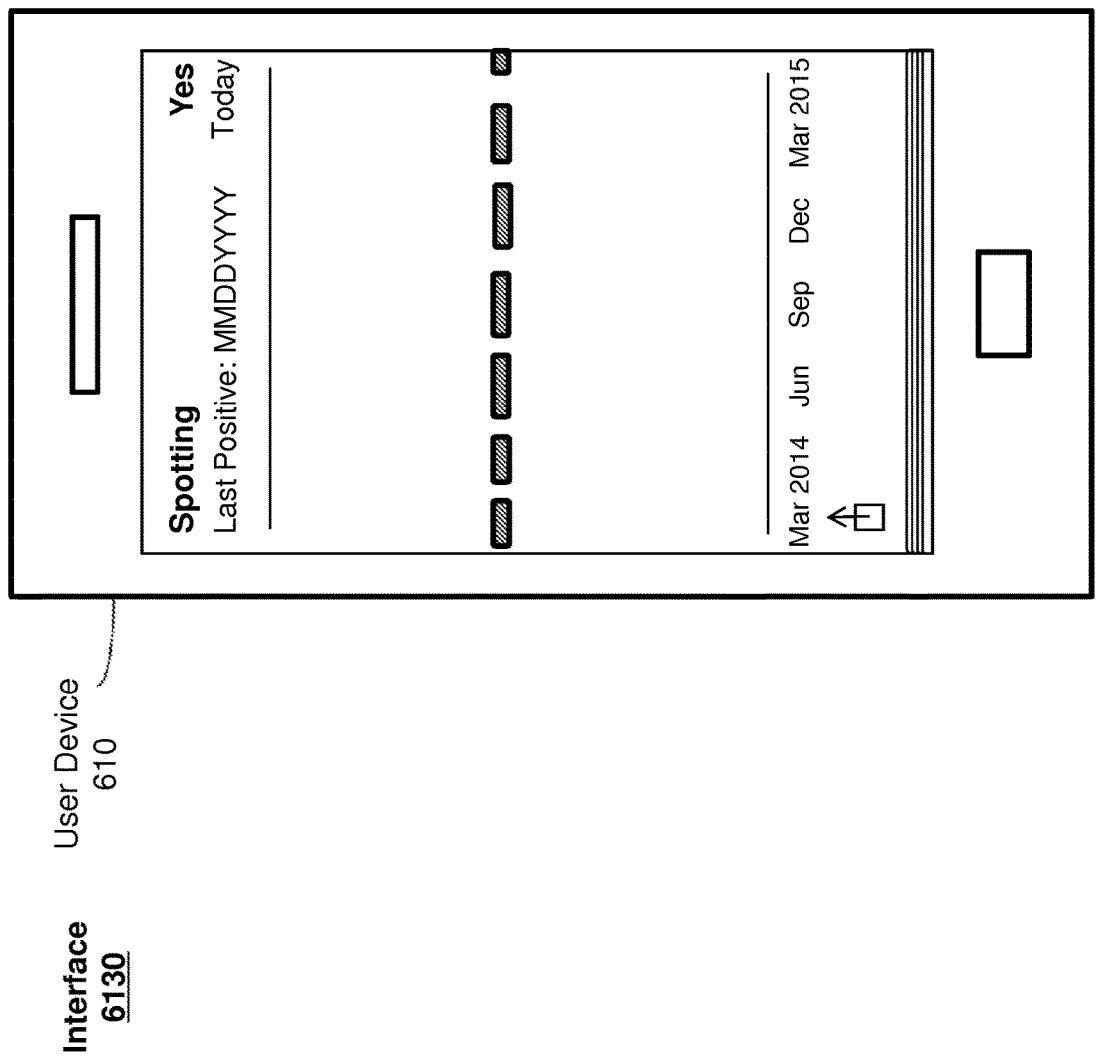

Turning to FIGS. 61A-61D, responsive to selection of option 5518 (FIG. 55B), one of interfaces 6100, 6110, 6120, or 6130 (FIGS. 61A-61D) is displayed, in some examples. As can be seen in FIG. 61A, interface 6100 depicts menstrual spotting information at the hourly level of detail for a given day. Interface 6100 includes indicators 6106 whose horizontal positions correspond to independent variables (e.g. times of day) of the data set, and whose vertical positions correspond to dependent variables (e.g., positive or no spotting) of the data set. Turning to FIG. 61B, interface 6110 depicts menstrual spotting information at the daily level of detail for a given week, with range indicator 6116 showing that spotting has occurred on multiple days of the week. Similarly, interface 6120 depicted of FIG. 61C depicts spotting information for a month, while interface 6130 (FIG. 61D) depicts menstrual spotting information at for a year. In some embodiments, a user navigates between user interfaces 6100, 6110, 6120, and 6130 (FIGS. 61A-61D) by pinching or de-pinching to zoom touch input on device 610.

As previously described with respect to FIG. 28, a category of wellness or non-wellness data can include one or more sub-categories. For example, the category "Reproductive Health" can include sub-categories "Menstrual Flow," "Cervical Mucus," "Basal Temperature," "Sexual Activity," "Ovulation," and so forth. The category "Lab Results" can include sub-categories "Blood Glucose" and "Blood Alcohol Content." It should be appreciated that list 5504 is provided only as an example, and that additional or fewer categories can be included within interface 5500. Additionally, it should be appreciated that the categories of interface 5500 can include additional or fewer sub-categories.

Figure 62A:
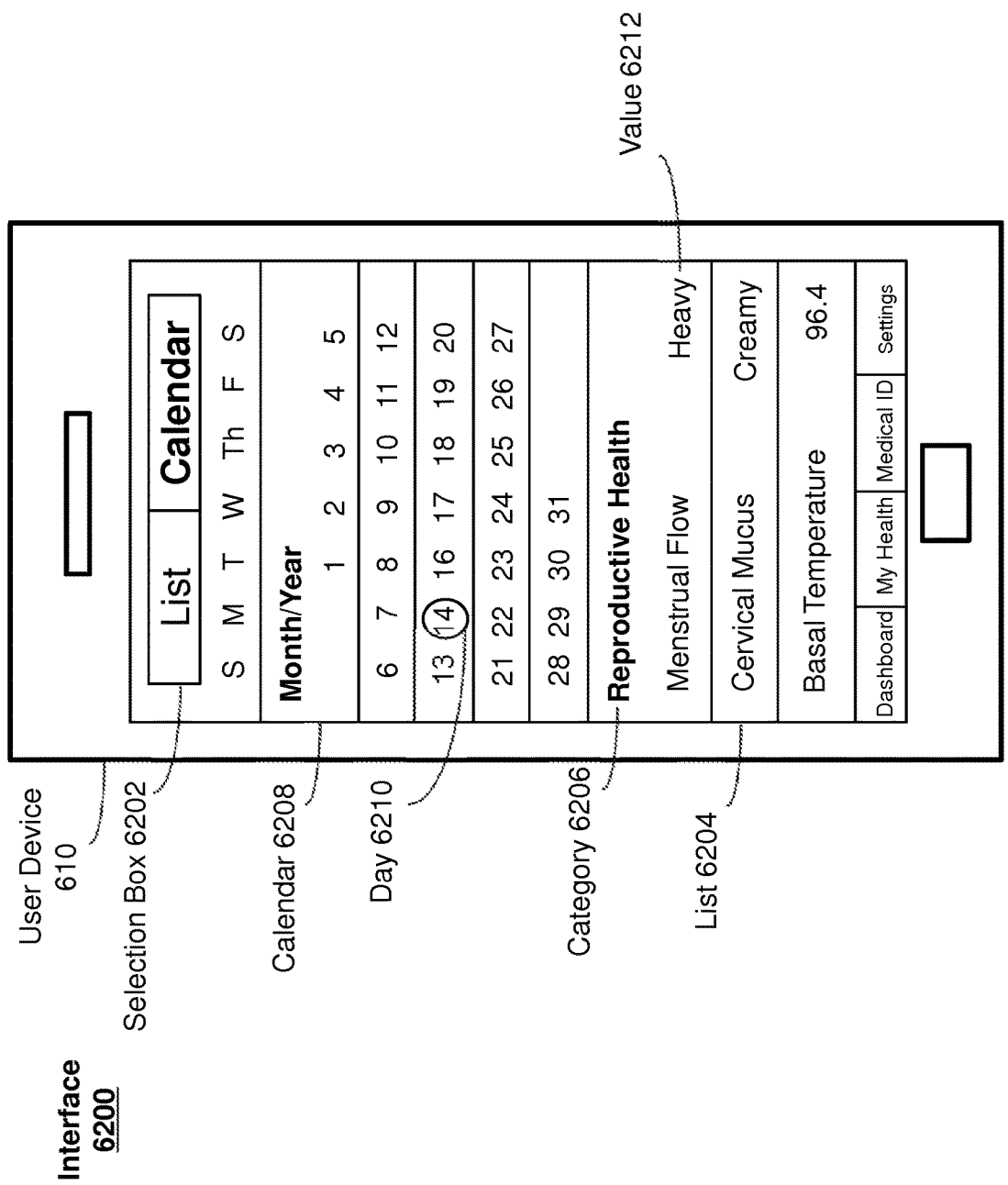
FIGS. 62A and 62B illustrate exemplary interfaces for displaying wellness or nonwellness data according to various examples.
Figure 62B:
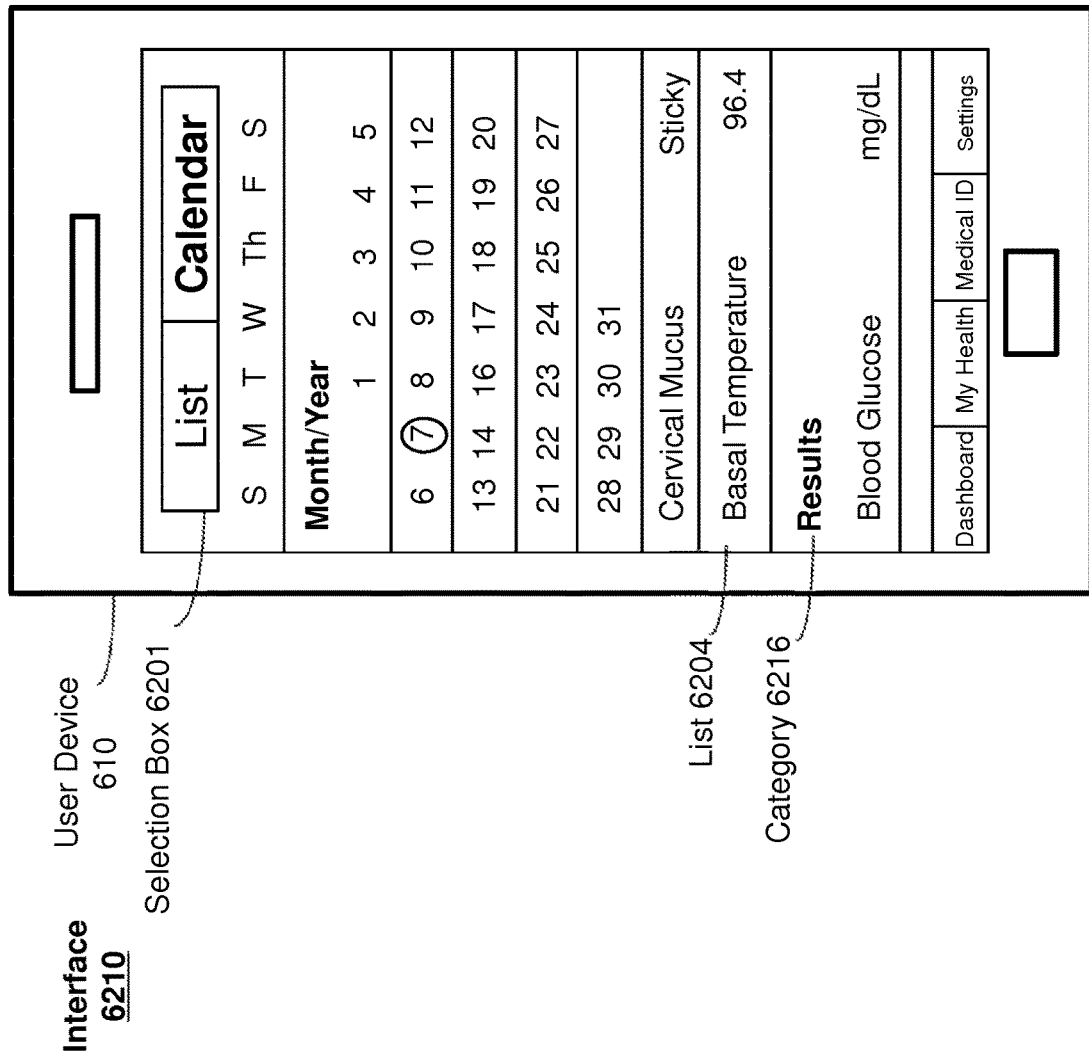

FIGS. 62A and 62B illustrate another example interface 6200 that can be displayed by user device 610 to display a user's wellness or non-wellness data. In this example, the calendar view in Selection Box 6202 is selected, rather than the list view as depicted in FIGS. 55A and 55B. When the calendar view is selected, interface 6200 displays calendar 6208 with a selected day 6210. Interface 6200 can include wellness or non-wellness data associated with the selected day 6210. For example, interface 6200 can include wellness or non-wellness data for a list 6204 of wellness or non-wellness categories, such as "Reproductive Health" category 6202. List 6204 also includes sub-categories, along with the value 6212 of applicable sub-categories for the selected day 5710. List 6204 of sub-categories is associated with the list 5504 of categories depicted in the list view of FIG. 55A. For example, list 6204 lists sub-categories such as menstrual flow, cervical mucus, and basal temperature as being associated with the category 6206 of "Reproductive Health."

In some examples, the list of sub-categories can be scrolled to display sub-categories associated with additional categories. For example, as depicted in FIG. 62B, scrolling list 6204 reveals sub-categories associated with the "Lab Results" category. In some examples, the categories (and associated sub-categories) are displayed in interfaces 6200 and 6210 in the order in which they appear in the list view of interface 5500; e.g., in the order of list 5504 (FIGS. 55A and 55B). Thus, in this example, scrolling list 6204 causes the sub-categories associated with the "Lab Results" category 6216 to appear after the sub-categories associated with the "Reproductive Health" category as this is the order in which these categories appear in list 5504 (FIGS. 55A and 55B).

Figure 63:
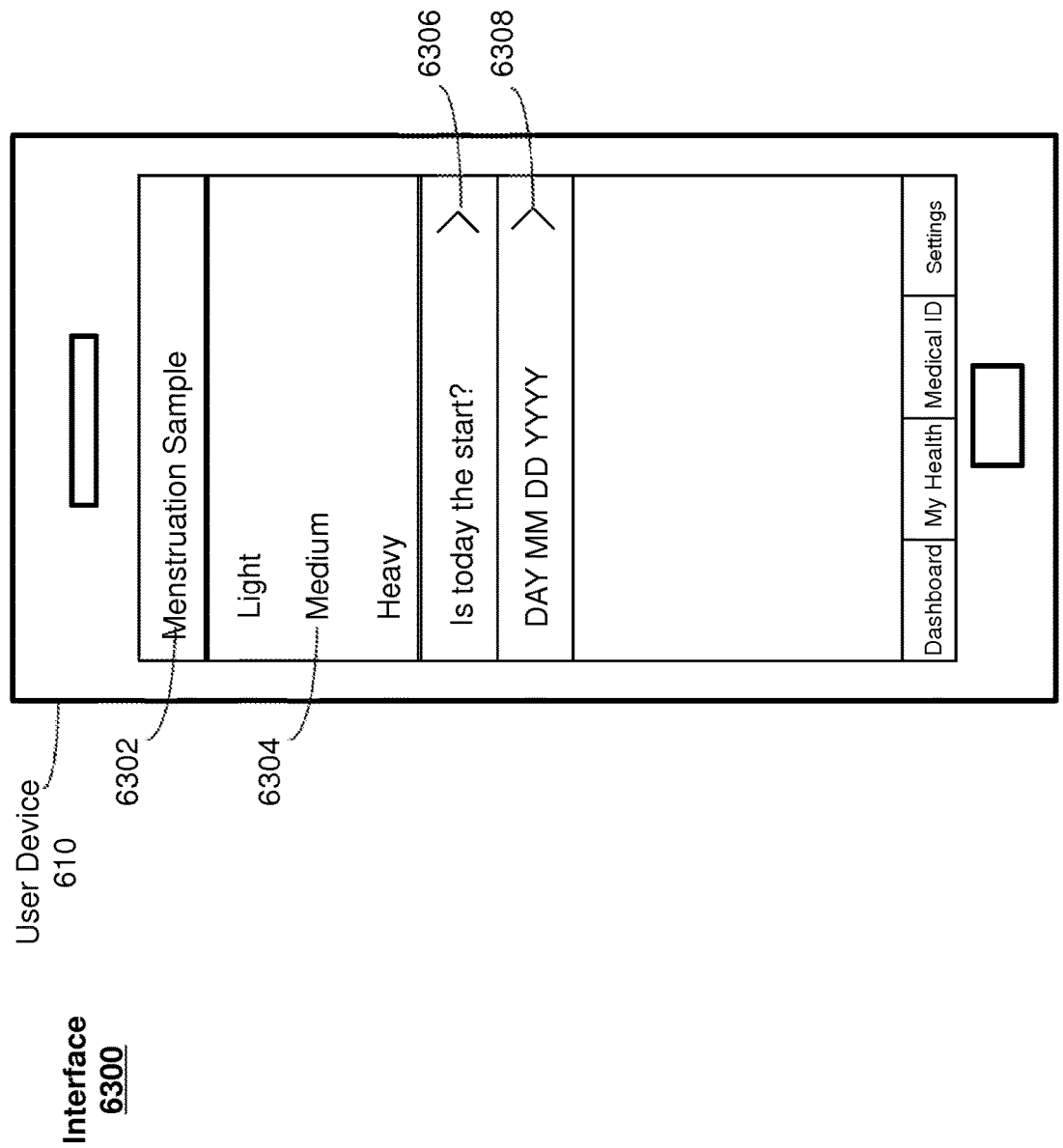
FIG. 63 illustrates an example interface for inputting wellness or non-wellness data according to various examples.

FIG. 63 illustrates an example interface 6300 for entering discrete wellness or non-wellness data, in this example menstruation sample information. Interface 6300 allows a user to enter a category value for the "Menstrual Flow" sub-category of the "Reproductive Health" category. Interface 6300 includes selection box 6302 to allow a user to select a data type corresponding to a category or sub-category. In the example depicted in FIG. 63, the selected data type, "Menstruation Sample," corresponds to data that can be entered for the "Menstrual Flow" sub-category. Interface 6300 includes data value picker 6304 to enable the user to pick a value for the menstruation sample. In this example, possible values that may be picked include Light, Medium, and Heavy. Restated, "Menstruation Sample" takes on values from a discrete set of values listed in picker 6304.

Interface 6300 also includes option 6306 for entering a date associated with the menstruation sample, and option 6308 for indicating whether the date is the start of the menstrual cycle. Information regarding the start of a particular cycle is useful for determining the range of a period of wellness activity. For example, information entered via option 6308 is used to derive the position of marker 5828 representing the beginning of a menstrual flow (FIG. 58C) in some examples.

FIG. 38A illustrates an example process 3800 for managing and displaying wellness or non-wellness data according to various examples. Process 3800 can be performed at an electronic device (e.g., device 610) with a display. In some examples, the display can include a touch-sensitive display. In other examples, the display can be separate from a touch-sensitive surface. Some blocks of process 3800 can be combined and/or the order of some blocks can be changed.

As described below, process 3800 provides an intuitive way to manage sources and destinations of data stored in wellness database 611. The process allows a user to specify which devices and applications can access data in wellness database 611, as well as to specify the devices and applications that can serve as sources for data to be stored in wellness database 611. Additionally, for the sources, the user can specify what types of data those sources can provide and which sources take priority over others. This can be advantageous when one device is more likely to produce more accurate results than another.

At block 3802, information identifying a plurality of approved sources of wellness data can be received by a user device (e.g., user device 610) from a user. In some examples, the information identifying the plurality of approved sources can identify one or more types of wellness or non-wellness data that are approved to be received from the plurality of approved sources and stored in a wellness database (e.g., wellness database 611). For example, the information identifying the plurality of approved sources can be received via an interface similar or identical to interfaces 3500, 3600, and 3700. In these examples, a user can specify which types of data can be provided by each of the plurality of approved sources to be stored in the wellness database.

At block 3804, information identifying a plurality of approved destinations of wellness or non-wellness data can be received by a user device (e.g., user device 610) from the user. For example, the information identifying the plurality of approved destinations can be received via an interface similar or identical to interface 3500. In these examples, a user can specify which destinations are approved to access data from the wellness database.

In some examples, the plurality of approved sources can include an electronic device or a software application. For example, an approved electronic device, such as a watch, a mobile phone, or the like, can provide wellness or non-wellness data to user device 610 to be stored in wellness database 611. Similarly, an approved software application on or otherwise associated with user device 610 can provide wellness or non-wellness data to user device 611 to be stored in wellness database 611. In some examples, the approved software application can be a software application associated with an electronic device and is capable of communicating with the electronic device.

Similarly, in some examples, the plurality of approved destinations can include an electronic device or a software application. For example, an approved electronic device, such as a watch, a mobile phone, or the like, can access wellness or non-wellness data stored in wellness database 611. Similarly, an approved software application on or otherwise associated with user device 610 can access wellness or non-wellness data stored in wellness database 611. In some examples, the approved software application can be a software application associated with an electronic device and is capable of communicating with the electronic device.

In some examples, the plurality of approved sources can be ranked amongst each other. In some examples, an interface similar or identical to interface 3500 can be used to display and adjust the relative ranking of the approved sources. For example, as shown in interface 3500, Device 1 can be ranked higher than Device 2 to prioritize data from Device 1 over data from Device 2, and Device 2 can be ranked higher than App 3 to prioritize data from Device 1 and Device 2 over data from App 3.

In some examples, process 3800 can further include, at block 3806, identifying a first wellness data entry and a second wellness data entry that are duplicates of one another. In some examples, this can include identifying a first wellness data entry in the wellness database that was received from a first approved source of the plurality of approved sources, the first wellness data entry comprising a first wellness data type and a first timestamp, and identifying a second wellness data entry in the wellness database that was received from a second approved source of the plurality of approved sources, the second wellness data entry comprising a second wellness data type and a second timestamp, wherein the first wellness data type and the second wellness data type are the same, and wherein the first timestamp is within a threshold length of time from the second timestamp. For example, a first data entry can have a type of "step data" and an associated timestamp of 2:30 p.m. on Mar. 1, 2014. The second data entry can have a type of "step data" and an associated timestamp of 2:31 p.m. on Mar. 1, 2014. If the threshold length of time used at block 3806 is 5 minutes, it can be determined that the first data entry and the second data entry are of the same data type and include timestamps that are within a threshold length of time from each other. This can indicate that the first data entry and the second data entry are likely duplicate entries representing the same actions performed by the user.

At block 3808, one of the first data entry and the second data entry can be prioritized or otherwise identified as being preferred over the other based on a ranking of the plurality of sources. For example, as discussed above, the plurality of approved sources can be ranked amongst each other (e.g., as shown in interface 3500). In some examples, if the first approved source providing the first data entry is identified by the user as being preferred over the second approved source, block 3808 can include using the first wellness data entry instead of using the second wellness data entry. For example, this can include deleting the second data entry from wellness database 611 or otherwise ignoring the second data entry for purposes of being displayed or presented to the user. In other examples, if the first approved source has been identified by the user as being preferred over the second approved source, then block 3806 can include prioritizing the first wellness data entry over the second wellness data entry. A data entry that is prioritized over another can be used in place of the other (e.g., displayed, used in calculations, or the like in favor of the other data entry).

In other examples, if the second approved source has been identified by the user as being preferred over the first approved source, then block 3806 can include prioritizing the second wellness data entry over the first wellness data entry. A data entry that is prioritized over another can be used in place of the other (e.g., displayed, used in calculations, or the like in favor of the other data entry).

Figure 38B:
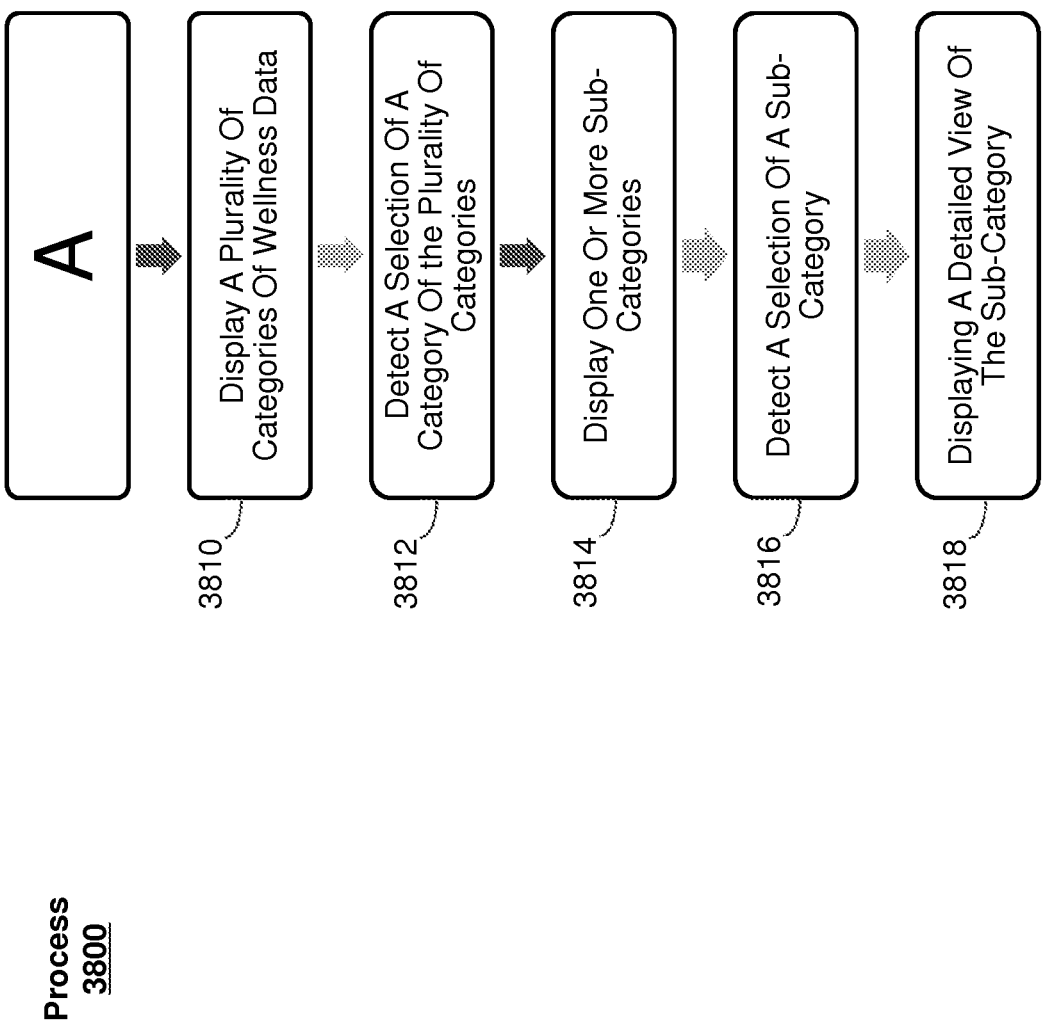

In some examples, as shown in FIG. 38B, process 3800 can further include, at block 3810, displaying, by the electronic device on the display, a plurality of categories of wellness data stored in the wellness database. For example, an interface similar or identical to interface 2800 can be displayed. The interface can include any amount or any type of categories of wellness or non-wellness data.

At block 3812, a selection of a category of wellness data from the displayed plurality of categories of wellness data can be detected at the electronic device. For example, a selection of one of the categories displayed in an interface similar or identical to interface 2800 made via a touch event by a finger or other device on a touch sensitive display, a click of a mouse or other device, a touch event on a touch pad, or the like, can be detected. In some examples, each of the displayed plurality of categories can include an indicator (e.g., indicator 2804) that can be color-coded based on the type of wellness or non-wellness data of the category. For example, the indicator associated with "Fitness" can have a different color than the indicator associated with "Vital Signs."

At block 3814, one or more sub-categories of the category of wellness data can be displayed in response to detecting the selection of the category of wellness data. For example, an interface similar or identical to interface 2900 containing a list of sub-categories falling within the category selected at block 3812 can be displayed. In some examples, the displayed interface can include indicators that can be color-cored based on the type of wellness or non-wellness data that it represents.

At block 3816 a selection of a sub-category from the displayed one or more sub-categories can be detected. For example, a selection of one of the sub-categories displayed in an interface similar or identical to interface 2900 made via a touch event by a finger or other device on a touch sensitive display, a click of a mouse or other device, a touch event on a touch pad, or the like, can be detected.

At block 3818, a detailed view of the selected sub-category can be displayed in response to detecting the selection of the sub-category at block 3816. For example, an interface similar or identical to interface 3200 can be displayed. The detailed view of the sub-category can include a graphical representation of the sub-category of data (e.g., graph 3102) and a numerical daily value (e.g., daily value 3104). The detailed view can further include options to show all data (e.g., option 3106), add a data point (e.g., option 3108), share data (e.g., option 3110), and show on dashboard (e.g., option 3112). The detailed view can further include a graphic representation of the sub-category (e.g., graphic 3114) and a text description of the sub-category (e.g., description 3122), In some examples, process 3800 can include displaying an interface similar or identical to interface 3400 in response to a selection of the add a data point option (e.g., option 3108). The interface can include one or more input fields (e.g., fields 3402, 3404, and 3406) for entering information associated with the wellness data entry. In some examples, process 3800 can further include receiving a wellness data entry to be stored in the wellness database that was input into the input field (e.g., input into fields 3402, 3404, and 3406).

In some examples, process 3800 can further include displaying an interface similar or identical to interface 3300 in response to a selection of the show all data option (e.g., option 3106). The interface can include a plurality of wellness data entries corresponding to the sub-category stored in the wellness database (e.g., entries in list 3302) In some examples, each of the plurality of wellness data entries can include a numerical value of the data entry, a timestamp, and an identification of a source of the data entry (e.g., indicator 3304).

In some examples, process 3800 can further include displaying a data sharing interface similar or identical to interface 3500 in response to a selection of the share data option (e.g., option 3110). The interface can include the plurality of approved sources (e.g., source list 3506) and the plurality of approved destinations (e.g., list 3504). In some examples, a request to reorder the displayed plurality of approved sources can be detected by the electronic device. For example, a selection of edit button 3508 can be received and movement of one or more of the sources in source list 3506 can be detected. In response to detecting the request to reorder the displayed plurality of approved sources, the displayed plurality of approved sources can be reordered in accordance with the detected request to reorder the displayed plurality of approved sources In some examples, the data sharing interface (e.g., interface 3500) can further include options to add an approved destination to the plurality of approved destinations and to remove an approved destination from the plurality of approved destinations (e.g., options 3512, 3514, 3516, and 3518).

In some examples, process 3800 can further include receiving, at the electronic device, a search query. In response, one or more sub-categories of the plurality of categories that match the search query can be displayed. The displayed one or more sub-categories that match the search query can be color-coded based on their respective categories. For example, a search query can be received from a search box (e.g., search box 2808) displayed within an interface similar or identical to interface 2800 or 2900. A search results interface similar or identical to interface 3000 can be displayed in response to the search query. The search results interface can include the one or more sub-categories that match the search query.

In some examples, process 3800 can further include displaying, on the display, a source interface comprising a list of known sources. For example, an interface similar or identical to interface 3600 can be displayed having a list of known sources (e.g., list 3606). The source interface can further include a numerical indicator associated a known source of the known sources that represents a number of new types of wellness data that can be provided by the known source. For example, the number "2" is shown for Device 1, indicating the two new types of data (e.g., Calories burned and flights of stairs climbed) are available.

In some examples, process 3800 can further include detecting a selection of a known source from the list of displayed sources. In response to detecting the selection of the known source, a list of types of wellness data that the known source can provide can be displayed. For example, a source from source list 3606 of interface 3600 can be received by a user selecting an option 3610 associated with the source. In response, an interface similar or identical to interface 3700 can be displayed. The displayed interface can include a list (e.g., list 3706) of known types of data that the source can provide. In some examples, the list of types of wellness data that the known source can provide can include a selectable option (e.g., options 3704, 3708, 3710, 3712, and 3714) for each of the types of wellness data that the known source can provide to approve or reject the associated type of wellness data.

In some examples, process 3800 can further include detecting a selection of the selectable option for a type of wellness data that the known source can provide at the electronic device. In response to detecting the selection of the selectable option, process 3800 can further include approving or rejecting the type of wellness data that the known source can provide in accordance with the detected selection of the selectable option. For example, user device 610 can accept or reject the types of wellness data shown in interface 3700 based on the positions of the switches of options 3704, 3708, 3710, 3712, and 3714.

It should be understood that the particular order in which the operations in FIGS. 38A and 38B have been described is merely exemplary and is not intended to indicate that the described order is the only order in which the operations could be performed. One of ordinary skill in the art would recognize various ways to reorder the operations described herein. Additionally, it should be noted that details of other processes described herein with respect to other processes described herein (e.g., processes 800, 1500, 1700, 2000, 2700, or 4400) are also applicable in an analogous manner to process 3800 described above with respect to FIGS. 38A and 38B. For brevity, these details are not repeated here.

Medical Identification Information

FIG. 39 illustrates one example lock screen interface 3900 that can be displayed by user device 610 while the user device is in a locked state. In some examples, the locked state can represent a state in which user device 610 restricts one or more functions from being performed. For example, user device 610 can prevent a user from running applications, changing settings, or the like, while in the locked state. In other examples, the locked state can represent a state in which user device 610 additionally or alternatively prevents access at least a subset of data stored on the device. For example, user device 610 can prevent a user from viewing photos or videos, accessing documents, or the like, while in the locked state. In other examples, the locked state can represent a state in which user device 610 additionally or alternatively restricts communications from the electronic device. For example, user device 610 can prevent a user from sending SMS messages or emails, or making calls to non-emergency phone numbers.

Figure 40:
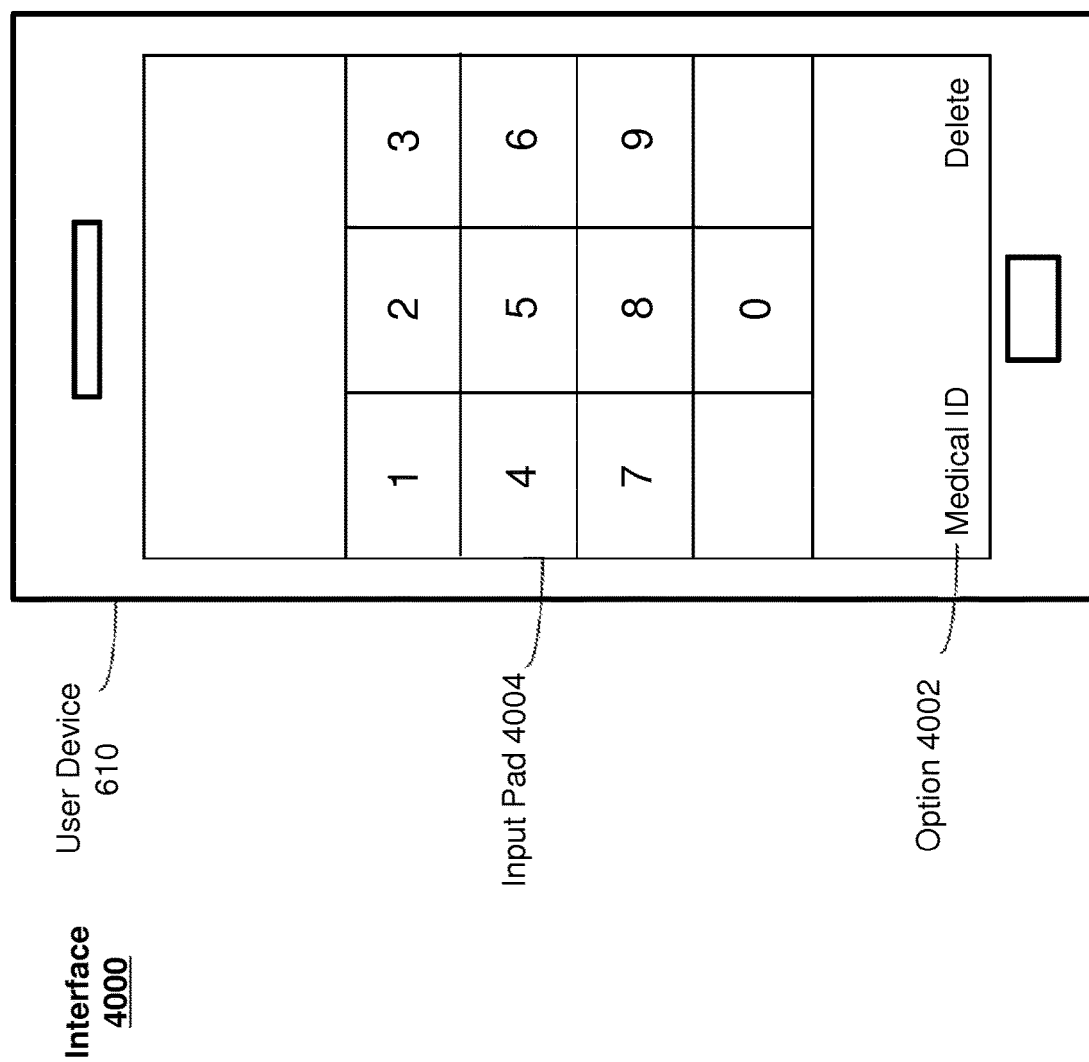
FIG. 40 illustrates example interfaces for displaying emergency medical information according to various examples.

As shown in FIG. 39, lock screen interface 3900 can include the current date and time. Lock screen interface 3900 can further be responsive to user input to allow a user to unlock the device. For example, a swiping gesture can cause user device 610 to display a numerical input pad to allow the user to enter a passcode to unlock the device. Lock screen interface 3900 can further include emergency option 3902 for accessing emergency features of user device 610. For example, FIG. 40 illustrates an example emergency dialing interface 4000 that can be displayed in response to a selection of emergency option 3902. As shown, emergency dialing interface 4000 can include numerical input pad 4004 for allowing a temporary user to enter an emergency phone number to dial while the device is in the locked state. In some examples, user device 610 can call a number entered using input pad 4004 if the entered number is predefined phone number (e.g., 9-1-1). In some examples, the temporary user can be a first responder or other person that encounters the primary user of the device when the primary user of the device is unable to operate user device 610 (e.g., because the primary user is unconscious or injured). Thus, emergency dialing interface 4000 allows the temporary user to place calls to predetermined emergency phone numbers without requiring the temporary user to unlock user device 610.

Interface 4000 can further include Medical ID or emergency information option 4002 for viewing medical information associated with a user by the temporary user. In this example, the user can be a primary user or owner of user device 610 that has customized the device by installing applications and/or entering personal information to user device 610. Thus, Medical ID or emergency information option 4002 can be selected by the temporary user to view emergency information associated with the primary user without requiring the temporary user to unlock user device 610.

Figure 41:
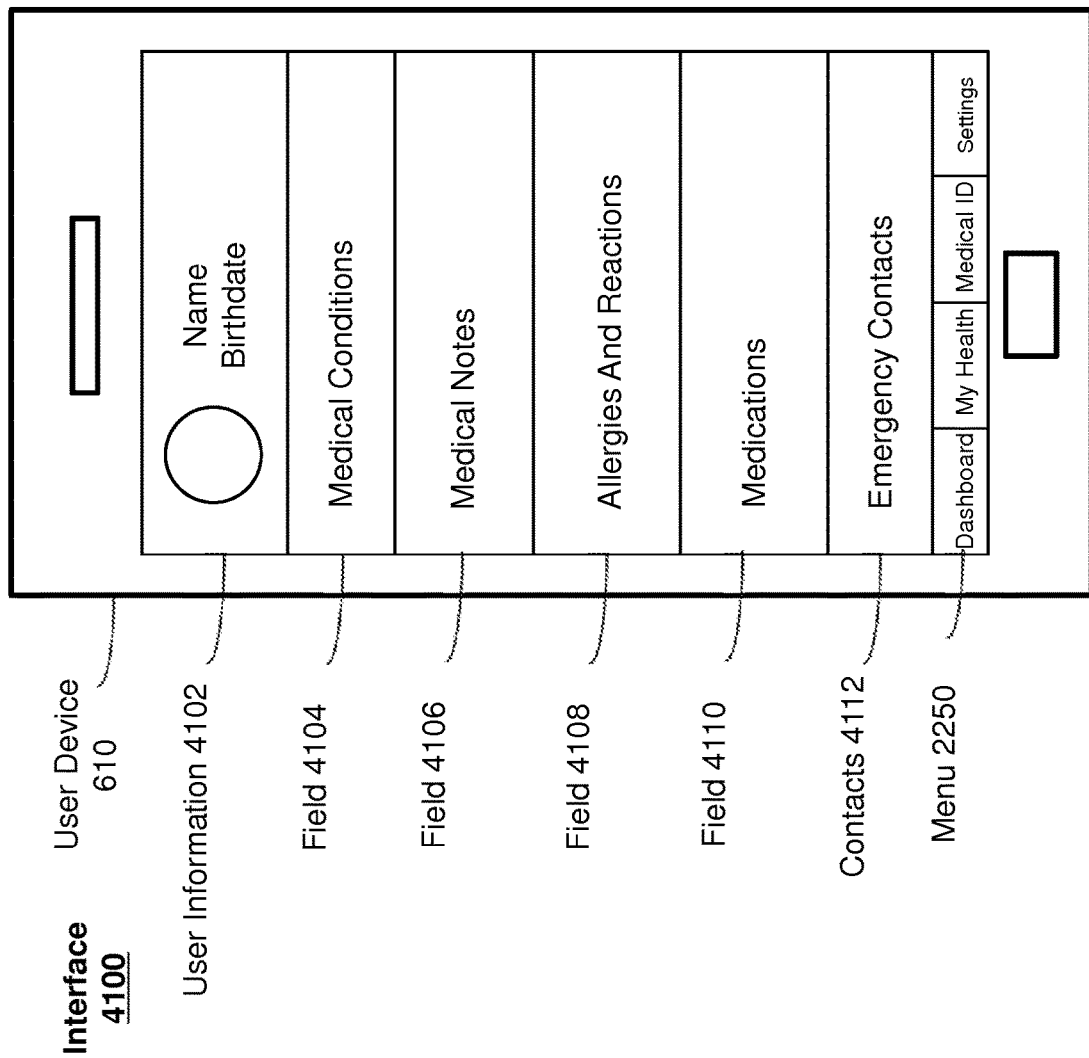
FIG. 41 illustrates example interfaces for displaying emergency medical information according to various examples.

For example, FIG. 41 illustrates an example emergency information interface 4100 that can be displayed in response to a selection of Medical ID or emergency information option 4002 in interface 4000. As shown, interface 4100 can include user information 4102 including the user's name and birthdate. Interface 4100 can further include a free-form field 4104 that can be used to store and display a description of any medical conditions that the user may have. Interface 4100 can further include a free-form field 4106 that can be used to store and display any other relevant medical notes about the user. Interface 4100 can further include free-form field 4108 that can be used to store and display a description of any allergies or reactions that the user may have to drugs or any other substance. Interface 4100 can further include free-form field 4110 that can be used to store and display a description of any medications that the user may be taking or that the user may require.

Interface 4100 can further include emergency contacts 4112. Emergency contacts 4112 can include a list of one or more people that the user has designated as being his/her emergency contact. Emergency contacts 4112 can include a name of each emergency contact and a relationship between the user and the emergency contact. For example, one entry for an emergency contact can include the name "Jane Smith" having a relationship with the user of "mother." In some examples, emergency contacts 4112 can further include contact information for the emergency contact, such as a phone number, email address, or the like. In other examples, emergency contact 4112 can exclude contact information for the emergency contact, such as a phone number, email address, or the like. This can be done to protect the privacy of the emergency contact. In either example, user device 610 can allow a temporary user to select one of the displayed emergency contacts to initiate communication with that contact (even if the phone number of the emergency contact is not displayed) while user device 610 remains in the locked state. For example, in response to a selection of one of the emergency contacts, user device 610 can initiate a phone call to the contact, send an SMS message to the contact, send an email to the emergency contact, or the like, while the device remains in the locked state. In some examples, when user device 610 initiates a call to an emergency contact in response to a selection of that emergency contact, user device 610 can flag the call as being an emergency call. In some examples, emergency calls can be accepted by a receiving device in any state of operation. For example, a call flagged as being an emergency call can cause the receiving device to ring while in a do-not-disturb mode, a silent mode, or the like. Additionally, an indicator can be displayed on the receiving device notifying the recipient that the call is an emergency call.

Figure 42:
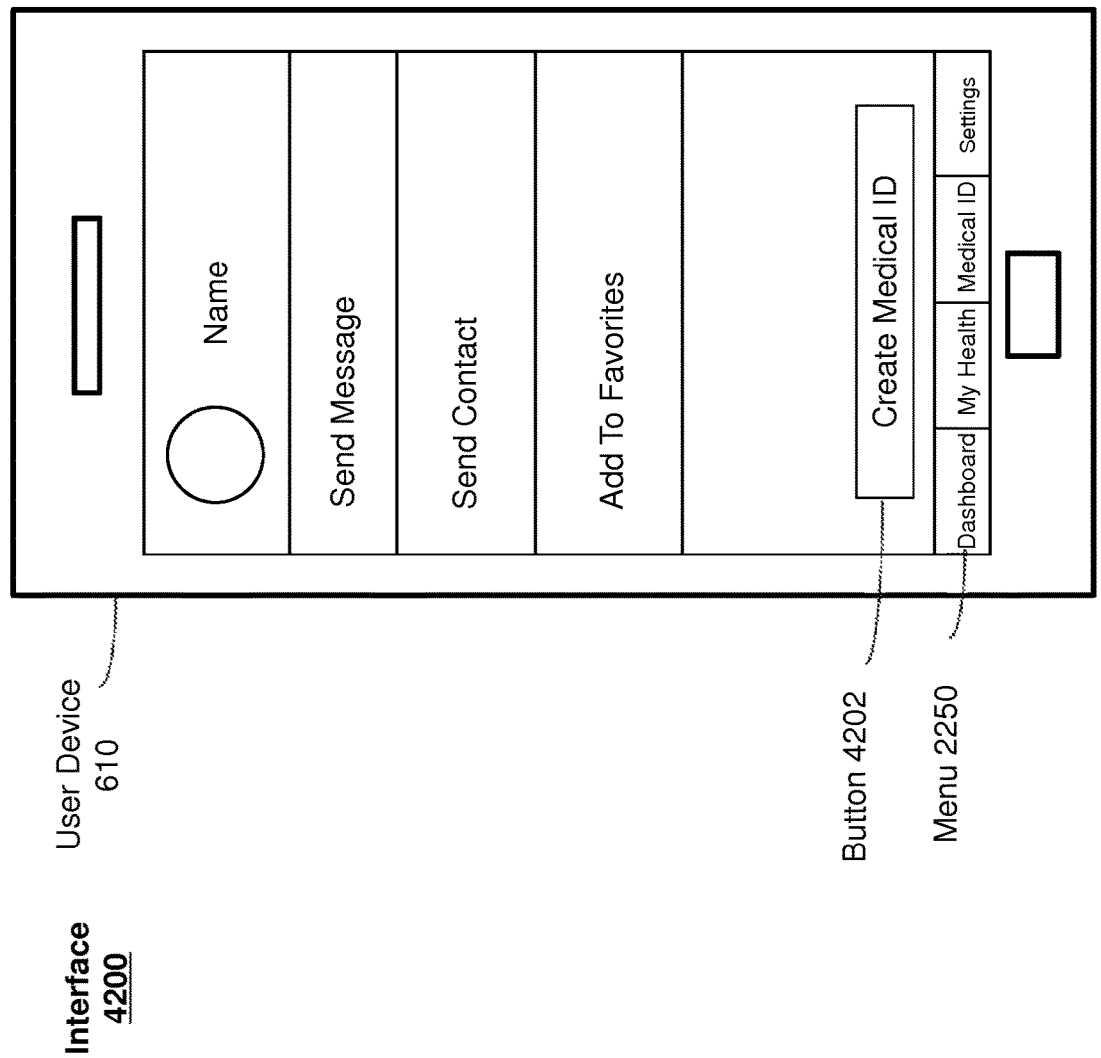
FIG. 42 illustrates example interfaces for displaying emergency medical information according to various examples.
Figure 43:
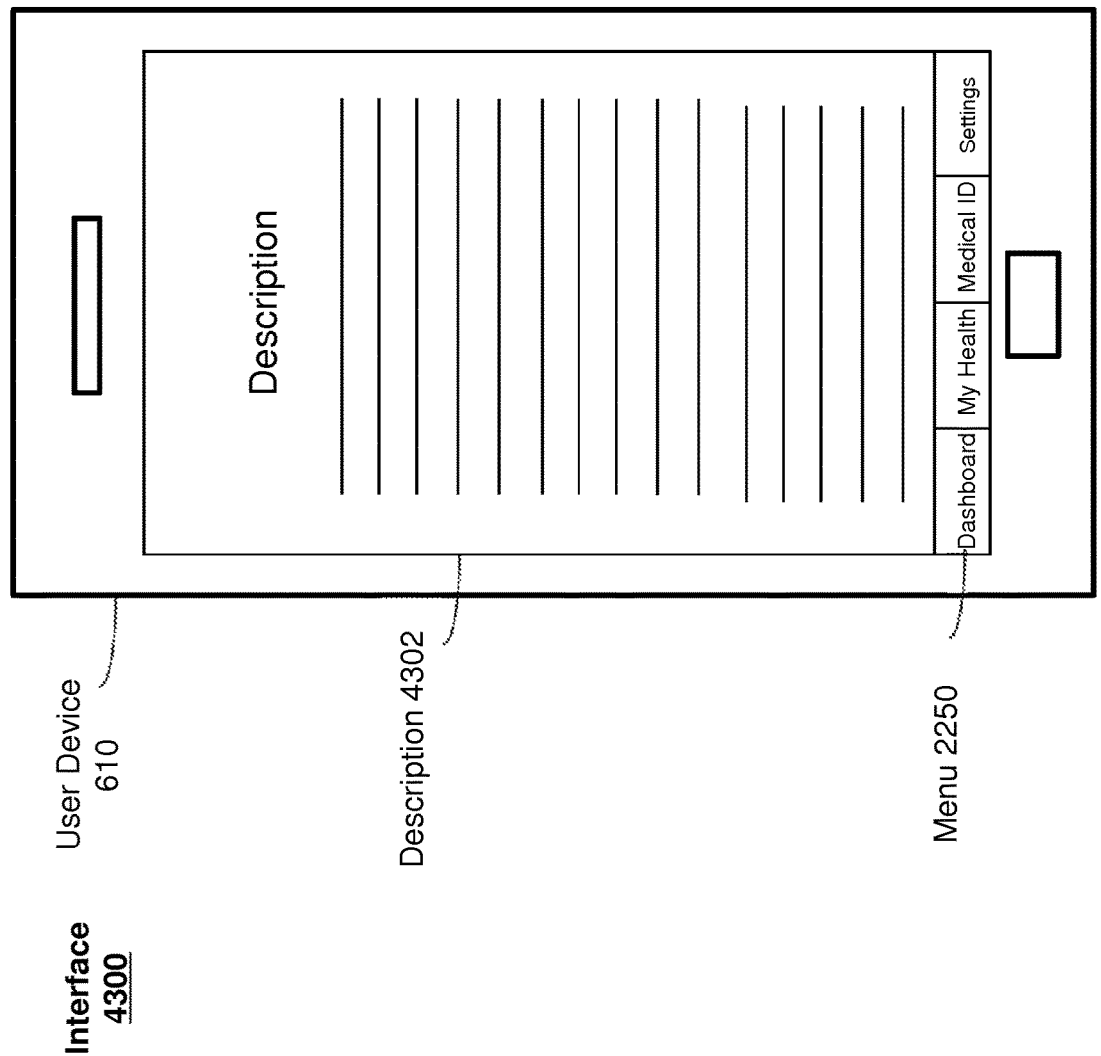
FIG. 43 illustrates example interfaces for displaying emergency medical information according to various examples.

In some examples, a primary user can create their medical identification from the contact list of user device 610. For example, FIG. 42 illustrates an example interface 4200 that can be displayed to display the user's contact list. As shown, interface 4200 can include a "Create Medical ID" button 4202 for creating a medical identification. FIG. 43 illustrates an example interface 4300 that can be displayed in response to a selection of button 4202. As shown, interface 4300 includes a text description 4302 that can provide information about the medical identification, such as the purpose of the medical identification, the privacy settings for information contained in the medical identification, and the like.

Figure 44:
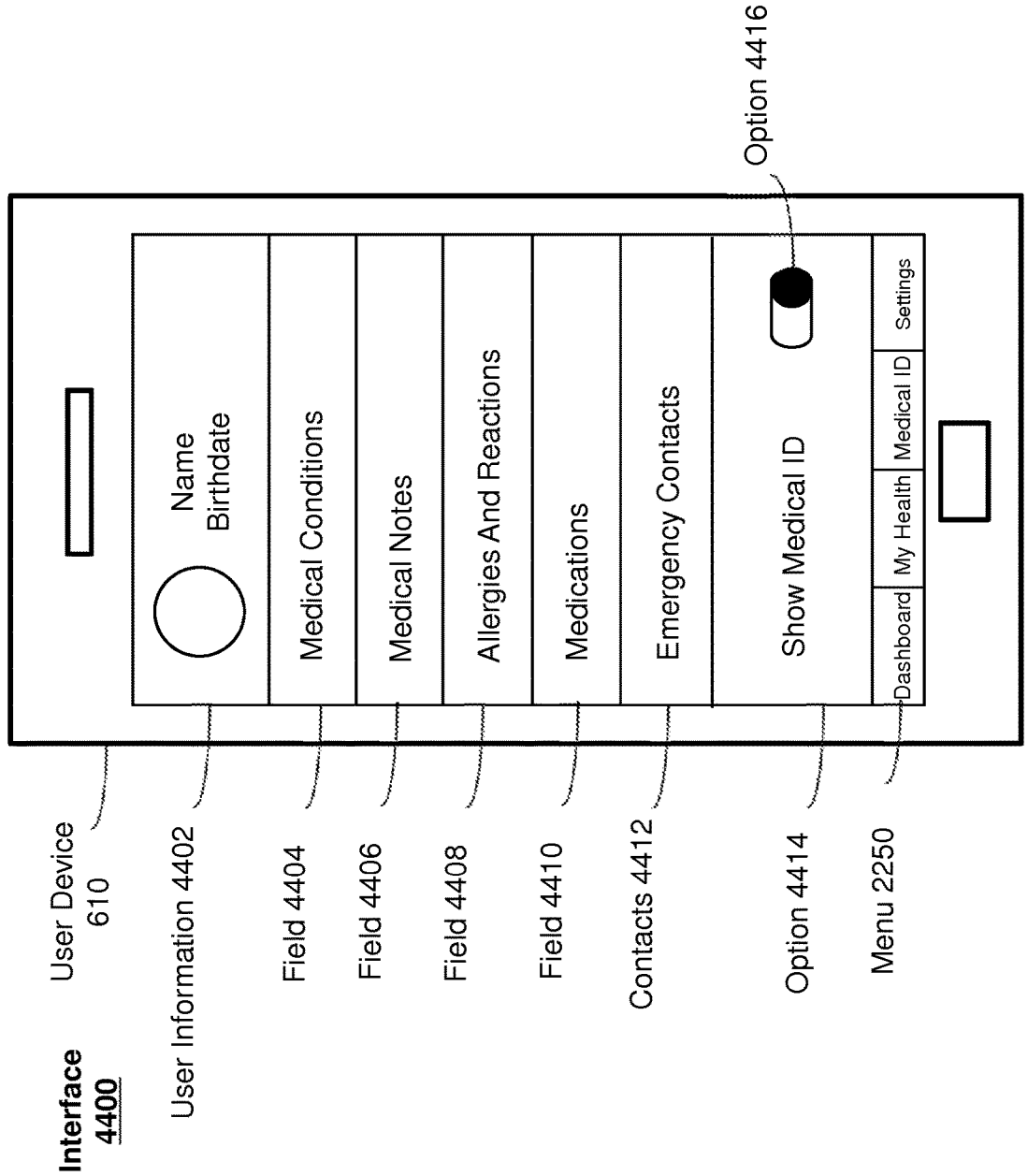
FIG. 44 illustrates example interfaces for displaying emergency medical information according to various examples.

FIG. 44 illustrates an example interface 4400 that can be displayed in response to a user accepting or acknowledging the contents of description 4302 in interface 4300. As shown, interface 4400 can include user information 4402 that can correspond to user information 4102 in interface 4100. In some examples, this information can be auto-populated by user device 610 based on information previously known about the user. In other examples, the user can enter this information manually. Interface 4400 can further include free-form text fields 4404, 4406, 4408, and 4410 that can correspond to fields 4104, 4106, 4108, and 4110 of interface 4100. Thus, information entered into fields 4404, 4406, 4408, and 4410 can be displayed in fields 4104, 4106, 4108, and 4110 of interface 4100. Interface 4400 can further include contacts 4412 to allow a user to enter one or more emergency contacts. In some examples, the one or more emergency contacts can be selected from the user's contact list on user device 610. In other examples, the one or more emergency contacts can be entered manually by the user. In yet other examples, the emergency contact can be selected from the user's contact list on user device 610 and additional information (e.g., relationship information) can be manually added by the user. Interface 4400 can further include "Show Medical ID" option 4414 having selectable option 4416. The position of the switch of option 4416 can be used to turn on or off the showing of the user's medical information while the device is in the locked state. For example, when moved to the right, as shown in FIG. 44, the switch of option 4416 can cause user device 610 to display option 4002 in the emergency dialing interface 4000 and to display interface 4100 in response to a selection of option 4002. However, when moved to the left, the switch of option 4416 can prevent user device 610 from displaying option 4002 in the emergency dialing interface 4000 and can prevent user device 610 from displaying interface 4100 in response to a selection of option 4002.

Figure 45:
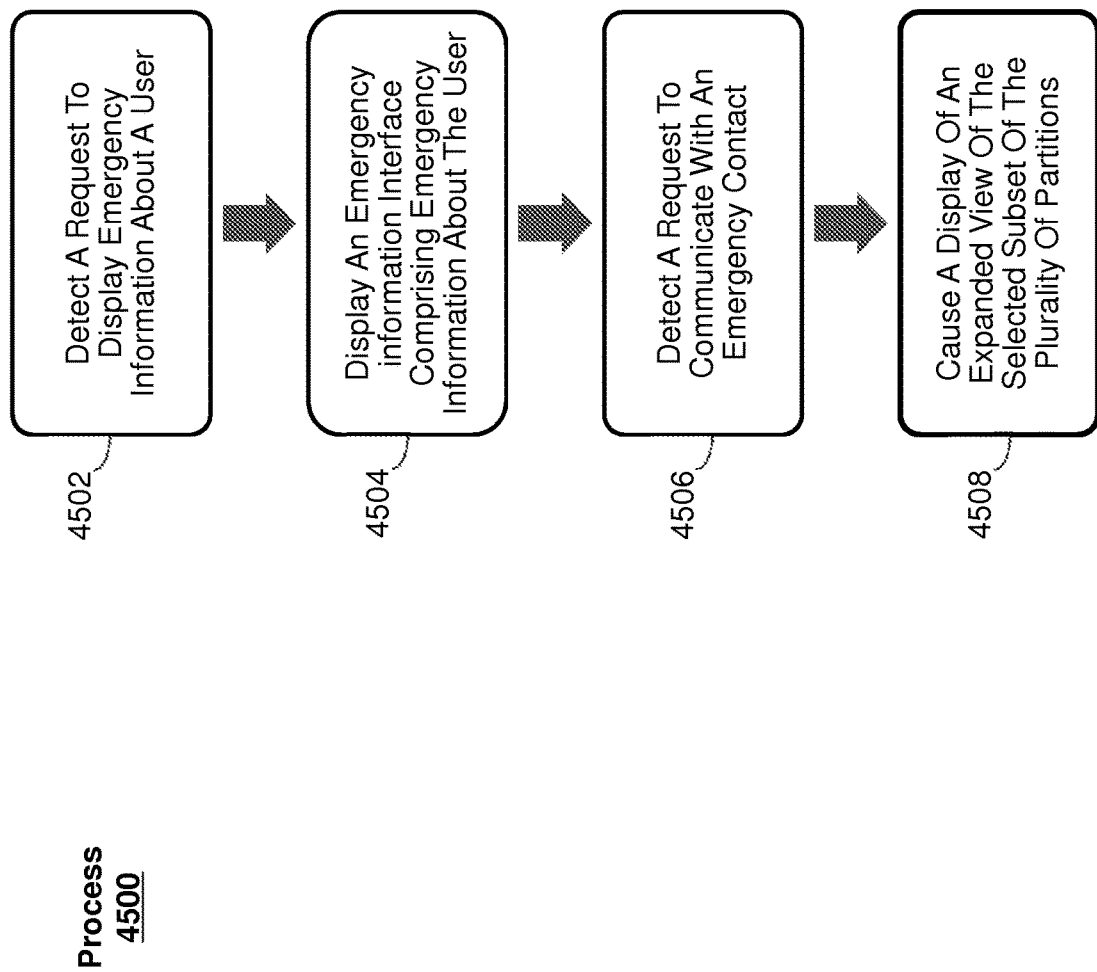
FIG. 45 illustrates an example process for displaying emergency medical information according to various examples.

FIG. 45 illustrates an exemplary process 4500 for displaying medical information on a locked device. Process 4500 can be performed at an electronic device (e.g., device 610) with a display. In some examples, the display can include a touch-sensitive display. In other examples, the display can be separate from a touch-sensitive surface. Some blocks of process 4500 can be combined and/or the order of some blocks can be changed.

As described below, process 4500 provides a way for a temporary user to view medical information associated with a primary user or owner of an electronic device while the device remains in a locked state. Process 4500 also allows a temporary user to initiate communication with the primary user's emergency contacts while the device remains in the locked state. This advantageously allows a temporary user that finds the primary user (e.g., in a state in which the primary user is unable to operate the electronic device or communicate) to assist the primary user in getting the appropriate medical care.

At block 4502, at an electronic device (e.g., user device 610) while the electronic device is in a locked state, a request to display emergency information about a user of the device can be detected. For example, the request to display the emergency information can be received while an emergency dialing interface similar or identical to interface 4000 is being displayed, and the request can include a selection of an emergency information option similar or identical to option 4002. The emergency information about the user of the device can include the user's name, birthday, medical conditions, allergies and reactions, medications, and one or more emergency contacts of the user. As discussed above, the user can be a primary user or owner of user device 610 that has customized the device by installing applications and/or entering personal information to user device 610. The request to display the medical information can be made by a temporary user, such as a first responder or other person that encounters the primary user of the device when the primary user of the device is unable to operate user device 610 (e.g., because the primary user is unconscious or injured).

At block 4504, in response to detecting the request, an emergency information interface comprising emergency information about the user of the device can be displayed without unlocking the device. For example, an interface similar or identical to interface 4100 can be displayed.

In some examples, the emergency information about the user can include information associated with an emergency contact. The information associated with the emergency contact can include a name of the emergency contact and a relationship between the user and the emergency contact. For example, information about an emergency contact can be displayed in a manner similar or identical to emergency contact 4112 in interface 4100. One example emergency contact can include the contact's name "Jane Smith," and the relationship "mother" between the user and the contact.

At block 4506, user device 610 can detect a request to communicate with an emergency contact while the electronic device is in the locked state. For example, a selection of a contact 4112 from interface 4100 can be detected.

At block 4508, user device 610 can initiate communication with the emergency contact in response to detecting the request to communicate. In some examples, initiating communication with the emergency contact includes sending an SMS message or email to the emergency contact. In other examples, initiating communication with the emergency contact can include calling a phone number associated with the emergency contact. In some examples, calling the phone number associated with the emergency contact can include flagging the call to the phone number as an emergency call. In some examples, the phone number associated with the emergency contact can be included in the information associated with the emergency contact displayed within the emergency information interface (e.g., interface 4100). In other examples, the phone number associated with the emergency contact may not be included in the information associated with the emergency contact displayed within the emergency information interface (e.g., interface 4100). However, a call or other communication can still be made to this emergency contact. This can be done to protect the privacy of the emergency contact.

In some examples, process 4500 can include displaying an emergency dialing interface prior to displaying the emergency information interface. The emergency dialing interface can include a numerical input pad and an emergency information option. For example, an emergency dialing interface similar or identical to interface 4000 can be displayed prior to displaying emergency information interface 4100. The emergency dialing interface 4000 can include a numerical input pad similar or identical to input pad 4004 and an emergency information option similar or identical to option 4002. In some examples, the emergency information interface (e.g., interface 4100) can be displayed in response to a selection of the emergency information option (e.g., option 4002).

In some examples, process 4500 can further include detecting a predefined phone number entered using the numerical input pad while the electronic device is in the locked state. In response to detecting the predefined phone number, process 4500 can further include calling the predefined phone number. For example, user device 610 can detect a predefined number (e.g., 9-1-1) entered in the numerical input pad (e.g., input pad 4004). In response to detecting the predefined phone number, user device 610 can call the predefined number while still in the locked state. In some examples, calling the predefined phone number can include flagging the call to the predefined phone number as an emergency call.

In some examples, calls flagged as being emergency calls can be accepted by a receiving electronic device in any state of operation. For example, a call flagged as being an emergency call can cause the receiving device to ring while in a do-not-disturb mode, a silent mode, or the like. Additionally, an indicator can be displayed on the receiving device notifying the recipient that the call is an emergency call.

In some examples, process 4500 can further include displaying a lock screen interface comprising an emergency option prior to displaying the emergency dialing interface. For example, an interface similar or identical to interface 3900 can be displayed having an emergency option similar or identical to option 3902. The lock screen interface can further include one or more controls for unlocking the device. For example, a numerical input pad can be displayed to allow a user to enter a passcode, or user device 610 can be configured to detect predefined gestures to unlock the device. In these examples process 4500 can further include detecting a selection of the emergency option and displaying the emergency dialing interface in response to detecting the selection of the emergency option. For example, user device 610 can detect a selection of option 3902 and display interface 4000 in response to detecting the selection of option 3902.

It should be understood that the particular order in which the operations in FIG. 45 have been described is merely exemplary and is not intended to indicate that the described order is the only order in which the operations could be performed. One of ordinary skill in the art would recognize various ways to reorder the operations described herein. Additionally, it should be noted that details of other processes described herein with respect to other processes described herein (e.g., processes 900, 1600, 1800, 2100, 2700, or 3800) are also applicable in an analogous manner to process 4500 described above with respect to FIG. 45. For brevity, these details are not repeated here.

In some examples, the interfaces shown in FIGS. 22-23, 28-36, 41-43, and 56-59 can include menu bar 2250 for navigating between the various interfaces. For example, in response to a selection of "Dashboard" in menu 2250, interface 2100 or 2200 can be displayed. In response to a selection of "My Health" in menu 2250, interface 2700 can be displayed. In response to a selection of "Medical ID" in menu 2250, interface 4400 can be displayed. In response to a selection of "Settings" in menu 2250, interface 3600 can be displayed.

Figure 46:
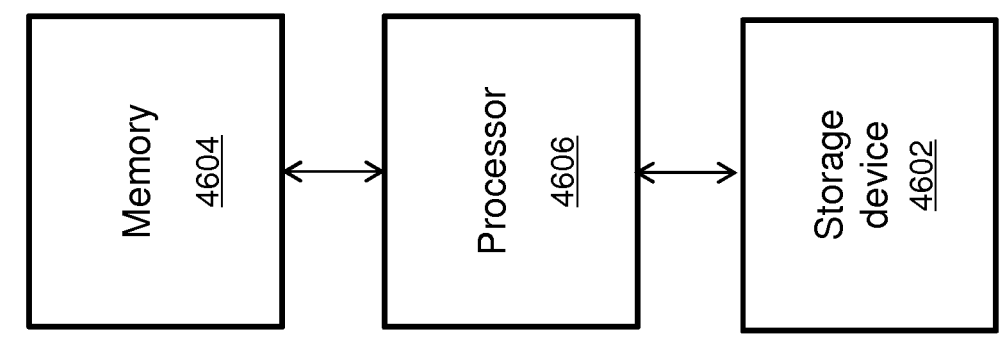
FIG. 46 illustrates an example computing system for aggregating and sharing wellness data according to various examples.

One or more of the functions relating to aggregating and sharing wellness data can be performed by a system similar or identical to system 4600 shown in FIG. 46. System 4600 can include instructions stored in a non-transitory computer readable storage medium, such as memory 4604 or storage device 4602, and executed by processor 4606. The instructions can also be stored and/or transported within any non-transitory computer readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer readable storage medium" can be any medium that can contain or store the program for use by or in connection with the instruction execution system, apparatus, or device. The non-transitory computer readable storage medium can include, but is not limited to, an electronic, magnetic, optical, electromagnetic, infrared, or semiconductor system, apparatus or device, a portable computer diskette (magnetic), a random access memory (RAM), a read-only memory (ROM), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The instructions can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

In some examples, system 4600 can be included within user device 610 or user server 614. Processor 4606 can be configured to perform processes 800, 900, 1500, 1800, 2100, 2700, 3800, or 4500. It is to be understood that the system is not limited to the components and configuration of FIG. 46, but can include other or additional components in multiple configurations according to various examples.

Figure 47:
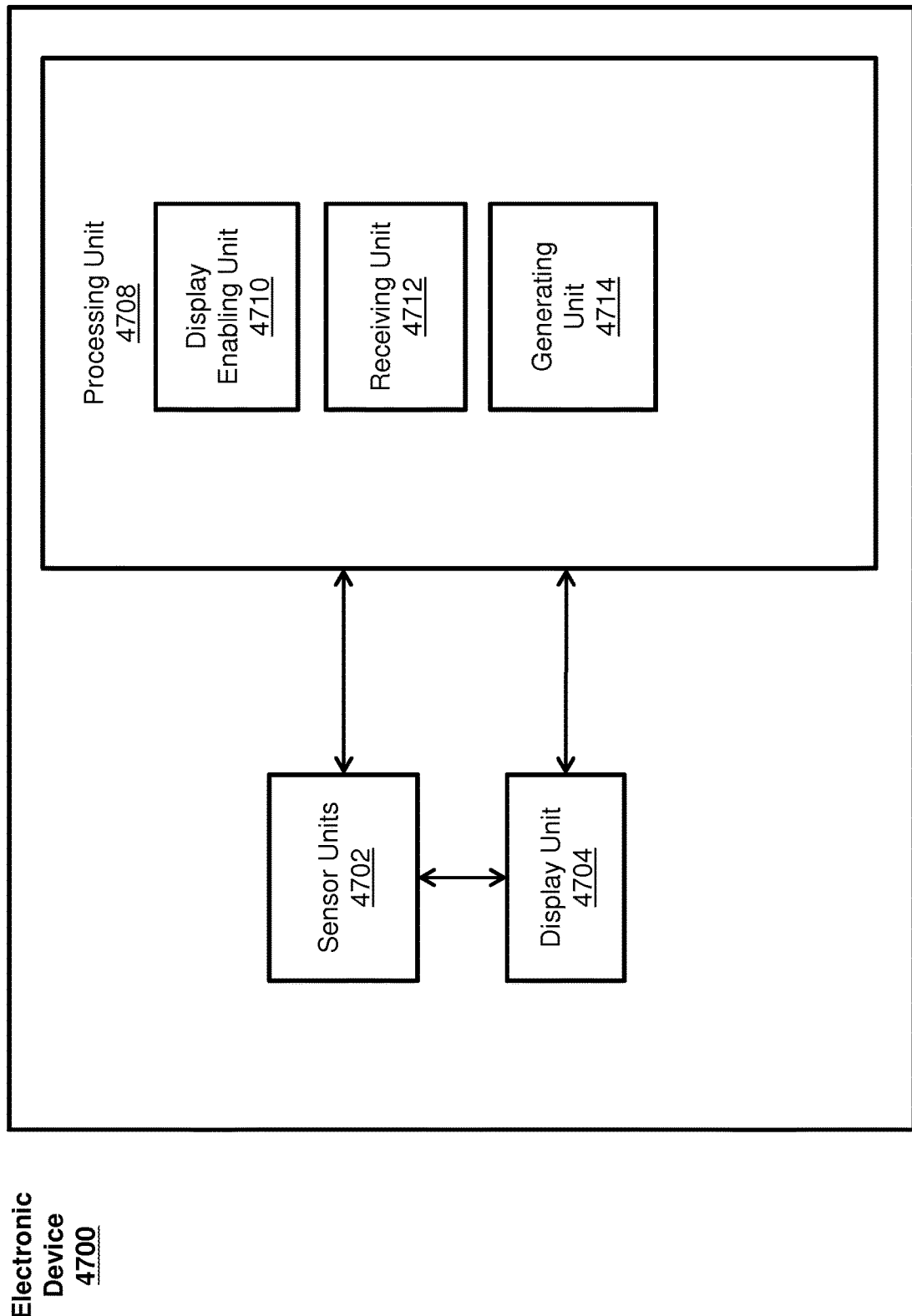
FIG. 47 illustrates a functional block diagram of an electronic device configured to display wellness or non-wellness data according to various examples.

In accordance with some examples, FIG. 47 shows a functional block diagram of an electronic device 4700 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 47 can be combined or separated into sub-blocks to implement the principles of the various described examples. Therefore, the description herein optionally supports any possible combination or separation or further definition of the functional blocks described herein.

As shown in FIG. 47, electronic device 4700 can include a display unit 4704 for displaying a user interface and, optionally, sensor units 4702 configured to receive touch input. Electronic device 4700 can further include a processing unit 4708 coupled to the optional sensor units 4702 and display unit 4704. In some examples, processing unit 4708 can include one or more of a display enabling unit 4710, a receiving unit 4712, and a generating unit 4714.

Processing unit 4708 may be configured to: enable display (e.g., with display enabling unit 4710) of an aggregated view of a plurality of types of wellness data, wherein the aggregated view comprises a plurality of partitions, each partition of the plurality of partitions associated with a type of the plurality of types of wellness data; receive (e.g., with receiving unit 4712) a selection of a partition of the plurality of partitions; and enable display (e.g., with display enabling unit 4710) of an expanded view of the selected partition of the plurality of partitions.

In some embodiments, in the aggregated view, each partition of the plurality of partitions comprises an identifier of an associated type of wellness data and a first portion of the associated type of wellness data displayed therewith, and wherein the expanded view comprises a larger view of the selected partition of the plurality of partitions and a second portion of the associated type of wellness data displayed therewith.

In some embodiments, the first portion of the wellness data comprises a most recent value of the associated type of wellness data, and wherein the second portion of the associated type of wellness data comprises a representation of the associated type of wellness data over time.

In some embodiments, the processing unit is configured to: enable the display (e.g., with display enabling unit 4710) of the expanded view of the selected partition by at least enabling the display of a collapsed set of partitions representing partitions of the plurality of partitions that were not selected.

In some embodiments, the plurality of partitions are ordered within the display based on a frequency of use of an associated type of wellness data, a time of most recently added value of the associated type of wellness data, or a time of day.

In some embodiments, the expanded view of the selected partition comprises a selectable element to share the wellness data associated with the partition through email or text message.

In some embodiments, the plurality of types of wellness data comprises weight data, blood sugar data, blood pressure data, activity data, or heart rate data.

In some embodiments, the electronic device further includes a plurality of sensor units coupled to the processing unit 4708 and the display unit 4704. The processing unit 4708 is further configured to generate (e.g., with generating unit 4714) at least one of the plurality of types of wellness data from sensor data obtained from the plurality of sensors.

In some embodiments, the expanded view comprises a graph of the associated type of wellness data, and wherein the graph comprises segments generated from wellness data obtained from different sensors.

In some embodiments, a partition of the plurality of partitions is a user-generated partition.

In some embodiments, the plurality of partitions have the appearance of a plurality of cards displayed in a stack.

The operations described above with reference to FIG. 16 are, optionally, implemented by components depicted in FIGS. 1A-1B or FIG. 47. For example, displaying operations 1602 and 1606 and receiving operation 1604 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 48:
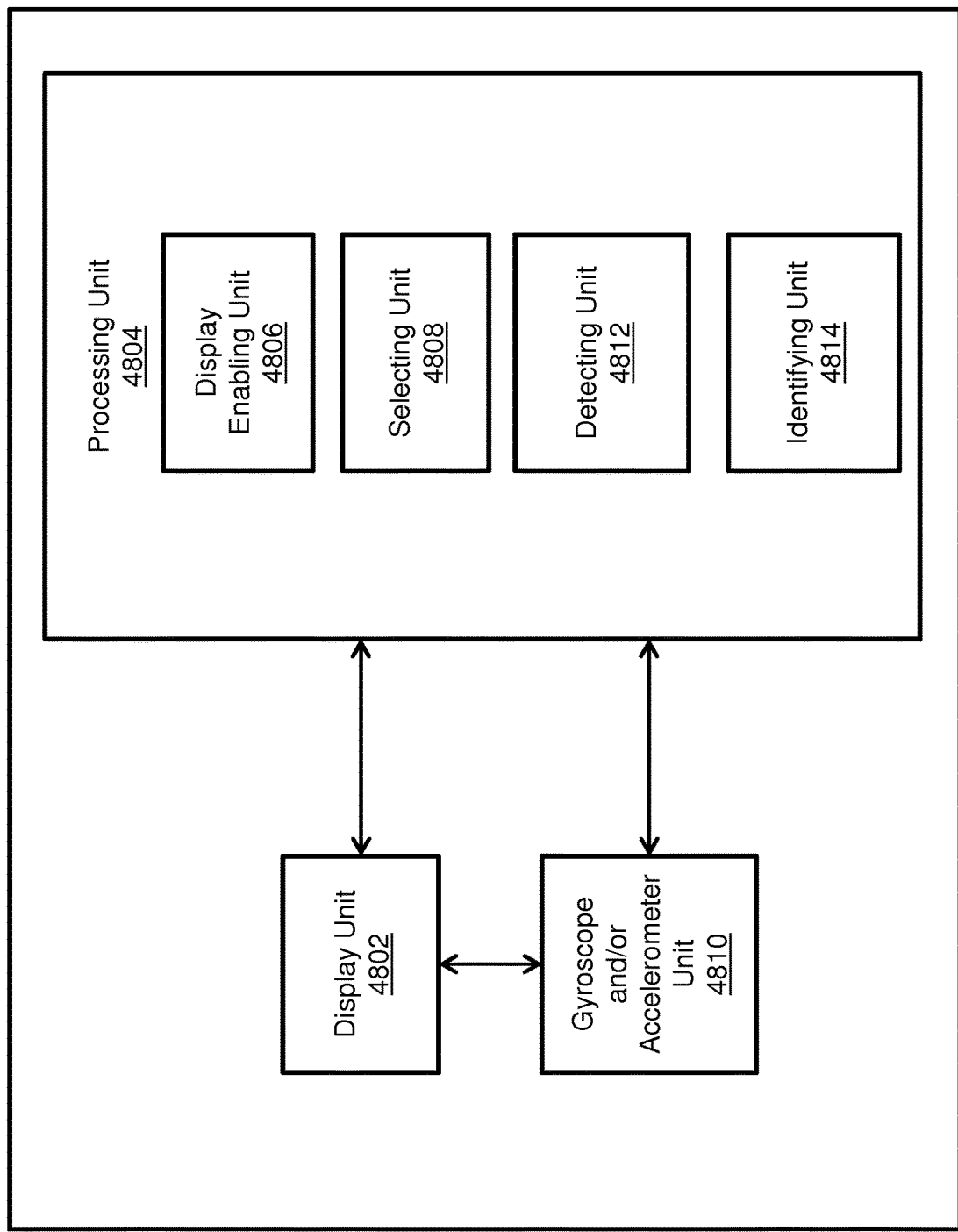
FIG. 48 illustrates a functional block diagram of an electronic device configured to manage and display wellness or non-wellness data according to various examples.

In accordance with some examples, FIG. 48 shows a functional block diagram of an electronic device 4800 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 48 can be combined or separated into sub-blocks to implement the principles of the various described examples. Therefore, the description herein optionally supports any possible combination or separation or further definition of the functional blocks described herein.

As shown in FIG. 48, electronic device 4800 can include a display unit 4802 for displaying a user interface and, optionally, a gyroscope and/or accelerometer unit 4810. Electronic device 4800 can further include a processing unit 4804 coupled to the display unit 4802 and optionally, to the gyroscope and/or accelerometer unit 4810. In some examples, processing unit 4804 can include one or more of a display enabling unit 4806, a selecting unit 4808, a detecting unit 4812, and an identifying unit 4814.

Processing unit 4804 may be configured to: enable display (e.g., with display enabling unit 4806) of a plurality of partitions, wherein each partition of the plurality of partitions is associated with a type of wellness data of a plurality of types of wellness data; in response to detecting a change in an orientation of the device, select (e.g., with selecting unit 4808) a subset of the plurality of partitions; and enable display (e.g., with display enabling unit 4806) of the selected subset of the plurality of partitions.

In some embodiments, the electronic device further includes a gyroscope and/or accelerometer unit 4810 coupled to the processing unit 4804 which is further configured to: detect (e.g., with detecting unit 4812) the change in orientation of the device based on data from the gyroscope and/or accelerometer unit.

In some embodiments, the processing unit is further configured to: detect (e.g., with detecting unit 4812) the change in the orientation of the device by at least detecting a threshold amount of change in the orientation of the electronic device.

In some embodiments, each of the displayed subset of the plurality of partitions comprises a graph representation of at least a portion of the associated type of wellness data displayed therewith.

In some embodiments, the processing unit is further configured to: select (e.g., with selecting unit 4808) a subset of the plurality of partitions by at least: identifying (e.g., with identifying unit 4814) correlations between the plurality of types of wellness data; and selecting (e.g., with selecting unit 4808) partitions associated with correlated types of wellness data as the subset of the plurality of partitions.

The operations described above with reference to FIG. 18 are, optionally, implemented by components depicted in FIGS. 1A-1B or FIG. 48. For example, displaying operations 1802 and 1808 and detecting operation 1804 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 49:
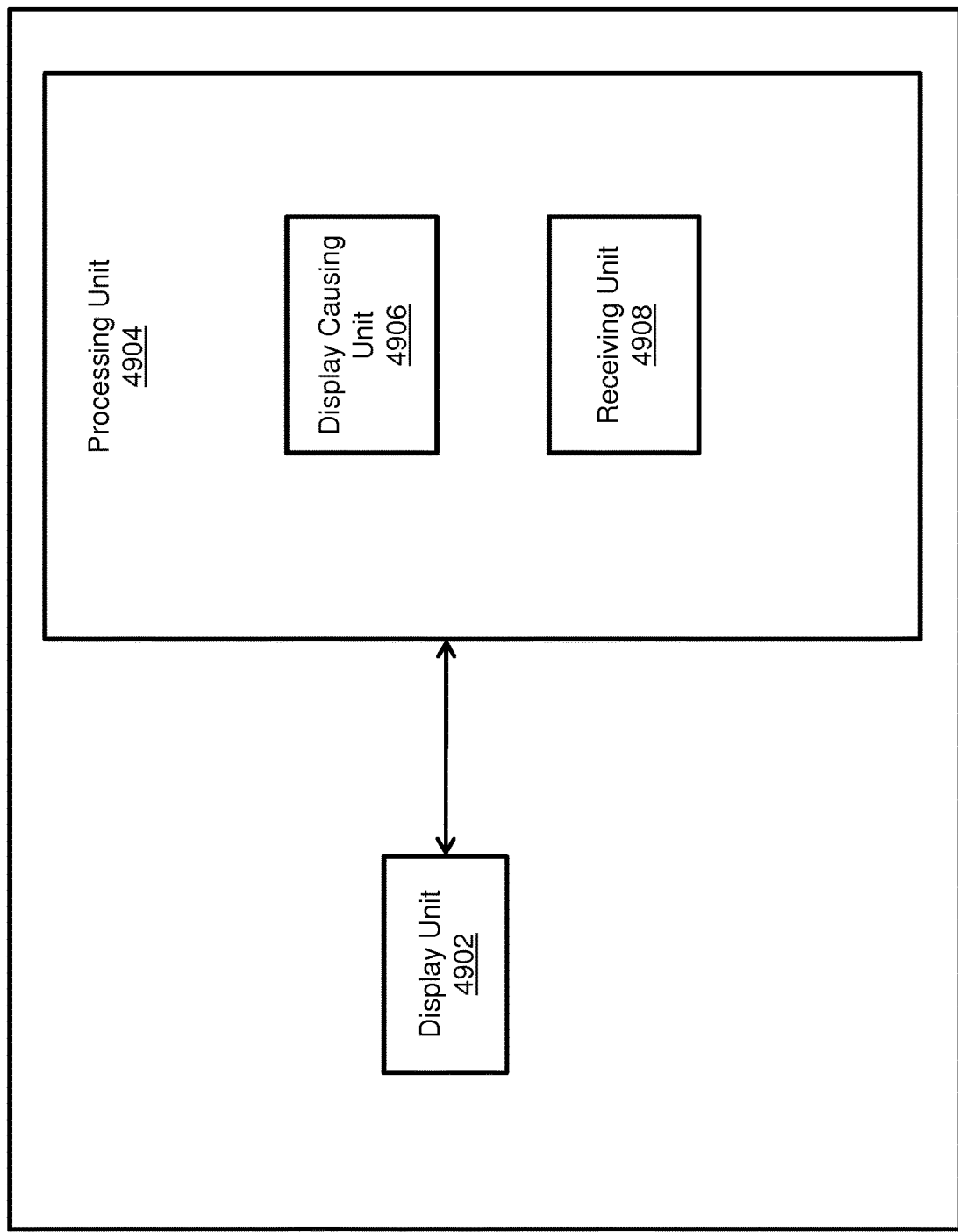
FIG. 49 illustrates a functional block diagram of an electronic device configured to display emergency medical information according to various examples.

In accordance with some examples, FIG. 49 shows a functional block diagram of an electronic device 4900 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 49 can be combined or separated into sub-blocks to implement the principles of the various described examples. Therefore, the description herein optionally supports any possible combination or separation or further definition of the functional blocks described herein.

As shown in FIG. 49, electronic device 4900 can include a display unit 4902 for displaying a user interface. Electronic device 4900 can further include a processing unit 4904 coupled to the display unit 4902. In some examples, processing unit 4904 can include a display causing unit 4906 and a receiving unit 4908.

Processing unit 4904 may be configured to: cause display (e.g., with display causing unit 4806) of a first plurality of partitions associated with a first user, wherein each partition of the first plurality of partitions is associated with a type of wellness data of the first user; and in response to receiving a request (e.g., with receiving unit 4908) to view a second plurality of partitions associated with a second user, cause a display (e.g., with display causing unit 4906) of a second plurality of partitions associated with a second user, wherein each partition of the second plurality of partitions is associated with a type of wellness data of the second user.

In some embodiments, the request to view the second plurality of partitions comprises a request to scroll the displayed first plurality of partitions in a lateral direction.

In some embodiments, the request to view the second plurality of partitions comprises a selection of the second user from a list of users.

In some embodiments, the first user has been authorized by the second user to view the second plurality of partitions.

The operations described above with reference to FIG. 21 are, optionally, implemented by components depicted in FIGS. 1A-1B or FIG. 49. For example, displaying operations 2102 and 2106 and receiving operation 2104 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 50:
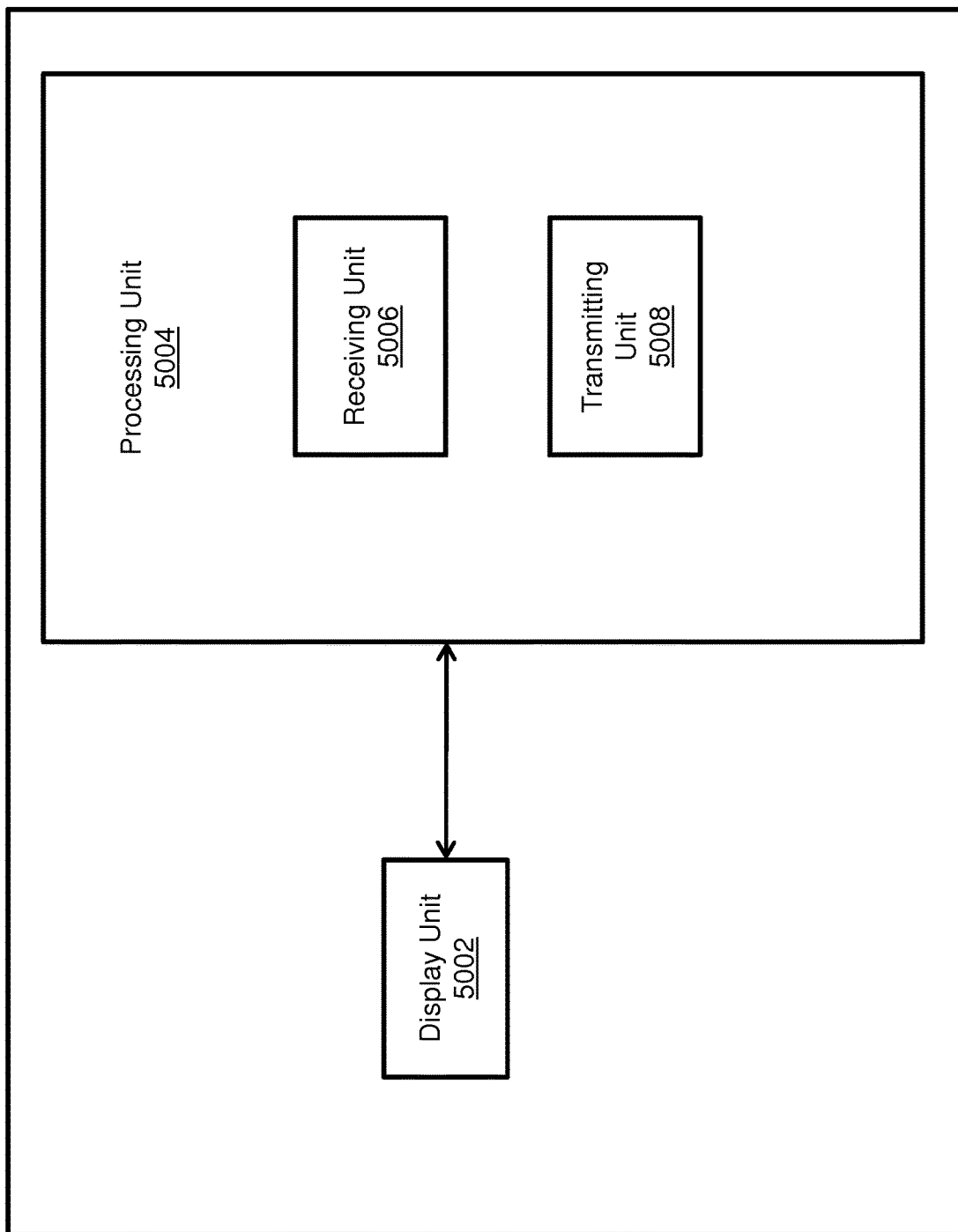
FIG. 50 illustrates a functional block diagram of an electronic device configured to display wellness or non-wellness data according to various examples.

In accordance with some examples, FIG. 50 shows a functional block diagram of an electronic device 5000 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 50 can be combined or separated into sub-blocks to implement the principles of the various described examples. Therefore, the description herein optionally supports any possible combination or separation or further definition of the functional blocks described herein.

As shown in FIG. 50, electronic device 5000 can include a display unit 5002 for displaying a user interface. Electronic device 5000 can further include a processing unit 5004 coupled to the display unit 5002. In some examples, processing unit 5004 can include a receiving unit 5006 and a transmitting unit 5008.

Processing unit 5004 may be configured to: receive (e.g., with receiving unit 5006) an identification of a user authorized to access a set of wellness data; in response to detecting an update to the set of wellness data, transmit (e.g., with transmitting unit 5008) a notification to the user authorized to access the set of wellness data notifying the user authorized to access the set of wellness data that the update to the set of wellness data has been detected; and transmit (e.g., with transmitting unit 5108) at least a portion of the set of wellness data to the user authorized to access the set of wellness data.

In some embodiments, the identification of the user authorized to access the set of wellness data comprises a name, a username, or contact information.

In some embodiments, the at least a portion of the set of wellness data is transmitted in response to receiving a request from the user authorized to access the set of wellness data.

The operations described above with reference to FIG. 8 are, optionally, implemented by components depicted in FIGS. 1A-1B or FIG. 50. For example, receiving operation 802 and transmitting operations 806 and 808 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 51:
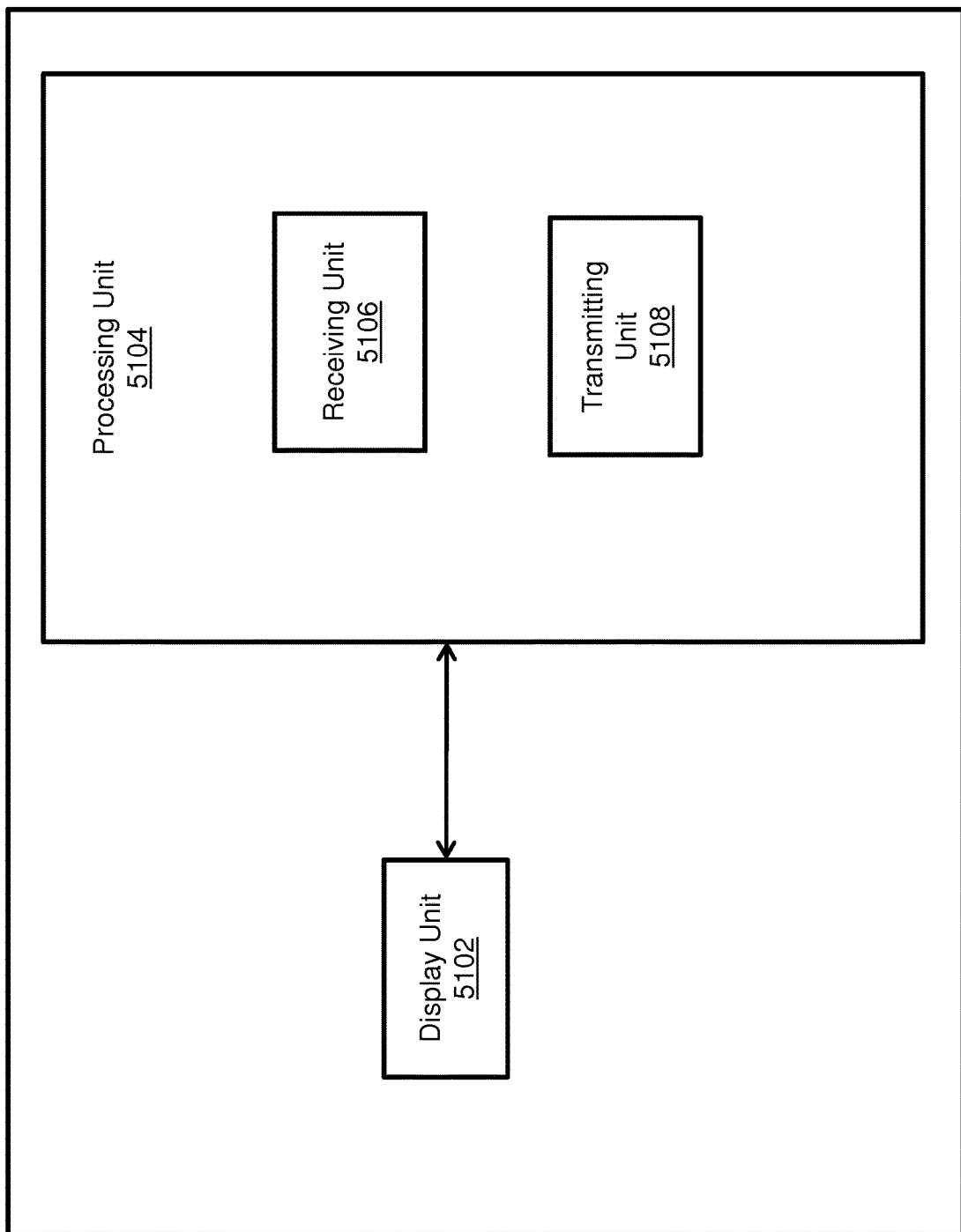
FIG. 51 illustrates a functional block diagram of an electronic device configured to display wellness or non-wellness data according to various examples.

In accordance with some examples, FIG. 51 shows a functional block diagram of an electronic device 5100 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 51 can be combined or separated into sub-blocks to implement the principles of the various described examples. Therefore, the description herein optionally supports any possible combination or separation or further definition of the functional blocks described herein.

As shown in FIG. 51, electronic device 5100 can include a display unit 5102 for displaying a user interface. Electronic device 5100 can further include a processing unit 5104 coupled to the display unit 5102. In some examples, processing unit 5104 can include one or more of a receiving unit 5106 and a transmitting unit 5108.

Processing unit 5104 may be configured to: receive (e.g., with receiving unit 5106), from a first user, a request to access wellness data associated with a second user; transmit (e.g., with transmitting unit 5108), to the second user, a request to authorize the first user to access the wellness data associated with the second user; and in response to receiving an authorization from the second user, transmit (e.g., with transmitting unit 5108) the wellness data associated with the second user to the first user.

In some embodiments, the first user is a health care provider and the second user is a patient, and wherein the request to access the wellness data associated with the second user is received prior to an appointment between the first user and the second user.

In some embodiments, the request to authorize the first user to access the wellness data associated with the second user is displayed on a mobile device of the second user.

The operations described above with reference to FIG. 9 are, optionally, implemented by components depicted in FIGS. 1A-1B or FIG. 51. For example, receiving operation 902 and transmitting operations 904 and 908 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 52:
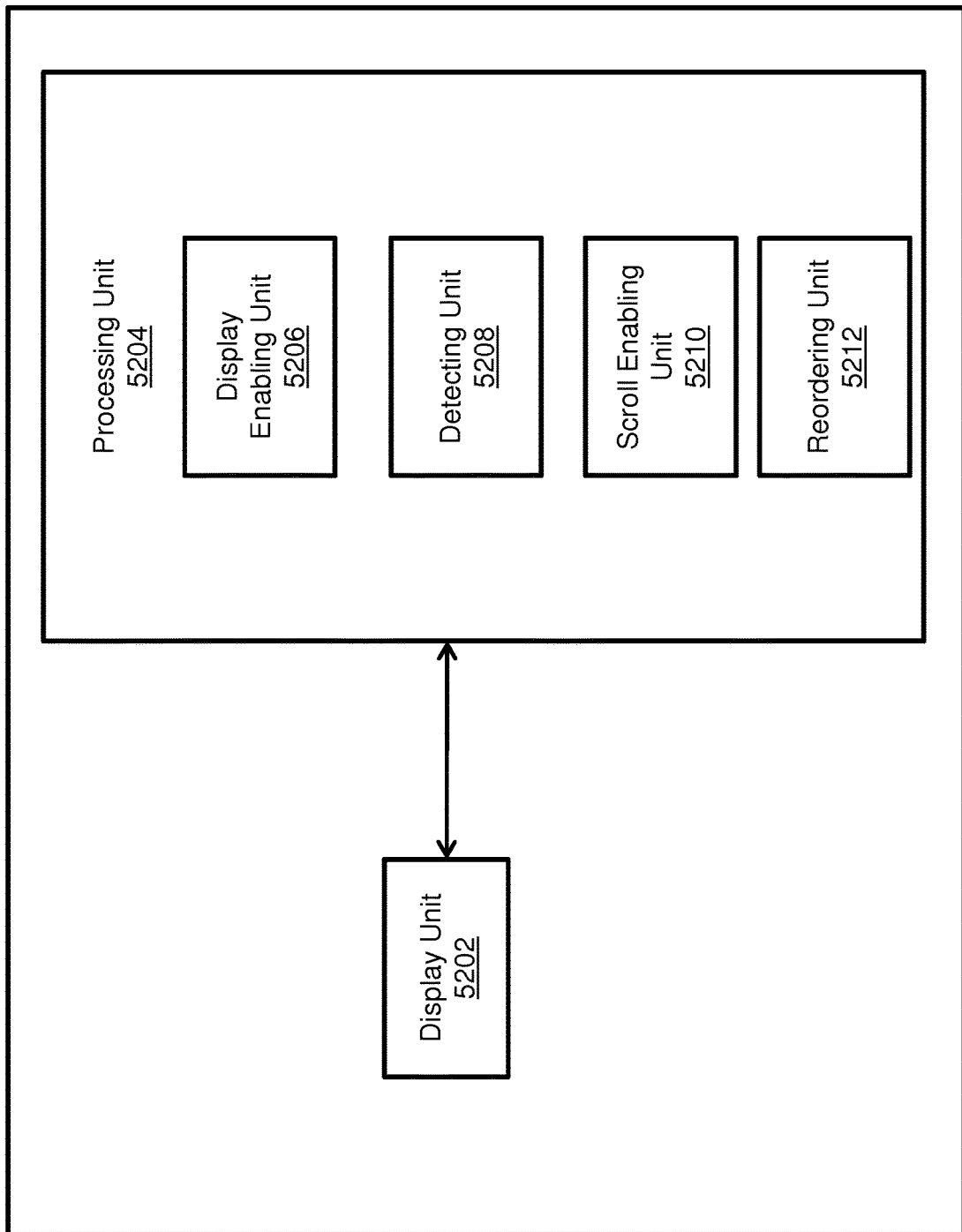
FIG. 52 illustrates a functional block diagram of an electronic device configured to display wellness or non-wellness data according to various examples.

In accordance with some examples, FIG. 52 shows a functional block diagram of an electronic device 5200 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 52 can be combined or separated into sub-blocks to implement the principles of the various described examples. Therefore, the description herein optionally supports any possible combination or separation or further definition of the functional blocks described herein.

As shown in FIG. 52, electronic device 5200 can include a display unit 5202 for displaying a user interface. Electronic device 5200 can further include a processing unit 5204 coupled to the display unit 5202. In some examples, processing unit 5204 can include one or more of a display enabling unit 5206, a detecting unit 5208, a scroll enabling unit 5210, and a reordering unit 5212.

Processing unit 5204 may be configured to: enable display (e.g., with displaying enabling unit 5206) of, on the display, a graph comprising a first data-set representation of a first data set in which a first dependent variable varies as an independent variable changes and a second data-set representation of a second data set in which a second dependent variable varies as the independent variable changes, wherein the first data-set representation is associated with a first range of vertical positions within the graph and the second data-set representation is associated with a second range of vertical positions within the graph; detect (e.g., with detecting unit 2108), at a respective location on the display, a user input; in response to detecting the user input: in accordance with a determination that the respective location is within the first range of vertical positions associated with the first data-set representation, enable display (e.g., with display enabling unit 5206) of, on the display, an indication that the first data-set representation has been selected; and in accordance with a determination that the respective location is within the second range of vertical positions associated with the second data-set representation, enable display (e.g., with display enabling unit 5206) of, on the display, an indication that the second data-set representation has been selected.

In some embodiments, the processing unit 5204 is further configured to: enable display (e.g., with display enabling unit 5206) of the first data-set representation in the graph overlapping the second data-set representation.

In some embodiments, the first data set comprises a first set of wellness data, and wherein the second data set comprises a second set of wellness data.

In some embodiments, the first range of vertical positions is uniquely associated with the first data-set representation, and wherein the second range of vertical positions is uniquely associated with the second data-set representation.

In some embodiments, the first data-set representation and the second data-set representation are colored-coded based on a type of data that they represent.

In some embodiments, processing unit 5204 is further configured to: enable display (e.g., with display enabling unit 5206) of the indication that the first data-set representation has been selected by at least enabling display, on the display, of a marker overlaid on the first data-set representation at a horizontal position corresponding to a horizontal position of the respective location on the display.

In some embodiments, processing unit 5204 is further configured to enable display (e.g., with display enabling unit 5206) of the indication that the second data-set representation has been selected by at least enabling display, on the display, of a marker overlaid on the second data-set representation at a horizontal position corresponding to a horizontal position of the respective location on the display.

In some embodiments, processing unit 5204 is configured to enable display (e.g., with display enabling unit 5206) of the indication that the first data-set representation has been selected by at least enabling display, on the display, of a numerical value of a first data entry of the first data set associated with a value of the independent variable corresponding to a horizontal position of the respective location on the display.

In some embodiments, processing unit 5204 is further configured to: enable display (e.g., with display enabling unit 5206) of the indication that the second data-set representation has been selected by at least enabling display, on the display, of a numerical value of a second data entry of the second data set associated with a value of the independent variable corresponding to a horizontal position of the respective location on the display.

In some embodiments, the first data set or the second data set comprises blood pressure data, and wherein the numerical value of the first data entry or the second data entry comprises a high value for diastolic blood pressure, a low value for diastolic blood pressure, a high value for systolic blood pressure, and a low value for systolic blood pressure.

In some embodiments, the first data-set representation or the second data-set representation is generated based on an average of blood pressure values.

In some embodiments, the first data set or the second data set comprises heart rate data, and wherein the numerical value of the first data entry or the second data entry comprises a high value for heart rate and a low value for heart rate.

In some embodiments, the first data-set representation comprises a first line in the graph, and wherein displaying the indication that the first data-set representation has been selected comprises highlighting an area below the first line.

In some embodiments, the second data-set representation comprises a second line in the graph, and wherein displaying the indication that the second data-set representation has been selected comprises highlighting an area below the second line.

In some embodiments, the first range of vertical positions within the graph expands based on a length of time that the user input is detected while a vertical position of the respective location on the display is within the first range of vertical positions, and wherein the second range of vertical positions within the graph expands based on a length of time that the user input is detected while the vertical position of the respective location on the display is within the second range of vertical positions.

In some embodiments, the dependent variable for the first data set is measured in different units from the dependent variable for the second data set.

In some embodiments, a vertical scale for displaying the first data-set representation is different from a vertical scale for displaying the second data-set representation.

In some embodiments, the vertical scale for the first data-set representation is determined based on the maximum and minimum values of the first dependent variable of the first data-set representation that are to be displayed in the graph, and wherein the vertical scale for the second data-set representation is determined based on the maximum and minimum values of the second dependent variable of the second data-set representation that are to be displayed in the graph.

In some embodiments, the vertical scale for the first data-set representation of the plurality of sets of wellness data is defined by: a maximum vertical position within the graph corresponding to a first multiplying factor multiplied by the maximum value of the first dependent variable of the first data-set representation that are to be displayed in the graph; and a minimum vertical position within the graph corresponding to a second multiplying factor multiplied by the minimum value of the first dependent variable of the first data-set representation that are to be displayed in the graph.

In some embodiments, the vertical scale for the second data-set representation of the plurality of sets of wellness data is defined by: a maximum vertical position within the graph corresponding to a third multiplying factor multiplied by the maximum value of the second dependent variable of the second data-set representation that are to be displayed in the graph; and a minimum vertical position within the graph corresponding to a fourth multiplying factor multiplied by the minimum value of the second dependent variable of the second data-set representation that are to be displayed in the graph.

In some embodiments, the processing unit 5204 is further configured to: detect (e.g., with detecting unit 5208) detailed-view input; and in response to detecting the detailed-view input, enable display of a detailed view of the first data set and the second data set, wherein the detailed view comprises a first partition associated with the first data set and a second partition associated with the second data set.

In some embodiments, processing unit 5204 is configured to detect (e.g., with detecting unit 5208) the detailed-view input by at least detecting a change in orientation of the electronic device while displaying the graph.

In some embodiments, processing unit 5204 is further configured to: detect (e.g., with detecting unit 5208) a request to scroll the detailed view; and in response to detecting the request to scroll the detailed view, enable scrolling (e.g., with scroll enabling unit 5210) of the detailed view.

In some embodiments, the first partition comprises a first graph representation of the first data set, and wherein the second partition comprises a second graph representation of the second data set.

In some embodiments, the first graph representation is non-overlapping with the second graph representation.

In some embodiments, processing unit 5204 is further configured to: enable display (e.g., with display enabling unit 5206) of the first partition in a color matching a color of the first data-set representation, and wherein the second partition is displayed in a color matching a color of the second data-set representation.

In some embodiments, the processing unit 5204 is configured to: enable display (e.g., with display enabling unit 5206) of the first partition in a color matching a color of the first data-set representation, and enable display of the second partition in a color matching a color of the second data-set representation.

In some embodiments, processing unit 5204 is further configured to: detect (e.g., with detecting unit 5208) a request to reorder the first partition and the second partition; and in response to detecting the request to reorder the first partition and the second partition, reorder (e.g., with reordering unit 5212) the first partition and the second partition within the detailed view.

In some embodiments, processing unit 5204 is further configured to: detect graph-view input; and in response to detecting the graph-view input, display the graph comprising the first data-set representation of the first data set and the second data-set representation of the second data set.

The operations described above with reference to FIG. 27 are, optionally, implemented by components depicted in FIGS. 1A-1B or FIG. 52. For example, display operation 2702, detection operation 2704, display operation 2706, and display operation 2710 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 53:
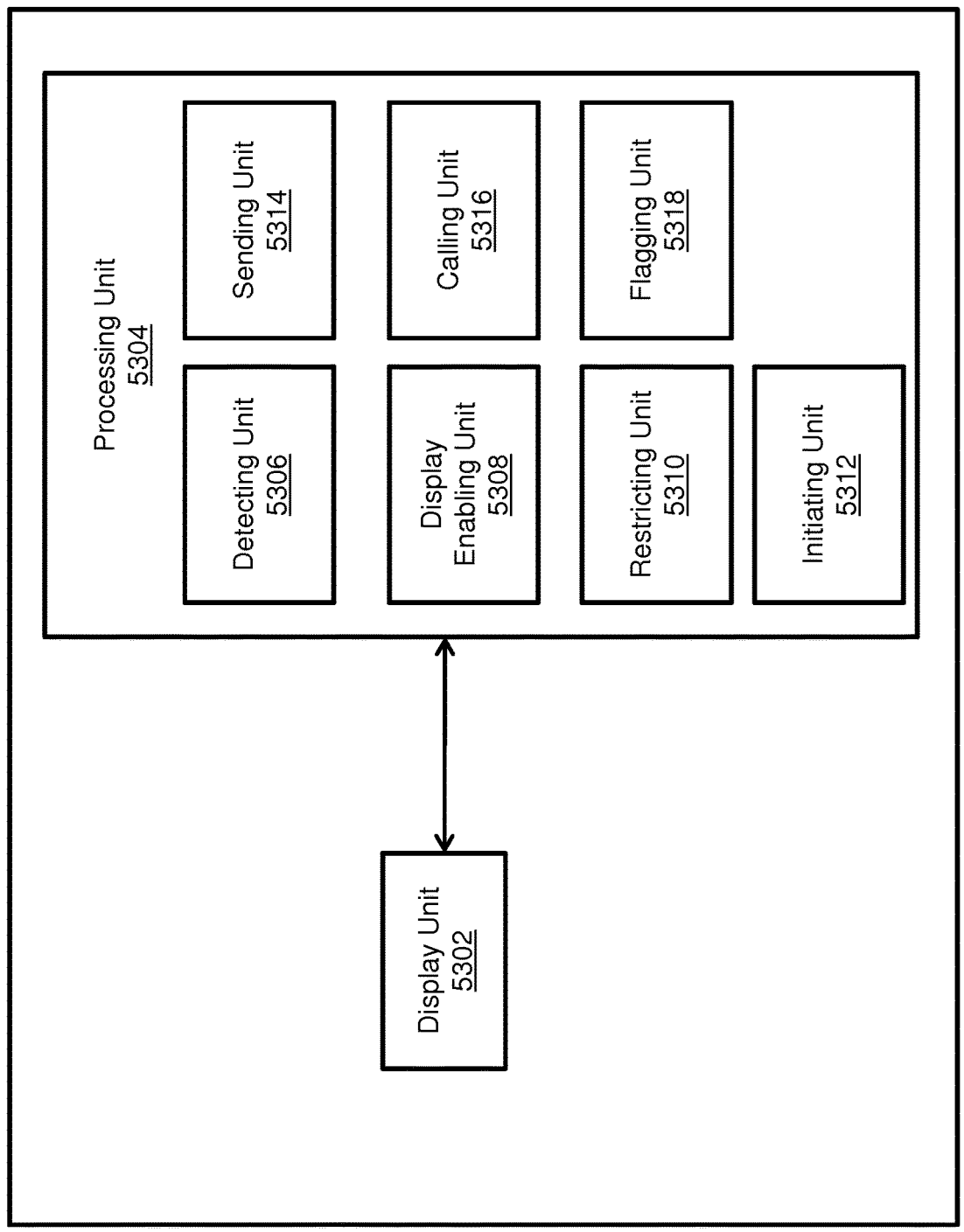
FIG. 53 illustrates a functional block diagram of an electronic device configured to display wellness or non-wellness data according to various examples.

In accordance with some examples, FIG. 53 shows a functional block diagram of an electronic device 5300 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 53 can be combined or separated into sub-blocks to implement the principles of the various described examples. Therefore, the description herein optionally supports any possible combination or separation or further definition of the functional blocks described herein.

As shown in FIG. 53, electronic device 5300 can include a display unit 5302 for displaying a user interface. Electronic device 5300 can further include a processing unit 5304 coupled to the display unit 5302. In some examples, processing unit 5304 can include one or more of a detecting unit 5306, a display enabling unit 5308, a restricting unit 5310, initiating unit 5312, sending unit 5314, calling unit 5316, and flagging unit 5318.

Processing unit 5304 may be configured to: while the electronic device is in a locked state: detect (e.g., with detecting unit 5306) a request to display emergency information about a user of the device; and in response to detecting the request, enable display (e.g., with display enabling unit 5308), on the display, of an emergency information interface comprising emergency information about the user of the device without unlocking the device.

In some embodiments, processing unit 5304 is further configured to: while the electronic device is in the locked state, restrict (e.g., with restricting unit 5310) use of one or more functions of the electronic device.

In some embodiments, while the electronic device is in the locked state, at least a subset of data stored on the device is not accessible.

In some embodiments, while the electronic device is in the locked state, communications from the electronic device are restricted.

In some embodiments, the emergency information about the user comprises information associated with an emergency contact, and wherein the information associated with the emergency contacts comprises a name of the emergency contact and a relationship between the user and the emergency contact.

In some embodiments, processing unit 5304 is further configured to: detect (e.g., with detecting unit 5306) a request to communicate while the electronic device is in the locked state; and in response to detecting the request to communicate, initiate (e.g., with initiating unit 5312) communication with the emergency contact.

In some embodiments, processing unit 5304 is configured to initiate communication with the emergency contact by at least sending (e.g., with sending unit 5314) an SMS message or email to the emergency contact.

In some embodiments, processing unit 5304 is configured to initiate communication with the emergency contact by at least calling (e.g., with calling unit 5316) a phone number associated with the emergency contact.

In some embodiments, processing unit 5304 is configured to call the phone number associated with the emergency contact by at least flagging (e.g., with flagging unit 5318) the call to the phone number as an emergency call.

In some embodiments, the information associated with the emergency contacts further comprises the phone number associated with the emergency contact.

In some embodiments, the information associated with the emergency contacts excludes the phone number associated with the emergency contact.

In some embodiments, processing unit 5304 is further configured to: prior to displaying the emergency information interface: enable display (e.g., with display enabling unit 5308) of an emergency dialing interface comprising a numerical input pad and an emergency information option; while displaying the emergency dialing interface, detect (e.g., with detecting unit 5306) a selection of the emergency information option; and in response to detecting selection of the emergency information option, enable display (e.g., with display enabling unit 5308) of the emergency information interface.

In some embodiments, processing unit 5304 is further configured to: detect (e.g., with detecting unit 5306) a predefined phone number entered using the numerical input pad while the electronic device is in the locked state; and in response to detecting the predefined phone number, call the predefined phone number.

In some embodiments, processing unit 5304 is configured to call (e.g., with calling unit 5316) the predefined phone number by at least flagging (e.g., with flagging unit 5318) the call to the predefined phone number as an emergency call.

In some embodiments, calls flagged as an emergency call are to be accepted by a receiving electronic device in any state of operation.

In some embodiments, processing unit 5304 is further configured to: prior to displaying the emergency dialing interface: enable display (e.g., with display enabling unit 5308) of a lock screen interface comprising an emergency option; detect (e.g., with detecting unit 5306) a selection of the emergency option; and in response to detecting the selection of the emergency option, enable display (e.g., with display enabling unit 5308) of the emergency dialing interface.

In some embodiments, the emergency information about the user comprises one or more of: the user's name, birthday, medical conditions, allergies and reactions, medications, and one or more emergency contacts of the user.

The operations described above with reference to FIG. 45 are, optionally, implemented by components depicted in FIGS. 1A-1B or FIG. 53. For example, detection operation 4502 and display operation 4504 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 54:
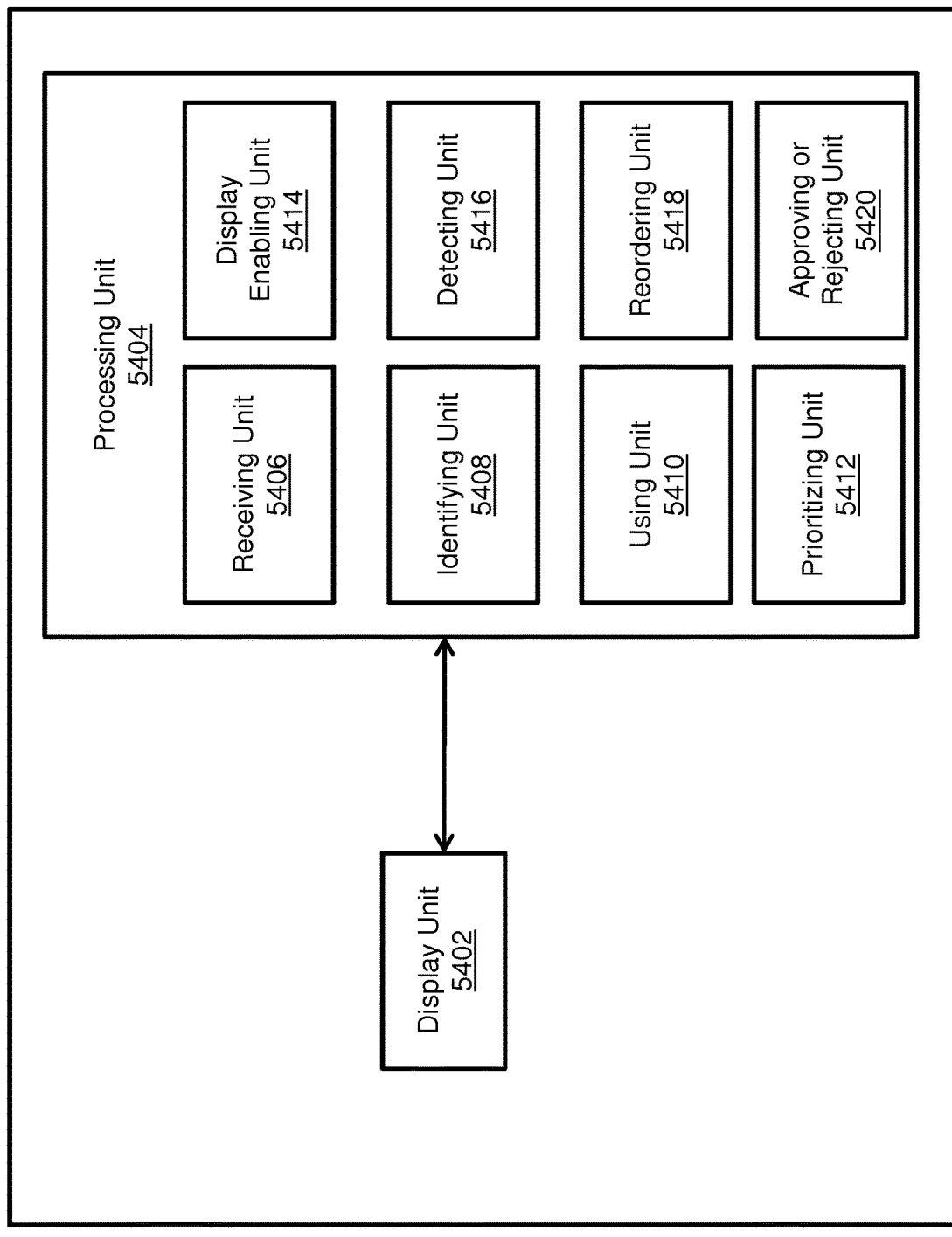
FIG. 54 illustrates a functional block diagram of an electronic device configured to display wellness or non-wellness data according to various examples.

In accordance with some examples, FIG. 54 shows a functional block diagram of an electronic device 5400 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 54 can be combined or separated into sub-blocks to implement the principles of the various described examples. Therefore, the description herein optionally supports any possible combination or separation or further definition of the functional blocks described herein.

As shown in FIG. 54, electronic device 5400 can include a display unit 5402 for displaying a user interface. Electronic device 5400 can further include a processing unit 5404 coupled to the display unit 5402. In some examples, processing unit 5404 can include one or more of a receiving unit 5406, an identifying unit 5408, a using unit 5410, a prioritizing unit 5412, a display enabling unit 5414, a detecting unit 5416, a reordering unit 5418, and an approving or rejecting unit 5420.

Processing unit 5404 may be configured to: receive (e.g., with receiving unit 5406), from a user, information identifying a plurality of approved sources of wellness data, wherein the information identifying the plurality of approved sources identifies one or more types of wellness data that are approved to be received from the plurality of approved sources and stored in a wellness database; and receive (e.g., with receiving unit 5406), from the user, information identifying a plurality of approved destinations of wellness data, wherein the information identifying the plurality of approved destinations identifies one or more types of wellness data that are approved to be accessed from the wellness database by the plurality of approved destinations of wellness data.

In some embodiments, the plurality of approved sources comprises an electronic device or software application.

In some embodiments, the plurality of approved destinations comprises an electronic device or software application.

In some embodiments, the plurality of approved sources is ranked amongst each other.

In some embodiments, processing unit 5404 is further configured to: identify (e.g., with identifying unit 5408) a first wellness data entry in the wellness database that was received from a first approved source of the plurality of approved sources, the first wellness data entry comprising a first wellness data type and a first timestamp; and identify (e.g., with identifying unit 5408) a second wellness data entry in the wellness database that was received from a second approved source of the plurality of approved sources, the second wellness data entry comprising a second wellness data type and a second timestamp, wherein the first wellness data type and the second wellness data type are the same, and wherein the first timestamp is within a threshold length of time from the second timestamp.

In some embodiments, the first approved source has been identified by the user as being preferred over the second approved source, and wherein processing unit 5404 is further configured to: use (e.g., with using unit 5410) the first wellness data entry instead of using the second wellness data entry.

In some embodiments, the first approved source has been identified by the user as being preferred over the second approved source, and wherein processing unit 5404 is further configured to: prioritize (e.g., with prioritizing unit 5412) the first wellness data entry over the second wellness data entry.

In some embodiments, processing unit 5404 is further configured to: in accordance with a determination that the first wellness data entry is prioritized over the second wellness data entry, use (e.g., with using unit 5410) the first wellness data entry instead of using the second wellness data entry.

In some embodiments, the second approved source has been identified by the user as being preferred over the first approved source, and wherein processing unit 5404 is further configured to: prioritize (e.g., with prioritizing unit 5412) the second wellness data entry over the first wellness data entry.

In some embodiments, processing unit 5404 is further configured to: in accordance with a determination that the second wellness data entry is prioritized over the first wellness data entry, use (e.g., with using unit 5410) the second wellness data entry instead of using the first wellness data entry.

In some embodiments, processing unit 5404 is further configured to: enable display (e.g., with display enabling unit 5414), on the display, of a plurality of categories of wellness data stored in the wellness database.

In some embodiments, processing unit 5404 is further configured to: detect (e.g., with detecting unit 5416) a selection of a category of wellness data from the displayed plurality of categories of wellness data; and in response to detecting the selection of the category of wellness data, enable display (e.g., with display enabling unit 5414), on the display, of one or more sub-categories of the category of wellness data.

In some embodiments, processing unit 5404 is further configured to: detect (e.g., with detecting unit 5416) a selection of a sub-category from the displayed one or more sub-categories; and in response to detecting the selection of the sub-category, enable display (e.g., with display enabling unit 5414), on the display, of a detailed view of the sub-category.

In some embodiments, the detailed view of the sub-category comprises a graph representation of the sub-category of wellness data over time and a numerical daily value of the sub-category of wellness data.

In some embodiments, the detailed view of the sub-category further comprises an input field for entering a wellness data entry, and processing unit 5404 is further configured to: receive (e.g., with receiving unit 5406) a wellness data entry to be stored in the wellness database that was input into the input field.

In some embodiments, the detailed view of the sub-category further comprises a textual description of the sub-category.

In some embodiments, the detailed view of the sub-category further comprises an option to view wellness data entries corresponding to the sub-category, and wherein processing unit 5404 is further configured to: enable display (e.g., with display enabling unit 5414), on the display, of a plurality of wellness data entries corresponding to the sub-category stored in the wellness database.

In some embodiments, each of the plurality of wellness data entries comprises a numerical value of the data entry, a timestamp, and an identification of a source of the data entry.

In some embodiments, the detailed view of the sub-category further comprises an option to share wellness data, and processing unit 5404 is further configured to: enable display (e.g., with display enabling unit 5414), on the display, of a data sharing interface comprising the plurality of approved sources and the plurality of approved destinations.

In some embodiments, processing unit 5404 is further configured to: detect (e.g., with detecting unit 5416) a request to reorder the displayed plurality of approved sources; and in response to detecting the request to reorder the displayed plurality of approved sources, reorder (e.g., with reordering unit 5418) the displayed plurality of approved sources in accordance with the detected request to reorder the displayed plurality of approved sources.

In some embodiments, the data sharing interface further comprises options to add an approved destination to the plurality of approved destinations and to remove an approved destination from the plurality of approved destinations.

In some embodiments, processing unit 5404 is further configured to: receive (e.g., with receiving unit 5406) a search query; and enable display (e.g., with display enabling unit 5414), on the display, of one or more sub-categories of the plurality of categories that match the search query, wherein the displayed one or more sub-categories that match the search query are color-coded based on their respective categories.

In some embodiments, processing unit 5404 is further configured to: enable display (e.g., with display enabling unit 5414), on the display, of a source interface comprising a list of known sources.

In some embodiments, the source interface further comprises a numerical indicator associated a known source of the known sources that represents a number of new types of wellness data that can be provided by the known source.

In some embodiments, processing unit 5404 is further configured to: detect (e.g., with detecting unit 5416) a selection of a known source from the displayed list of known sources; and in response to detecting the selection of the known source, enable display (e.g., with display enabling unit 5414), on the display, of a list of types of wellness data that the known source can provide.

In some embodiments, the list of types of wellness data that the known source can provide comprises a selectable option for each of the types of wellness data that the known source can provide to approve or reject the associated type of wellness data.

In some embodiments, processing unit 5404 is further configured to: detect a selection of the selectable option for a type of wellness data that the known source can provide; and in response to detecting the selection of the selectable option, approve or reject (e.g., with approving or rejecting unit 5420) the type of wellness data that the known source can provide in accordance with the detected selection of the selectable option.

The operations described above with reference to FIGS. 38A and 38B are, optionally, implemented by components depicted in FIGS. 1A-1B or FIG. 54. For example, receiving operation 3802 and identifying operation 3806 may be implemented by event sorter 170, event recognizer 180, and event handler 190. Event monitor 171 in event sorter 170 detects a contact on touch-sensitive display 112, and event dispatcher module 174 delivers the event information to application 136. A respective event recognizer 180 of application 136 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 may utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data can include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates examples in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed examples, the present disclosure also contemplates that the various examples can also be implemented without the need for accessing such personal information data. That is, the various examples of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. An electronic device of a second user, comprising:
one or more processors; and
memory storing one or more programs configured to be executed by the one or more processors, the one or more programs including instructions for:
receiving a request from an electronic device of a first user to access wellness data associated with the second user;
in response to receiving the request and in accordance with a determination that the first user is authorized to access the wellness data associated with the second user:
encrypting the wellness data associated with the second user; and
transmitting the encrypted wellness data associated with the second user from the electronic device of the second user directly to the electronic device of the first user; and
in response to receiving the request and in accordance with a determination that the first user is not authorized to access the wellness data associated with the second user:
displaying, on a display of the electronic device of the second user, a prompt including a request for the second user to authorize the first user to access the wellness data associated with the second user;
subsequent to prompting the second user, receiving an input indicative of whether the first user is authorized to access the wellness data associated with the second user;
in accordance with a determination that the input indicates the first user is authorized to access the wellness data associated with the second user:
encrypting the wellness data associated with the second user; and
transmitting the encrypted wellness data associated with the second user from the electronic device of the second user directly to the electronic device of the first user; and
in accordance with a determination that the input indicates the first user is not authorized to access the wellness data associated with the second user, forgoing transmitting the wellness data associated with the second user from the electronic device of the second user.

2. The electronic device of claim 1, wherein the first user is a health care provider and the second user is a patient; and wherein the one or more programs further include instructions for:
receiving, from the first user, a request to access the wellness data associated with the second user, prior to an appointment between the first user and the second user.

3. The electronic device of claim 1, the one or more programs further including instructions for:
prior to determining whether the first user is authorized to access the wellness data associated with the second user:
receiving, from the electronic device of the first user, a request to authorize the first user to access the wellness data associated with the second user.

4. A method comprising:
at an electronic device of a second user:
receiving a request from an electronic device of a first user to access wellness data associated with the second user;
in response to receiving the request and in accordance with a determination that the first user is authorized to access the wellness data associated with the second user:
encrypting the wellness data associated with the second user; and
transmitting the encrypted wellness data associated with the second user from the electronic device of the second user directly to the electronic device of the first user; and
in response to receiving the request and in accordance with a determination that the first user is not authorized to access the wellness data associated with the second user:
displaying, on a display of the electronic device of the second user, a prompt including a request for the second user to authorize the first user to access the wellness data associated with the second user;
subsequent to prompting the second user, receiving an input indicative of whether the first user is authorized to access the wellness data associated with the second user;

in accordance with a determination that the input indicates the first user is authorized to access the wellness data associated with the second user:
  encrypting the wellness data associated with the second user; and
  transmitting the encrypted wellness data associated with the second user from the electronic device of the second user directly to the electronic device of the first user; and
in accordance with a determination that the input indicates the first user is not authorized to access the wellness data associated with the second user, forgoing transmitting the wellness data associated with the second user from the electronic device of the second user.

5. The method of claim 4, wherein the first user is a health care provider and the second user is a patient; and
  wherein the method further comprises:
    receiving, from the first user, a request to access the wellness data associated with the second user, prior to an appointment between the first user and the second user.

6. The method of claim 4, further comprising:
  prior to determining whether the first user is authorized to access the wellness data associated with the second user:
    receiving, from the electronic device of the first user, a request to authorize the first user to access the wellness data associated with the second user.

7. A non-transitory computer-readable storage medium storing one or more programs configured to be executed by one or more processors of an electronic device of a second user, the one or more programs including instructions for:
  receiving a request from an electronic device of a first user to access wellness data associated with the second user;
  in response to receiving the request and in accordance with a determination that the first user is authorized to access the wellness data associated with the second user:
    encrypting the wellness data associated with the second user; and
    transmitting the encrypted wellness data associated with the second user from the electronic device of the second user directly to the electronic device of the first user; and
  in response to receiving the request and in accordance with a determination that the first user is not authorized to access the wellness data associated with the second user:
    displaying, on a display of the electronic device of the second user, a prompt including a request for the second user to authorize the first user to access the wellness data associated with the second user;
    subsequent to prompting the second user, receiving an input indicative of whether the first user is authorized to access the wellness data associated with the second user;
    in accordance with a determination that the input indicates the first user is authorized to access the wellness data associated with the second user:
      encrypting the wellness data associated with the second user; and
      transmitting the encrypted wellness data associated with the second user from the electronic device of the second user directly to the electronic device of the first user; and
    in accordance with a determination that the input indicates the first user is not authorized to access the wellness data associated with the second user, forgoing transmitting the wellness data associated with the second user from the electronic device of the second user.

8. The non-transitory computer-readable storage medium of claim 7, wherein the first user is a health care provider and the second user is a patient; and
  wherein the one or more programs further include instructions for:
    receiving, from the first user, a request to access the wellness data associated with the second user, prior to an appointment between the first user and the second user.

9. The non-transitory computer-readable storage medium of claim 7, the one or more programs further including instructions for:
  prior to determining whether the first user is authorized to access the wellness data associated with the second user:
    receiving, from the electronic device of the first user, a request to authorize the first user to access the wellness data associated with the second user.

* * * * *